(12) United States Patent
Whatcott et al.

(10) Patent No.: US 8,703,736 B2
(45) Date of Patent: Apr. 22, 2014

(54) THERAPEUTIC TARGET FOR PANCREATIC CANCER CELLS

(75) Inventors: Cliff Whatcott, Phoenix, AZ (US); Haiyong Han, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 13/439,830

(22) Filed: Apr. 4, 2012

(65) Prior Publication Data

US 2012/0252753 A1 Oct. 4, 2012

Related U.S. Application Data

(60) Provisional application No. 61/471,310, filed on Apr. 4, 2011.

(51) Int. Cl.
*A61K 31/551* (2006.01)

(52) U.S. Cl.
USPC .......................................................... 514/49

(58) Field of Classification Search
USPC ........................................................... 514/49
See application file for complete search history.

(56) References Cited

U.S. PATENT DOCUMENTS

2011/0294789 A1\* 12/2011 Nikolich et al. .............. 514/218

OTHER PUBLICATIONS

Kaneko et al. Expression of ROCK-1 in human pancreatic cancer: Its down-regulation by morpholino oligo antisense can reduce the migration of pancreatic cancer cells in vitro. Pancreas 24:251-257, 2002.*
Burris et al. Improvements in survival and clinical benefit with gemcitabine as first-line therapy for patients with advanced pancreatic cancer: A randomized trial. J Clin Oncol 15:2403-2413, 1997.*

\* cited by examiner

*Primary Examiner* — Wu-Cheng Winston Shen
*Assistant Examiner* — Yih-Horng Shiao
(74) *Attorney, Agent, or Firm* — Polsinelli PC

(57) ABSTRACT

This invention provides a therapeutic target for pancreatic cancer. The invention further provides methods of screening of new therapeutic agents using the target. The invention also provides a pharmaceutical composition comprising fasudil or derivatives thereof for pancreatic cancer treatment, and a kit comprising such a pharmaceutical composition.

15 Claims, 19 Drawing Sheets
(8 of 19 Drawing Sheet(s) Filed in Color)

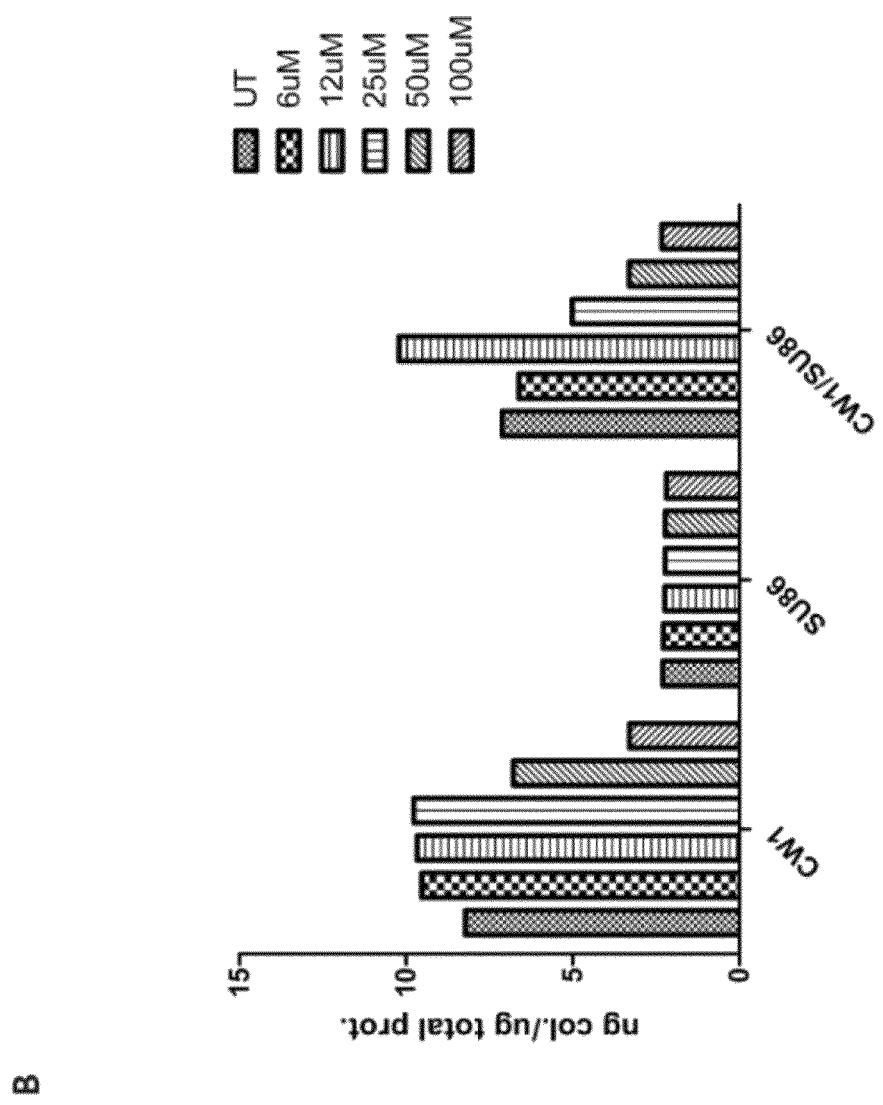

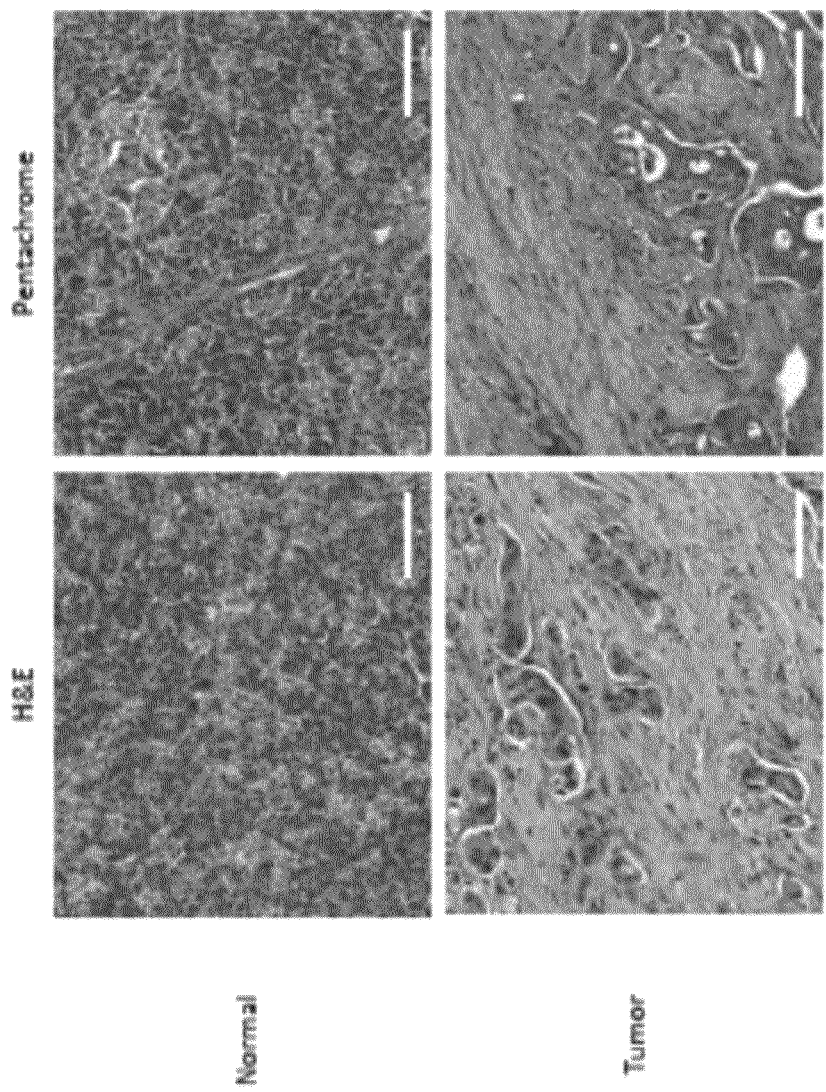

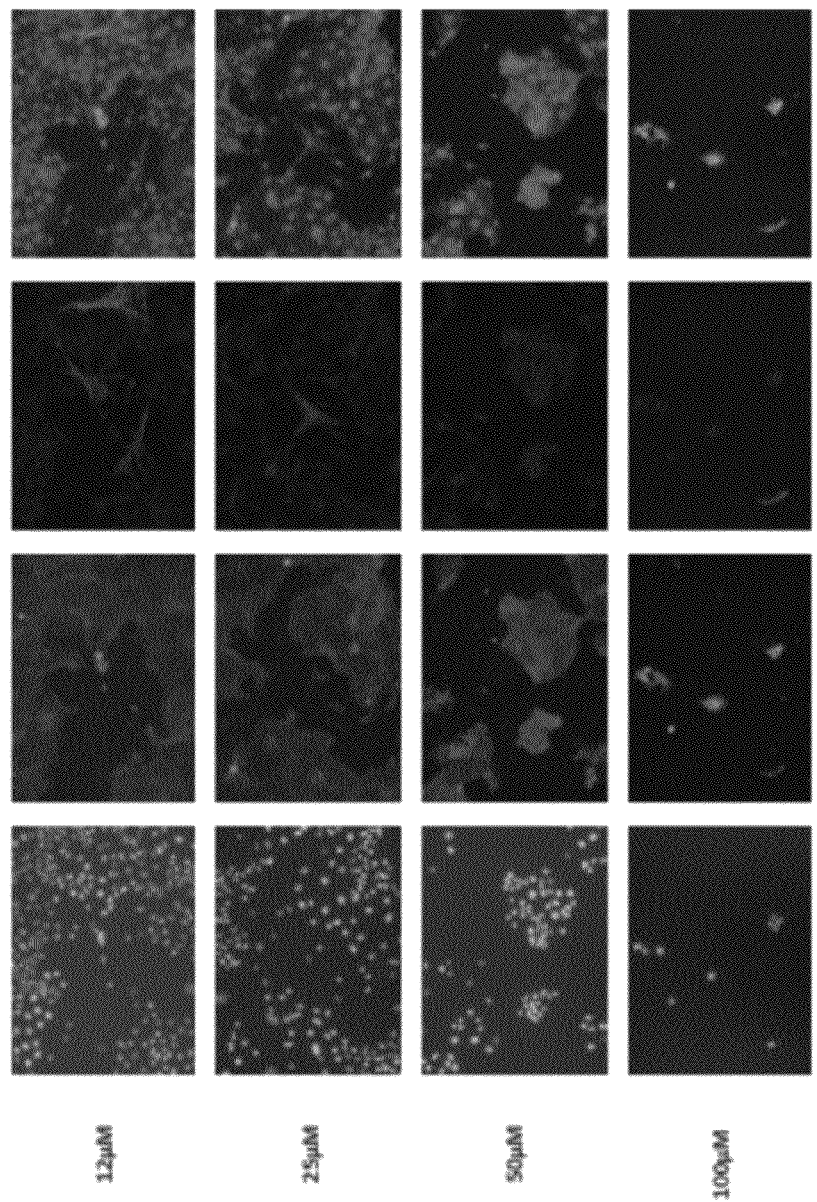

US 8,703,736 B2

THERAPEUTIC TARGET FOR PANCREATIC CANCER CELLS

CROSS REFERENCE

This application is related to and claims the priority benefit of U.S. provisional application 61/471,310, filed on Apr. 4, 2011, the teachings and content of which are incorporated by reference herein.

FIELD OF THE INVENTION

This invention relates to a therapeutic target, ROCK1, for pancreatic cancer. Further, the invention relates to methods of using the therapeutic target in screening for agents to develop pancreatic cancer treatments. The invention also provides a new application of a known ROCK1 inhibitor, fasudil, in treating pancreatic cancer.

BACKGROUND OF THE INVENTION

Pancreatic cancer is the fifth most common cause of tumor-related deaths in the industrialized world. Fewer than 10% to 20% of patients are candidates for surgery at the time of presentation, and fewer than 20% of patients who undergo curative resection are alive after 5 years. Despite recent progress, there is no modality for early detection of pancreatic cancer. There have not been many reports of effective treatment of advanced pancreatic cancer either local or metastatic disease. Therefore, there is a need to develop new treatments that are effective for pancreatic cancer, and methods to prevent pancreatic cancer progression.

It is known that the gene expression patterns are complexly different between normal and cancerous cells. With regard to various cancer researches, it was proposed that the genomic landscape consists of the most frequently mutated genes, and hundreds of less frequently mutated cancer-associated genes. Using breast cancer as an example, many studies have investigated genomic instability such as copy number alteration and DNA amplification and deletion affecting commonly amplified regions in the genome. However, most of these global genomic studies of high-frequency genetic events have not revealed any additional genes that contain alterations potentially affecting breast cancer development, which is true to pancreatic cancer research as well. Therefore, there is a need to take a different approach, i.e., looking into low-frequency alterations, to identify novel genes that may facilitate treatment development for pancreatic cancer.

SUMMARY OF THE INVENTION

One aspect of the present invention provides a method for identifying a treatment responding subgroup of subjects having pancreatic cancer, comprising: (1) receiving a sample from a subject; (2) detecting abnormality of ROCK1 gene in the sample relative to the ROCK1 gene of a sample free of pancreatic cancer cell a sample having treatment non-responding pancreatic cancer; and (3) identifying ROCK1 inhibitor sensitivity as being present in the subject providing the sample. The abnormality of ROCK1 gene may be gene overexpression or gene amplification relative to control. The subject or the subgroup identified thereby would respond to the treatment comprising administering an effective dosage amount of a pharmaceutical composition comprising one or more ROCK1 inhibitors selected from the group consisting of fasudil or its derivatives, Y27632 or its derivatives, and any combination thereof. In some examples, the pharmaceutical composition may further comprise gemcitabine. In one example, the method for identifying a treatment responding subgroup of subjects having pancreatic cancer may further comprise administering an effective dosage amount of a pharmaceutical composition comprising one or more ROCK1 inhibitors selected from the group consisting of fasudil or its derivatives, Y27632 or its derivatives, and any combination thereof. The novel application of fasudil includes inhibiting pancreatic tumor cell proliferation, migration; and reducing stromal contribution to pancreatic tumor growth.

Another aspect of the present invention provides a method of inhibiting pancreatic tumor cell proliferation, and the method comprises the step of administering a pharmaceutical composition comprising fasudil or derivatives thereof to a subject in need thereof. In one example, the subject in need of such a pharmaceutical composition is one having abnormality of ROCK1 gene. The abnormality of ROCK1 gene in such a subject may be gene overexpression or gene amplification relative to the ROCK1 gene of a sample free of pancreatic cancer cell or a sample having a treatment non-responding pancreatic cancer. The treatment that a subgroup of pancreatic cancer patients would or would not respond to comprises administering an effective dosage amount of a pharmaceutical composition comprising one or more ROCK1 inhibitors selected from the group consisting of fasudil or its derivatives, Y27632 or its derivatives, and any combination thereof. In some examples, the pharmaceutical composition may further comprise gemcitabine. In other examples, the pharmaceutical composition may further comprise at least one pharmaceutically acceptable excipient, which may be selected from the group consisting of a binder, a filler, a non-effervescent disintegrant, an effervescent disintegrant, a preservative, a diluent, a flavoring agent, a sweetener, a lubricant, an oral dispersing agent, a coloring agent, a taste masking agent, a pH modifier, a stabilizer, a compaction agent, and combinations thereof.

Other aspects and iterations of the invention are described in more detail below.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 9 depicts the histochemical analyses of human pancreatic tissue samples from pancreatic cancer patients by comparing to control sample from normal pancreatic tissue. Both normal and tumor pancreatic tissues were subjected to hematoxylin/eosin (H&E) and pentachrome (Russell-Movat's) staining analysis. Pentachrome staining: Green/blue=mucins, Yellow=collagen, Red=muscle/fibrinoid. Scale bar=100 µm.

DETAILED DESCRIPTION OF THE INVENTION

Figure 1:
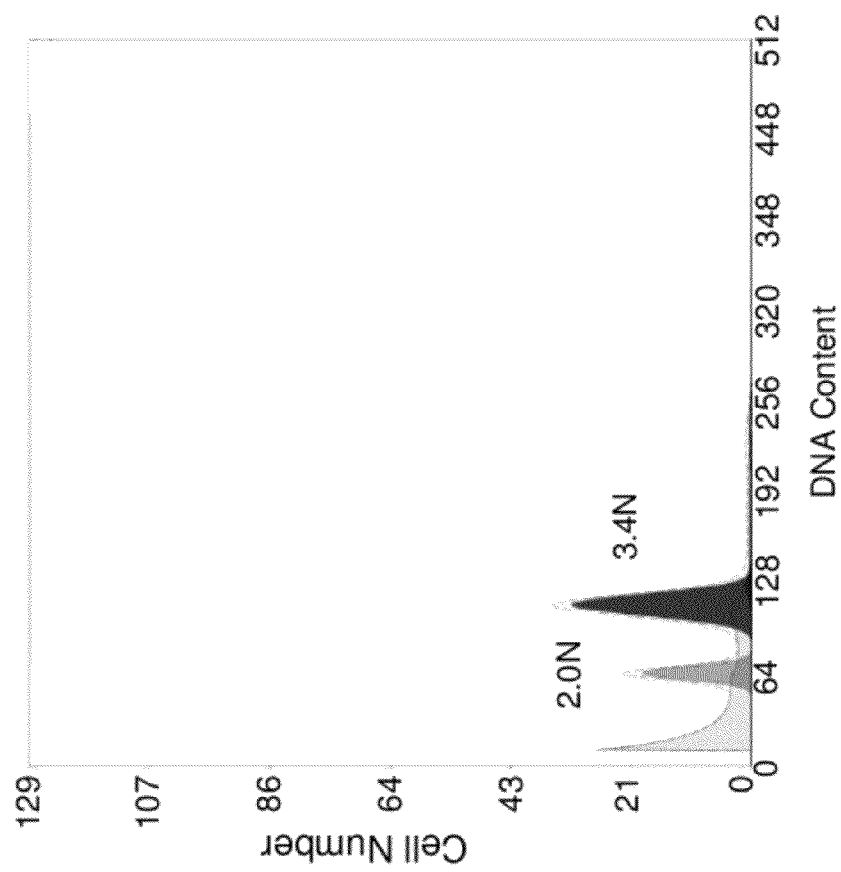
FIG. 1 depicts a low frequency amplification of the ROCK1 gene locus at a 12% frequency in human pancreatic tumors.

The present invention provides a therapeutic target for pancreatic cancer. Specifically, the inhibition of the target reduced pancreatic cancer cell proliferation and migration. In this regard, the present invention provides a method for screening inhibitors to therapeutic targets such as ROCK1.

It has been known that the gene expression patterns are complexly different between normal and cancerous cells. Gene amplification, or gene copy number alterations, in genetic events that characterize cancer progression often shows both high- and low-frequency alterations. Characterization of these DNA copy-number changes is important for both the basic understanding of cancer and its diagnosis and treatment. Using breast cancer as an example, many studies have investigated genomic instability such as copy number alteration and DNA amplification and deletion affecting commonly amplified regions in the genome. However, most global genomic studies of high frequent genetic events have not revealed any additional genes that contain alterations that potentially affect breast cancer development. In contrast to commonly amplified regions or genes, there are regions or genes with a low frequency of amplification, affecting relatively small regions of genomic DNA and appearing with a low frequency in cancer samples.

Comparative genomic hybridization (CGH) or Chromosomal Microarray Analysis (CMA) is a molecular-cytogenetic method for the analysis of copy number changes (gains/losses) in the DNA content of a given subject's DNA and often in tumor cells. CGH will detect only unbalanced chromosomal changes, such that the method surveys DNA copy-number variations across a whole genome. With CGH, differentially labeled test (i.e., tumor) and reference (i.e., normal individual) genomic DNAs are co-hybridized to normal metaphase chromosomes, and fluorescence ratios along the length of chromosomes provide a cytogenetic representation of the relative DNA copy-number variation. Array comparative genomic hybridization, or aCGH is a technique to detect genomic copy number variations at a higher resolution level than chromosome-based comparative genomic hybridization.

The present invention provides a pancreatic cancer therapeutic target identified through a focal amplification of a low frequency genetic event involving the ROCK1 gene. ROCK1 is a multifunctional member of the AGC (protein kinase A/G/C) kinase family that has been implicated in the modulation of stress-fiber assembly, cell contraction, apoptosis, and in the migration and invasion of multiple cancer cell types. This invention discloses that ROCK1 has increased expression relating to pancreatic cancer cell proliferation and migration.

I. ROCK1 Regulation

Rho-associated coiled coil-containing protein kinase 1 (Rho kinase, or ROCK, UniProtKB/Swiss-Prot Accession No: Q13464) belongs to a family of serine/threonine kinases that are activated via interaction with Rho GTPases. Rho GTPase family proteins, which include Rho, Rac1 and Cdc42, control a wide variety of cellular processes such as cell adhesion, motility, proliferation, differentiation and apoptosis. ROCK is one of the effectors of Rho.

ROCK has a molecular mass of about 160 kDa. The ROCK family contains two members: ROCK1 and ROCK2, which share 65% overall identity and 92% identity in the kinase domain. The ROCK1 gene locus is at chromosome 18q11.1 (SEQ ID NO: 1). The ROCK1 gene mRNA sequence is represented by SEQ ID NO: 3. The ROCK protein (SEQ ID NO: 2) contains a catalytic kinase domain at the amino terminus, followed by a central coiled-coil domain including a Rho-binding domain (RBD), and a carboxyl-terminal pleckstrin-homology (PH) domain with an internal cysteine-rich (CR) domain. ROCK has auto-inhibitory activity. In the inactive form, the carboxyl terminal PH domain and RBD of ROCK interact with the kinase domain, which forms an auto-inhibitory loop. The kinase domain contains the conserved motifs associated with serine/threonine protein kinases. ROCK inhibitors such as Y27632 and fasudil bind to the kinase domain and inhibit ROCK1 and ROCK2 with similar potency.

Both ROCK1 and ROCK2 phosphorylate a variety of protein substrates at serine or threonine residues. The majority of ROCK substrates have been identified from cell culture experiments. In most cases, only ROCK2 has been tested. Because ROCK1 and ROCK2 share 92% identity in the kinase domain, it has been assumed that they share the same substrates. However, ROCK1 and ROCK2 may have different targets as only ROCK1, but not ROCK2, binds to and phosphorylates RhoE. Most of the ROCK substrates are cellular proteins associated with the regulation of the actin cytoskeleton. As an exemplary example, one of the ROCK protein substrates is myosin light chain (MLC). ROCK can increase MLC phosphorylation through direct effect on MLC. However, MLC phosphatase (MYPT1) is also a ROCK protein substrate. Therefore, ROCK can increase MLC phosphorylation indirectly by inactivating MLC phosphatase as well.

Several ROCK substrates are involved in the regulation of both cell death and survival. Caspase 3-mediated ROCK1 activation is responsible for the increased MLC phosphorylation relating to cell apoptosis in a variety of cell type. However, the importance of ROCK in regulating apoptotic caspase cascades is highly cell type-dependent and/or apoptotic stimulus-dependent. Under some conditions, ROCK activation or inhibition is not important for mediating apoptotic signals. For example, inhibition of ROCK does not affect caspase 3 activation and progression of apoptosis in anti-Fas antibody-treated Jurkat cells and TNFα-treated NIH3T3. Inhibition of ROCK disrupts actin stress fibers but does not induce apoptosis in 3T3 cells.

On the other hand, the phosphorylation of PTEN (Phosphatase and tensin homologue) by ROCK stimulates its phosphatase activity and when activated it is a negative regulator of phosphatidylionositol (PI)3-kinase/Akt pathway, which has important roles in a diverse range of biological processes including cell survival. However, based on other research, ROCK appears to be involved in both positive and negative regulation of PI3-kinase/Akt signaling, and the outcome may be cell type-dependent and stimulus-dependent.

To add another layer of complexity, ROCK activity can be regulated by several distinct mechanisms. ROCK1 and ROCK2 can be distinctly activated or inhibited by a number of positive or negative regulators, and in turn, can have distinct cellular or physiological functions. Using Rho/ROCK pathway as an example, the kinase activity of ROCK is increased after Rho binding. The interaction between RBD and active GTP-bound form of Rho disrupts the interaction between the catalytic domain and the inhibitory carboxyl-terminal region of ROCK. The Rho/ROCK pathway is activated by numerous extracellular stimuli. Therefore, the consequence of Rho-dependent ROCK activation is highly cell type-dependent, ranging from a change in contractility, cell permeability, migration, and proliferation, to apoptosis.

II. ROCK1 as a Therapeutic Target

Among the various aspects of the present invention is the provision of a target for pancreatic cancer treatment, specifically for inhibiting pancreatic cell proliferation and migration. Generally, a target may be any form of molecular structure produced by a cell, expressed inside the cell, accessible on the cell surface or secreted by the cell, whose activity may be modified by a drug and the modification results in a desirable therapeutic effect. A target may be in a form of protein, carbohydrate, fatty acids, nucleic acid, catalytic site, or any combination of these such as an enzyme, glycoprotein, ion channels, receptors, cell membrane, virus, cell, organ, organelle, or any uni- or multi-molecular structure, or any other such structure now known or yet to be disclosed, whether alone or in combination.

Specifically, in this invention, a target may be represented by a nucleic acid sequence, a protein or peptide or the fragments thereof encoded by the nucleic acid sequence. Examples of such nucleic acid sequence include miRNA, tRNA, siRNA, mRNA, cDNA, or genomic DNA sequences. In one embodiment, therefore, the term "target" encompasses a gene and a gene allele thereof, and the products (i.e., RNA and protein) of the gene or a gene allele thereof, whose expression or activity is directly or indirectly associated with a particular phenotype or cellular condition, or physiological characteristic.

An allele includes any form of a particular nucleic acid that may be recognized as a particular form on account of its location, sequence, chemical modification of the sequence, expression level, expression specificity or any other characteristic that may identify it as being a form of the particular gene. Variable alleles of a particular gene may differ from each other because of point mutations, silent mutations, deletions, insertions, frameshift mutations, single nucleotide polymorphisms (SNPs), inversions, translocations, heterochromatic insertions, differentially epigenetically modified, or any combination of thereof, relative to a reference gene. An allele may be compared to another allele that may be termed a wild type form of an allele. In comparison to the wild type allele, a different allele may be called a mutation or a mutant. Mutants may also be interchangeably called variants. In some cases, the wild type allele is more common than the mutant. In the example of gene mutation, the mutation may be in the coding region or the non-coding region. The non-coding region comprises transcriptional and translational control elements. Suitable transcription or translation control elements include but are not limited to upstream control elements, enhancer elements, TATA boxes, cis-regulatory regions, activator binding regions, repressor binding regions, transcription initiation sites, polyadenylation control elements, transcription termination sites, ribosome binding sites, translation initiation sites, and translation termination sites.

An allele of a gene may have overexpression, underexpression or no expression. Alternatively, an allele of a gene may or may not produce a functional protein. A gene allele may produce a protein with altered sequence, function, localization, stability, dimerization, protein-protein interaction, or temporal or spacial expression specificity. A genetic mutation or variance may be any detectable change in genetic material such as DNA, or a corresponding change in the RNA or protein product of that genetic material.

At the protein level of a target, there may be conserved variants to a given amino acid residue of the protein, peptide or fragments thereof. In a conserved variant, the amino acid has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Depending on the location of the variance in the overall context of the protein, some substitution may have little or no effect on the apparent molecular weight or isoelectric point of the protein or polypeptide.

Amino acids other than those indicated as conserved may differ in a protein or peptide so that the percent protein or amino acid sequence identity between any two proteins of similar function may vary as determined according to an alignment scheme such as by the Cluster Method. The term "sequence identity" in the context of protein refers to the extent in which two amino acid sequences are invariant, i.e., the two sequences have the same amino acid at the same position. Sequence identity is generally expressed as a percentage. Two amino acid sequences that are identical in sequence and length have 100% sequence identity. The concept of a variant encompasses a polypeptide or the fragment thereof which has at least 60%, 75%, 85%, 90%, or 95% amino acid identity as determined by algorithms, such as BLAST or FASTA, and which has the same or substantially similar properties and/or activities as the native or parent protein or enzyme to which it is compared.

Another example of allele or variant is a gain-of-function variant. Gain-of-function variants of a polypeptide encompass any variant in which a change in one or more amino acid residues in a polypeptide improves the activity of the polypeptide. Examples of activities of a polypeptide that may be improved by a change resulting in a gain of function variant include but are not limited to enzymatic activity, binding affinity, phosphorylation or dephosphorylation efficiency, activation, deactivation, or any other activity or property of a protein that may be quantitatively measured by some method now known or yet to be disclosed.

In one embodiment of the invention, the target for pancreatic cancer is ROCK1 which comprises the coding nucleic acid sequence and its alleles, the polypeptide products and variants thereof.

The presence or absence of an allele may be detected through the use of any process known in the art, including but not limited to using primers and probes designed according to a specific allele for PCR, sequencing, hybridization, or immunohistochemical analyses.

III. Method for Screening Substrates to a Therapeutic Target

Disclosed herein are methods for identifying agents that alter the expression or activity of a therapeutic target, and may result in a desirable therapeutic effect. Preferably, the target for a therapeutic agent is ROCK1. The methods include contacting an agent with at least one cell comprising a therapeutic target having increased expression in comparison to a control cell, the target being ROCK1. In one exemplary example, an agent that has therapeutic effect may be identified by determining the effect of an agent on the expression level of a target. In a particular example, an agent that down-regulates the target expression as compared to the target expression in the absence of the test agent identifies that agent as an inhibitor of a target. Specifically, in the present invention, the target is for pancreatic cancer cell proliferation and migration and the agent is an inhibitor to the target, and thus, inhibits and may alleviate these properties of the pancreatic cancer cell.

Agents that interact with a therapeutic target to result in a desirable therapeutic effect may include a pharmaceutically active ingredient or pharmaceutically acceptable salt thereof, a drug, a toxin, a chemical, a small organic molecule, a large molecule or peptide or an antibody. Large-molecule pharmaceuticals refer to pharmaceutical agents having a molecular weight greater than about 1000 Daltons, e.g., peptidic drugs, vaccines and hormones. The term "antibody" is used herein in the broadest sense and refers generally to a molecule that contains at least one antigen binding site that immunospecifically binds to a particular antigen target of interest. Antibody thus includes but is not limited to native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term, thus, includes full length antibodies and/or their variants as well as immunologically active fragments thereof, thus encompassing, antibody fragments capable of binding to a biological molecule (such as an antigen or receptor) or portions thereof, including, but not being limited to, Fab, Fab', F(ab')2, facb, pFc', Fd, Fv or scFv (See, e.g., CURRENT PROTOCOLS IN IMMUNOLOGY, (Colligan et al., eds., John Wiley & Sons, Inc., NY, 1994-2001).

The screening or creation, identification and selection of appropriate therapeutic agent through the target identified herein can be accomplished by a variety of methods. One approach is to use structural knowledge about the target protein to design a candidate molecule with which it will precisely interact. An example would be computer assisted molecular design. A second approach is to use combinatorial or other libraries of molecules, whereby a large library of molecules is screened for inhibitory effect with regard to the target gene or protein expression, or ability to inhibit the transcriptional factor activity of the target protein. In a further example, a panel of antibodies may be screened for their ability to inhibit the target protein.

Cancer and precancer may be thought of as diseases that involve unregulated cell growth. Metastasis involves migration of tumor cells away from the site of the primary tumor, entry into the circulation, and proliferation at a new site. Cell growth involves a number of different factors. One factor is how rapidly cells proliferate, and another involves how rapidly cells die. Cells can die either by necrosis or apoptosis depending on the type of environmental stimuli. Cell motility is yet another factor that influences tumor growth kinetics and metastasis. Resolving which of the many aspects of cell growth a test agent affects can be important to the discovery of a relevant pharmaceutical therapy for pancreatic cancer cells. Screening assays based on this technology can be combined with other tests to determine which agents have growth inhibiting and pro-apoptotic activity in pancreatic cancer cells.

Some embodiments provided herein involve determining the ability of a given agent to inhibit the increased expression of a target in pancreatic cancer cells. In one preferred embodiment, the target is ROCK1. Various cell lines can be used, which may be selected based on the tissue to be tested. Certain cell lines are well characterized, and are used for instance by the United States National Cancer Institute (NCI) in their screening program for new anti-cancer drugs. Suitable pancreatic cancer cell lines include, but are not limited to A818.1, AsPc-1, BxPC-3, Capan-1, Capan-2, CF PAC-1, Colo 357, FA6, HPAF2, HPDE6, Hs766T, MIA PaCa-2, MDA Panc-3, PaCa-3, Panc-1, PaTuI, PaTuII, QGP-1, Rossi, RWP-1, Suit-2, Su8686, SW-979, T3M-4, and derivatives thereof. Cell lines can also be constructed to overexpress ROCK1 for screening inhibitory agents for pancreatic cancer cells, or specifically pancreatic cancer cell proliferation and migration. In addition to cell line cells, cells or samples originating from biopsy or other in vivo or ex vivo analysis of pancreas may be used. In some aspects of the invention, the sample may be a body fluid sample, such as peripheral blood, serum, plasma, lymph fluid, ascites, serous fluid, pleural effusion, sputum, cerebrospinal fluid, amniotic fluid, lacrimal fluid, gastric fluid, pancreatic fluid, mucus or urine, from which free floating DNA, RNA, protein, peptide or fragments thereof may be detected and compared to control samples. Samples include single or multiple cells, whole organs or any fraction of a whole organ, in any condition including in vitro, ex vivo, in vivo, post-mortem, fresh, fixed, or frozen. Alternatively, a sample may be any cell source from which DNA, including genomic, somatic, and germline DNA may be obtained.

Significant tumor cell growth inhibition, greater than about 30% at a dose of about 100 μM or below, is further indicative that the agent is useful for treating neoplastic lesions. An $IC_{50}$ value may be determined and used for comparative purposes. This value is the concentration of drug needed to inhibit tumor cell growth by 50% relative to the control. In some embodiments, the $IC_{50}$ value is less than about 100 μM in order for the agent to be considered further for potential use for treating, ameliorating, or preventing neoplastic lesions or tumor metastasis.

In another embodiment, agents can be screened for induction of apoptosis, or cell death, using cultures of pancreatic tumor cells comprising ROCK1 as a target. In some examples of such screening methods, treatment of cells with test agents involves either pre- or post-confluent cultures and treatment for one to seven days at various concentrations of the agents. Apoptotic cells can be measured in both the attached and "floating" portions of the cultures. Both are collected by removing the supernatant, trypsinizing the attached cells, and combining both preparations following a centrifugation wash step (for example, 10 minutes, 2000 rpm). Following treatment with a test agent, cultures can be assayed for apoptosis and necrosis, for instance, by fluorescent microscopy following labeling with acridine orange and ethidium bromide. Many methods for measuring apoptotic cells are known to those of ordinary skill in the art; for instance, one method for measuring apoptotic cell number has been described by Duke & Cohen (Curr. Prot. Immuno., Coligan et al., eds., 3.17.1-3.17.1, 1992). For example, floating and attached cells are collected by trypsinization and washed three times in PBS. Aliquots of cells are then centrifuged. The pellet is resuspended in media and a dye mixture containing acridine orange and ethidium bromide prepared in PBS and mixed gently. The mixture then can be placed on a microscope slide and examined for morphological features of apoptosis.

Apoptosis also can be quantified by measuring an increase in DNA fragmentation in cells that have been treated with agents. Commercial photometric enzyme immunoassays (EIA) for the quantitative in vitro determination of cytoplasmic histone-associated-DNA-fragments (mono- and oligo-nucleosomes) are available (e.g., Cell Death Detection ELISA). The cell death detection assay is based on a sandwich-enzyme-immunoassay principle, using mouse monoclonal antibodies directed against DNA and histones, respectively. This allows the specific determination of mono- and oligo-nucleosomes in the cytoplasmic fraction of cell lysates. According to the vendor, apoptosis is measured as follows: The sample (cell-lysate) is placed into a streptavidin-coated microtiter plate ("MTP"). Subsequently, a mixture of anti-histone-biotin and anti-DNA peroxidase conjugates is added and incubated for, for example, about two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by a washing step, the amount of nucleosomes is quantified by the peroxidase retained in the immunocomplex. Peroxidase is determined photometrically with ABTS7 (2,2'-Azido-[3-ethylbenzthiazolin-sulfonate]) as substrate.

Statistically significant increases of apoptosis (i.e., greater than 2 fold stimulation at an agent concentration of about 100 μM) are further indicative that the agent is useful for treating neoplastic lesions. Preferably, the $EC_{50}$ value for apoptotic activity should be less than about 100 μM for the agent to be further considered for potential use for treating neoplastic lesions. $EC_{50}$ is understood herein to be the concentration that causes 50% induction of apoptosis relative to vehicle treatment.

In another embodiment, agents can be screened for inhibitory effects to the activity of ROCK1 as a regulator of its substrate, which may be a protein or the gene encoding the protein substrate. In one preferred embodiment, the screening of inhibitory agents is achieved through determining the expression or activity of MLC, known to be specifically regulated by ROCK1.

The methods of determining the expression of a gene or the activity of its gene product, whether for the target itself or the substrate of the target, include but are not limited to microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing. Other examples include any method of assessing biomarker protein expression such as flow cytometry, immunohistochemistry, ELISA, Western blot, and immunoaffinity chromatography, HPLC, mass spectrometry, protein microarray analysis, PAGE analysis, isoelectric focusing, 2-D gel electrophoresis, or any enzymatic assay.

Other methods used to assess a gene or protein expression include the use of natural or artificial ligands capable of specifically binding the protein. Such ligands include antibodies (as defined in paragraph 0038), antibody complexes, conjugates, natural ligands, small molecules, nanoparticles, or any other molecular entity capable of specific binding to a target. Ligands may be associated with a label such as a radioactive isotope or chelate thereof, dye (fluorescent or non-fluorescent,) stain, enzyme, metal, or any other substance capable of aiding a machine or a human eye from differentiating a cell expressing a target/substrate from a cell not expressing such.

Differential expression may be assessed by a detector, an instrument containing a detector, or by aided or unaided human eye. Examples include but are not limited to differential staining of cells in an IHC assay configured to detect a target, differential detection of bound RNA on a microarray to which a sequence capable of binding to the target is bound, differential results in measuring RT-PCR (Reverse Transcription-PCR) measured in ΔCt or alternatively in the number of PCR cycles necessary to reach a particular optical density at a wavelength at which a double stranded DNA binding dye (e.g., SYBR Green) incorporates, differential results in measuring label from a reporter probe used in a real-time RT-PCR reaction, differential detection of fluorescence on cells using a flow cytometer, differential intensities of bands in a Northern blot, differential intensities of bands in an RNAse protection assay, differential cell death measured by apoptotic markers, differential cell death measured by shrinkage of a tumor, or any method that allows a detection of a difference in signal between one sample or set of samples and another sample or set of samples.

Techniques using microarrays may also be advantageously implemented to detect and/or assess gene expression. Gene expression may be that of the target or the expression of another set of genes upstream or downstream in a pathway of which the target is a component or a regulator. In one embodiment, microarrays may be designed so that the same set of identical oligonucleotides is attached to at least two selected discrete regions of the array, so that one can easily compare a normal sample, contacted with one of said selected regions of the array, against a test sample, contacted with another of said selected regions. Examples of microarray techniques include those developed by Nanogen, Inc. (San Diego, Calif.) and those developed by Affymetrix (Santa Clara, Calif.). However, all types of microarrays, also called "gene chips" or "DNA chips", may be adapted for the identification of mutations. Such microarrays are well known in the art.

IV. Pharmaceutical Compositions Comprising ROCK1 Inhibitors

Fasudil (5-(1,4-diazepan-1-ylsulfonyl)isoquinoline) is a potent and selective Rho-kinase inhibitor and vasodilator. One of its derivatives, Fasudil Hydrochloride (INN) (hexahydro-1-(5-isoquinolinesulfonyl)-1H-1,4-diazepine hydrochloride), has been used for the treatment of cerebral vasospasm, which is often due to subarachnoid hemorrhage, as well as to improve the cognitive decline seen in stroke victims. Fasudil ameliorated myocardial ischemia in patients who were most likely having coronary microvascular spasm. Fasudil has also been found to be effective for the treatment of pulmonary hypertension. It was demonstrated recently that Fasudil could be used to enhance memory and improve the prognosis of Alzheimers patients. The invention disclosed herein, however, is directed to a new application of fasudil or derivatives thereof, or combinations with cytotoxic agents or derivatives thereof, e.g., gemcitabine, as a therapy for pancreatic cancer, especially for inhibiting pancreatic cancer cell proliferation and migration.

Another known ROCK inhibitor is Y-27632 (4-(1-aminoethyl)-N-pyridin-4-yl-cyclohexane-1-carboxamide), a pyridine derivative, was found to suppress ROCK-mediated formation of stress fibres in cultured cells and dramatically corrects hypertension in several hypertensive rat models. Administration of Y-27632 preferentially lowered brain levels of Abeta42 in a transgenic mouse model of Alzheimer's disease. Oral administration of Y-27632 in rats significantly reduced the colonic inflammation. In vitro study suggested Y-27632 may be a potential treatment for bladder dysfunction.

Therefore, another aspect of the invention, based on the new application of fasudil, provides for pharmaceutical compositions comprising fasudil, the derivatives thereof or any combination of the above. The derivatives of fasudil may be known or yet to be discovered. In general, the pharmaceutical composition will comprise an effective dosage amount of fasudil, i.e., an amount of fasudil sufficient to provide treatment to the subject being administered the pharmaceutical composition. The amount of fasudil in such pharmaceutical compositions, therefore, may range from about 97%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, or about 3% by weight of the total amount of the various forms of fasudil.

A variety of excipients commonly used in pharmaceutical formulations may be selected on the basis of several criteria such as, e.g., the desired dosage form and the release profile properties of the dosage form. Non-limiting examples of suitable excipients include an agent selected from the group consisting of a binder, a filler, a non-effervescent disintegrant, an effervescent disintegrant, a preservative, a diluent, a flavoring agent, a sweetener, a lubricant, an oral dispersing agent, a coloring agent, a taste masking agent, a pH modifier, a stabilizer, a compaction agent, and combinations of any of these agents.

In one embodiment, the excipient may be a binder. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, peptides, and combinations thereof.

In another embodiment, the excipient may be a filler. Suitable fillers include carbohydrates, inorganic compounds, and polyvinilpirrolydone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

The excipient may be a non-effervescent disintegrant. Suitable examples of non-effervescent disintegrants include starches (such as corn starch, potato starch, and the like), pregelatinized and modified starches thereof, sweeteners, clays (such as bentonite), microcrystalline cellulose, alginates, sodium starch glycolate, and gums (such as agar, guar, locust bean, karaya, pecitin, and tragacanth).

In another embodiment, the excipient may be an effervescent disintegrant. By way of non-limiting example, suitable effervescent disintegrants include sodium bicarbonate in combination with citric acid, and sodium bicarbonate in combination with tartaric acid.

The excipient may comprise a preservative. Suitable examples of preservatives include antioxidants (such as alpha-tocopherol or ascorbate) and antimicrobials (such as parabens, chlorobutanol or phenol). In other embodiments, an antioxidant such as butylated hydroxytoluene (BHT) or butylated hydroxyanisole (BHA) may be utilized.

In another embodiment, the excipient may include a diluent. Diluents suitable for use include pharmaceutically acceptable saccharides such as sucrose, dextrose, lactose, microcrystalline cellulose, fructose, xylitol, and sorbitol; polyhydric alcohols; starches; pre-manufactured direct compression diluents; and mixtures of any of the foregoing.

The excipient may include flavoring agents. Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot).

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; stevia-derived sweeteners; chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2, 2-dioxide, particularly the potassium salt (acesulfame-K), and sodium and calcium salts thereof.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose.

Depending upon the embodiment, it may be desirable to provide a coloring agent. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present invention depending on the embodiment.

The excipient may include a taste-masking agent. Taste-masking materials include cellulose hydroxypropyl ethers (HPC); low-substituted hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and combinations thereof.

In various embodiments, the excipient may include a pH modifier. In certain embodiments, the pH modifier may include sodium carbonate or sodium bicarbonate.

The weight fraction of the excipient or combination of excipients in the pharmaceutical composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the pharmaceutical composition.

The pharmaceutical compositions detailed herein may be manufactured in one or several dosage forms. Suitable dosage forms include transdermal systems or patches. The transdermal system may be a matrix system, a reservoir system, or a system without rate-controlling membranes. Other suitable dosage forms also include tablets, including suspension tablets, chewable tablets, effervescent tablets or caplets; pills; powders such as a sterile packaged powder, a dispensable powder, and an effervescent powder; capsules including both soft or hard gelatin capsules such as HPMC capsules; lozenges; a sachet; a sprinkle; a reconstitutable powder or shake; a troche; pellets such as sublingual or buccal pellets; granules; liquids for oral or parenteral administration; suspensions; emulsions; semisolids; or gels.

The dosage forms may be manufactured using conventional pharmacological techniques. Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., prilling, spray drying, pan coating, melt granulation, granulation, wurster coating, tangential coating, top spraying, extruding, coacervation and the like.

The amount of active ingredient that is administered to a subject can and will vary depending upon a variety of factors such as the age and overall health of the subject, and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk reference.

V. Kits

The invention further provides kits comprising a pharmaceutical composition comprising fasudil and/or its derivatives for treating pancreatic cancer. The kit may further comprise a complete regimen of components that facilitate the administration of the pharmaceutical compositions. An example of such a kit includes one or more units of effective amounts or dosages of the compositions. The unit dosage would be enclosed in a preferably sterile container and would be comprised of the compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the kit comprises the container that encloses the unit dosage. The kit may further comprise instructions for the safe and effective use of the pharmaceutical composition for treating pancreatic cancer.

EXAMPLES

The following non-limiting examples are intended to further illustrate and explain the present invention. The invention, however, should not be limited to any of the details in the examples.

Example 1

ROCK1 is Overexpressed in Human Pancreatic Tumor Cells and Amplified in a Small Subset of PDAC Patient Samples ROCK1 is amplified in a subset of pancreatic tumor samples: A low frequency amplification of the ROCK1 gene locus at chromosome 18q11.1 was identified in pancreatic ductal adenocarcinoma (PDA) patient tissue samples by aCGH analysis. The ROCK1 gene locus is focally amplified in pancreatic ductal adenocarcinoma. A focal amplification was identified in the aneuploid population of multiple cell-sorted tumor samples at chromosome 18q11, which is confirmed to be ROCK1 gene locus. ROCK1 amplification (as measured by aCGH) was observed at a 12% frequency in human pancreatic tumors. The low frequency amplification was detected in 4 out of the 34 cases analyzed (FIG. 1).

Figure 2:
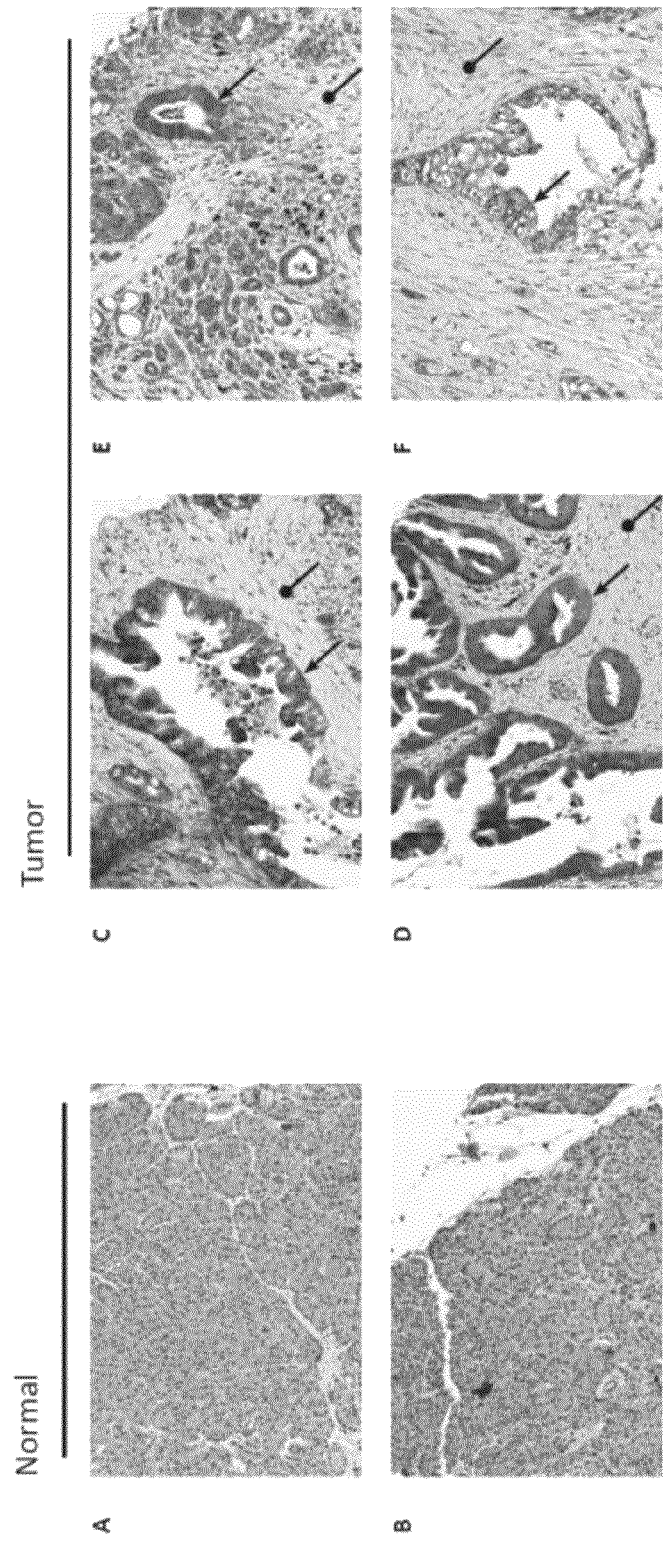
FIG. 2 depicts an increase in ROCK1 expression observed using immunohistochemistry (IHC) analysis in (A) and (B): normal samples; and (C), (D), (E) and (F): tumor tissue samples.

Increased ROCK1 expression is observed in pancreatic cancer patient tumor samples: As shown in FIG. 2, an increase in ROCK1 expression was observed using immunohistochemistry (IHC) analysis in tumor tissue samples (FIG. 2C-2F) relative to normal (FIG. 2A-2B) or adjacent normal tissues. Tissue microarray analysis (TMA) allows multiple analyses on multiple samples on sections from a single paraffin block. ROCK1 expression in epithelial cells (pointed arrow) was increased, yet was largely absent in the stromal compartment (circle-tipped arrow). Immunohistochemical (IHC) analysis of a pancreatic cancer tissue array showed increased expression of ROCK1 in pancreatic epithelial cells relative to the surrounding stromal cells, or adjacent normal pancreatic ductal cells. Among the pancreatic epithelial cells with increased expression of ROCK1, 76% (53/70) of tumor samples exhibited 2+ or greater (scale 0-3+) in staining intensity by IHC analysis, versus 40% (19/47) of adjacent normal tissue samples (P<0.0001). Table 1 shows the preliminary staining intensity scoring of tumor, adjacent normal tissues or normal tissue ductal epithelial cells.

TABLE 1

Preliminary ICH, Pancreas TMA Score

| Tissue Pathology | Score | | | | | % 2+ |
|---|---|---|---|---|---|---|
| | 0 | 1 | 2 | 3 | N/E | |
| Tumor (n = 133) | 8 | 38 | 42 | 33 | 12 | 62.0% |
| Adjacent Normal (n = 59) | 7 | 24 | 17 | 4 | 7 | 40.4% |
| Normal (n = 12) | 4 | 4 | 3 | 1 | 0 | 33.3% |

Figure 3A:
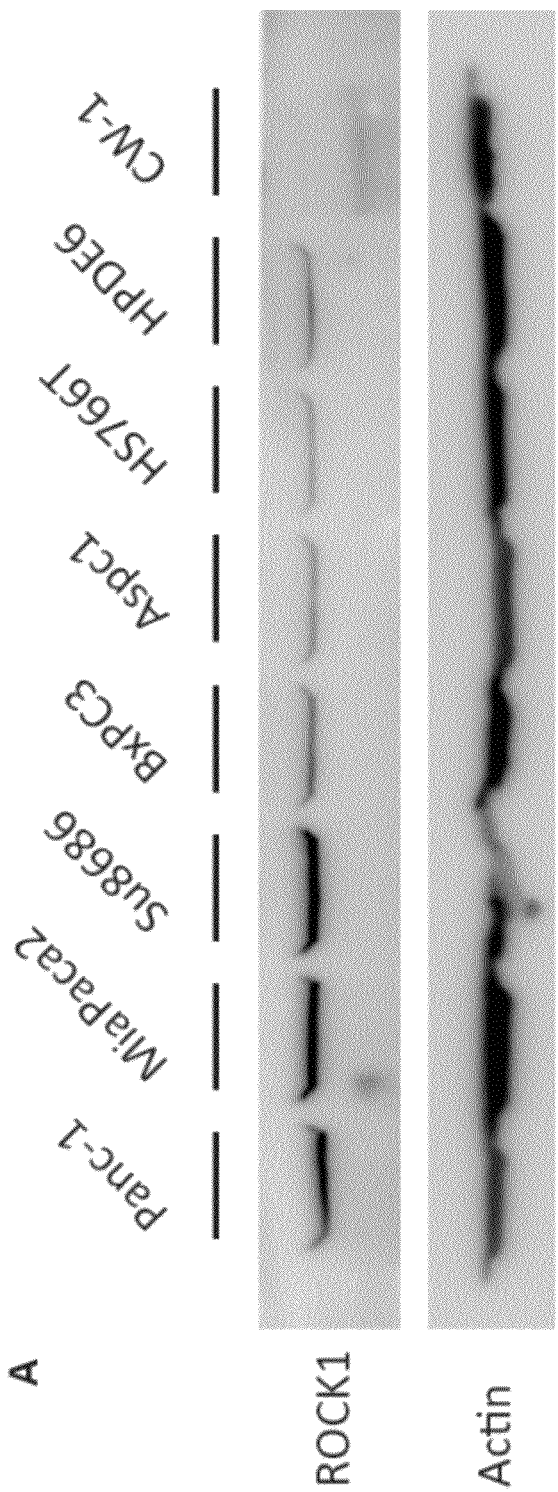
FIG. 3 depicts (A) the Western blot analysis of ROCK1 expression in pancreatic cancer cell lines: Panc-1, MiaPaca2, Su8686, BxPC3, Aspc1, CW-1, and HS766T and a normal pancreatic epithelial cell line HPDE6; (B) the densitometry of the protein expression of pancreatic cancer cell lines relative to the normal HPDE6 cell line.
Figure 3B:
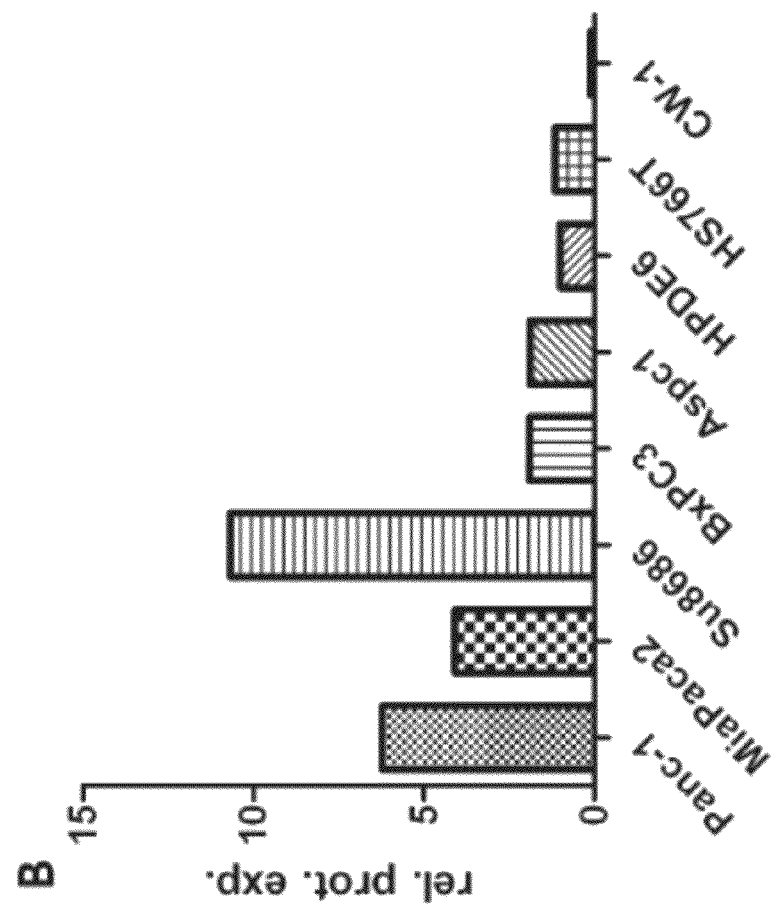

ROCK1 expression in pancreatic cell lines: ROCK1 was generally observed localizing to ductal epithelial cells, and not in the stromal compartment of patient tumor samples. Increased ROCK1 expression was observed in human tumor samples relative to normal and adjacent normal tissues. Further, ROCK1 is observed in multiple pancreatic cancer cell lines, with 100% showing greater expression than the normal HPDE6 cell line. Western blot analysis of ROCK1 expression in pancreatic cancer cell lines and a normal pancreatic epithelial cell line HPDE6 was shown in FIG. 3A. ROCK1 was most highly expressed in the Panc-1, MiaPaca2, and Su8686 pancreatic cancer lines (FIG. 3A). Lower levels of expression were seen in the BxPC3, Aspc1, HPDE6, and HS766T epithelial cell lines, with the expression in CW-1 myofibroblast cell being the lowest. Densitometry of the protein expression, relative to the normal HPDE6 cell line is shown in FIG. 3B.

Figures 4A, 4B:
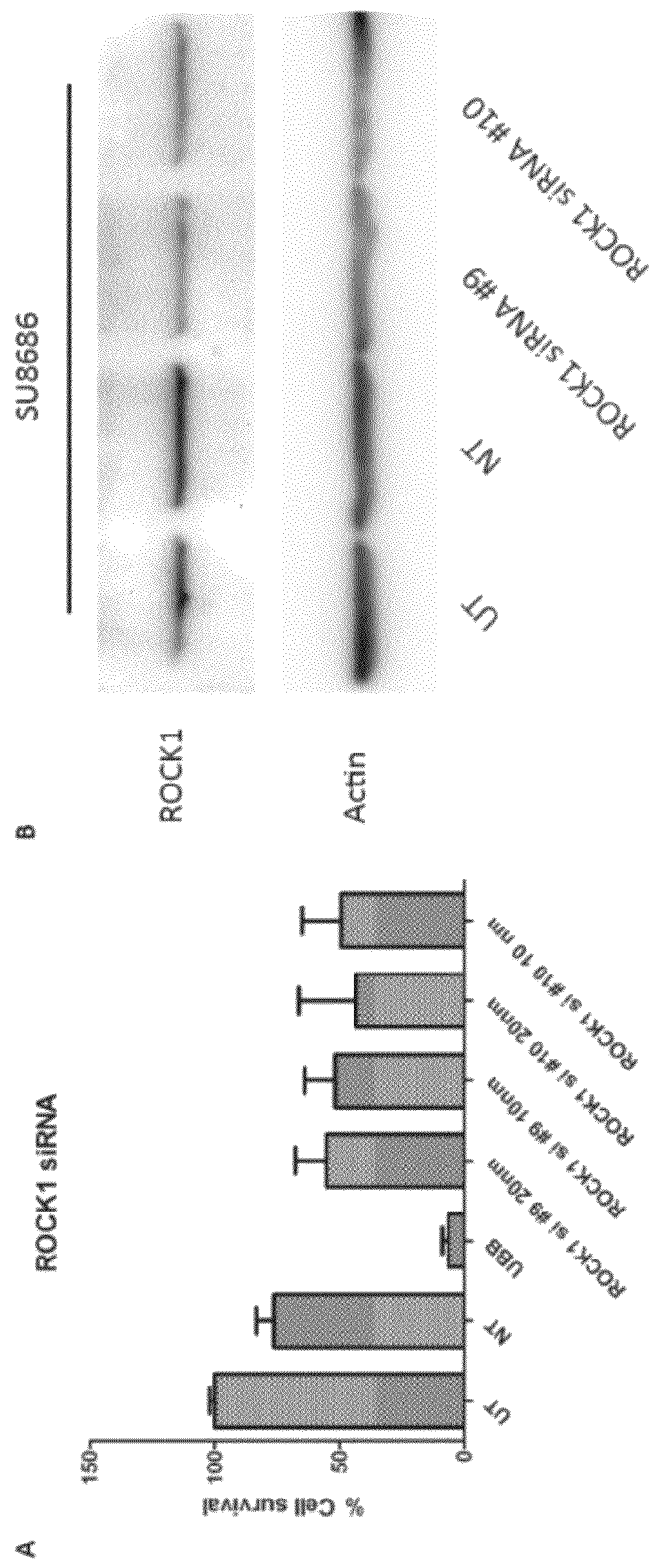
FIG. 4 depicts (A) there was no significant change in cell survival at 96 hr time point after siRNA treatment in SU8686 cells; (B) that incomplete knock-down of ROCK1 was observed for both siRNA treatment using Western blotting in SU8686 cells; (C) no significant reduction in cell proliferation, measured by an SRB cell viability assay, was observed in Panc-1 cell over 0-100 hr time period after siRNA treatment; although (D) knock-down of ROCK1 expression was observed for both siRNA treatments using Western blotting in Panc-1 cells. "UT" stands for untreated, "NT" stands for non-targeting siRNA, "UBB" stands for ubiquitin B cell death control siRNA.
Figures 4C, 4D:
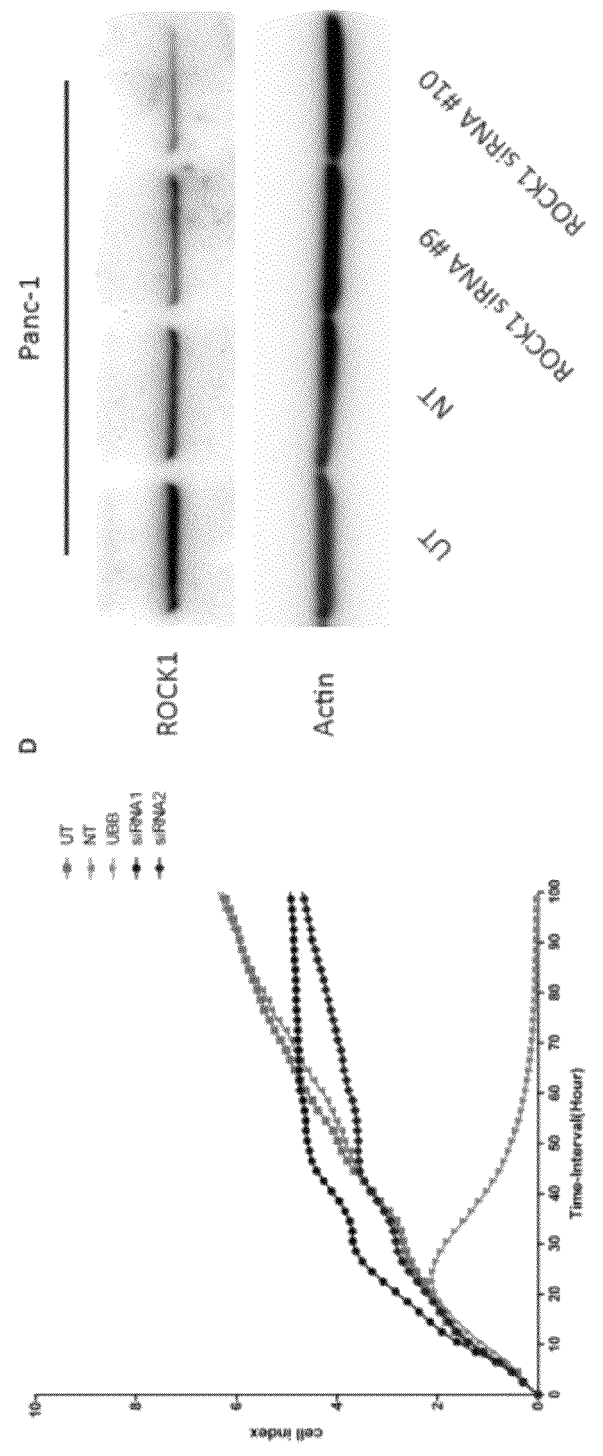

Effect of ROCK1 knockdown by siRNA on cell growth: Each of the pancreatic cancer cell line SU8686 and Panc-1 cells was treated with two different ROCK1 siRNAs: ROCK1 siRNA #9 and #10. The knock-down of ROCK1 was observed for both siRNA treatment using Western blotting in SU8686 cells (FIG. 4B). The knock-down of ROCK1 was observed for both siRNA treatments using Western blotting in Panc-1 cells as well (FIG. 4D). However, ROCK1 knockdown by siRNA does not significantly decrease cell proliferation in pancreatic cancer cell lines. FIG. 4A showed the cell survival at 96 hr time point after siRNA treatment in SU8686 cells. Panc-1 cell survival data over 0-100 hr time period were shown in FIG. 4C, and no significant reduction in cell proliferation, measured by an SRB cell viability assay, was observed (FIG. 4C). Untreated, non-targeting siRNA treated, and ubiquitin B cell death control siRNA treated cells were used as control for FIG. 4 experiments.

Example 2

Effect of ROCK1 Inhibitors in Pancreatic Cancer Cell Line Cells

Figure 5:
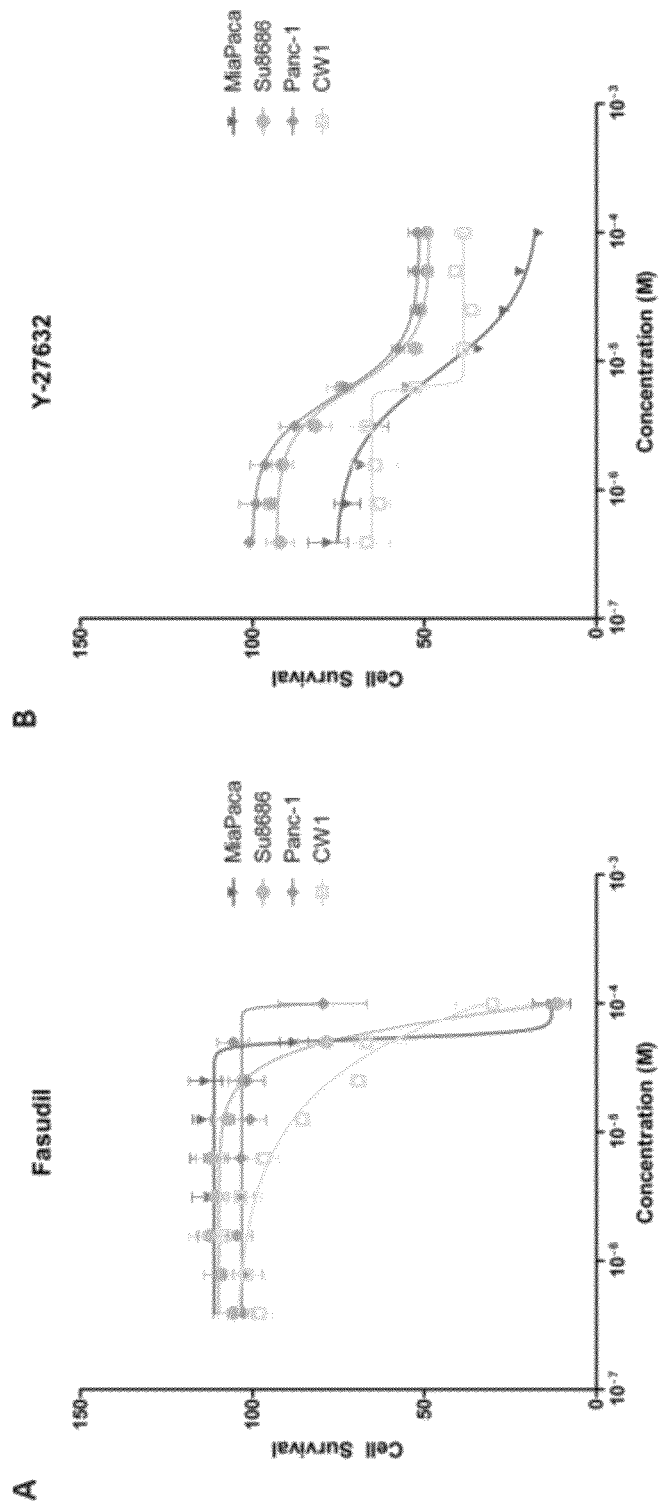
FIG. 5 depicts (A) the drug dose-response curves for fasudil exposure in MiaPaca, Su8686, Panc-1 and CW1 cell line cells; (B) the drug dose-response curves for Y-27632 exposure in the same above mentioned cell lines; and (C) the drug dose-response curves for Gemcitabine as a reference.
Figure 5C:
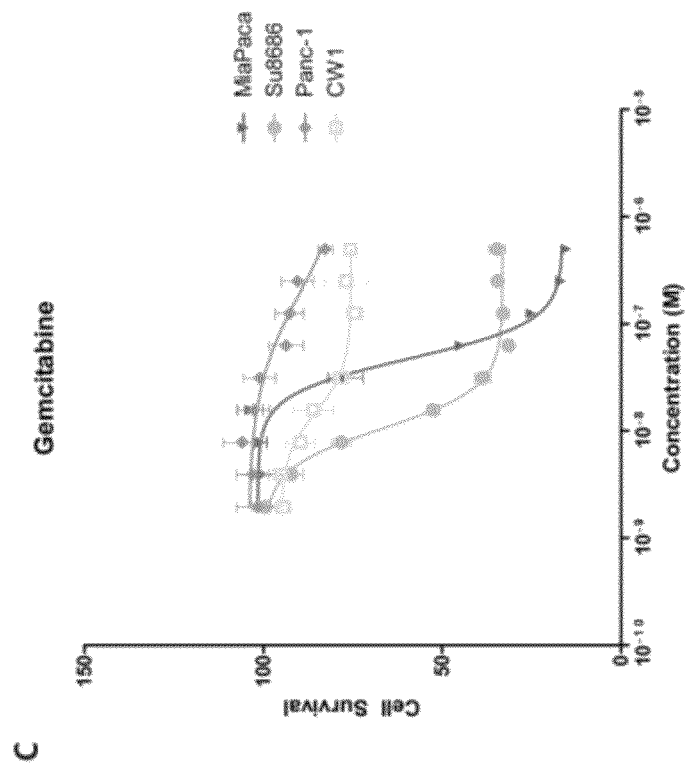

Efficacy of ROCK inhibition evaluated by drug dose-response curves: The small molecule ROCK1 inhibitors, fasudil and Y27632, were analyzed for their effects in pancreatic cancer cell lines. Drug dose-response curves were created to assess the efficacy of ROCK inhibition at 72 hours of drug exposure. FIG. 5A presents the drug dose-response curves for fasudil exposure in MiaPaca, Su8686, Panc-1 and CW1 cell line cells. FIG. 5B presents the drug dose-response curves for Y-27632 exposure in the same above mentioned cell lines. Gemcitabine, a nucleoside analog, replaces one of the building blocks, cytidine, during DNA replication and thus arrests tumor growth, which leads to cell death. Gemcitabine is shown for reference as illustrated in FIG. 5C. $IC_{50}$ values for each inhibitor to each cell lines are shown in TABLE 2, which demonstrated moderate ($IC_{50}$s range from 6-71 μM) inhibition of PDA cell proliferation by fasudil and Y27632. In some situations, agents with an $IC_{50}$ value less than 100 μM may be considered further for potential use for treatment. When the $IC_{50}$ value is too low, it means that the agent has high toxicity to cells and thus may not be proper for treatment purposes. Therefore, based on the $IC_{50}$ value in TABLE 2, fasudil was selected for further exploration in developing pancreatic cancer treatments.

TABLE 2

ROCK1 inhibition, $IC_{50}$ values (μM)

| | Inhibitor | | |
|---|---|---|---|
| Cell line | Fasudil | Y27632 | Gemcitabine |
| Su8686 | 71.2 | 27.9 | 0.017 |
| Panc-1 | >100 | >100 | >100 |
| MiaPaca2 | 55.0 | 6.8 | 0.056 |
| CW1 | 66.0 | 6.4 | >100 |

Figures 6A, 6B:
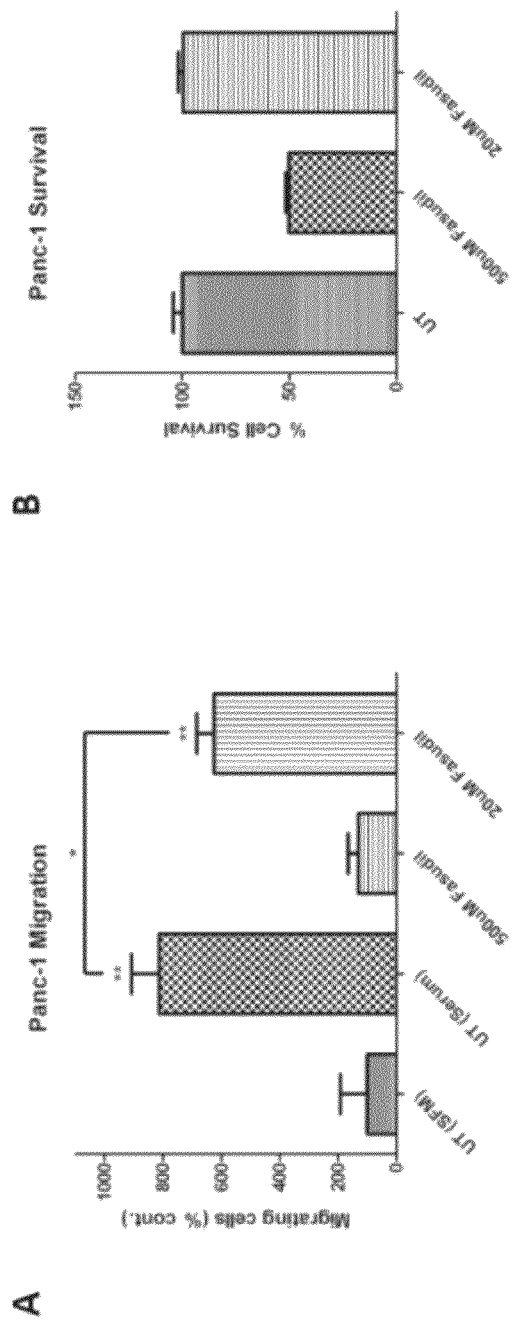
FIG. 6 depicts (A) a significant reduction in migrating cells was seen at both 500 µM and 20 µM, relative to the serum (chemoattractant) containing media control; and (B) 500 µM fasudil resulted in 50.3% cell survival at 24 hours, however, no significant cytotoxicity was observed at 20 µM. *p<0.05, **p<0.01; and "UT" stands for untreated; "SFM" stands for serum-free media.

Fasudil reduces pancreatic cancer cell migration: Panc-1 cells were treated with the ROCK1 inhibitor, fasudil, in a modified Boyden Chamber Assay. A significant reduction in migrating cells was seen at both 500 μM and 20 μM, relative to the serum (chemoattractant) containing media control (FIG. 6A). To further study the effects of fasudil at these concentrations on growth, an SRB (Sulphorhodamine) cell viability assay was performed. As shown in FIG. 6B (*p<0.05, **p<0.01), 500 μM fasudil resulted in 50.3% cell survival at 24 hours. However, no significant cytotoxicity was observed at 20 μM (FIG. 6B, *p<0.05, **p<0.01). In both FIGS. 6A and 6B, "UT" stands for untreated; and "SFM" stands for serum-free media.

Figure 7:
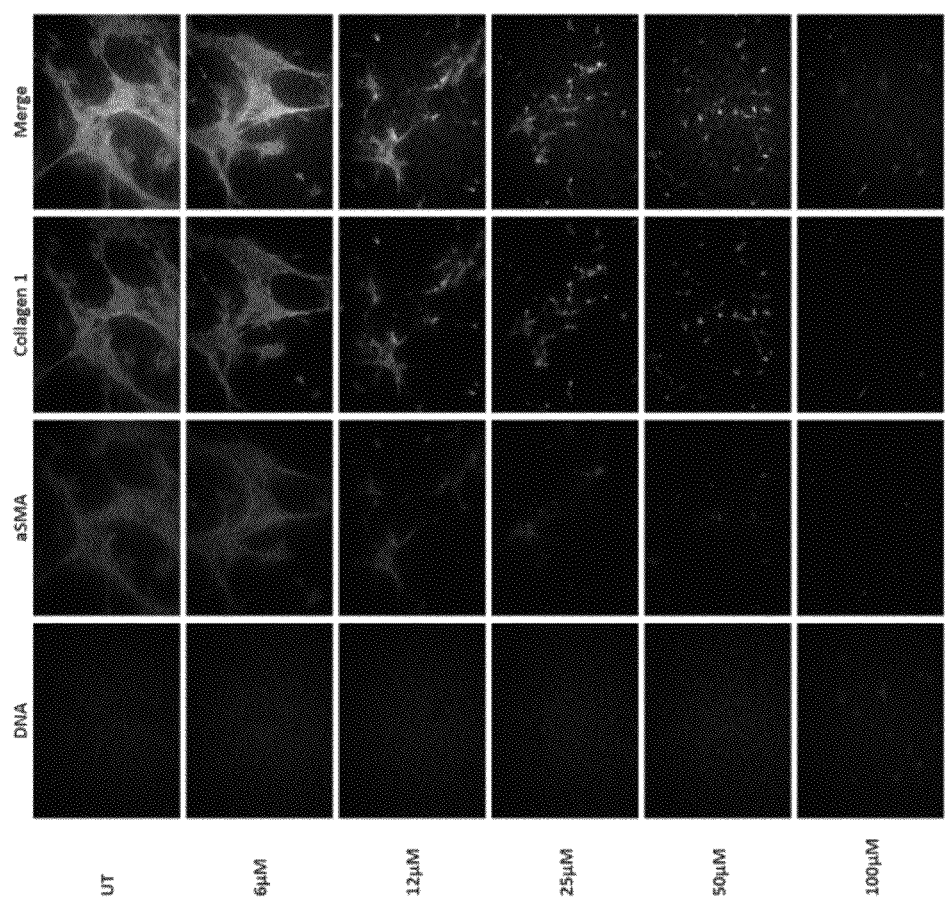
FIG. 7 depicts the effects of fasudil on the proliferation and expansion of the stromal compartment in a co-culture of human pancreatic cancer-derived myofibroblasts and SU8686 cells. Cells were fixed and stained for the myofibroblast markers: alpha-smooth muscle actin (aSMA), in red, and collagen 1, in green.

Fasudil selectively inhibits proliferation of aSMA-positive fibroblasts: Despite the fact that ROCK1 was generally observed localizing to ductal epithelial cells, and not in the stromal compartment of patient tumor samples, the effects of fasudil on the proliferation and expansion of the stromal compartment in a co-culture of human pancreatic cancer-derived myofibroblasts and SU8686 cells were examined. These cells were seeded and then treated with fasudil for 72 hours at the concentrations indicated in FIG. 7. Subsequently, cells were fixed and stained for the myofibroblast markers: alpha-smooth muscle actin (aSMA), in red, and collagen 1, in green. aSMA and collagen 1 expressing myofibroblasts, were selectively inhibited at 50 μM, 25 μM, and 12 μM of fasudil; whereas a significant reduction in cell proliferation was seen for both cancer cells and myofibroblasts was observed at 100 μM, relative to the untreated samples ("UT").

Figure 8A:
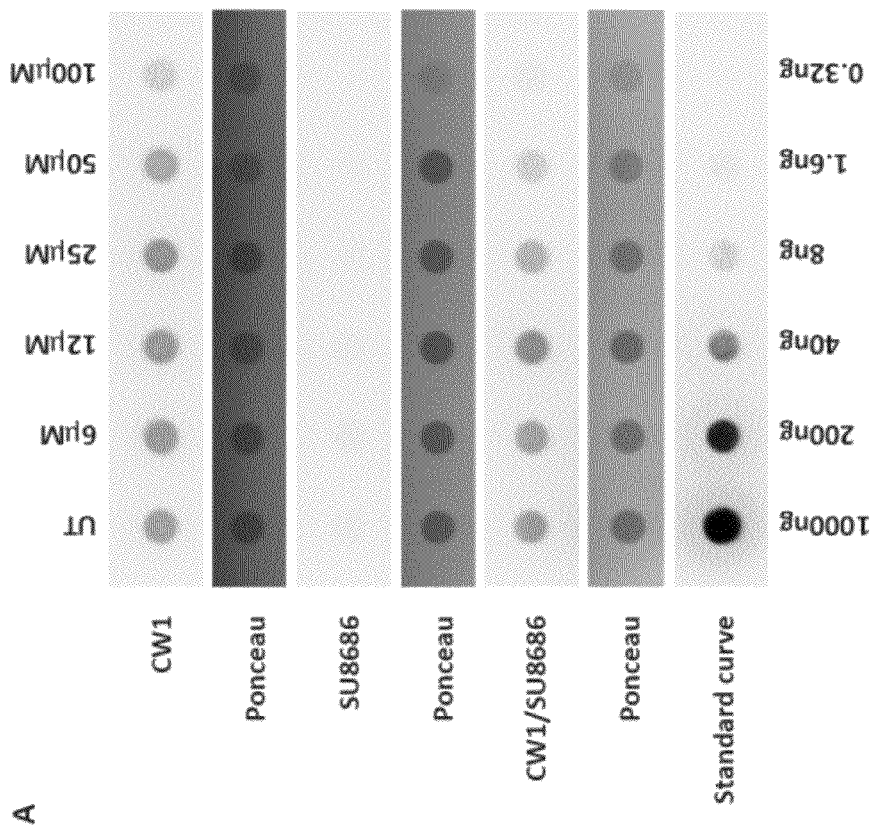
FIG. 8 depicts (A) CW1 myofibroblasts and SU8686 expression of collagen 1 in single culture, as well as a co-culture samples; and (B) calibrated collagen concentrations in each sample with treatments of 100 µM, 50 µM, and 25 µM fasudil relative to the untreated sample.

Fasudil reduces collagen synthesis in co-cultured pancreatic cells: The effects of fasudil on the expression of collagen 1 in single and co-cultures of human myofibroblasts and SU8686 cells were examined. These cells were seeded and then treated with fasudil for 72 hours at the concentrations indicated. CW1 myofibroblasts and SU8686 expression of collagen 1 in single culture, as well as a co-culture samples are shown in FIG. 8A. Treatment conditions are shown at top of the figure panel, and standard curve concentrations are shown below the figure panel (FIG. 8A). Calibrated collagen concentrations were shown in FIG. 8B (20 μg total protein loaded per sample). A significant reduction in collagen synthesis was seen with treatments of 100 μM, 50 μM, and 25 μM fasudil relative to the untreated sample (FIGS. 8A and 8B). This and above findings showed that ROCK1 is a valuable therapeutic target for the inhibition of migration or invasion in pancreatic tumor cells, as well as in reducing the stromal contribution to tumor growth.

Increased collagen deposition is observed in pancreatic cancer patient tumor samples: Histochemical analyses of human pancreatic tissue samples from pancreatic cancer patients were conducted and compared to control sample from normal pancreatic tissue. Both normal and tumor pancreatic tissues were subjected to hematoxylin/eosin (H&E) and pentachrome (Russell-Movat's) staining analysis. H&E analysis reveals increased proliferation of the pancreatic stellate cell population (FIG. 9 left column). Pentachrome analysis demonstrates increased collagen expression in the stromal compartment in tumor tissue relative to normal tissue (FIG. 9 right column).

Figure 10:
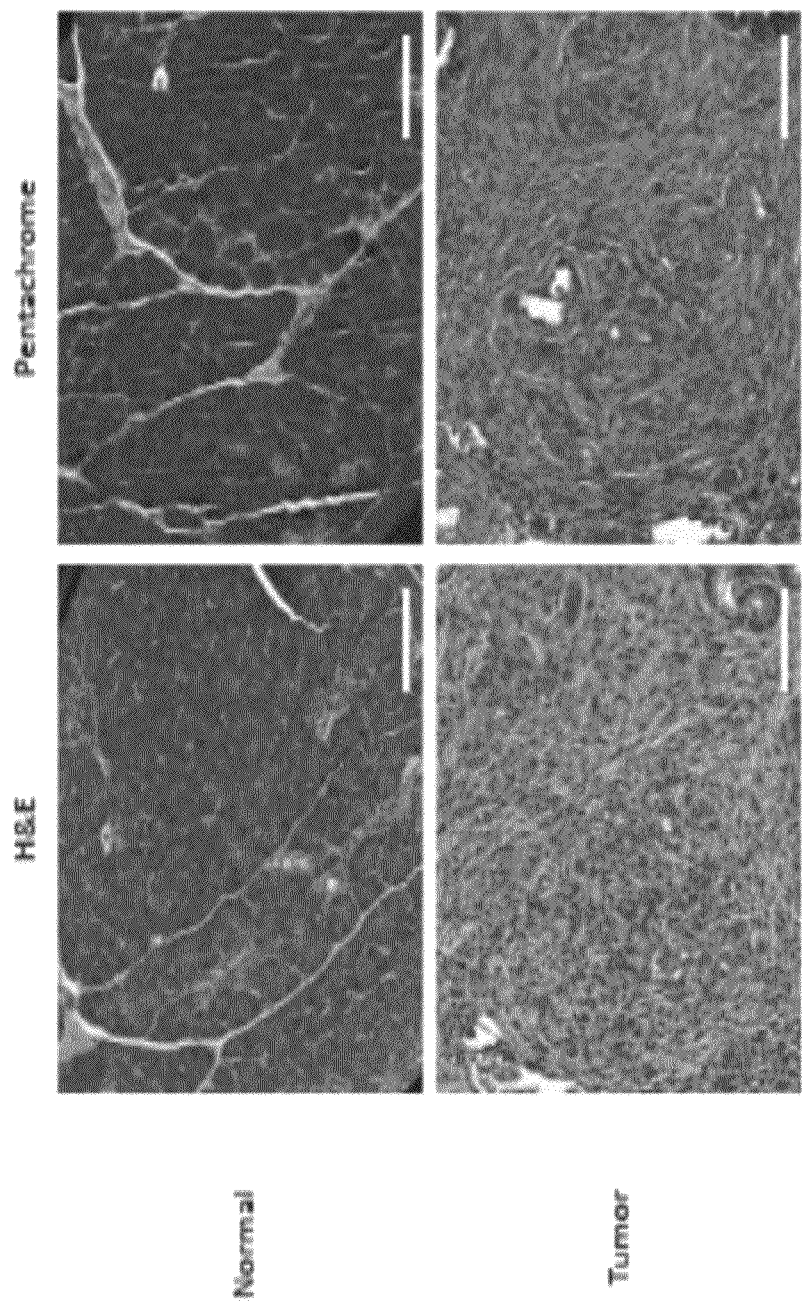
FIG. 10 depicts the histochemical analysis of KPC mouse pancreatic tissue samples. Both normal and tumor pancreatic tissues were subjected to H&E and pentachrome staining analysis. Pentachrome staining: Green/blue=mucins, Yellow=collagen, Red=muscle/fibrinoid. Scale bar=100 µm.

Increased collagen deposition is observed in the KPC (GEMM) model for pancreatic cancer: Histochemical analysis of KPC mouse pancreatic tissue samples. The KPC model, also called the KrasLSL$^{G12D/+}$; p53R$^{172H/+}$; Pdx-1-Cre$^{tg/+}$ model, is a well-validated, clinically relevant model of PDA (Pancreatic Ductal Adenocarcinoma). KPC mice develop a spectrum of premalignant lesions called Pancreatic Intraepithelial Neoplasia (PanINs) that ultimately progresses to overt carcinoma with 100% penetrance. The tumors generally have a moderately differentiated ductal morphology with extensive stromal desmoplasia, similar to the most common morphology observed in humans. Both normal and tumor pancreatic tissues of the KPC mice were subjected to H&E and pentachrome staining analysis. H&E analysis reveals increased proliferation in the pancreatic stellate cell population (FIG. 10 left column). Pentachrome analysis demonstrates increased collagen expression in the stromal compartment in tumor tissue relative to normal tissue (FIG. 10 right column).

Figure 11:
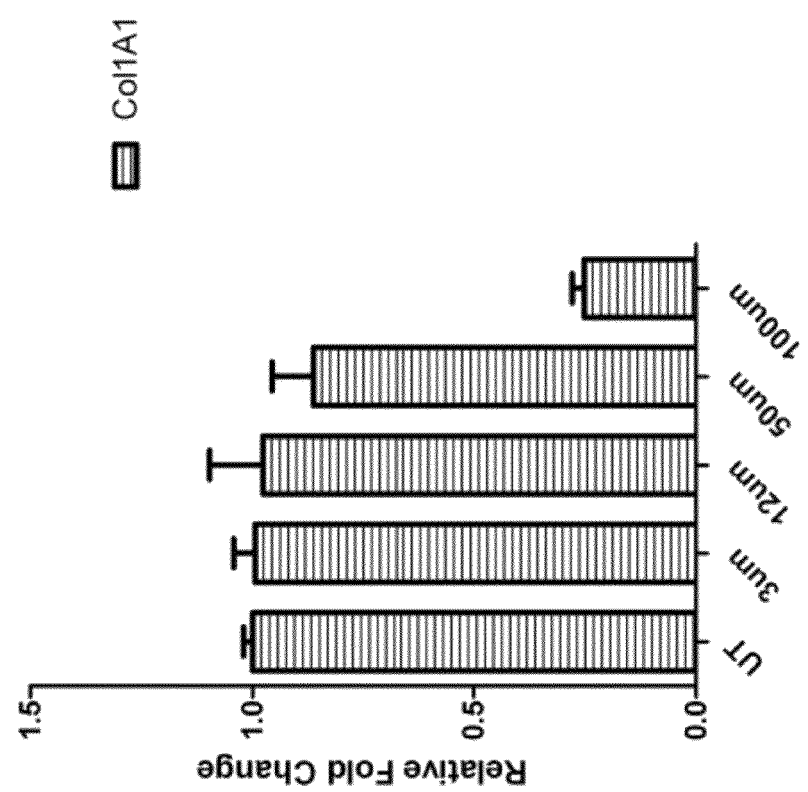
FIG. 11 depicts the analysis of collagen expression in cultured cells: quantitative PCR analysis of collagen 1 mRNA levels performed on cultured human stellate cells treated with differing concentrations of Fasudil.

Fasudil inhibits collagen expression in cultured human stellate cells: The analysis of collagen expression in cultured human stellate cells exposed to Fasudil was carried out using quantitative PCR analysis of Collagen 1 mRNA levels. The analysis was performed on cultured human stellate cells treated with differing concentrations of Fasudil at 0, 3 μm, 12 μm, 50 μm, and 100 μm. A three-fold decrease in collagen expression was seen at the highest concentration of fasudil (FIG. 11A). Dot blot analysis was performed on protein lysates of co-cultured tumor/stellate (SU8686/CW1) cells treated with Fasudil at concentrations at 0, 6 μm, 12 μm, 25 μm, 50 μm and 100 μm. Decreased collagen expression was noted in both monocultured stellate cells (CW1) and co-cultured tumor/stellate cells (CW1/SU8686) (FIG. 8B).

Example 3

Figure 12A:
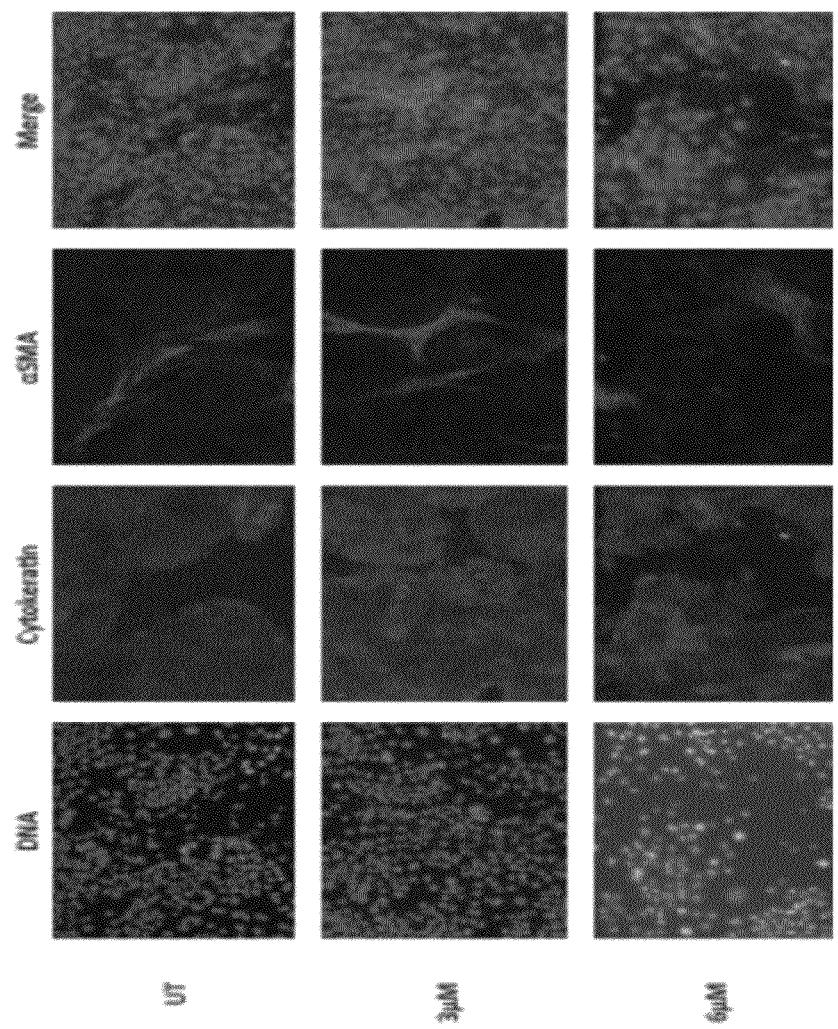
FIG. 12 depicts the effects of dosage effect of fasudil on the proliferation and expansion of the stromal compartment in a co-culture of human pancreatic cancer-derived fibroblasts and SU8686 cells. Cells were fixed and stained for the epithelial cell marker, cytokeratin, in green, and αSMA, in red. (A) 0 µM, 3 µM, and 6 µM fasudil treatment; (B) 12 µM, 25 µM, 50 µM, and 100 µM fasudil treatment.

PDAC Treatment Using Fasudil to Target ROCK1 for the Inhibition of the Stromal Contribution to Tumor Growth Fasudil inhibits stellate cell proliferation and function: The effects of fasudil on the proliferation and expansion of the stromal compartment in a co-culture of human pancreatic cancer-derived fibroblasts and SU8686 cells were compared. Cells were seeded and then treated with fasudil for 72 hours at the concentrations ranging from 0, 3 μm, 6 μm, 12 μm, 25 μm, 50 μm to 100 μm. Subsequently, cells were fixed and stained for the epithelial cell marker, cytokeratin, in green, and αSMA, in red. A significant reduction in cell proliferation was seen for both cancer cells and stellate cells at 100 μM, relative to the untreated sample as shown by DNA, cytokeratin and αSMA staining (FIG. 12). It is noted, particularly, that aSMA expressing cells (stellate cells), were selectively inhibited at 50 μM, 25 μM, and 12 μM.

Figure 13:
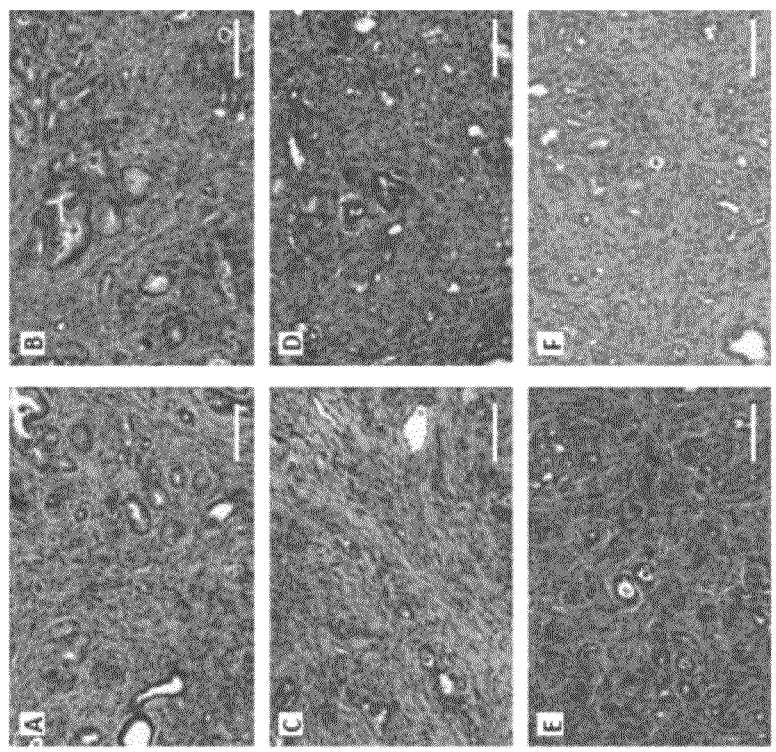
FIG. 13 depicts the effects of fasudil on the proliferation and expansion of the stromal compartment in the KPC mouse model for PDAC with representative images showing tissue from mice treated with (A,B): vehicle; (C,D): gemcitabine; or, or (E,F) gemcitabine plus fasudil. Scale bar=100 µm.

Effects of fasudil treatment on the stromal compartment in PDAC: The effects of fasudil on the proliferation and expansion of the stromal compartment in the KPC mouse model for PDAC were examined. Mice were enrolled in this study after meeting criteria—tumors were at least 3-5 mm in diameter in at least one dimension—upon regular inspection by high resolution ultrasound. Enrolled mice were then treated for two cycles before being sacrificed with vehicle (control), gemcitabine, or gemcitabine plus fasudil. Each cycle of gemcitabine treatment consisted of 80 mg/kg gemcitabine via intraperitoneal injection every third day for a total of four doses. Fasudil was dosed at 100 mg/kg, twice daily for each day on cycle. Representative images, each of which is from a different mouse, are shown of mice treated with vehicle (FIGS. 13 A and B), gemcitabine (FIGS. 13 C and D), or gemcitabine plus fasudil (FIGS. 13 E and F). As seen in FIG. 13, some reduction in the stromal compartment was observed in the gemcitabine plus fasudil treated mouse tumors in contrast to that under vehicle or gemcitabine only treatment.

Figure 14:
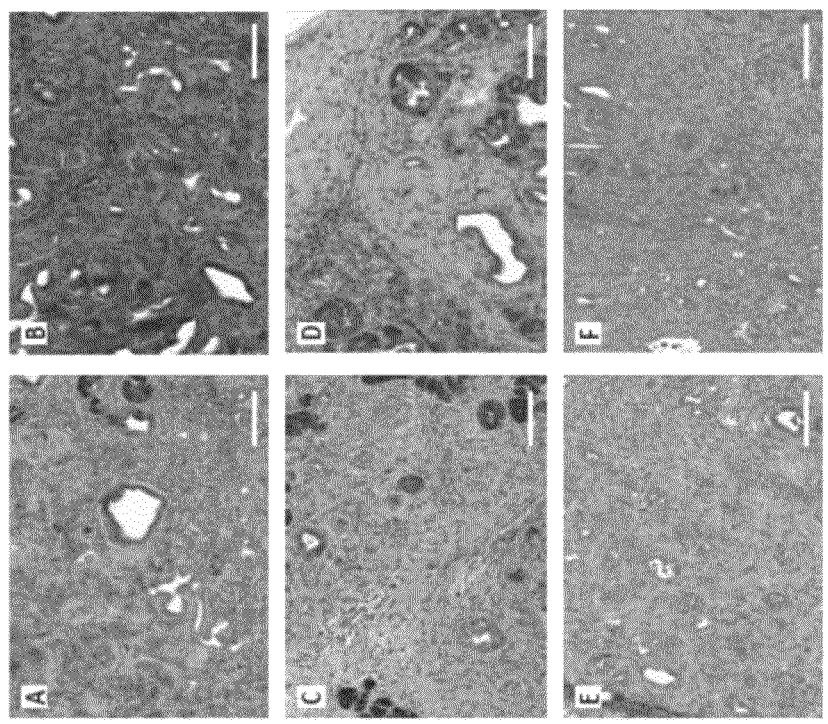
FIG. 14 depicts the Pentachrome staining analysis of the effects of fasudil on the expression of collagen in the stromal compartment in the KPC mouse model for PDAC with representative images showing tissue from mice treated with (A,B): vehicle; (C,D): gemcitabine; or, or (E,F) gemcitabine plus fasudil. Scale bar=100 µm.

Effects of fasudil treatment on collagen expression in PDAC: Russell-Movat's pentachrome analysis was carried out to examine the effects of fasudil on the expression of collagen in the stromal compartment in the KPC mouse model for PDAC. Mice were enrolled in this study after meeting criteria—tumors were at least 3-5 mm in diameter in at least one dimension—upon regular inspection by high resolution ultrasound. Enrolled mice were then treated for two cycles before being sacrificed with vehicle (control), gemcitabine, or gemcitabine plus fasudil. Each cycle of gemcitabine treatment consisted of 80 mg/kg gemcitabine via intraperitoneal injection every third day for a total of four doses. Fasudil was dosed at 100 mg/kg, twice daily for each day on cycle. Representative images are shown of mice treated with vehicle (FIGS. 14 A and B), gemcitabine (FIGS. 14 C and D), or gemcitabine plus fasudil (FIGS. 14 E and F). Significant reduction in collagen expression was observed in the gemcitabine plus fasudil treated mouse tumors relative to vehicle treated tumors.

The KPC model exhibits high levels of collagen expression in the stromal compartment of pancreatic tumors, similar to that in pancreatic cancer patient tumors. In this invention, Fasudil was shown to not only selectively inhibit human fibroblast proliferation, but inhibit collagen synthesis in primary human fibroblast cells as well. Histochemical analyses demonstrate significantly reduced collagen deposition in fasudil treated mouse tumors. Therefore, ROCK1 is demonstrated to be a valuable therapeutic target for the inhibition of the stromal contribution to tumor growth in PDAC, and the new indication of fasudil provides an effective PDAC treatment through inhibiting human fibroblast proliferation and collagen synthesis in fibroblast cells.

What is claimed is:

1. A method for identifying a pancreatic cancer responding to inhibition of pancreatic tumor cell proliferation by a ROCK1 inhibitor treatment in a subject in need thereof, comprising the steps of:
   a) receiving a pancreatic cancer sample from the subject;
   b) detecting an abnormality of a ROCK1 gene comprising SEQ ID NO: 1 in the sample from the subject; and
   c) identifying in the subject who is sensitive to the ROCK1 inhibitor treatment according to the detection of the ROCK1 abnormality in the sample provided by the subject,
   wherein the abnormality of the ROCK1 gene comprises
   (i) gene overexpression, detected by comparing the level of ROCK1 gene expression in the sample from the subject to a control sample free of pancreatic cancer cell or a control sample having pancreatic cancer non-responding to the ROCK1 inhibitor treatment, and/or;
   (ii) gene amplification, detected by comparing ROCK1 gene copy number in the sample from the subject to a control sample free of pancreatic cancer cell or a control sample having pancreatic cancer non-responding to the ROCK1 inhibitor treatment.

2. The method of claim 1, wherein the treatment is administered as a pharmaceutical composition comprising one or more ROCK1 inhibitors selected from the group consisting of fasudil, fasudil hydrochloride, Y27632, and any combination thereof.

3. The method of claim 2, wherein the pharmaceutical composition further comprises gemcitabine.

4. The method of claim 2, wherein the pharmaceutical composition comprises one or more ROCK1 inhibitors selected from the group consisting of fasudil and fasudil hydrochloride.

5. The method of claim 1, wherein the subject is a mammal.

6. The method of claim 5, wherein the subject is a human.

7. A method of inhibiting pancreatic tumor cell proliferation in a subject in need thereof comprising the step of administering an effective dosage amount of a pharmaceutical composition comprising one or more ROCK1 inhibitors selected from the group consisting of fasudil, fasudil hydrochloride, Y27632, and any combination thereof to the subject.

8. The method of claim 7, wherein the subject has an abnormality of the ROCK1 gene comprising SEQ ID NO: 1, and wherein the abnormality of the ROCK1 gene comprises gene overexpression or gene amplification relative to the ROCK1 gene expression or gene copy number of a sample free of pancreatic cancer cell or a sample having a pancreatic cancer non-responding to the ROCK1 inhibitors.

9. The method of claim 7, wherein the pharmaceutical composition further comprises gemcitabine.

10. The method of claim 7, wherein said pharmaceutical composition further comprises at least one pharmaceutically acceptable excipient.

11. The method of claim 10, wherein the pharmaceutically acceptable excipient is selected from the group consisting of a binder, a filler, a non-effervescent disintegrant, an effervescent disintegrant, a preservative, a diluent, a flavoring agent, a sweetener, a lubricant, an oral dispersing agent, a coloring agent, a taste masking agent, a pH modifier, a stabilizer, a compaction agent, and combination thereof.

12. The method of claim 7, wherein the subject is a mammal.

13. The method of claim 12, wherein the subject is a human.

14. A method of inhibiting pancreatic tumor cell proliferation in vitro comprising the step of administering an effective dosage amount of a pharmaceutical composition comprising one or more ROCK1 inhibitors selected from the group consisting of fasudil, fasudil hydrochloride, Y27632, and any combination thereof to a sample having pancreatic tumor cells.

15. A method for treating a ROCK1 inhibitor-responsive pancreatic cancer, comprising the steps of:
   a) identifying the pancreatic cancer according to claim 1;
   d) administering an effective dosage amount of a pharmaceutical composition comprising one or more ROCK1 inhibitors selected from the group consisting of fasudil, fasudil hydrochloride, Y27632, and any combination thereof to the subject,
   thereby proliferation of the ROCK1 inhibitor responsive pancreatic cancer is inhibited.

* * * * *

UNITED STATES PATENT AND TRADEMARK OFFICE
Certificate

Patent No. 8,703,736 B2                                                                                          Patented: April 22, 2014

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Cliff Whatcott, Phoenix, AZ (US); Haiyong Han, Phoenix, AZ (US); Daniel Von Hoff, Scottsdale, AZ (US); and Michael Barrett, Scottsdale, AZ (US).

Signed and Sealed this Second Day of September 2014.

BRANDON FETTEROLF
*Supervisory Patent Examiner*
Art Unit 1672
Technology Center 1600

SEQUENCE LISTING

<160> NUMBER OF SEQ ID NOS: 3

<210> SEQ ID NO 1
<211> LENGTH: 162112
<212> TYPE: DNA
<213> ORGANISM: Homo sapiens

<400> SEQUENCE: 1

```
gctggttccc cttccgagcg tccgcgcccc gcatgcgcag tctgcccggg cggtctccgt      60
ttgtttgaac aggaaggcgg acatattagt ccctctcagc ccccctcgcc ccacccccca     120
ggcattcgcc gccgcgactc gcccttcccc cggctgggac cgcagcccct cccagaagct     180
cccccatcag cagccgccgg gacccaacta tcgtcttcct cttcgcccgc tctccagcct     240
ttcctctgct aagtctccat cgggcatcga cctcgccctg ccccaccgga caccgtagca     300
gcagccccag cagcgacggg acaaaatggg agagtgaggc tgtcctgcgt ggaccagctc     360
gtggccgaga ctgatcggtg cgtcgggccg ggccgagtag agccggggac gcggggctag     420
accgtctaca gcgcctctga gcggagcggg cccggcccgt ggcccgagcg gcggccgcag     480
ctggcacagc tcctcacccg cccttttgctt tcgccttttcc tcttctccct cccttgttgc     540
ccggagggag tctccacccct gcttctcttt ctctacccgc tcctgcccat ctcgggacgg     600
ggaccccctcc atggcgacgg cggccggggc ccgctagact gaagcacctc gccggagcga     660
cgaggctggt ggcgacggcg ctgtcggctg tcgtgagggg ctgccgggtg ggatgcgact     720
ttgggcgtcc gagcggctgt gggtcgctgt tgcccccggc ccggggtctg gagagcggag     780
gtccctcag tgaggggaag acggggggaac cgggcgcacc tggtgaccct gaggttccgg     840
ctcctccgcc ccgcggctgc gaacccaccg cggaggaagt tggttgaaat tgctttccgc     900
tgctggtgct ggtaagaggg cattgtcaca gcagcagcaa catgtcgact ggggacagtt     960
ttgagactcg atttgaaaaa atggacaacc tgctgcggga tcccaaatcg gaagtgaatt    1020
cggattgttt gctggtgagt agcgctgttc tcttttgctt gtctggggtt ttgcatgtct    1080
ttccttcctc ttgcattagt ctggttcgct gcaaaagtct caggtgtgca taatcgtctt    1140
ggaaaatgct agatttctgt ttcctgaaga atcttggagt accattaaca tctcatggtg    1200
tggtcctatt tgccatttga ctggctctgt actaactact ctgaactttt aattctgact    1260
cagttcatga gtacccgaaa gatacttaca aactgctatt gcaggcatcc tataaaaagt    1320
tatcacgtca gagttactgc aatgtataca gtttgttgaa tggcgatcgt agtaattaat    1380
gttaatctttt ctgatccgtt tgacagttaa attggaaaga ctactttgca tttttttttcc    1440
tttttgcgat ttagctccta ggggtttagt ttttagcctt gaaaatgata acggagaatt    1500
gctattgagg aagtgatttt tgagccaaaa tttcataggt gatttgagtt tgaaggaact    1560
ttttgctaaa ctattgtaaa aaaccaagat aattggtcat aggtaattac agtgttaact    1620
tatttttattg tattattggt tacaaaagta cgtaccatac agttattgta actgtcttttt    1680
tggtggtgtg gcacttaaca ttgtcacttg taaaacattc taaagagggt tttatgacat    1740
gaaaaaccac aatcccattt taaaaatagt taagtggttg ataatacagt tatctgtaaa    1800
taattggaat tcttaggttt gatacatttc ctctgtaaat gtatcaaagt tgttcagagt    1860
ttctgaacaa ctaagggtta tataatatttt cttggtccaa acaaaaccac ataatctcta    1920
aaataaggtt tcaggagca tgtatatgga caggatttca caatgtcttc ggtgaaataa    1980
tgttagatat gctcaatttt ggggattaag attaaggaaa caaataata ccattcaaag    2040
```

```
aaataataca attcaaaaat cgcatcttga atcaaaggaa aattaatgta gattgtttaa    2100
aattaacgtg catttcagtt actctaaatt tctgtttatt tgtattttc cacgtgtatg    2160 ggttttacaa caagcttccc aaagctttca gaattgttgt aagcatccct gaccaggaaa    2220
taagactatt gtgggttgtt tgaaatgtct caccacatta tggatgctct ttatattgag    2280
agatagtaaa gaaggttgat gcgtaataga ttttaaaaca ttttattaaa cgagataagt    2340
ggaaggaatt agaatatatc ttgtagtaag gatttctata acttctaaga agtctgattt    2400 atctttttaat atttatccag ttttcatata tttttgattt tattttgctt ttcgatctcc    2460
ttattacatg agtggtgtta tagggagggt ttagtagctt tcttttttctt taaatcatct    2520 tctggcctct tgctatagct tcatttggtg gggacccttta tttacatgtg gaggatacaa    2580
ggaaatataa gtcatgactc tttccctgag agtccaatct atttaatgga agacaaaacc    2640
ttgtctcaca tatatacaca gaaacaaagc taaacacttc acagattgag aaaatgtgat    2700
aaattccaga tgattgttta gataatgtat gttcttggaa attgagagaa agaagtcact    2760
gtgagttgag agagccaaag tatgttttat aatggatgga taggatttag gtagagggta    2820
ctcaagagga gtggaggata acgtgaatag agggtggaga catgactggc tatgacatgt    2880
ttggggaaac aaggaagata aggttggaag gaaatattag cgttagattg tggaggattt    2940
gattggtagg ctaaggattt tggattgcct ttacactgtt gtggctatta aatatttata    3000
aataagaccg tgctaggatg aatgaagaag atgaatctgg tgtgtggaag atgggttagc    3060
atgggaaaag attggagaga cagtgagatt ggacagtttt ttaaaattgt tattattgta    3120
atagtccaga aatgattgaa gcccaaaatt ggggcatgag aatgagaaaa gaagaattaa    3180 tggaactttta ttggcaggga aaagatgggg aaccaaagag agaggcaata gtcagatgac    3240
tctaaagagg ttgagcctgg attataggga gaatggtaaa aatagcaaag tcaggtttgg    3300
aaattgcttg tgaagaatag gcctacagat aaattcaatt ttagattcgt tgtgtttgag    3360
gggatagtgg agcaatcatg agaaaatgac ctgtagactg ttggagatac agaactgagc    3420
tcataattac agataatgat ttagaagtca tttgcacaaa ggtgcaagtt gatataatgg    3480
taaagggaga acaatggag ggaaaatga gggtgaaaga tgaaggttga acaaagagga    3540
agagtggagg aggtaagcca tcaaggcctc cagagttagg acagccaggt atcatggagc    3600
ccaacacttc taaaacaaca ttttgttaaa gagaatagtc aacagacaga tttggttgtt    3660
ttttcccctt caaatcttat aatcttgtcc tcttttttctg tttagttcca cagctgttta    3720
ttgatagctg ttactgaaat tttattaccc cgtcaatctg aacttggtaa agactgaatt    3780
ttcctttttt tttttctgag atggaatctc actctgttgc ccaggctgga gtgcagtggc    3840
gcgatcttgg ctcactgcaa cctccgactc ctgggttcga gtgattctcc tgcctcagcc    3900
cccacgagta gttgggatta cacgcgtgca ctaccacgcc tggctaattt ttgtagtttt    3960
agtagagatg gggtttcacc atgttggcca ggctggtctt gtactcctta ccccaaggaa    4020
tccgcctgcc ttggcctccc gaagtactgg gattacaggc gtgagccacc gtgcctggcc    4080
caagactgaa tttcctttag agacaaaaaa tccttttttct gggtttgtag tatctagcat    4140
gaattttctt cgcatgatgt tttatgttta acattgagca ttcgttcgtt cattcattca    4200
ttgtgtcatt cagggtgacc tatcaggtga cttcagcttt ttcagtgagt ctgttcttgt    4260
tcttccctat ctggactttg gacctctcat gtattatagg aacaaaactc cttttacatt    4320
ggttgccttt ttctgttatt ttgacttttg ttgatttgtg taactgatac ttacttatta    4380
gtgtgtatta tgtgccacgt gcagtccttt agttctagag ttgttttttgt aatcccaaaa    4440
```

```
ataaggtttt caaattgttt cttctctacc tcctttacta gattcatgct tagaaatgga    4500
aacttccaaa tcttttggtt tcagaaattt gctggtgtat gtccttttaa actaccttac    4560
ctactaaaca gcttttttgt tgagacacta atgatgaata gcatccgtaa tctgaaattt    4620
gaagtgctca aaatctgaaa cttttgagt gctgacatga cgccataagt ggaaaatcca    4680
cctgaccttg tgagatgggt tgcagtcaaa atgcagtcag aactttgttt catgcacaaa    4740
attattaaaa tattgcaaaa aataaccttc aggttgttgt gtataaggta tgtatgagac    4800
gtaaatgaat ttcttattta gacttggtcc ccatcccag ggtatcttat gtatatgcaa     4860
atattttaaa atctgaaaaa gtctgcagtc tgaaacactt ctagttccaa gcattttaaa    4920
caagggatac tcaacctgca gtagtttaga ataatgtagc tggaagaact ctgataagtg    4980
gctatccaat ctttctcga acacctgtaa ttttttcaa gaactaagta agttcaatct      5040
tcatatcatg tataaatgct aaaatagtct gcaaatacta agatacatta tgataaccat    5100
tcacttgttt cctagagcat tcaaattagt caacttggt tttctgtagg tcagattctt     5160
tccagtgtcc taatggttgt cttcttact gtccatgtta cagtttataa ggattatcgg     5220
gagctatttc tcttttccgg acttccttat cttctaatta ttttgtctag gcctgtaat     5280 aatttctcag tgattttgag tacctttgaa aacagaataa gggatggagt ttagttaagt    5340
ctatttaatc tttgcagagg aaaaaatgct tatgatttgt aaattaaata ggaaaaacaa    5400
ggccgggtgc agtggctcgc tcctggaggg ctgaggccag agaattgctt gagcctagga    5460
cggggaggtt gcagtgagcc gagattgtgc cactgcactc cagcctggac gacacagtga    5520
gaacttgtct caaaaaaaag gaaaaacaaa aatggttggg agggttatag atacatttgt    5580
tttgaagttt gacatacttt tcatgaaaat atcttgcttg tagcatattt attggcacat    5640
cgcttcatga tgcctgttaa gaacatgacc tttccacttc tcttctggct ggtggaggtg    5700
tagcaacggg tgagcggagg agacagaagg gaaccagtat tagtcaaata gtgcctgttg    5760
agttctaaca ctgtgctgtt tgtcactact atttcttatt agggagtttt tcagaatgtg    5820
gaagataaat gtaaatgaaa tttctggtgt tagtctttga gttttcttc ctttaaatta    5880 tcttcctggg ctctcttgac ctagtgcttt cccatctttt cattcttctt tttttctttt    5940
cctcaatctt tggcctatca tacttatctt tgtcttcact ctcttgaaga attcatccat    6000
tcttacagct tcaattatta ttatctctat gtacatgata cccaaatctt tattttagt     6060 cttttgtttc aaaccttaaa tatctgactg ccttgtaagc atttctactt ggatgtcatg    6120
ttagtctcaa atccctcata ttccaaaaca agcttcctcc cataaactta tctgttttgt    6180
cattaattcc actattgtcc ctgtcgctaa actgaaattt tgttgtgaa cttttttgac     6240 agtgttagtc cacacattgg gttattacag cagattttgg gtagcatttt cgaatctgga    6300
ttattgctgt ctaatcccct gtatgccttg ccagttgaat tgatctgttt tgggggtata    6360
ttactcttgg aatgaaaaga cctgaggtca ttaaatcttt gagccttaaa gttgtatctc    6420
tgccagtgtt cctagtttgt gagttaatag gtgttattag tatcaattgc atatctggtt    6480 agttggacc agactttttt ggatgttagt atgttcagg aacttctttt aaaaaaacaa      6540
gttactctcc taattcattt ttattcattc agcaaatctt tgtatagggc ctaaacttgg    6600
attgaaatct aggctctgac atgtatttgc tgaaatattt tagggagtta ttttaacctc    6660
tcaatgctgt ttcatcttca gaaaaataag aggggataaa agtactagat tgttgtaaga    6720
attgaataat atagtcaaag caactatcat agcatttggt atttagtaag catttgtaat    6780
attgtcatat ttataatatt tctgttatat actagtcagt gtgcttagtc tagaagttga    6840
```

```
tatttattgt cgtctctaag tacagagtaa tttatctggc acctcaagcc gctcataaat    6900
tcataatcta gctgtgcgtt attgacgtct aagccaattg taactgaaaa ttgagacatt    6960
tattaataga ttcaataaat ggggaagatc ttttagagac tgtttatttg tttagttgtg    7020
atttataata tggtatatac tttgtgccaa gggtttagtt ggatataaaa ggcaattggg    7080
aactaattta tggagattga gttgttatct tgttctcttt ctgtgtgtat cttttatact    7140
ttcagtgtgt gttctgtaaa taggccctct tgcactacag gcaccctgtg ggtgtgtaga    7200
gacgtggctc agagtaacgg ctgagatatg aattggttaa ttcattaatc ttttgagtca    7260
gaaatgtttt ttttccgccc agtccgaagt gccgtggcgc tatcttggct tactgcaagc    7320
tccacctcct gggttcacgc cattctcctg cctcagcctc ctgagtagct gggactacag    7380
gcgcccgcca ccgcacccgg ctaattttt gtattttag tagagacagg gtttcaccgt    7440
gttagccagg atggtctcga tctcctggcc tcgtgatccg cccgcctcag cctcccacag    7500
tgctgggatt acaggcatga gcgccgcacc ctgcccagaa atgttttaa tccagaagaa    7560 ggaactacat ataaaatttt atgttgaata aagagtaaat tctcagtttt agattagact    7620
ttgcataact ttacaccagt tttgcttcac gattataagt tttggtgtta tggatatatg    7680
gtgaaaacta cagattctat tacgataatt gatagaaaaa cccacttatc aggaaatatt    7740
atatatagag ttctattgct gaagataatc caatagctct acttctccat tcctcatccc    7800
cactaaaaag ggggtatatc catttagttt aagtccacag tatagctgtt ggatacgaca    7860
cacatgtgtt caagaagatg aacaggtagt actgcaattc acaatggaaa gtattcttaa    7920
aaatatgcca ttagtgtggt gtgaaaagaa cactggactg aaaattcaga gcatagtctt    7980
gttttgctat taaatctctg tgtaatgaag tacatcattt ttctcatcta ggcttcagtt    8040
tccctatttg tagaacaaag agttggacca gatagttgct gatgtctctt gtgtctctga    8100
aaattctatg ataggcctgg catggtggtc tgtaatccca gcacttttgg aggccaaggt    8160
gcaagtatcc cttgagccca ggagtttgag accggcctgg gcaacagaga gggacctcgg    8220
ctctacaaaa aaaataaaaa tattacctgg gtgtagtctc agctacttgg gaggttgagg    8280
taggaagatc gcttgagccc aggagattga ggctgcagtg agccatgttg gtgccacggc    8340
actctagcct ggttgtcaaa gtgagactct gtctcaaaaa aaaaaataa taaaataaaa    8400 tttattaaac aaaatctatg agactttgtt tattacactt caattaaaac ttcaaaaaat    8460
tgtctttgat ttattattta agaaataaaa cttaaacagt taaatgatgt tggggtagaa    8520
atgtaagact gtcaaccatc tttagtaagt gcttttttg gaactagttc ctaaattaat    8580
ttcaatagtt atatttgcca ttatttttg aatttgtgac ttacgttcat aattgtaggg    8640
gtttgtactt tctgaacata ggaagtgtaa tttttattt gtatatctat taaaatgtaa    8700
agatatgatt tcttctctca gtatacttgc cctctctgtt tgggattatg aaatatagag    8760 tgtatttta ttacagttcc taaacaatta ataggaaggt agatgttcaa attaacgtcc    8820
aaagtctgat atctcaggga ggtgagagtt tatcttatac ttgtgttata ttaagggtag    8880
gccaacctgt gcccctctta attgatccat acttctgata ccagattttt ggcaagaaat    8940
tgaaaatttt ctcagattgt tgtcttgaac tacttttttt ttttttgaga cagggtctgg    9000
ccctgtcacc caggctgaag tgtggtggca tgatctcagc tcactgaagc ctccacttcc    9060
cgagctgaag ccattcttct gcctcagcct cttgagtaac tgggactaca ggcaagcgcc    9120
accatgcctg gctaatttt gtattttttt tggtagagat ggggttttgc catgttgccc    9180
aggctggtct caagtgagcc attggcctca gcttcccaaa gtgtaaggat tacaggcgtg    9240
```

```
agccacagca cccagccctc aaactaattt tgaaacagtg gactgcaatt aactttcctt    9300
tttctctttt ctgttattca ttcattcatt tgacaaatgt ttatttggtg tgtactgtgt    9360
gctaggaatt ctgctatgca atggaacacc atggtgagta aaaacaaaca tgtcccactt    9420
tcatggaatt tatagtgtca ggaaaaggat taattaaatg tctatcacac taagatagga    9480
gtggggtatg gtgaagggca ggtaagagat atgatcatga ctttcccttta aggtttggtt    9540 tacttgtagt aaagcaatta agtgtatagt tttcagatat gaggctgtag attgtatcag    9600
attcacttga ggcacttgtt aaaaatggaa tctgggatct tgcgtagaca aacaaaatca    9660 caatttttg gatgattct taggatttgc atgagatgtg gattcttaga cacactcaag    9720
tttgaaaact gtagttacag tggaaagaat gtgaattttc attctgtttg gtaattttat    9780
gataaaaatt tcaaatatac gcagaagtag ggaaaatagg atagtgaact cctgttactc    9840
agattttgca gttttcaaaa tgtcatcaca tttgatttca ttaatcaccc ttttcttac    9900 caaaatattt taaagtaaat tccatatatt gtcatttcat ccttacatac ttcaataagc    9960
atctttgaaa aaaaaaagg acattttctt acataatcat aatggccatt atcatgccta    10020
gcaaaattaa aagtgctttg gtatcattaa ttcccagttt atattcatat ttctgattgt    10080
ctaaaacagt gtctatttta cagttgcttt attagaatct ggatccaaag tccaaatgtt    10140
gcttttcttt ggttaggtcc tttaagagtc ttttaagtct cttaatatag agaaatctca    10200
ttcccccaac ttctccaact cccctttcccc tgcatgttga aggaactagg tcagtggtac    10260
tatacaggac cttgtttac attctggatt ttctttttta ctttcctaat gatgtaattt    10320
aacttcttcc tgtattttcc atatttccta taaaatggta gttagatcta aaagcttgat    10380
ttacttattt cagatttcta gtcaagggta ctcaatagat tgtatttct tttgcctcac    10440 acggaggtgc ataatgtctg cctggcctgt agtgatgcta aggttgatca ttctgttcag    10500
gtggcatcag tctgtgatag cttcctgtaa gaatcgttca ttaacctttc atctaatggt    10560
tccattcatt catgatcttt aactgaatcc ctgttatttc attagggaat agcaaaataa    10620
tgattttcta attctgttat tccttttcaca tttattaact gtaattcctc tgttaagagt    10680 agaacttta catattaata tcaactaggg ctgtatgttt accatgaaat ccaattcatg    10740
aaatacagga tgaatacttc aatcttttcc ttaattgcca cttgttatag caaggtatt    10800 tggagactta ttatgataga tatgccacaa actgggtaac ttgagggag tttaagtaaa    10860 ggactgttta caaaggtata gataatattt aaggaaactg gtagggatgg tacagtgctc    10920
tgtgactagt cacagtgagg aagggagttg cgatcgcctc aaggccagca ggaaacaggg    10980
aagaggaaag cagctgagga gggtagctct atggaagagg tctgtctgat ggggagtgtg    11040 cttcaagta aagaggagct tgtggatcaa gtattaaggg agacagagga atatatcccc    11100 taccttatt ctcctccctc cctacatgca gtctccttct gagatctccc attacctgaa    11160
aagctaatat gcaaaagagc ctgttgatat gatccatatg agtcacaaac aagacataac    11220
caacatttat ttatttattt cgctctcagt ctttttttt ttttaaatt tttggcatca    11280 ttataaacac atttaaaaat attttggtg tgttttcagt caattatgt catccttgct    11340 gatactcagt ttgtcctgtc tttggctgat gggggcttct tcaggttgat tctcatgtta    11400
tttgtatatg accctaatta tctttgatag agcttcctttg tttttttt tttgctgcag    11460 taaggtactc aggctcatct tgtacatttc ttgcctcaga cttggaaatc agccattcct    11520
ccaggaaact ctttccttt ggtggggaat gctactcttt actattggat gaaattgttt    11580
cttgtccttg ttcagtgaat agagctatga tattttattt ttgagaagaa gaaaaagtga    11640
```

```
ctgattattt caccaacttc ttgtcagtta ggctctttca ttttaggttt ttttttttttt    11700 tcttttttc  cagtacttaa aaagtgcttt ctttactttt tgatgtaatt ttattttatt    11760
gtgtatgtga acatttaca  tgcttttttgg ttggtttggg ttttttttgtt tttgttttga    11820 gacagtcttg ctctgtcgcc cagactggag tgcagtggca ccatcttggc tcactgtaac    11880
ctcctccctc caggttcaag caattcttct gactcagtct ccctagtagc tgggactaca    11940
ggcatgtgcc accatgcccg gctaatttttt gtatctttag tagaggtagg gttttgccat    12000
gttggccagg ctggtctcga actcctgagc tcaagtgatc ttgcctgcct cagcctccca    12060
aagtgttggg attacaggca tgagccactg cgcccggcct gttttttgag acagggtctt    12120
gctctgtccc ccaggctgga gtgcagtggc atgatcacgg ttcactgcag cctcttcctc    12180
ctgggctcaa gcgattctct cacttcagtt tcctgagcgg ctgggactat aggcacgtgt    12240
taccatgcct ggctgatttt aaaaatgttt tgtagagatg gagtctcgct gtgttgccta    12300
ggccaggatc aaactcctag gctcaaggga tcctcccacc acaaccccc  aaagtgttgg    12360 gattaaaggt gtgagctact gtgccaggcc catttacgtg gtttaaaagt taaaactata    12420
tcagatatat tcagaatatt cttactttga tccacgtctc tctaccctgt tcttttccct    12480
ttactctttt ttttgatttg acatttcagt gtttattctt ataaatataa gcaaatatgt    12540
atccatatac acatatacat agatatatac atagatatat ttatattctt ttttaatcac    12600
tttcttacgc aaaaagtagc atgttacata ttggtgtatg attttcctcc ttcctttta     12660 cagctgagtc ctgttccatt ttgtgggtgt tagcattgtt aattcagtct cctatggatg    12720
gacatttgag ttgtttatat ttttaccagt gtgtctttgg agtagattcc tagaagtgag    12780
attgctgggt taaagacaca tgcatatata attttgctca ctgttaaaat attctccctc    12840
tcctaagagt tgtgctattt tacatttcca ctagtaatga tatgggattg tctgttgtcc    12900
tcaccaacaa tatgttgtaa gacttttgaa tttttgtcca tttaataggt gacaagtgct    12960
atttcagtat aatttgaatt tgaattttat tttctatttt ttctattcta acattaatat    13020
caatttctgt tcttctcatg agtaaggttg aatatctttt catatttaa  gggctatttg    13080 aattccttct gtgatctgcc cgtccatatt ttttgttcat tttaaattgt ttttcttctc    13140 agttttaga  agctctttat gtattaggga gcttagccct ttttctgtgg taaaatgcag    13200
attttttttt ttttttgcaa tttttcatgt tttagactttt gcttctgcat tttgttactt    13260
tgccgcacaa ttttttaaatg tctccaaatt atcaatctttt tgttgcttca aaattttgag    13320
tcatagttag aaagatttcc cctatgtcca gatcataaag gaattcatcc atattttctc    13380
tgatgcttaa tgttttttttc agttttttact ttgaaatcta ctcggaattt atcatgtatg    13440
gtaaattttg agatacatcc aatttttatct ttattcaaat ggctatctgt ttatctccac    13500
agcatttatt ttaaaaaatgc ctatgtttgt tggttgacaa tgccactttc ttcatatatt    13560
aaatttccat gtgtacttgg gattatttct aaccttctgt tccattggtc tctcttgctt    13620
tttcatgtgc taataccaca ctgtgtcaat tataaaggct ttctaatatc tcttcagctt    13680
ttaaaatgtc tagtagggcc atctccaccc ctgctctccc atgcacatac accgtcacat    13740
tgaagcacat gggtgttttt tagggataac tagcttccaa ccctggcttt gttgtttact    13800
agcccttggt ccttggacag tttactaaag cactgtgata tccatttatc ccatctctga    13860
aatgggatga tgatgcctac cttatattgt tgtaaggatt acatgacacc agcagaactg    13920
ccttgtcagg catgaattct ggagtcgac  tgggattttt cactcccacc caggtcgacc    13980
acttattagc cctgtgactt tgggtaaagt tcttaagagg aactcaaaca catcaccttc    14040
```

```
aaataagatt aatcatagac cctcatagaa ctcttaagag tattaaacgt ggtaatgcat   14100
gtaagtgctt tgcagagttc acaacattta gtagatgtta gctgtttgta atcatcgtca   14160
tcattatata tccttatgat ttgtccttgg gaaaaactac ttttgatcta agtggattat   14220
tatctatctc ccagctctgc tggccaggtt tttatttagt tgtgtaatct tggacaagtt   14280
acctaacttt tttgagtctg aatatattta atctgcaaaa tgagaatcat gataatacgt   14340
cataggctta attaggagga ttaaatgaaa taatttatag gtggtgccat ggttacatac   14400
aagtattagt agttaattct tttcctttgt ttacttttat agtataggtt ggatgaaggt   14460
tccagtatag gcaaaaatac tacttggggg taaagtagag tgtgatactt tatttgaaat   14520
gttccctgaa tctgatcttt acttttttgtt actgctgcac tacccaaatc caaattttca   14580
tcccaacatt cttggatttg tgggacagcg tagcagcttt ccaatataat ctatactaca   14640
tcttttctta actttggtgc ttttttgtcat gtggtctcag tgtacctatt tacttagtct   14700
ttattcccag catttcccaa aatagactgc gctctactgg attttcttgc tttctatagt   14760
atctcaccta ctcttttccta cttttgctgt cgtatttcca ggacctacct ttctctcccc   14820
ttgagttctc ccccatgtcc tcctcacaca attttctcat ctttatagtc tgacataaat   14880
cacaactgtg ttaaactgtt actttctttt ttgaactcct gtagtctcat gaaatttaga   14940
aattgatcat agttgtcttg tatagggcta ttttgtttgt taatcttacc taatgagaat   15000
tccttgaggg ctaagcataa ttctagacat cagtgttcag tattacttat tgattggtgt   15060
gaatgattat ctccccttttc cccattcctt tgttttttttcc ctttctttct ctgaattagt   15120
tgatcatacc tatctggtat agggctatct tgtttgttaa tcatacctaa tgagaattcc   15180
ttgtgggcta aacataataa ttctagacat catgttcaat aatgctcatt aattattgtg   15240
aatgattatc tcccctattt ccattctctt gttctttccc tttctttctc tgaattagtt   15300
aggactcttt cagttgtaag tgatagaacc aacataaat atttgtagac aggctgggca   15360
tggtggctca cgcctgtaat cccagcactt tgggaggctg aggcaggcag atcacctgag   15420
gtcaggagtt caagaccagc ctggccaatg tggtgaaacc ctgtctctac taaaaataca   15480
aaagttagct gggcatagtg gcaggcgcct gtaatcccag ccactcggga ggctgagaca   15540
ggagaattgc ttgaacccgg gggggcagag gttgcagtga gccaagattg tgccactgca   15600
cttcagcctg tgtgacagag tgagactcca tctcaaaaaa aaaaaaaatt cgtagacaaa   15660
aaataatttt aaaaatgctt tattttaaat ttttatggga acatagtaga tatatgtatt   15720 tatgggtac atgtgatgtt ttgatatagg catacaatgt ataatagtca catcaggta   15780 aatggagtat ccatcaccta caacacttgc catttctttg tgttaagaat gttttgattc   15840
tactcttatt ttttttttta atttcaatt tttgtggata catagtaggt gtatatatta   15900
tggggtacat gggatgtttt gatacaggca tgctgtgtgt aatcacatca tggaaaatga   15960
ggtatccatc ctctcaagca tttatccttt gtgttacaat ccaattattc tccattagtt   16020
atttaaaaat atatgattaa attattattg actatagtta gcctgttgtg ctatcaaata   16080
ctagatctta ttcatttttt ctagctagtt tttttttttt cttgtaccca ttaactatcc   16140
ccccagtccc tttctcccct actacccttc ctatctctgt ctccatgagt tgaattgttt   16200
tgagttttag atcccacaaa tgaatgggaa catgtgagat ttatctttct gtgtctggct   16260
tatttcactt aatgtaatga ccttgagttc tatctatgtt gtgcaaatga taggatttta   16320 ttcttttttta tggttgaata atatcccatt gtgtatatgt accgtatttt ctttgtccat   16380
tgatcatgga cacttaggtt gcttccatat cttgggtgtt gtgaatagtg gtatgataaa   16440
```

```
catgggagtg cagatatctc ttcgctatac tgatttcttt tcttttgcat atgtacctag   16500
aagtgggatt gctggattct atgggtagtt tgattagttc tttgaagaac cgccaaactg   16560
ttctccatag tggttgtact aatttacatt cccgttaaca ttgtaggaga gttcccgttt   16620
ctccacatcc tcagttgtat tcattattgc ctcttggatt aaaaaaaaaa gctactttaa   16680
ctggggtgaa atgataccac attgtagttt tgatttgcat ttctctgatg atcagtggtg   16740
ctgagtacct tttcatatac ttgtttgcca tttgtatgtc tttttttttt ttttttttt    16800 tgagacagag tttccctctt gttgcccagg ctggagtgca atggcgcagt cttggctcac   16860
cgcaaccttt gcctcccagg ttcaagcgat tctcctgctt cagcttcccg agtagctggg   16920
attacagcca tgcaccacca cacctggcta atttttttgg tgttttagt agagatgggg    16980 tttcttcatg ttggtcaggc tggtctcgaa ctcagacct caggtgatct gcccaccttg    17040
gcctcccaaa gtgctgggat tacaggtgtg agccaccgcg cctggccatc tttttttttt   17100
tttgagacag gatctcattt tgttgcccag gctggagttc agtggtgggg tcatggctta   17160
ctgcagcatt gacctctctg gctcagatga ttctctcacc tcagcctctt gagtagctgg   17220
gactacaggt gcgtgccacc atgcccggcc aatgtttgta ttttttttc tttttttgta    17280 gagacagggt tttgccatgt tgcccaggct ggtctcaaac tcctcggctt aatgatcctc   17340
ctcccaaagt gctgggatta taggcatgat agacgtcttc tttggagaaa tgtctattca   17400
gatcctttgc ccatttaaaa attggattat tagactttt ttctcctgag ttgtttgagc    17460
tccttatata ttctagttat taatcccttg tttgcacata ttttctccca ttctttaggt   17520
tgcctcctca ctttgttgat tctttaaaaa agaattttgg attcaggaaa acctagtctc   17580
attaaaggta aagattaagt tgaacttcag taaaaactag aatttgggct taaatgcaag   17640
caaggctcat tctctgtgtt ctcttacgtt tttctttgtg ttggcatcat tctctcagat   17700
tgtagactgg ttttagtcac atgtggaaaa tatggctgcc tacagcactg gaactttata   17760
tctaacagct tcagctttga ccattgactt cagatctttg agtcttgagt atagagctct   17820
ggaggaaaag attcattagt tacatttagg tcagttgcca ggtgcccact ccttgactaa   17880
tttttttttt tttttgaga ttgagtcttg ctctgtcacc caagctggag tgcagtggca   17940
tgatctcggc tcactgcaac ctccacctcc caggttcaag cgatcctcct gcctcagcct   18000
cccgagtagc tgggactaca ggtgcacacc accacacctg gctaatttt tgtatttta     18060 gtagagatgg ggtttcacca tattagccag gatggtttca atctcctaac caagtcttga   18120
tctgcctgcc tcggcctccc agagtgctgg gattacagat gtaagccatc gtgcctggct   18180
ccttgactaa ttaattgtga tcaggcgggt agggtcacat gagaactttg agaatgggga   18240
ggcagtttgc aggaaaatga gggcagtagg gcagggcaga cagtgccgta ggtgtacatt   18300
atgctaccct ttcttcctc tttgtcctta gagaagtcat atacactctt ctaaagtgca    18360
gttttctcaa tctgtaaaat tgaattaaca ataatttatt tcatgggta ctgaggagga    18420 ctaaatgaga taatttagaa agcagcattt gaaacttcac aaaaacaata gagtaacctg   18480
gtgataagtg gctgtacctt ggtctctcac aacgtgccct gtgcttattt ggcctggccc   18540
caaaggtttt gcaaatgatg tgactgcagc tggttttcca gatcggcttc tttggtgttg   18600
tccaccagag aacttgtgat tacaagacga gtgccagtag cttctaagac tatttgttca   18660
ggtacagtgg aaaaagtctt ttcttcttac cttcaaatag aatctctaat tgatctgacc   18720
aatttagata taatgtaccc atatctgaat caatctcagt caaaataatg gtgtgctgat   18780
gagcataggt ctgcatcatg tgctccagtc ttggaactgg ggaagagcca gcttatacca   18840
```

```
agatacatta cggttgcatg aaggaggggt ggaaattgga gttcatttac cattattaaa   18900
ttatctgaca tttaaaataaa tattgccagc cgtttgccaa acctcaactt aagaccacca   18960
actgagatac acttggacct ttaagagagg gatacctgtg tgctgcattg ccttgatgat   19020
atgtcatagt gaggattacc aaatgcctgt tgatggatcc agtcacatta gaaccaaata   19080
cagattcttg tgattcatca cagctccacc atatgagaat tgaagaaaaa gtcttgtttc   19140
ccatttaata aattattta tcttttaaaa aatgtggttt aaaaaatgcc aggctatatg    19200
aagaggatga gcattttctg acacttgcta aaaagaagtt gtgttggttt tttttttttt   19260 ttttttttt taaagatgag gtcttgctta cccaggctgg agtgcagtgg tgcgatcatg    19320
gctcactgca gccttgacct cccaggctga agcagtcctc ccacctcagc ctcccgagta   19380
gctgggacta cagacctgtg ccatcacagc tggctaactt tgttgcattt tagtacagat   19440
gaagtcttaa cgatgttgcc cagcctggtc ttgaactcct gggctcaagc aatcctccca   19500
ccttggcttt ccaaagtgct gggattacaa gcagtgcctg gccggttttg ttttattttg   19560
tttggttgat ccaattttt tagtgggggaa gggaaaatca aattttatac agaagccaaa   19620
taaagagatt cccttaatca tcattgtaac tctccaatac cttgttcctt cacctgtcaa   19680
aaggaaggga ttggctgttt agtaatttat gaagacatta ttttaatgtg aagaggctat   19740
aaaataatag ttttacaatt ggtccctgaa cagcatggtg gttagaggtg ctgactcccc   19800
taataattga aaatctgcat gtaactttga ctcctcccca aatttaacag tttttatt    19860 tattatttt ttgagacagc gtctcgctct gttgcccagg ctggagtgca gtggcatgat   19920
ctcggctcac tgcaaccttt gccccaccgc ccacccccgg ttcaactgat ccttgggctt   19980
cagtcttcag agtagctggg attataggca tacgacacca cgctgggcta atttttgtgt   20040
ttgtagtaga cacgggtttc accacgtagg ccagcctggt ctcaaactca tgggctcaag   20100
tgatccactc gcctcggcct cccaaagtac tgggattaca ggtgtgagcc actctgccca   20160
gccccagatt taacaattaa cagccttact aatgtaaaga ttcaactagc acatattttg   20220
tgatatatgt acatagttat ttaatttttg agatggaatc tcgctctgtc acccaggctg   20280
gagtgcagtg gcatgatctt gactcactgc aacctctgcc tcctgggttc aagtgattct   20340
cctgtctctg cctcccgagt agctgggact acaggtgcgt gccaccacac ctagctcatt   20400
tttgtatttt tagtagagac gggggtttcac catgttggcc aggctggtct tgaactcctg   20460
acctcgtgat ccacccacct cggcctccca gagtgctggg attacaggca tgagccacca   20520
ttcctggcta ttatatatct tatatactgt attcttacag taaagtaagc tagagaaaag   20580
aaaatattag gaaaatcata agggagagaa aatatattta ctattcatta agtggaggta   20640
gatctcataa aggtcttcat cctcgttatc ttcatgttga gtagctgagg aggaggagag   20700
attggtcttt gtatcagggg tggcagagag ggaagaggta aaagagatgg aagggaggc    20760 aagagaggca tactcggtgt atattttatt gaaaaaaaaa atccacatat aagtagatct   20820
atgcagttcc aactcatgtt gtttaagggt caactgttac agaaaaacag atattttcac   20880
agattaaaaa ggtttaaaaa tttactgttc ctatgagatt aatttttttt ccctaaatgg   20940
taataaattt tgcttactta gcttttatgc ttctgatcta ttgtactttg agatactgat   21000
gctcttacat gtaagctctg tgagaacagg tatctcattg tcttgttcac tgttgtatca   21060
ctggttctta gagccctgct tggcacatta taagttttca ataaacattt atttgttgtt   21120
gtcgaatttc tggaaaatat cttttgctta tttgtttctg taacaagagc tgaagatggt   21180
tgacatcatg ttagggaata ggatataatt gataatttgt ttaaatgtaa actgtaccta   21240
```

```
tccgggggat aacatttaa  aactgcagga ggtctgtatg aaaatataga tattctgctc  21300
cccaccccag tacctcttga attttgaatg aaggaccaaa agccaataat gtgttgtttt  21360
gtgtgtgtgt tttttgatac agagtctcaa aaataaaggg aatcacttta tttggcttct  21420
gtatgcagtg gtgggatcat gattcactac agcctcaacc tcctgggctt aagtgattct  21480
cccacctcag cctcctgagt agctgagatt acaggcatgc taattttacc tggctagttt  21540
ttgaatgttt aatagagaca gggtcacact gtgttgccca ggctggtctt aaactattag  21600
gttcgaggga tcctcccgcc ttggcctccc aaagtgttgg ggttacagat gtgatgaaat  21660
gtgtcaacat ttggctgcat aattcaagga accagtattt tctaagtgac caatcaatgc  21720
atgatgttat aaaatcatcc atgaataaaa gatccattca aagtagaaga tagaccaata  21780
aattttaatg ttgcaaactg tgcaaaaagt tcagaaacca ttgatataat ttcagattct  21840
acaatgccac taatctttaa gaaacacccc tcgtcaaatt tgatgtagta gcaaataatt  21900
tccagttatc tgaaaagact gttaacatac tcttcccttt tccaactaca atctcagact  21960
taataatggt tcactttatg attttccac  tttatgatgg tgtgtgtaaa gctatatgca  22020
ttcagtagaa accgtacttt gagtacccat acaaccgttc tgttttcac  tttcagtaca  22080
gtattcaata aattacatga gatatttgac actttgttat aaaataggct ttgtgttaga  22140
tgattttgca caactgtagg ctgatgtaag tgttctgaac atgtttaagg taggctacac  22200
taatctatga tgttagcaga ttagatgtat taaatgcatt ttcaacctac aatattttca  22260
acttacaagt ggtttatcag gatgtaaacc ccacccatta taagtctagg agcatctgtc  22320
catatctgtg tgaagttaga ttttcacgct tcaaaccaag gcaatgtatt gtcatagatt  22380
gaatgcaggc gcagatatga gtgtccagtt gtcttctatt aagctagatg ctaaagagat  22440
ttgtaaaaat gtaagataat gccattcttc ttcccaatta aaaaaagttt taggccggct  22500
gcggtggctc acgcctgtaa tcccagcatt tgggaggcc  aaggcgggtg gattgcctga  22560
ggccaggagt tcaagaccag tctggccaac atggtgaaac cccgtctcta ctaaagatag  22620
aaaaaaatta gccgaatgtg gtggcgtgcc cctgtaatcc cagctacttg gaggctgagg  22680
caggggaatt tcttgaacca ggggaacttc ttgaaccagt ggaggttgca gtgagctgag  22740
attgcgccgc tgcactctag tctgggcaac agagcaagac tccgtcttaa aaaaaaaaag  22800
ttttaataaa atatgttatt tataataaca tataatggga attttttta  aattcctgtc  22860
ctagtttatt tctgctgcta taacagaacc aagactgggt aatttataaa gaacggaaat  22920
ttgttttctc atagttctgg agtctgggaa gaccaagatc aaggcaccag caggtttggt  22980
tctctgatga gggtctagtc tctgaatcca agaaggtgcc tggaaagctg catcctccag  23040
aagggagggg tcagtatgtc ctcacatggt agaaggcaaa aggacaaaaa gggtccaaac  23100
tccctaatca aacctgttca tcatggcatt aatatactta taaggactct gccctcatga  23160
cctttacacc ttcccaaagg ccccacctct taacactgtt tctctgggga ttaagtttcc  23220
aataaatgaa ttttggcact ttcagaccat agcaaatttg ttcagatgat cccttttctag 23280
tttcttgaga aaggaactta gattattaat tgaaaattat tattcttttt cttttcttaa  23340
aaaatttatt ttaagacagg gtctcactct gtcacccaga ctggagtgca gtgacgtgat  23400
catagctcac tctagccttg accttttcagg ggctcaggct atccttctgc ctcagcctct  23460
cctgagtagc tgggaccaca ggcgtgtgcc tcgatgcccc gctaattttt aaattttttt  23520
gtagagacga ggtctttcta ttgttaccca gatgggcctt gaactcctga gctcaagtga  23580
tccttccacc tcagcctccc aaagtattag gattattggc ctgagccact gcgcctggcc  23640
```

```
atcattactc ttttctaatc atttaatgct atacattttt cttttagcag tgatttagct    23700
gtattccaca aattccagtg ttgtgttctc attttcattc agttcaatgt atattttat    23760
ttcctttgag gctttccctt tgacccagaa attatttaga aatctgttgt ttagtttcca    23820
agtgtttgga gatttcccta ctatctttt cttatttatt gtagtttgta cattttggtc    23880
aaagaacaca ttctgttatg attttaattc ttttttaattt gctgaggttt gaattatggc    23940
acacaatgtg gtggtctgtc ttggtaatag ttccatgagc acttgtaaag gatgtgtatt    24000
ctgctatttt gggttagaat gtgatataaa tgtcaattag atcttgttga ttaattgtgt    24060
tgagttcttg atgattttgt gcccagttct atcaattttt aagagagaag tattcaagtt    24120
gccgactaaa attgtagatt tgtctatttc tcttttcatt tttgtcaggt tttgcttcac    24180
ttgtgttgca gttctgttgt tctgagcgta catggttcag attattgtgc cttcttggtg    24240
gattgactct tttgtgatca tataatttc cattctgtgc ctggccattt tctttctctg    24300
aagtctgcct tgtctgacac taatatagcc acacccactt tcttttgatt aatatttgca    24360
tggtaaatca tttcccattc ttttacttcc aacctacctg tattgttgca ttttaagtga    24420
atttcttgtc tgtggatggg tcatgtttat gtatccaggt ctaccaatct gtttcttaat    24480
ttgaattgtt gtctagacca tttatatttc ataaactat tgttatgtta gggtttaaat    24540
ctgctgttat attctttctt ttctgttttt acctccctgt tttttgtatc tgtgttcctt    24600
ttttgccttc ctgggccact tgaacattta ttgtaattcc cttttgactt atctgaaagt    24660
gttttttgtgt gtatatgtct ttgtatagct ttttaaattg gttactctag gtattaaatt    24720
aggcatagaa aacatcacat tatattggtt ttgatattt actagttcaa ttgaaaggta    24780
gaaattttc ctccttttttg tcatttttacc cttgttcgta atatattcat gtttaatatc    24840
ttcttacatg cattgagaaa caagcaacat tataattttt gctttaactt tcaagacaag    24900
aaaaatgtat tatctttttcc catatttta cattttgttc ttcttttctg atatatgata    24960
taccagattt atttctttca tcgtcttcta tttagagaat ttcctttaac cattattta    25020
gaatgtctgc ttgtgacaaa tctcttggtt tttcatcatc tgagaatgtc ttaattttt    25080
tttttttttt cagtggatgt agaatttcgg tttgacattt taaaaaattg gcttaggttt    25140
ctttgggtgt gtcctgtttt gatgtttggt cagctccttc aacctgtagg tttatgtctt    25200
ttgccaaatt tggggaattt ttagccatca tttgttttag tcccttttag ccccattcta    25260
ttttttcttgt ttgtcttctg ggcatccagt gatacaaatg ttaaatcttt tgttatagtt    25320
ccatggaaaa tgaatgattc tcttcatttt cttttccatg atcaaggtct gattgtatga    25380
taatttgtat aagaaatttta agaaaataac aattagctga gttttaaaaa attatttca    25440
ggctgggcgc ggtggctcac gcctgtaatc tcagcacttt gggatgccta ggtgggcgga    25500
tcacttgagg tcgggagttc gagaccagcc tgtcccacat ggtgaaatcc tgtctctact    25560
aaaaatacaa aaattagcca ggtgtggtgg tgcatgcctg taatcccagc tactcaggag    25620
gctgaggcag gagaatagct tgaacctggg aggtggaggt tgcagtgagc cgagattgcg    25680
ccactgcact ccagcctggg cgacagagtg agactcagtc tcaaaaaaaa aaaaaaaaa    25740
ttatttccat actactacta accaaagaat gtatgacatg tatttatttt tccccaaaat    25800
aacaaattag atacttaaaa gatcgtttg agaaatgaca aactctctct ccccaaagtc    25860
tgaaccatct gaacttcttc agttactcat gccaggagaa aactttgatt gtgttcaccc    25920
atacctataa aactttaagg cagtagggag gaaatcctcc ttgaaattat ccgtgaatat    25980
atttttgtga ctcatttgga taaatctta aaaaataaaa aacagtcctg tgtggttgtt    26040
```

```
actgatacta tcttgtttta cagatgagaa cattgaggtg gtgatgggtt aaataacttg   26100
ctcaagatca catgactact aaatattcta gcttggaata tgagacagga tgccatttct   26160
gtagaagtat tctcttactt tacaaggtta atgtcttaac ttggtatctt aagcctgttc   26220
tcccttacat cttttggaac cttgttaaat catgtatctt ctataaaaat atcttttcta   26280
cctaaaaatg tttcatcaag tttaagtttt aaatcatgca aacttctagt ctttctcatt   26340
tatttagcca tttttctcat tcttcattt tccattaatt tttctaccaa ccataagctg   26400
gtatgtgcac cttctcctct aacgaagcat tctaattaag attaataatg cccttaaaaa   26460
ttggcagtaa aatatacgta acatgaaatt tgcctttttt tttttttga aatgggttg    26520 tccaagctgc tctgaaattc ctgggctcag gcgatcctcc cacttcactt tcctgagtag   26580
ctgggattac aggtgcatgc cactgcatcc gcctccgttt taactgttcc tgagtacaat   26640
ttggtggtgt taaagcacat tcacaatttt gtgttttcac cagtatctgt ttgcactata   26700
tcatctgtct caaacaaact ctgtatccat taaacagtaa ctcttttatt ccctgtccct   26760
ccagcctatg gtaatctcca ttctactttc tgtttctgta aatttgccat ttctaggtac   26820
tgtgtataag tggaatcata caatatttt ccttttttgt ctggcttatt tcatttagca    26880
taatgtttac agattttatc tatgttgtag tatgtgtcag catttccttt tttaaggctg   26940
aataatacta cagtgtatgt acataccacc ttttatccat tcatctgttg gtgtacaatt   27000
gtgttgtttc taccttgagc tattttgaat atgctgctgt gaacattggt gtacaaatat   27060
ctgttcgaat cccttcttc ggttcctttg ggtgtatacc cagaagtgga attactgatc    27120
aggtggtaat tttatgagaa actgatacac tatttttcac agcagctaca ctgttttaca   27180
ttcccaccag cattgccaag ggttccagtt tcattacgtt tcattccagt ttcattctaa   27240
cacttgttct tttctgattt tttaaaataa taactatcct aatgggtgtc aagtgatgtt   27300
tcattgtggt tttgatttgt atttccctaa tgatttatga tgttgagcat cttttcatgt   27360
gcttattggc catttctgtc tttggagacg ttttttattca agttttttgcc cattttaaaa   27420 ttgagttgtt ttgaatttta ggagtgccct acatattttg cgtaataatc tcttatcaga   27480
tatattattt gcaaatattt tctcccattc tgtggattgc catttcactc tgttaatact   27540
gttctttgat gcacaaaagt ttttaatttt gatgaggttt agtttgtttt tttttgttg    27600 cctgtgttct tggtctcatg tacaagagat catggtcaaa ttcaatgtcc tgaagcttcc   27660
ccctatgttt tcttctaagc attttatagt tctagctttt atgttttggt ctttgatccc   27720
ttttgagtta atttttggtat atggtatatt gtagggctc ccacttgatt ctcttgcatg    27780
tggatatgca gttttccag caccatttgc taaaaagact gtccattatt gaatggttat     27840
gtcacacatg ttgaaattaa ttgaccatat gtatgtgtgg gtttgtgccc cttttccccc   27900
cgccattcca ttttctgca caattgaccc ttgaacaaca tggggattag gggcactgac     27960
cactaccctc tctccataca tttgaaatac atgaaataca tacttttta atttccccaa    28020 aacttaacta ctaatagcct gctgttgact gaaagcctta ctgatagcaa aaccagttga   28080
ttaacaacac gtattttgta tgttatatgt aaatatatgt actgtattct tacataatgt   28140
tagccagcaa aaagaaaata ttactaaaat cataaggaag agaaaatata tttactgttc   28200
attaaatgga agtggatcat cataaaggtc ttcatattca ccatcttcac attgagtagg   28260
ctgagtagaa ggaaaaggag gagttggtct tgctgtttca tgggtagcag aggtggaagg   28320
aggtataagt ggactcatgc agttgaaact tatgttgttt gagcaccagc tgtatgtgct   28380
tgtccttatg ccagcagtac accatttttgg ttactgtagc tttgtagtga tttttgaagt   28440
```

```
cagtgaattt gagtcctcta actttgttct ttttcaagat tgttttggct atttgtgatc   28500
tgagattaca tttgaatttt aggatgaggt tttctatttc tgcaaaaaac accattggga   28560
ttttgatagg gattacattt aatctgtata ttactttgag tagtattgcc attaaaaaaa   28620 atatttttc cagtccatga acataggatg tcttttcatt tatgtcttct ataatttcag    28680
caatgtttta tggttttcag tgtacatgtc tttagcctca gttaaattta ttcttcagta   28740
ttatttgttt tgatgctttt ataaatgaaa ctgctcttaa gttctgtttt ggattattca   28800
ctgttagtat atagaaatgc aactgatttt tgagtattga ctaacctgta acttggctga   28860
atttggttat gggctctgac ggattttttt gttttgtttt gttttggtgt gtgtgtaatc   28920
tttagttttc cacctatagg atcatgtcac ctgtgaatag ataatttat gtctttgttt    28980 ccaatttgga tgccttttat ttcttttttct tacctaattg ctctggcaaa aacttccaat  29040
aatgagttga atagaagtga caaaaggtga catctttgtc ttgttcctga tctcaggaga   29100
aaagctttca gtctttcatc attgagtatg atgttagctg tgggattttc atatgtggcc   29160
ttcaccatgc tgaggaagtt tctttccatt ccctgtttgt tgattgtttt ttattatgag   29220
agggtgttga atttgtttga acattttatc tgtatctaat gaggtgatgt ggttttttgtc 29280 ctttattcta ttaatgtggt agattacatt aaaatatttt tgtatgttaa atcaactgtg   29340
cattcctggc ataaatccca cttgatcctg gtgtgtactt cttctcatat gtgctatatt   29400
ctacttgctg ttatttttat gggcattttt atgtctatat tcatatgttt cataaactct   29460
gatatgtaat ttttgtgtga tattttttagt tttgctatca gggcagtgct gcactcatag  29520
aatgagttag gaaatatttc cttctcttca gttttttgaa agagtttgaa aaggattcgt   29580
gttaattctt ctttaaacgt ttggtagagg ccggacatac tgcctactca caatctgtaa   29640
tcccagcact ttgggaggcc aaggcaaaca ataacgttg agctcaggag ttcaagacca    29700
gcctgggcag catggtaaaa ccccatccct aaaaaaaaaa attaaccagg tgtggttgct   29760
cacacaagct actcaggagg ctgaggctgg aggatagctt gaagtccagg aagcagaggt   29820
tgcagtgaac tgagactgtg cccctacact tcaccctggg caacagagtg agaccctgcc   29880
tcaaaaaaag gaaaaaacaa acaaataaaa atacataaat gtttgttaga attcaccagt   29940
ggagccatct ggcccaggga ttttctttct tgagaggttt attattacca tttctgtctt   30000
cttacttgtt acagttattg gtgtattctg actttccatt tctttatggt tcattttttgg 30060 cagattgtat gcttctagga atttgtccat tttatgtaag ttaccctttt tttctggtgt   30120
gcagatgttc ataatattct attacaatta tttgtagaat tgataggaat gtcgtcactt   30180
ttatttctga aattactaat ttgagtcttc tctctttttc ccttagtcag cttaaccaaa   30240
tatgtgccaa ttttatcttt tcagaagacc tactttgggt cacattggct ttctctgtta   30300
ttttcctatt ctgtgtttta tttatcttca ctttaatctt tattctttcc ttctgtcagc   30360
tttgggtttc atttgctttt ctttttctag ttccttatag tattaagtta ggttattttt   30420
attgatttta aaagcttttt ttcttttttaa aatgtaagca tttatagcta taaatttcct   30480
cctttgcact gatttttcag catcctacta ggtttggtac attgtatttt cattttcatt   30540
tgtctcaaag tattttctaa tttcccaatg atttttttctt tgacccatag ttttaagagt  30600
tcattgtcta atttccacgt ttgtaatttt ccagttttttcc cctattattg tttagtagtt 30660
tcattccatt gtgattggaa aagatacttt tgtgtcatttt ggtctttttaa aagttattaa  30720 aacttgtttt gtggcataac ataataagtc tattcttgag aatgttccat gtgtacttga   30780
gaaaaatgtg tattttgtta ctggatagag tgctctctct ctctttataa tctgttaggt   30840
```

```
ccagttggtt tatagtgtcg ttcatgtcct ctgttttttt attaatcttc tgtctggttc   30900
tattcattac tgaaaatgga ttattgaaat ctccaactat tgtagaact atgtatttct    30960
ttcttaaatt ctttcaatgt ttgcttcaca tatcatgggg cttgtatatt tatataccaa   31020
atgtacatat ttgacgcata taaatttatg ataatatatt tttggtgaat taactctttt   31080
atcaatatgt aatgtctttt ttgtctgtta accatttttt taacttaagg tctgttttgt   31140
ctgatattag cctacccacc tcagtgcttt ttttatttac tatttgcatg gagtatttt    31200
tcccatcttt cacttttaac catttgtctt tggacttgaa gtgagttcct tatgggcagc   31260
atatagttgg atcatggtgt ttttgtttgt tttttaaaat ccattttgtc agtctctgta   31320
gtttgattgg agagtttagt ccatttatac ttaaagtgtt agttttagc tccagaattt    31380
gtttggtttc ttaatatagt ttcttctct tgttgacat tctcattttg gtcatatata    31440
attttcctag tttcctttag ttccttttct gtgttttcct tcaactcttt gaacatattt   31500
aagacagttt ttaatgtctt tatcaagtcc aatgtctggg cttcttggat atggtttctg   31560
ttcatttatt tcattcctcc cagccgtgtt tttctgttcc tttgtatatc ttgtggtttc   31620
tttatggaaa attggccgtt taactgttat aatgtggtga ttttggaaat tagattttct   31680
ctattctcca gggtttgcta gtgatatggc tttgatgagt gggggaacac cagggtcttc   31740
gtctcgagtc gaattagaaa aaaactacag gaacacacgt ggatcacata ccgaaaggaa   31800
ggagaacgct tttgttctca cttctctttc tagatgggta acagatcgtc ttcaacatgc   31860
actcccctgg agtgtatttt aaagcactgg gactccttcg accctaaaac tttgaagaaa   31920
aagcagtatt ctactgcaca agggcatggc cttcctatcc tcttcgtaaa cctggcctgg   31980
ggagacttaa ttttaatatt atccaacagt tagaactttt ctgcacacag gagggcaaat   32040
ggactgaggt cccctatgta caggcttct ttgctctgcg agacaaccca gacctttaca    32100
agttctgtac aatcgaccca gttcttttag tagccatggc aggcaaaccc acagggagta   32160
gttccccaga gctaaagcgg gctccagagg agcaatctaa gacagctact gaagtcccaa   32220
cccttccggt tccactccag ttgtaccatc agcaccacca tctccagtat gtcctactct   32280
cccctcttca ctcttacccc tccaggaaat gcctgatggg aatggtgcca taagggttca   32340
agttcccttc tcattgcagg acgttaagca aacaaaggga gacttaggtc aattttctga   32400
tgaccctgat aggtatatag aaattttctg aaatttaact caggtgtttg atctcacgtg   32460
gagggatgtt atgttgctgc taagttaaac cctcactaca gctgaaaagc agacagttcc   32520
gcaggcagca gaaaaatatg gaggtgagca acatgcctcc atacagcaga ccaaggaaaa   32580
aaagaggaga aaaggaaggt gaggaagagg tgaaaacttc actcctgcaa ggaagggaag   32640
cagttccggt aaataaccct aactgggatc ccaataactc agcagatgaa tggaaaagga   32700
agcactttt aaggtgtata ttagaaggcc tgcgaaagac cacagctaaa cctctcaatt    32760
actccaaact gtccatgata gaccaaaaac cagacaagaa tcccacagct tttatggaaa   32820
ggctgagagg ggcactaata aagcacactt ctctataccc caatttagtt gagggacagc   32880
tcatcctgaa ggacaagttt attacacagg cagctcccaa tattagaaga aagctacaga   32940
agcaagcagt agaaccagat agcaccctag aaagcctcct gagaatagcc acttcagtct   33000
tttacaaaag ggattgggag gaggcccgag aaaaggagag gaagtacaag agaaaaacag   33060
aggctctagt agcagcatta caagcttgta aagtcctgaa tccccaaggt gcatccacta   33120
gctgttatca atgtggtcag tcagggcatt ttaagaagga atgccagga agcaagacaa    33180
agccaccttg accctgtcca gcctgtggtg gagactactg gagacagacc tgctttggtc   33240
```

```
ttttgttctg ggttcagaac tagtctcaca gatggtccag caggactgat gggtcccaga    33300
gctcaaactc catccactca gactgccatt acagcacagg tgccccgggc tttcctgcta    33360
gacaagagct gcgaaaaacc ttccaaagga ccctttttt tcctctctat ctgcctaaaa     33420
taatttctta ataactccta ccacactagg ttctctctct ctctctctct ctctctctgt    33480
gtgtgtgtgt gtgtgtgtgt gtgtgtgtgt aggtgggtgt tttgagatag agtcttgctc    33540
tgtcacccag gctggagtgc agtggtgcca tctcagctca ttgcagcccc tgcctccgg     33600 gttcaaacga ttctcgcacc ctagcccccc aaacggttgg gaccacaggc gcacgccacc    33660
acacccggct aattttttgta tttttagtag agacgggggtt tcgccatatt ggccaggctg   33720
gtctcgaact cctgggctca aatgatctgc ctgccttggc ctcccaaagt gctgggatta    33780
caggcatgag ccactgtgcc tggccagttt gttttttatt gctgatggct gtagtacaaa    33840
tgactgcagt ccatttgttt tgagactttt ccaaattgtt tttgcaaaga ctattcctta    33900
ctgtgagtga ttactgaagt cttggttcct ttagcttgta ttcagctaat gtttggacag    33960
agatttcctt gaatgtgaga tgctccaata cataccaaaa aagcctcaga aaacaaaaag    34020
agaaccacct ctcagtcttt gcagatttgc cctctgctgg ggtactcctt taccacttag    34080
ctaggcttgt tctgagtttc aggatgaaac tcacatgaga tgagagctta ggatcttctc    34140
aggattttcc ttagcatgct tttttttgcct gggcttcaca cggcttttta tattctcctg    34200
tatacatggc tgcttttgaa tcatctaatt tcccaaaaaa gtctcgcccc acttctcctc    34260
tgggcctaga tggtctattg tatgtgttgt gtccattagt cctccctact cccccatctt    34320
ttacctcagg tgtgtcagta ggttttgtag ttagcttcct tgtagccttt atgagcagca    34380
ccagctgctt ttcctgcctg tgttctgaat tatgtgaaac agagtttagg ttcttgcctt    34440
agtccttcag gtatctccca tacaagatag aatgaacata cacagtatgg tcttattcta    34500
ccctcttggg ttcaaggtgt gggggagtag aagaggagg aaccagtctg ctacctgctc     34560
aagacttaag actgtccttg gccgggcgcg gtggctcacg cctgtaatcc cagcactttg    34620
ggaggccgag gcgggtggat catgaggtca ggagatcgag accatcctgg ctaacaaggt    34680 gaaacccgt ctctactaaa aatacaaaaa attagccggg cgcggtggtg ggcgcctgta     34740
gtcccagcta ctcgggaggc tgaggcagga gatggcgtg aacccgggaa gcggagcttg     34800
cagtgagccg agattgcgcc actgcagtcc gcagtccggc ctgggcgaca gagcgagact    34860
ccgtctcaaa aaaaaaaaa aaaaaaaaa gactgtcctt ttctctggca gggggtggga     34920
caagagcaag taaactgcca taacactttc ctaccatttg ggatagcttt tacttgattg    34980
gatatttgct tgttttttgc tataaaccta aattttccag aactattgca gacctgcttc    35040
agatagcttt ttacttttga tgtttctgtc ggtgaaggag agcttggagc ttcctagtcc    35100
accaatttgc tgacatctga tagtgactta aaataaatta tggctctgtg tgtgtgtgtg    35160
tgtgtgtgtg tgtgtgtgta tgtaccaaga ggggaggatc acttgaggtc agaaatttta    35220
gtccaacctg gccaacatgg tgaaacccca tctctactac aaatacaaaa attttatgt     35280 gtgtatatat atgtacacac acacaaacgt atcataaaac ttatcattta actgttctt     35340 ttttgtttga gacagactct ccctctgtca cctaggctgg agtgcagtgg cacgatctcg    35400
gctcactgca atctccacct cctgggttca agtgattctc ctgcctcagc cttctgaata    35460
gctgggatta caggtgcctg ccaccatgcc cagctaattc ttgtattttt agtagagacg    35520
gggtttcacc gtattagcca ggctggtctt gaactcctga cctcaagtga tcctcctgcc    35580
ttggcctccc aaagtgctgg gattacaggc atgagccacc tagcccattt aactgattct    35640
```

```
aaatgtatag ttctgtggca ttaatcattc acgttgttgt gcgaccatca gtgatgttta    35700
aatggcaaat gatttggctt cttttgcatt ctctattctg tttgacttcc tgagatgttt    35760
taaattcatt cttaaggcat ttcttctttt taagttcctt ctcagcttcc ttggtactat    35820
tctgtctttc ttctctgtgt cctcctccac cattttttgct ctgtgtacct cttttttttc   35880
tttccttttt tttttttttt gagacagagt cttgctctgt caccaggctg gagtgcagtg    35940
gtgctatgtc ggctcactgc aacctccgcc tcccgggttc aagcgattct cctgtctcag    36000
cctcctgagt agctgggact acaggtgcgc atccccatac ccggctaatt ttttgtattt    36060
tagtaaagaa ggggtttctc catgttggtc aggctggtct caaactccga cctcaggtga    36120
tccaccagcc tcggcctccc aaagtactgg gattcaggt gtgagccacc atgcccagcc     36180
tgctctgtgt acctgttaaa tgttagtgtt tcccagtgtt ctattcttca gtctttctct    36240
actctccctg tttattcttg ttggatgatt gcatatgttc tcatggattt aagtgtgctc    36300
tcatgactcc caaatctgta ttgtagtccc aatctctctg ttaaacccaa acttatattc    36360
agctgccatc tagttattca tgaaatgata tcccaaagga cctcagatgt agtgtgtctg    36420
aaatatttat catctctcca aattatatta tctgccttgg ttaatgaagt cactgtctac    36480
tcacatcaac ttgaagatca tataatcatt ttcaacccctt cctgttcctc tttcaattat   36540
tcatcagatt cttttgcctc taatgcccca ttcctgttta cccagttttt cagtctttta    36600
tccttttatg cttgtattac cacagtatcc tcctagttgc tttcatctcc acctgtctct    36660
tctactttta atttatcatc tttatcattg ccagactact aaaataaaaa ccagttatgc    36720
cactttctcc cccgcagaaa ttcctgtggt tccaaattat cagaaggtaa attcttctcc    36780
tggtatgtta tacctttaac attctctccc tgatcatcac agctttgact ccttctcctt    36840
catctccttc tcacctttcc cagtccagaa cattctatcc tcattctctg aattctcgtt    36900
gcttttcacc tctagattgc cttgccccac ttctgtctta ttccttcata attctattct    36960
tcaaggttca gctcaaattt catcttctct gtgaagcccc aaatagcctt ttctctattt    37020
atgtagtacc tactataac acttgatatc ctgtatttac ttttctacc tactaactaa      37080 cttctgaact ctgagagaca ggaagtattt tttttctgct ttcctgcaga agaggaggca    37140
gatttagaaa taataatta cagtataaca gctaaataca taatttctgt aatagcacaa     37200
aggaggttat gtaacatttc ccctcagggc actggggaag gcagcacaaa gtaagggaca    37260
tttgaggcag tcttaatgta agaatgttca cattccagcg ggagaataga gcaggtgcaa    37320
aggccccata gggtagagtg agcctggctt atttgggaaa tggctggtag cacactgtgg    37380
cctaagccca gctatgtatg tgtagagaaa caggctggac aaaggtatga ttggagactg    37440
attgggaaga gccattgttt gttgtactag ataatttgga acattattta cttatttatt    37500
gactataaat gtcctgggca gcattgacat gggtatagta atgtcacacc agttaaacag    37560
attttaactg tatttaatat caggttgtta aaattcccta aggaaattct gttttcattt    37620
tcatagctgt gcttaatttt gatgaattat ttctttatca agtgaagaga gattgacaga    37680
ctgattgatt tttagagaca gggtcccact ctgtcaccag gctgtagtg cagtggcaaa     37740 atcatagatt actgtagcct tgagctcctg ggctcaagcg atcttcctgc ctcagcctct    37800
caagtagctg ggactgcaag catgcggcac cacgcccagc tatttttttt acttttattt    37860
ttgtagagat agggtcttgc tatgttgtct aggctggtct tgaactcctg gtttcaagtg    37920
atcctcctgt ctcgatctcc caagtgctgg gattgcagt tgtgagccac agcatctggc     37980
ctaagggact tagttaaaac aacattctac tacatatacc aaaaacattt tctttaaatg    38040
```

```
gtatatcctc tcttaccaaa gttggtcagc agtctttagt accagtggtc agcccatttt    38100
agaagtagtt tgattttcag aagccccagt tttgctgcca tagttttcaa tggatttga     38160 gggtggggtg gtgtttctcc aaaaatatgt ctgttaggtt tagaataata accatttagg    38220
ttttgaaaat ttacctaaaa atgaatgttt cttataatag tgtaactgtc ctttcctagt    38280
gccattaaat tctcatacct tataatgtgt tacttttaat ggatttaatc ctaaatgatg    38340
ttttacacct gactcatatt tgttaattca gatttatcca gaaaactaaa gtttgtagta    38400
gtgttgaata attttctttt gcttctgctt tcacttgaac tctgttgtgg cataacacaa    38460
tggacctcta cctcctcttc ccctgctcc  ccctgccata tcagtgcttc tcaggaaatg    38520
tgaagtgttt ttactttaga gatcactgta aaatgttata cttttaattg attatgcctg    38580
cctttgtgtg tatatgtgaa aatacttctc ttatgtaact accttctttt aaaatgtaac    38640
tgctacaact ggtctactac ccttgttcaa ctattagtag caaagaattt aattactgta    38700
attttttgac attgattggc ccctctgtta catattttct cctccacttt tgttttttt     38760 tttttttttt ttttttttt  ttttttttgg agacggagtc tctttcaccc aggctggagg    38820
catgattttg gctcaccgca acctctgcct cccgggttca gcgattgtc  ctgtctcaac    38880 ctcccgagta gctgggatta caggtaccca ccaccaccat gcctgactaa tttttatatt    38940
tttagtagag atggggtttc accattttgg ccaggctggt ctctaactcc tgatctcagg    39000
cagtacgcct gcctcggcct cccaaagtgc tgagattaca ggagtgaacc accgtgcctg    39060
gcctcctcta catttttaaa ttgatgatta agctatatga tggacatgtt gtgaaagtag    39120
aaggtagttt tgctcatgcc taaatcataa aattaagtga aggatcagtg gaagtatatc    39180
ctttgattat cattcctcgt gaattgtttt tgcacttgga tgaatgttat gttaacattc    39240
cgagtcctgg tactagaatt tggacttta  ggaagtgtgg aagtcttatc tgcattattt    39300
tatgaacttt cagagtattg aataaaagct aaggttcctg cctcatttat agttggacat    39360
acacattcct tgcattgtgc agcttttcca ctgcattaaa atggaagcct gcatccctct    39420
ctcccacccc agtgtcttga ctccccttag aaacctcagt tggtatatgc tttggttaag    39480
ttagaagaat acattcttgc caactttatt tccctaataa aggcacacaa gttttgctta    39540
tgggtgatgc tgaaaagtaa tagactatcc catggtattg tagaattaaa gtgtgtggta    39600
ccaggtccaa acacttagtg actatatgta attagtggag gcagctcatt tttcattaac    39660
aaacacatga tcaaatactt ggtcacgcaa aactcagatg cccatgtgta acaacaacaa    39720
aagtactttg gattactgca ttggggaagg gtttaacatc atgacctaag atttactttt    39780
aaggttttat gaccacgtga ctaaaatgtc tgttttctgt gtaggtcatt cctgttaata    39840
gggagactaa cattcagagc tttcaaatgt cagtaacaga aataaaagag agagaagtga    39900
gactattaag gtccagacac ttcacatgtt aactcattta attctcacaa atctgttatg    39960
tgttgtaatc attatccctc attttacaaa aaagaaaact gaggctcaga aaggttatgt    40020
gacttgttct cccaacggta tcatgtaaat atactatttt tttctttaaa atgcttttgc    40080
ctggttcttt attttttaa  tgttttgacc tgtctggaac tgattacatt attaagcatc    40140
acgcaaaaac cattcttttc catagtgcta ttcaattata caaacaacat ttactaaaga    40200
gtgagacttt atagtgaaga ttgcttagga ttatctgaag ttcttccagt tcctgccatg    40260
cagcaggata tagtctgaat agatgctttc ccacttcaac actgcttggt ataccttcac    40320
actgccatgc acttgcttag ataatattta aaatatccact taaaagcaaa agttcggcca    40380
ggcgtggtgg ctcacacctg taatcccagc actttgggac tctgagacag gagcaattgc    40440
```

```
ttgaggtctg gagttcaaga ccagcctggg caatatggtg aaactctgtc tataaaaga   40500 cgaaatttag ccaggtgtgg tagcgtgagc ctgtagtccc cgctactcaa gaggctgagg   40560
caggaagatg gcttgagccc aggaggtgga ggttgcattg agccaacatt gcaccactgc   40620
actccagcct ggccaacaga gcaagaccct caaaaaaaaa aaaaaaaaaa gcagaaaaaa   40680
tgcaaaagct caggtgtgtc ctttactgct agctttccct agaaagtgcc tcaaagaaag   40740
aaagaagacc catgacaatc taatacattt ttataattaa aaatgtatat agcttgcatt   40800
tgtgattatg cagtatttat tttatattaa acctcacatt ttattattat ttagctgtta   40860
ccttataaaa tatttatagt aacaaatgta ggttttgat gtctaagata aagataaatg   40920
cagtagtaag gagaagtaat gcaaaataaa atttcatgtc cttatgaggg gaaaagtgca   40980
tggattgaaa tcacttgcag ccaatctgtg gtaattttct tgcccctggg cctggcagac   41040
ttagaaggta aaagaactg catatgaaat gaaaaccact tttctcccag tactcatcta   41100
accttgtaga gggtgttaaa tgtacacaag atgtgttagg ggaaattaaa tattaaagcg   41160 tatatttat tctttcataa aaaggagac tgtataatgt gatccaaaaa actaaccatt   41220
gtttgtttgt ttctttagga tggattggat gctttggtat atgatttgga ttttcctgcc   41280
ttaagaaaaa acaaaaatat tgacaacttt ttaagcagat gtaagtaatt ttttgtggag   41340
gttaatgaca gacttcatat aactacattt tcacttatgt cattcaagcc cttatttttt   41400
cttctattta cttttggtg atttcatcaa tgatttctac atagaattta gtaggaagtg   41460
tgaaagaaac aatttggatg cctgttagga gaaccaaaat atttgaaga gaaagggatg   41520 aaaaatagtt aaaataagta ttcaaaaaac tgtgcattga gtttgaataa ctgcacattg   41580
agtttgagta actgctgaga catgagaatt tttctccatg aaagctgttt tatatttaaa   41640
ttttacagat attcttttcc gaaggctcct ttttagattg gattttatca tttaaaaatt   41700
tgattaaata acttataatt tcaaacttt aatcttaaag aattgataag atttagatca   41760
taaagtcctc cttactttat ttatttctgt ttctgaacta taaatattga tacatgtaag   41820
tttgattggt tttggtgtta tcttcaatt ttggttatat atgttttatt acaaaggttt   41880 tgttttcta aatagtcata tctttttgat tttttaaatc acttctatac tttgaaatct   41940
tgtattagaa tttttaatt ttatgatctt ttagtttttc aattttttaaa aaattattgt   42000 tttattttcg ttttgaata tggtgccaga ttctgaactg agaagttttt aagtataaaa   42060
gttttaatta tttctcatgt cctatggaca tagcagtaaa atttattaa tatttacagt   42120 tgcttacctc cctacctgac aacatagtga aggaactaaa aagatggaga ggcttgacta   42180
tttatcttaa tggtaactgg catttataga gatggtgtag ataaggggta aatgctcctt   42240
agtacaaagg cagagggtgg ggcatggttt tttttaaagt aatggctagc aagaatgaaa   42300
ttcatgcttc cttaaactgt gctactttgt tgctttcata atgttaagta tgcttgtata   42360
ttttataaat agagacatta atgctttagt agaaataagt gaaataaaag tgtaaatcta   42420
aagtaaactg ttttaactgg taaacctgta caatttattt taattttaa attggagaaa   42480 aatgcagaga ataatataac aaaattttag ggcagtcata tgtagcagta ggtaaaaatc   42540
atgaccaagg atagtttatg ccaggattac taagttagta taaaattcaa aaatcagtta   42600
gcttaattta ccacattaac atattttaaa aaggaaattt agtagatgca gaaaaagcat   42660
ttgataaaat ttaatatcca ttcacaattt taaaatatct gtctgcaaac taggaagtga   42720
aggaagcttc ctttccccaa taagggaat ctacaagaaa cctacagttt agattgtatc   42780
tacttgttta agacgaatgc ttttcccta agattggaaa aggcaaatct gtcctctctt   42840
```

```
accacttttta tttaacattg tcttagaagt tctagccagt gccatcaggt aaaataaaga    42900
aaagccgtac agattgaaaa ggaagaagta aaactttccc aatttagaca gcatgatttt    42960
ccatatagaa aatcctcaag attctgcaaa aaagctacat gaactaataa gtacattcag    43020
caaggttgaa agttagaaga ttaatatcca aaaagcagtt gcacatacat ttattaacaa    43080
caagcaattg ggaattaatt tattataaca aatacagcac catttacaat agaagcaaaa    43140
acatgaaaaa tttaggagta aatttgacaa atatgtgta aacctgttta ctgaaaacta     43200
tacagcattg tagacagaaa ttaaggaaga cctaacaaga tattcaatgt tcatggattg    43260
tacaattcaa tattaaaatg ttaacagtcc ccaaattaat tgatctatag agtccgtata    43320
ttctcagaac cttagcagac agttttttgt ataaggtgac cagcaattct gtaattcata    43380
tggaaatgta aaggacctgg aacagccaaa acagtttcga aaagtaagag caagttggag    43440
gattaaggtc aatatcaaga cagtatagtc ttgatgaaag aataaacaca tagttcagtg    43500
gaacagaaaa gagcatctag aaatagacct gtgcatgcaa gtatatggtt aattgatttc    43560
aacaaaggtg acaggataat tcaatgttca agcctcagtt tccactgtat acaaaaatta    43620
actcaaaata gatcatcaac gtaaatgtaa gagctaaaac aataacactt ctagaagaaa    43680
acatagaaca tatttgccac tttccttagg caagttttttc ttagatagga cacaaataac   43740
acaaaccatt tttgaaaaag gataaattag acttatcgaa atttaaaata gttctcttca    43800
gaagacactg ttcagaaaat gaaagataa gccaaaggct gggaaaaat agttgcaaag       43860
catgtaaaag aagaaagaat agtccttttca accagtggtg ttcagacaac tggatatccg   43920
tacgcaaggg aatgaatttg gactcctacc tcatatcatg tacaaaaatt aaccgaaaat    43980
ataaaagtta aaaatgtaaa actcttagga gaaaacatag gttgaaatct tcatgacctc    44040
ggactaagca gtggtttctt agacgtaata ccaaaagcac aagcaacaaa agaaaaatag    44100
ataaactgga catcatcaaa ataaaaaact tttatttatg cttcaaagat actatcaaga    44160
gtgaaggcca ggcatggtgg ctcacgcctg taatcccagc actttgggag gctgaggcgg    44220
gcagatcagt tctgtccagg agttccagac cagcctggcc aacatggcga acccccatct    44280
ctactaaaaa tgcaaaaatt agcagacatg ttggcagaca cctgtaatcc cagctacttc    44340
agaggctgag gcaaggagaa ttgcttgaac ccaggaggtg gaggttgcag tgagccaaga    44400
ttgcaccact gcactccagc ctgggcgaca gagcaagact ttgtctcaaa aaaaaaaaaa    44460
aaaaaaaga gtgaaaagac aacttacaaa ataggaaaac attagcaaat catatgtcca    44520
ataaaggact ggtatctaga atatataaac aagtgtaaca actcaataat aataagacaa    44580
atagttcagt ttaaaagtag gaaaaatatt tgaatagaca tttctccaaa gaagatgtaa    44640
aaaatggccag taaacatgtg cagaactgtt catggtggtt agtcattagg aagttgcaaa    44700
ttatggccac aataagatac tagtacacct ctattagaat gattaaaact ttctaaactg    44760
acaatatcaa gtatttatga aaatgcattg cagctggaac cctgtacatt gctgactggt    44820
aaatggtaag gcactttgga aaacagtttg gttgtttctt ataaagttat acatgcactt    44880
tactatatga ccccaggaat tctgctccta gatatttact gaaagaaat gaaagcatat     44940
gtctgcacaa agagctgtat taaaatgttt aaggcaactt tatgtttgct gaaaactgga    45000
agcaactcaa gtgcccgtca gctgatcaat ggataaattg tggtacaacc acatagtggg    45060
atattactga ataataaaaa gtaatgaatt actgctatgt gcaatatcca gcaatctcag    45120
aagcattctg ttaagtgaaa aaagccagac acaaaaaggc tacatactgc atgattccat    45180
ttgtaggaca tgctggaaat gcaaaacttt gagctagaaa tcctatggtt gaggtaaaac    45240
```

```
ttcaggagtt agaaaagggt atgaagaaac cttggaattc tgtaacctct ttgtggtgat    45300
gattacatga gtatatgtgt tagtcagaaa tgcattgaaa tctatataca aaaagcatca    45360
tttactctat gtttattagt tatattaaca aactcaacct taaaaaacat gaagtttaat    45420
gctcatttag taatcagcct aattctaaac caatatgtta cttcaagaaa aaaaattact    45480
tctatgtaag ttaattttt aaggaaaaca atgtatgtgg ctaccatgaa atcataataa    45540
aatttaaaga catgaacaaa aacaaggtga ataaacatgt tataagtgta aataaacata    45600
acaaacttat tttttcaata taattagaac attctccttc aattactggc attgtgtttt    45660
tatgtttcac acagagcaat agatttgtat aggatagcat tttacatacc gctgaaattc    45720
ttttatatag atttagcttt catcagcaag cacatcaaaa ttatttttatt aaaggtaaat    45780 ttttgttttg tttctaattg cttttttgctg acatatatca gatgtagtga tctaagaata    45840
tacctggaat atgggataaa atatttttct ttaaaaaatt cagcttaagt catattaaat    45900
taagcctcaa atataatttt taatcatcag gtttaattat attgcaacct gttaattttt    45960
atctctttgt gttaagaagt gtgtggaaac aaaagggaaa ggagaatctg tgaacatttg    46020
actgaatagt gaaatataaa gatttacttt tctgggctct ggtgtatgat acctaaataa    46080
taaggctgca agaagatgt ttatcagcct cacatacctg ataaggaaag atttcaggtg    46140
acattttcat aggagttaga gagatgatac caagataaaa ttaagcgatt gttgtgggag    46200
ttagtcacag ttttgaagac acatgttggg agccagaaca ttgggaggat gaagggagag    46260
aaaatttggg aacagtgatt atgattgtat atgcttataa accattatgg atgtcacaga    46320
gactttaggg tacaagattc ataattatat gttaatagaa aaacatgttt atcaaacaaa    46380
tcttagtcta aaagaagata atggagaagg taagaccatt gaatgaagaa aattcatgaa    46440
cctccgggta taaatgcaag agagctcatt tgtttggctt aaaaaaaaaa cagaactgat    46500
attttatgtc atatactata tctttttataa tatagattac aaaagtgaca taatagctat    46560
ggtagtgata aaagcataca gtacagttgg taaattttg gttgctttgg cactagtaca    46620
attactgaga agtaatgcg aataatcact attcagagtt agtgatcaaa agcgatgatc    46680
atttagaatg ttacacagac cttgagacaa agcattcagt tcactttaga ccagggtttc    46740
tcaagtggca ccaatgacat tttaggtcag ataactcttt gctgggaggc tgttctttgc    46800
atcgtatgat gtttagcagc acccctggcc tctgccttct taatgccagt agcatatcct    46860
aacacctatc cccagttgtg atcaccagaa atatttctag acattgccaa atatcccttg    46920
agaggcaaaa ctgcctaaga ctttatgttg atgaaggaaa gaaatagtgg gcgcagttag    46980
acacgtgctc caagcttaga aaatgtaatc aaaagcaata aatattagaa ggttgcagcc    47040
atagaaagca aggttcttcc acagggagtt ctcagctgag attataaagt tttatgaacc    47100
agatcagaag tatgaataca tatccaggga taaatacaaa agagtagtat aaatctatta    47160
aaaatgtgtt aggctagaag actataatga gccacaactt gtgaaaagct cttaagccct    47220
ttacaagtca ttctctcttc tactcccatc cttcctggtt agaattagga ttcaagatgt    47280
gtgagaaaag gataatttca ctacatgaga ccattcttga aatagttttt gaatgaccag    47340
ttactaaaga catgaagaac aagactgttt ttcttagaaa ctgtagctct taccatctca    47400
tggatggaaa cacacacaga tataccttat aatagtagaa gtttgtagag aatgtaatga    47460
tacacagatc ttgaatgggg taaagaaagg cttccaaaag aaagtaatat ttgagtctta    47520
aaacatgggc tagattttc aatggaggaa ggacagttct gagagggagg accatttaaa    47580
tcacagagtc ttccaaaagt atgacatctt tgaggaacca ggagtttggt gtaaattgaa    47640
```

```
cttggtttat aatgagagag aaagggtcgg gaggacggac tgcagggggat gagactgaaa    47700 tggcaggctg gggcttttgg gttaatgggt tggatattaa aaaaaattac ttagttgctt    47760
gttttttctt ttcaaattct catgagtttt aaaaacttag ataaagaaat tgaagtaagt    47820
tcaaggaaga ggagaaagtt tgagtgtttt aaatacctct aaatcaaggc agtttacacc    47880
tattgaatta acatgctgag gtgattgaag atctttagag aaactttgga gaatgatgga    47940
gttcccaaaa aactaaagat aggtaaatgg tctggttata ataaaccaaa gaaaagactg    48000
ataagtgcag atttctgaac agtggcagtc ttcatacaga ggcttgactt tccctctttt    48060
tccaacacaa ctattgttta agcttcttca ttttcattta aatgatcaca aaaatcttcc    48120
attcagtctc aataatacat ctacttttgc ctatgtacag ttacctacgt tgctgccaga    48180
ggattctttt tgaatagtaa atttaagtca aattccattc ccagcttttt ggtggatttt    48240
ctaaacttga tgctatctaa gcttctaaat tacattctta actgtacacc tctcctcctt    48300
gtttccttac acatcagcta cacgctgaca tttatttcct ggaaagtacc atgacacctc    48360
cataagactt ttcagatgtt gttttctct ttctagaatt ctttccaacc cacccaactc    48420
aaagcagtca tcctttaaat ttcaaataag ccttcatttt tgttccctaa cctcttggtt    48480
atctaggctt catggatctg accttctgag catgtacttc tatggcatct tgtatactta    48540
tcacaggtta tatttatttg tatgactatt taattggtac ctgctgtggt ttgaatgccc    48600
ccaccaaaac tcattaaagt ttaattgcca gtgctagtag gtggggacgt taagaagtga    48660
ttaggtcatg tgggttccac ccccatgaat ggattaatgc tgttattgtg ggaaggggtt    48720
ataaaagtga gctcttgtgc atgtatgctc ttactcttcc acttgtctac cattgaatga    48780
cccttgccag atgcccttttt ttctttata aattacccat tctgtggtat tctgttatag    48840
cagcaaaaaa cagactaaga cagtatccat tctccttttt ctccttctcc tgtcactaga    48900
ttttaagtgc catgagagca ggggcattta tgtttttact gccaaacctg acagcatagt    48960
aagtacttgt tatatatgag ctcagtgcat tagacgttgg atactgactt gttagagatg    49020
atctagaaag tccaggtggt ctctgacttt aaaatttcca gctttatgag ggtttcattg    49080
gaacataact ccatcataaa tctaggcaca tcactggtga tgttaacgct tatcatttgg    49140
tttaaggtag tgtctggcaa gcttctccac tagtaagtta ccattttctt tttccaaacg    49200
ctgtggaggg gagcgtattc cctttccata ctctcctgga ggggagactt tacacgtatt    49260
atttggaatt ctgtagggaa gatttgcctt ttctccccca tttattaatt tagtcattga    49320
tttatataat ataaactgca tatatttatt tcatactttg ggttgtaatc cagtagtgtg    49380
ttatttatta ggttggtgca aaagtaattg cagttttttgc cactattttt agcaaaaatc    49440
tcaattgctt ttgcaccaac ctaatacttt gttacttaaa ttgttctcat ttttgccttt    49500
tgggagctcc ttcaggttgg acccagctcc tactcctgtg ttctttgaca tgttcttact    49560 tttttttaaaa aaaggaacac ttcttttactt tctggcatta cacgatgctc caggctcatc    49620
ttatattttc cctcagccct gaaatcagcc attttttcca aggagctctg gttcctttta    49680
ttggagaata tatttagaa accaagatct gggtgctagg tgtgcttatt gctactggtg    49740
atcactgttt caaggccctc tcagctgcca tagctaggaa atatatgtat gcatgtatac    49800
cagcctgtga ctatacacat aactataatt ctataccgtgt acacatgtta aacgtgttta    49860
gactgatatt accagctcta aactagtatc acaagattca ttctagcttt tgcccttgcc    49920
tgtttgtaac ttttttttctc tgatgatgag aaacctggct cccattattg gtatttactt    49980
actcaaccct aatattcatg taaaataaac catacaccct gtgagaaatg gatttaccaa    50040
```

```
ctggaacaca atatctttgt acagttcctt ttttgtcttt agccttagtt tccagctaaa   50100
acagttttcc agcattacgt agttcagctt cttttccctc accaccttca atgagggcat   50160
gtcatcttgt tagtcataca tttagattca tttgttagaa tctggattcc atcctgagat   50220
cccccagaat cccaattgat ttttttaaatt tgcataaagt gtgtatagtt ctgtgggtct  50280
taacaaacac atagtcttgt ctgcaacacc ccaataccat tcggaacagt tccatcaccc   50340
ccactcctgg gaaacactga tctcttttc tgttcctata gttttacctt ttccagaatg    50400
tcattaaatg gaatcataca gtgtatagcc ttttgattct gtctttttt cacttagcaa    50460
aaatgcattt aaggctgggc acagtggctc ttgcctgtaa gcccagcacc ttgggaggct   50520
gaagcgggca gatcacctga gatcaggagt caagaccag cctggccaac atgacaaaac    50580
cccgtctgta ttaaaaaata cgaaaattag ccgggtatgg tggcaggtgc ctataattcc   50640
agctacttgg gaggctgagg caggagaatc aattaaacct gggaagtgga ggttgcagtg   50700
agccaagatt gcgccattgc actccagcct gggtgacaga gcaagactct gccttgaaaa   50760
aaaaaaaaaa ataaaagcat ttaagattcc ttcatgttgt ccatgttgtg tgaagtagtt   50820
gcttttcct ttttttcccct aaattgcaga gcaaccttct attgaatgga tatacctttgg  50880
tttgtttgtt cattcctctg ttgaagaaca tattcgttat ttcctgtttg gggcaattat   50940
gaataaagct gccgtaaata ttcgtgtaca agttttttgca tgaatttagg ttttttttt   51000
ttttttttt ttgagatgga gtttcgctct tctcgcccag gctggagtgc aatggcacaa    51060
tctcagctca tggcaacctc cacctcccag gttcaagcag ttctcctgcc tcagcctccc   51120
tagtagatgg gattacaggc atgcgccaca atgcccggct aattttgtat ttttagtaga   51180
gacagggttt ctccatgttg gtcaggctga tcttaaattc ccgacctcag gtgctctgtc   51240
tgcctcggcc tcccaaagtg ctggaattac aggcgtgagc caccgtgccg gccatgaatt   51300
tagtttgaaa ttcacttggg cagatatgta aatacacaga tgtagcattg ctaggttgtt   51360
tgctaagaac aggtttaact tcttaagaaa ctgccaaact gtcttccaaa gtggctatac   51420
catttttatta tacattccca ccaacaatga atgagagttt ctgttgttgt gcatccttgc   51480
cgcatttgct actgtcaatt ttcatttgca taatgtcttt catagagcaa aaattttaat   51540
tttgatgaaa tctaacttat atttctgcat tgattgtgct ttttgtgtca tataaaaatc   51600
attgccaaac tcaagattga tttttaaag caactttatt aagttatcat ttacatgcta    51660
taaaattcac ccgtttgaag tatacaattc agtgagcttt tgggtgtat gtgtattttc     51720
agagttgtgc aaccattacc acagttgctt ttacaacatt ttcatcactt cgtaaggtaa   51780
cctcataccc attaacagtc agtctccatt tctctccagg cttccagccc tagacaacca   51840
ctaatctatt ttctgtctct atagatttgc cgactctata gagacatttc ctatagaagg   51900
aatcatcaat aaaatggtct tttgtgactg ccttctttgg cttagcatgt tttcattgtt   51960
catagtgtta taccatgtgt cagtatttca ttttttaattg ccagtaatat tccattgtat  52020
ggatatacca cattttgttt atctgcttat cagctgatgg acatttgtat tgattctctt   52080
ttggctttta tgaataatgc tgctatgaac atttgtgtag aagttttgt gtagacatat    52140
gtttttattg ttcttgcgta gatacctaga agtggaattg gtgggtcata tggtaattct   52200
atatttaaca ttttgagaaa ctcaagatgg attttttaaat atatacttt attactttgg   52260
agtaaatata tatggctttt ctgttgttcc tgaatagata aatgcagcat gtgttatct    52320
ccatttgtat ataatgtcat taagtgtttt taatatttca gtagcatcga gcacaagtat   52380
aatctctatc cttaaggatt gtggggacat acaacgtaat agaagaaaca gacctataga   52440
```

```
aacaattcca gttcagattg ttaggtgaaa tatagggaaa taatgtccca gagaagggag    52500
tcataccttg tgcttgagag ggaatcagga atgtctaaag aggagataaa agattagatc    52560
ttgtttaata gtaacttggt cagataaggt ggtgggggaa gtcattttag gctagtgata    52620
acatctggaa aggcacagag agatgaagca gtatgggctt atatagataa ttgcaaataa    52680
ctaggcattg ctagagcatg gttgtgggga gtatcttatc tagaactata agactggaca    52740
gtcactaatg atatatatat attttttttgc catgttgagg agtttgaatt taggagtctg    52800
gattttttat atttattttt tgttgatctg tttatcaaac tggattactc tgtgtgtatg    52860
tgggtgggtg gatgcgtgcc tatgtgccta tgcagtcaaa atgtagcaca tcttcctaga    52920
gtgtgatttt atttgaacat ttggacatga ataattttc ttaattaaaa cagtgctggt     52980
tgcagtggct cacatctgta atctcagcac tttcggaggc cgaggcaggt agatcacttg    53040
agcccaggag ttcgagatcg gcctgggcaa catggcaaaa ctgtgtctct gcaaaaatac    53100
aaaaattagt tgtgcatggt gttgtgtgcc tatagtcccg gctacttggg aggctgcggt    53160
gggagaatcg cttgaactcc gaggtggagg ttgcagtgag ctgagattgc atgacagcgt    53220
gagaccctgt ctcaaggaaa aagaaaagaa aaatcagatt tttatggaat tgaatataac    53280
attcttgtga attttcaaa taagtttaat ttttgagctt tttagggctg ctttcactac     53340
tctaaaagta tgcaatgtat actgggcttt tttaggcaga gtagcagtat tctggtcaaa    53400
cagtacaagg tacataatgt ttattatgat atttttaccta ttgtgacatt taaaaaaact   53460
ttgaacattt ttgaaattag aatgtatctt agaatctcta gtggtacata aagtaatggt    53520
acgttttata atctaggatc ttagggtagg caaaatacat cttttgtttt tttcattaga    53580
aaagcaacaa agggtcatta taaaaaactt aaaatatata gaaatgtgg cagaataatc     53640 tgtagtctca ccaaactcag agatgactgc agttattgtt ttggcatatt ttcttctggc    53700
ctttaaaaaa atccatatct gtgtatcagt atataattat gttttttagaa atcaagttc    53760 atatactgta tacagtttgt tctatttctt tgcacaacat tatatgctga acataattct    53820
atgtaattaa atattcaaca caatttttaaa tgttacctaa tactctatgt atatgaaatt   53880
atttgctctt taaaattgta aaaactactt tattgtagat atcttggtcc cacattgtat    53940
ctcatttcct taggataaat tcctagaagt aaaatttact gggtataaag ttgattttta    54000
tttattttta atttaattta atttttttct tgatacagag tctcggtcag tcacccaggc    54060
tggagtgcag tggcccaaac tcggcttact gcaacctcca cctcttgagt tcaagtgatt    54120
cttatgcctc agcctcctga ttagctggga ttacaggcgc ccaccaccgt gccggctaat    54180
ttttgtgttt ttagtagaga cggggttttg ccatgttggc caggctggtc ttgaactcct    54240
gacctcaagc aatccgcctg ccttggcctc ctgaagtgct gggattatag gcgtgagtca    54300
cagcgcctgg ccaattttta aaacagtatt aggaaaaatc atccatttgc tttcttgaaa    54360
attagattga agagtttata tatgattgaa atgcttttga attttggta acccagaagc     54420 tgtaagttag ccttttttgca ctggcccttt tgctaacttg tgatcatttg gagaaagatt   54480
aactctaaac gactagctct aatgattagc tagttagtgg ttgtcaagac tgtggttcct    54540
atttatgact caatttgctc attttatttc ttgctgaata tgttgcatag tagtatttca    54600
cttctctgaa tcttagcttt ctgccagcat cacctgactc aatatagttg acaatcagaa    54660
attgctaaaa gagtctagat ggtcacaaca tcctatttgg aggttttaga atgaaggaag    54720
acttaccaga tttgtgattt tgcaaatatt attttgcata aaactaattt tgtgaataac    54780
aaagaggtca aaatctgcca taggaaaaga tacaacagtt taagaaggat cggaagttct    54840
```

```
gagaagtttg ctgttttagg taaggtggcc agggtaggcc ttgttaaaag gtgacatttg   54900
aaaaaagagt tgaagtagtt gagggagtta gccatgtgga tgtctgaggg aagagagtgg   54960
catacagagg agcagctagt gcaaaggcct gaagggagga gagtgtacct ggcctgtttg   55020
aagaacatca aggaagccag tgtggctgga gaggattagg caaggggggag aattgtagga   55080 tgatatcata gaggtaagga aatggggagg ctaggtcatg tagagtcttg taggccattg   55140
taaaatcttg ggcttttgct ctgggtgaga tggcaagaca ttagagactt ttgagcagag   55200
aagtgacatg atctgacttg tgttttaaga acatcaccct atgttgagaa tagacacagg   55260
gcaatcagtt aagagtctat cacagtaatc caaggaagag atgatggtga cttggtctag   55320
catggtagca atgtagaggg tgagaagcta tcagattaca gatatatttc aaagagagag   55380
ccaacatatt ttcctgaaag ataggatgtg gagtgtaaga aaaaaaggag tcaagaatgc   55440
cccctaggtt tttgtcctga gcaaaattga gccatcggcc aaagtgtggg acacataggt   55500
ataagttttg ggtgagaata tttcttcagt ttttggcaca ttaaatttga gatgttttc    55560 aaaagaggat atattttgaa agtaattgaa tagataagtt tgaagtttaa gagagacatg   55620
tagactagag ataaaaattt ggaagttgat atgtagatgg tttttaaagc ccaccagaga   55680
agtgagtgta gatagagaag aagtcaccat tgagggctga gccttggaat gctccagtgt   55740
taagaaatct gagagaaggg gaggaaccag ccaaggcaac tgaaaactac taaggttgaa   55800
aagtaaaatc ttcagtattg ttggaagaat gttgtgtcct gaaagtcaag taaagaaagt   55860
gtatcaggag agagtgattg aagtgttaaa gccactgata tatcaagatg agggctgaga   55920
attggtcatt ggatttagca acatgatgct catttgtgac tttgacaagt agttttgaaa   55980
gaaaggtaag agccgacctg aagtggattt tagagcaaat agtaggaaag atttagtcac   56040
agaaattata gacaactttt gagaaatttt gctgcagtgg ggagttgagt aatgggacag   56100
tagctgctga gagaaatgag atcaagagtt tttttttgtt tccctaagat gggagagaaa   56160
acagcatggt gggatccggt taggagggt aaagcttagt aatagaggag aaaggggaga   56220
attgcttgag caatgtcctt gaactacagt aatgaaaaag gatgacatct agtgcatgag   56280
tggagggttt aagttaagat agaagtagtc tcccatagta aaatatgaaa agacaaaata   56340
tatgcttgta catgctgata gttaagtgtg taagtggtgg taagtcagtg gtagttttct   56400
tctgattgtt tcgttcgttt cagggtagta gccaaacaag atcattagct gtgaacgagg   56460
atcagtggga gagctgtggg aggtgtgtgt gaagaaagaa gaaaacttga aatacgtctc   56520
taggagagtg ggagagtgac tagaaattta ggattgccaa gtagaactaa gggccagctt   56580
gatgtttgtg attatgaatt ttaaaatagg atcagtcatt gtgattttat gtatttattg   56640
agacatattc aactgcatgg gtgctgcat agagtagttg gagagttgga tttaactata   56700
ataggattgt cgttttgcca aactaagtaa agtgaggcag aagagagctc atgacattaa   56760
aggtatatgc aagggagtga ttataataat tgaccatgta atttaagctg gctaggtagg   56820
aaaaagaggc tatcagtgca acgagggaaa gtatgagtgt agtagaatca atggattgga   56880
ggtcctggtg gggttggggt tgttggagtt aagatgctag aggaactaag caggaaagct   56940
ataagagagt gcttagagag tgtaagtttt ctaattgaaa ttgttggaag attataatta   57000
tgagtaatga caaggtctag tatatgacca tggaaatgag tgaccaaggt aaggtagagg   57060
acaagatcat tgaaggagag aagtataggt gttgagaggc caaggtactg taagtattat   57120
ctgtgggtat attaaagtta ttaagaatta aaacaggaga atattggaga gaagttcagt   57180
aaatcaggaa gtaaaactgt ctagcgatga gacgtggtga cctctgagag tcagtagatt   57240
```

```
acagcaacaa tgagaggtgg gaaatacaac ctaatataat gaaaatcaaa gctagcagat    57300
ttaggggtgg ggatgtgggg gatctcccac tttcagggtc ggttgtctaa ggcatgtgga    57360
aaagtaaagg tccccacttg agagctgtgg ggaagcagtg ccctcagaag gccactgggt    57420
tttattagag caggagttgg tgaactacag cccacaggcc aaatctcacc caccactgtg    57480
gctcatgaac taagcatgtt ttttgtattt tttcatgatt gaaaaaaaag tcaaagaat     57540 atataattaa agaatataca attgcatata taagtttgaa gtttaagaga gactagacta    57600
gagataaaaa tttggaagtt gatatgtaga tggtttttaa agcccatcat gatcatgatg    57660
gtgaaataat gaaacaatat catgaatgtg aaataatagg aaattcagat ttcagtgtcc    57720
ataaataaag ttttcttggg acgttgctac actttaaaaa atgtattgtg tatagctgct    57780
tttgttctac aacacctaag ctgagtagct acaacagcga ccatatgtga tgctctcctt    57840
gcttcacact gctgctcagc acagtagaaa tcacagtgat gctgttacag cttgacagtt    57900
ttgagtgcta tatgtatcac catatcacaa cattttattt gttttctatt accagtacat    57960
acgcatgtgt caaagcaaga agagaagagt atacttgaaa tgttgtcttt ttttttccct    58020
cccctaaaag actgtcacac aggcaggagt gcagtggcac attcatagct cactgcagcc    58080
ttgaactcct aggctcaagc agtccttctg cctcagcctc ccaagtagct gggactacaa    58140
gtgcatgcca ccatgggcct ggctaatttt taaattttt gtaaagacaa gtcttggtat     58200
gttgtccagg ctggtttcaa actcctggcc ttgagcaatc ctcctgcctc tgtgtcccaa    58260
agcactggga ttacaggtgt gagccatcat gcccagccca aatgttgtcc ttttgaagc     58320 ataatggaga atgaattatt tttatcaagt taggtggcaa agcatttttt taaattatgc    58380
aatgacagta tagctgtgct aaaggaatac agtgtacttt ggacattccc agactaagca    58440
ctcactatga tcttcctgac tcataggaca gcaacagtga gaaaaaatag aaaatttaaa    58500
acagagtatc tcatcccagt aaaatttctt cataaagaaa aatgttcatg caggcttgac    58560
caaaaaaaaa aaagaggctg caatgttatg taagtgtatg agtggtttat tcactagcct    58620
agcagagaaa gctgttcact gatggtgtgt gattgcagca gccaaacaaa tgtgtacaga    58680
gagaaaaact tgcctaagac tgttagcctt tgggcaagaa tagctgctca agaattggg     58740 ggtattggga gtggcatcaa tagtcaatta aaaaataacc aattttgagt tgttttcctt    58800
gactcttgtt tatttgagga atcagtgcag agtttgaagt gactgaagaa ttagcctgtg    58860
tatatagtct ccccttacag acttgggaaa gcttggtctt attttcttta gaatatgtat    58920
cacaatgtga aattaagtta catatttatt tatgtactta ttatttttct ttagagcagc    58980
agtccccaaa cttttggca ccagggacca gttttgtgga agacagtgtt tctatggaca     59040
ggatgggggt tgggggtgg cagacgggat ggttttatga aactattcca cctcagatca     59100
tcaggcatta aaaaagatt ctcataagga atgtgcaacc tggatccctc gcatgtgcag     59160
ttcacaatag ggtttgtgcc cctgtgagaa tctaatgccg ctgctgatct gacaggaggt    59220
ggagctcaga tggtaatgct tgcctaccca ctgctcacct catgctgtgt ggcccagttc    59280
ctaataggcc atgaaccggt acaggtccac ggctcagggg ttgggaatcc ctgttctagt    59340
gcatgcattg ttttctgtct caatggagcc ataagcctac aaagttcagg ctatatagta    59400
cccctagacc aagagtgggt ttcttacatg actactttac aataaatagg cttcgtttaa    59460
gatcctgaga tttgggtagg tgtgaataca tagtcctgag tgtttgggaa actaaagtcc    59520
aatgcttaga atttaccat taagttcttt attagttcta ggttggaccc ttggtgagat     59580
gaactaggaa aagtagaacc atagaatctc tgagtttgat tgaaagccat ccaacagagg    59640
```

```
catttacact tgttagcacg taaacctgta ttagaacaag ctagaatcca aggcagtaga   59700
acatagaaag atcttttaga tttcaaatga cttgtctgcg gtctttgtca agactctaca   59760
gcctattcta gctcatagct agagccaaga atctttttt caacgtaaca ggctattata   59820
ttatccaggt tcagaacttt ctctctcatc tggggtatta caatactctt aaaattctcc   59880
ccacctcctg tcttgacttt attgaactca tcttctacgt atttcctaga gtagttttcc   59940
tgaaatgtaa gtttgactat gttgttttat ccatcataat tccttttcat ggcttcctgc   60000
ccatagtagt ggtgcttctc agttcccagc agattccaga gcattcctca gggactgtat   60060
tatggaagag cctgaagtag atgaggctct gtctcttctc tgacaccttt aacctcattt   60120
agaacagagc agtttctttg atctatttca tgtagagagc tactttaaac tttaatgtga   60180
aaacggtttt cggtacttaa atattagttt tattactgta actactggct gataggtaaa   60240
gttcaagctc ctgaacttac ctggggctct ccagcctctt ctgtcagtcc ttactacaaa   60300
cttgatactc cagcaacata gaacttagat acagttcctc tgtgcttggt ttacattgct   60360
tgtctgctta tattgttcac ttgttctttc ctttttttga gacagagttt cgctctgtcg   60420
cccagactgg agtgcactgg tgtgatcttg gctcactgca accttcacgt cctgggctta   60480
ggtgatcctc ccacctcagc ctcctgagta gctgggacta caggaaactg ccactgcacc   60540
cagctaattt ttaaaaaaat attttttgta gagacagggt ttcatcatgt ttcccaggct   60600
ggtcttgaac tcctggactc atacattccg cttgcctcag cttcccaaag ttttgggatt   60660
acaggcatga gccaccacac ctggcctgtt ctttctttca ttctctatca tctagctaac   60720
cgctactatt cagtttagac ttttttcagg taccatcatt tacagaaagt cttcctagct   60780
atctctcacc cagcaggctt tagttaggtg tcctccttag tactcaaaaa actgtttatc   60840
ttccttatta catttttga attctttttt tcattgtttc tgttttattt gctagagttt   60900
gaactcttaa agaataggaa ctacatttta agttatgtt tatttatctc cagtgctgta   60960
cagcctgatg tatggtagat agaaatattt gtgcagcgaa ttaattgatt attgttcatc   61020
tttctggtgc atcttgcagt ggatatgtaa cctaaaatta aaggtactta taactttgta   61080
gaaatttgct ctctgttaca tgtatttatt ggtcataaag tacacaaaca cttgagttta   61140
aatgcatttg aaaggaaaa caagaatatt aatacagctc ttattaggaa ctggaactga   61200
agtttaatag ctgctgtgta ttttgtacaa ctctgaaatg tgaagctttt ccatgtaatc   61260
tcatgccagt gttgacccat gtggattaaa atagccctat tttaatctat gaccaaatta   61320
ggaattagaa tatctatcca gtggggattt gtgaattatt gtagtttgta gtatgacaag   61380
tttatataaa taattgcagt gattttcact gtgtgtttca agttaaaatc taggttcaaa   61440
tagagaaatg taatgctata agtattaaag attaccagtt ggaaaattta ctgttttttt   61500 ttttttagt gtgtttgcct ttgatatctt aaattacatc ttttttaaa ggatcactaa   61560 aactgacctt ataaaagaa aaatttattc cagtattaat ctaaaatatc tactcatgtt   61620
tcctaaattc agatttgatg tgtacttaaa ataccaggaa ctaattagct aattattttc   61680
agcttttgtt tgtagtgtaa tatttgtttt taaaacattc tgttaagtca aattttgatt   61740
aataaaaacc tttagtagtt gtaatgaagt tattctggaa tttactttaa aaaatcttag   61800
caaattgaac atttagctac tttatagctt caagttcac catattttca ataattctt   61860 catgaagttt gttgttttc attgtgtttc ttaagaactc gaatgtaaaa taagtagtgc   61920
tagttgtaat gctttagtga tttaaaatga taaactttc ttttcataca gataaagaca   61980
caataaataa aatcagagat ttacgaatga aagctgaaga ttatgaagta gtgaaggtga   62040
```

```
ttggtagagg tgcatttgga gaagttcaat tggtaggtta ttttaatgag aatacaaaag    62100
gactttatta aattaaaata atccacttgt gtgtttaaca tattatttgg gaaaatactg    62160
tttttataga attgttgctt taagttcctt tagacattgt tgcctgaggg tatggaagcc    62220
tagtgtcaaa tctagccata gtgggaagtg ttttccccaa gtatctgtgg cagaaaagaa    62280
gtgtcaggca tcagaagata aatctttgct cctaatatta gactaaaatg ctgtagaaca    62340
gtaagcttta taaacaggaa gcagcttaca tagccgtgtg gaggggggaa agtgtcttgt    62400
aatataggaa ataaaaattt ttttaaaaca ttacttctga taattaaagt cttgacatta    62460
gctacttgga ataatttggc agaagagaag aaataaaaat aactgaaaca gtaaggctaa    62520
attatttagc aagtattaaa agcacttagt aaattgttct gtgaaacctt gagctttaaa    62580
tgttaacaaa aggttcatta ttttcccttt tcaattttaa aggtaaggca taaatccacc    62640
aggaaggtat atgctatgaa gcttctcagc aaatttgaaa tgataaagag atctgattct    62700
gcttttttct gggaagaaag ggacatcatg gcttttgcca acagtccttg ggttgttcag    62760
gtatgacttt gctactcttt cattattgct gcattagttt gtaactaaac atgtctgaga    62820
agcttagttt gtgttttaga atagtagtag agaatttact ggcagttaca aaattgtcta    62880
attacctttt aaatcttaaa atttaattgt attgaatcat ttctagcaag aaaggctaga    62940
acaaaataac catgcttctg tagaatttat atataggaaa tttaatttaa atgtagaatt    63000
tgtgctgggc gtgatggctc atgcctgtta tctgaatact ttgggaggac aaggcgggag    63060
gatagcttga gcccaggggt ttgagaccag cctggacaac atagtgacac ctatctctac    63120
aaaaaattaa aaaattatt gaggcatggt ggtacacgcc tgtggttcca gctactgggg    63180
aggctgaagc aggaggatta cttgagtcca ggaggtcgag gctatagtga gccgtgttca    63240
catcactgca ctccagcctg ggcaacagag tgagaccctg tctcaaaaat aaaaataata    63300
aatataaaat ttaaatacag aattttaaat tagatatttt taaatacaga agatatagaa    63360
aacttaatct acttagattt gagggaagtc gtatattatt aaaatttaaa tagatacttt    63420
tagttaatat tgaattttt tccccaaaca tgaggctctc attttgttta gctgtctcct    63480
catttatctg tctcttattt tgtgaagagg agataataag agaaatgaag ggaaagtgag    63540
aggaaaccaa gttaagctag gtcaccaaat aatacttgtc tttcggtttt cagtggaaag    63600
aaaaactaga agtcagtagt tttaggtcct cgtcttgatt gccataggcc tttctctgaa    63660
gctgtggcca tgttacttaa catctctggg ccacaatttc cttgttcata agtctgaaag    63720
ttgtctttga ttggttatgt tcaattgtgg aggtacctta ggcaaaatca tggggtcaag    63780
tggggttttg ggtagattat aattctgagt tttctctctg cttttatgag ttcagcttca    63840
tgttttatct gtcttatgta ttgggatcct taatgcaaaa tgtcatacgg gggaagttaa    63900
actgggctag accatttcta attttctaac atgttttgt gatttattta taatatataa    63960
tgaagtctgt cctaaaaag cataccagta attggaatta aaaggatatg aaaaatgttg    64020
aaggtttatg ccatagcact ttttttttt ttttgagacg gagtctcgct ctgtcgccca    64080
ggccggagtg caatggtgcg atctcggctc actgcaagca agctctgccc cctgagttca    64140
cgccattctc ctgcctcagc ctcccgagta gctgggacga caggtgcctg ccaccacgcc    64200
cggctattat ttttttgtatt tttagtagag acgggtttca ctgtgttagc cagcatggtc    64260
tcgatctcct gacctcgtga tccgcctgcc tcggcctccc aaagtgctgg gattacaggt    64320
gtgagccacc gtgcccggtc accatagtac ttttaaactt gaaatgtcta tgttttttacc    64380 aactatgtag atcagagttt ctcaggctta atactattga cattttgggc cagataattc    64440
```

```
tttgttgttg ggggctatcc tttatattat ttcagttact aatgtgttta tttaggatgt   64500
ttggcagcat tcctggcctc tacacagggg atgctagtag tgactcttcc cacctcacac   64560
acagttgtga caaccaaaaa tgttttcacc actagttaac aaccactgat acatgaacgt   64620
tcagtgtctg ttagtgaaaa aatatgtgac ataattgtta ctttcagggc tatttacaat   64680
ttaggtattc agagctttat ttctctggat atattgtcta taaatagggt gaaactgtca   64740
ccaaattaac agtatttctt tatggggccc aaatgacaaa ttatatactt taatctggga   64800
tagtcatgaa atgccacttt gtttcttatc cttctctctt cccccaaaat acattttta    64860 cattaaaata actgagtctg gccgggtgt ggtggccccc atgcttgtaa tctgagcact    64920
ttgagaggct gagacaggaa gatcacttga gggcaggagt tcaagactgg ctcccaatct   64980
ctacaaaaaa acaaaaaatc aaaacaaagt aactgaatct ataactaaaa ttattaaaca   65040
cagttgaaaa aaatgaaaca ttaagaagat tttaagacaa acatctgggt aaattagaga   65100
tcatcttctc tagggcttgt ttttttttagt ttaattctaa acttcttgta tttacttaaa  65160
atgttatttt ataaatttgc ccttcttttt atttgatccc cagtcacata atatatttat   65220
gcctgatatc ctcgctaatt tcacattagt ggattttgct gttactattt gaaccctagc   65280
tgctgccttc ctcctacttc tgtgttagct attactgctc ctcctcctga ctgctgtcat   65340
ttgttgagca tctgttgcac taagtgctttt ctatattcag taatcttttt taacaaccct  65400
caaccctgaa agacagttaa tctgttaggt gcactgttac tttatggatt agtttatgat   65460
ttggttcatt aagcctttat taagcaattg ctaaccgcca ggcatctgga tacttgacta   65520
agcagcaggt ataaaagtta aacgaagtat agtccttaca gtgttttaga agagattata   65580
gtctcataga ctcgggtagg ttaagcaaat tactagtcac acagctaata agaaacagct   65640
gaggccgggc gcagtggctc atgcctgtaa tcccagcatt ttgggaggcc agggtgggcg   65700
gatcacgagg tcaggagatc gagaccatcc tggctaacac ggtgaaaccc catctctact   65760
aaaaatgcaa aaaattagcc gggcgtggta gcgggtgcct gtagtcccag ctcctcggga   65820
ggctgaggta ggagaatggc gtgaacctgg gaggcggagc ttgcagtgag ccgacatcac   65880
gccactgcac tccagcctgg gcgacagagc gagactccgt ctcaaaaaaa aaaaaaaaaa   65940
aaaaaaaaaa aacagctgaa actgtaagcc aaatttatca aagacttctt gagcattgtg   66000
atattgatat aaatttaata gtagaccccca ctgatgcaca agttaaatta gaaatacagt   66060
atttctttgc ctaggagatt tgtatattta ctgaaaatat tacagtttaa aaaaattctc   66120
agtaaaagaa attcaaatag tgtagaaaat tatgaagaaa ggatatctcc atgtaactct   66180
tctgaataat tatgttatag tcattttgca tatacaaggg tctttgtggc atttatgttt   66240
gtcttttttt aaaactagac ttgcaacttc tgtaatttga ttattttact taaatctttt   66300 attaacatttt ttgccacttt ttaagtgaaa caattttgtt taacattaat gaatgtgttt   66360
tgtttgtttt ttctatttgt atagcttttt tatgcattcc aagatgatcg ttatctctac   66420
atggtgatgg aatacatgcc tggtggagat cttgtaaact taatgagcaa ctatgatgtg   66480
cctgaaaaat gggcacgatt ctatactgca gaagtagttc ttgcattgga tgcaatccat   66540
tccatgggtt ttattcacag gtaaagataa aagtgcttta aattttctca tttgttgagg   66600
gaaatagcta aaaataactt taacatttct tactctcagt tcacccattc ttcttccgta   66660
tgacataagt gacctttcag aactcaagac tctggccagg cgctgcctca cgcctgtaat   66720
cccagagctt tgggaggccg aggcaggcag atctcttgag ctcaggagtt tgacaccagc   66780
ctggacaaca tggtgaaacc catctctaca aaaaaaaaaa aaaaaacac aggtgtggtg    66840
```

```
gcatgcacct gtggtcccag ctccttggga ggctaaggtg ggaggatcgc ttgagcctgg   66900
gagcagaggt ttcagtgagc tgagatctag tcactgcact tcagactggg tgacagagtg   66960
agattctatg tcaggaaggg gggaaaaaaa gaactccaaa ctttgaagtt tataatttta   67020
gcatttcaat ttaatgttga tataaatgta ttctttaata tcccttaatc tgatcatata   67080
gcctttaaat ggtgttctga aaagtaaaac ttgtaaacta gttttctaag gtatgtgcca   67140
ggagttaaac actttgatgt taattttta aatatgtaac ttaatttgct tttaattagt   67200
gaataggtcg tatttattca ttagacgaat agtttcattt gttgtacaaa cactgcttga   67260
atcctgtgtg cagttgctgt gcctacatgt cagggatcaa aaatgaaagt gacttagacc   67320
ctgccgtggg gttttttat gtacttacct atctaatatg tttcaatcac cttttatgtc   67380
tgagtgttgt attttgatg gtctgtctct ctcaaatgat ttgattttcc ctctgaaaga   67440
atgaaacttt taaaaaagga atatatatgt tttcttctga ggcattaaca tataaagaag   67500
tttctttgat gaaatttaat ttatagatgt ggatagagaa cacatacaga tcaaagatgg   67560
ccttacctag attgaggatg cttgacctaa ataactgcc tcatataatt tttacagtgt   67620
ctaatctgtt tcagaaaata ctgtactatt ttttccctcc tgcagagatg tgaagcctga   67680
taacatgctg ctggataaat ctggacattt gaagttagca gattttggta cttgtatgaa   67740
gatgaataag gttaattaac tagattttaa tttagttttt gctaattcaa ggtagatgct   67800
tctttagaaa atggtttaag aattctttag aaaatggtgt aagaatttac taaccatagc   67860
tggacttgtc cagaattaat atgaccttat ttgttgaact agataccatg gtttcaatgt   67920
tgtattagta acttgttagt gatttatttt ttcctctcta tttagggtaa atatggattg   67980
ccagatttac taaatccttc ataacaactc taatatacac tactggtaac taggaatgga   68040
attagcttaa atgtcactaa atacttatgc cagtgttaaa attagacttt cataaaaatt   68100
ggattccagt aatgtgtgta tttttagtg ttttacttca gttaacatat aaaagatttt   68160
actgctatt ttaggagtga gtcttaaaag atacctatcc tcactgttta tataataaat   68220
aacatataca cagctgtata tgtatataca tattatgtat atgtatatac atatacatta   68280
tgtatatgta tatacatata ataataaca taaataaata tgttatttat ataataaata   68340
acatatacac agctgaagga gctgaaggag ctgtgtatat gttattcctt cacttcatat   68400
acacagtgaa ggaaacactg catgagaact tctgtatgaa catttagtta taatgctgtt   68460
tcattaatac cagcgaatat aggtaacagc taacaagtct ctcaggtttg ttggggagg    68520
gcagttaaaa ttcacatcaa atagacattc agtgtgcttt acactattat gccctttcc    68580
catacatatg cttccccagt ttgtatttgt acagtcagct tttgtatgtt tcttttgtag   68640
tttcaaacat agttaaatag ctattttagt agaaaataat gaagtcagtg tttataccaa   68700
tatgttgtaa aatgccctat cctatgaact ccccagtgta tttgcactgg cctgtgtact   68760
tgttctcagc agttaaatgg tttcatgata ttggcacaac ttggggaata ataaatgtgg   68820
cagtatgttt ttctagtgag cattattaca aaataatcac tggtgtgtgt atatatgtga   68880
atacacatat aatgtgtgtg tatatgcatt cacatgtata cacatacata cattatatgg   68940
tatatatgta tatggtgtgt atatagtatg tatatatatg attaagctgt gttaattttt   69000
gtcaggtttc cattcagttt taatatatga tatttttatag ctcaaagatt tggagtccca   69060
taggtaatat taataagaaa gtcattttaa ataattgaga ctttatatcc taattcaaaa   69120
tttgacctgc cgcgcttttt aggaaggcat ggtacgatgt gatacagcgg ttggaacacc   69180
tgattatatt tcccctgaag tattaaaatc ccaaggtggt gatggttatt atggaagaga   69240
```

```
atgtgactgg tggtcggttg gggtatttt atacgaaatg cttgtaggtg agtaaggaag    69300
attttatgtc tctctattac agttgttcat ctcaaaactt gccacttggc tctttctaat    69360
atatttatta tattaagcaa tcttgatttt atttgtgggt aataaacatg atccaaacct    69420
gcttcgtatg tgtttttaaa agcatttaga ggcttagagc aactttgtga tgtgttcttt    69480
tatatattag gtgtatgttt ttagtttaat acatacctaa taatcttttt aaacgggtaa    69540
ctttgactct tcctttgaaa ctgacttttt aaaaatgtat ttcattttgc ttttgttttc    69600
tttatcaatt tttcaggtga tacacctttt tatgcagatt cttggttgg aacttacagt    69660 aaaattatga accataaaaa ttcacttacc tttcctgatg ataatgacat atcaaaagaa    69720
gcaaaaaacc ttatttgtgc cttccttact gacaggtaaa taattttaaa actgagcctg    69780
tattaattct gaggacttct catcttctgc tccattttta aggtccatat ctgagcttct    69840
acatgtaaat tgttagaata taaatgacag tgaaacctga tgtaatttta tgatattcta    69900
gatgtctttt gtagatctca actcacttat catacctaag aaaattgtgat aataatacag    69960 tcttggctga tggctaaact agatgacttt tttcttttat tgttcaattt ttaacttggt    70020
taattataaa aattactgtg tatttactg aatctaaaaa aattttttaa cataacatct    70080
ctgaaattag agtacatctc acagtcaatg gtatgagttg ggagcatcct ttttcatagt    70140
ggtataaaaa cggtgataca ccttatactt taaaccattt tagatttgat gatgtatggt    70200
atatggttgt tgaaagagtc aatagtataa agccattttt aaaagtatac tatctttttt    70260
cttctagaca taatagttgg tgttccatct tgtagatcca acaagcattt taataataat    70320
gtctgtctgc atttttgaaa gaaaaatggc atattatata tacctttgtg gtttactttt    70380
gaaatttgaa agtgaaccag atgtattagt aagattatat ttaatgttta tgattgtata    70440
ttgttaaata ttagggagac ctagtacttt taaatatgtt tcaagttgag atttgcttta    70500
acttgtctcc cttcattatg tcctttagag cttgaagtat ggttttcaa atgttactt    70560 tttttttttt tttttttttt taaatagaga cagggttttg ctctgttgcc caggctggtt    70620
tcaaactcct gggatcaagt gatcctccca cttcagcttc ccaaagtgct gggattacag    70680
gcctgagcca cccatgcctg gctaattttt acattgattg attgattgat tgagacagag    70740
tctcactctg ttgcccaggc tggagtgcag tggcatgatc tcggctcact gcaacctcca    70800
cctcccggat tcaagtgatt ctcctgcctc agcctcccaa gtagctgtga ctacaggttc    70860
ctgtcaccat gcctggctaa ttttttgtatt tttgatagag agggtttcac tatgttggcc    70920
aggctggtct tgaactcctg acctcatgat ctgcctgcgt tggcctccca aagtgctggg    70980
attacaggtg tgagccaccg cacctggcca atttttacat tttaatataa agcattgtat    71040
tatgctgttt attaggtgct agggatatag tagtgaggaa gatacagagc cacttttctc    71100
aaatacctca tagtcctttg ggggaattag ataagcaaat cagacattta tagtacacac    71160
agctaattac catgagataa gtaccatgtg ccggagaacc atggagaggt ttctaatcc    71220 agtttgagag ttagtgaaag cttcttggaa aaattgtcac atgtctaagc caacttatct    71280
tttagcttat gcaaaaactt agaatttaga gtattttctt tatttataag cactgtacta    71340
gggaaaaaag gtgctaactt tctttttcca attcagctaa aatcacattt ttaaaaactt    71400
tttgctcacc aaaaagagg ctggtatcag taacttgtcc agtgaaagct ctgaattctg    71460
tggcagtatc aagaattagt agtcattggc ttttgaatgg tcagaaataa ttaatagatt    71520
ataaattgga agttcaaaat tttaaatgtg tttctggagg ttttggtag catctggtat    71580 tgctgcctaa gtaaagtttt ggttggggaa aaaaagcct aactttacca ttgtaagaaa    71640
```

```
aaaataacac acacacacaa aaaactgtca agaaaatgca tggtgctttta ttcattttgc   71700 taatgaagta aggtggtgat taatctggat ttttgttgtc agtagaaaag tcatgggtgt   71760
tttttgtagt tattctttag ttttcttttt tttgagacgg agtctcgctg tgtttcatcc   71820
aggctggagt gcggtggcgc aatctcagct cactgtagcc tctgcctccc gggttcaagc   71880
gattctcctg tctcagcctc ccaagtagct gggactacag gcgtgttcca gtacacccgc   71940
tagttttata ttttttagtag agatgggggtt tcacagtgtt ggctgggctg gtctcgaact   72000
cctgacctca ggtgatccac cccacctgag cctcccaaag tgctgggatt ataggcatga   72060
gccaccatgt ccagcctttc tttagttttc ttttaaaaaa attctttaat gttctcaatc   72120
tttaacatat tttctatttg ggctgatact atgctgacaa tataatttca ccttagaact   72180
atatttgtcg tcctacactg atttaatatc ctgcccacaa ataaacctgg acaggttata   72240
ataagatctt aaatgattga ttacttttct ccttctgtca ttattcaggg aagtgaggtt   72300
agggcgaaat ggtgtagaag aaatcaaacg acatctcttc ttcaaaaatg accagtgggc   72360 tgggaaacg ctccgagaca gtaagttttt ttttttcttt catattttag tgaatatttg   72420
aaagtagttg tggtagtttg ttgaaactac attgctaaat atttgtgtgt atctgatgaa   72480
aatcagaagc cacaaatact atatgggaat tgtcctaacc tattaatttg ataatattgg   72540
gcagattata ttgttactcc tcttatgtcc cacgcaggat acccagatga aatataaatg   72600
taatggattt aggctcacca gtcataattt tacatttgat cttgttgaa ttgttcattt    72660 taggcgttag ttatcttatt atggaggtgg tcaataagta gtaagtaatg agattaaaat   72720
atatgttttt gtgagaagac aagttattct cttgttttta ttaaaaccca aaatataaga   72780
aggttctatt attaattcca gaattcaatt taattttatt tatgagttta taggatattg   72840
tgatatactt gattccatca ggcttttgca gctggcaatt cagaaacaaa aatgtattgt   72900
ataagaaact aattttcagt cagtttagaa cactttctta cttttttaaaa aaagttaaaa   72960 ttacaagatg attcacagaa aactctacaa catagctgaa tcaaaattat catgacacca   73020
aaggttctca tcatcttcgt ggatttggga ggtaaagaat tcatctttcc cctgctgaca   73080
tcttaggatt tttttcctg ttcatctatc agagaaagga taatgtatct cagtccctaa    73140
cttgctgcct tagcaatagc agtgaatagt aacaatggaa atgaactcag ctaccttatt   73200
ttagaaagtt acacagtagt tatttgtctt aaggactgcc tatctagttg agacagtgaa   73260
ggatagtact ttgcagagag atggaaatct tgttaattct gatgaaataa atcatgtagg   73320
tttgctaata ttagtgaagc attctagtta tcaaatattt taaagaaca attgtattgc    73380 cttcaagtac tatagcacag tacttacatt gtgctgagct ataaaattgt ctaaggagga   73440
gaaagggaaa ataaatcctc tggaaattaa gaaattatac aacaaagaac atcattgaat   73500
gaccagctgt ctgagaagct gtaagagcag cttgactttg ggagaatttt attagcaatt   73560
atatactagg aaataaggaa cttcctcctc ttcagaatta aatgtgacat aattattatc   73620
ttcatgctgc aagtgaaatt gttgcatgac aaagagatga tcagggagtg agaaatggtt   73680
acatcaaaac acttttttgtg ttttttattca ggttattctc ttagtaaagt ttaagaaggc  73740
tgaagacgta caaatattat tataaatctg aataaaactt tgaagggaac tgaagaaaat   73800
acaaaataat attttgtatt gctttaaatt ctttttcaaa gttaagcaat gcataaataa   73860
ttatagaata accacacaat aaatcaaccg caaaagtaac aaggatattt ttcctttat    73920 gtattgaaaa accgatcact tgaaagagga ggtaatttag tcaacaacta tttactgaac   73980
acctgttgta tattgatcac tgttcaattt cagacactgg gaaaacagca gtgatcaaac   74040
```

```
caccaaaagt tttctttctc ccttctggag ctcatagtct tatggaatta gggagtccag   74100
atcagtggca ttttattata ttgctgtacc tccttcataa aactacttaa gatctgcatt   74160
atctatggtt ttattctagc gtggttagat ttagcatact taaaagaatt ttggtagttt   74220
ttcctaattc taagaggtcc tgttttgtgg ttattggaaa aaacaaagaa aaattgaaat   74280
ctgtagaact tattgttctt tgcttccctt cccctcttcc taccccttct ttacttccca   74340
cccctaaaat accaagaatt cttttattct gaactgacct ctttgacctg ctaaattttt   74400
aaaacttatg taacagttat aattcctttt aattttttg ggtttccatt ttccgtggca   74460
aaattgcttt ctaatacaaa taatagtttt ttttggtatt tttaccactt aacatgtctc   74520
cacattgcaa tggcaattaa tcttcacctt gtgttccttg gtaatgtggg agcaggatac   74580
aaaatagcct gattttggc agaatttcca tgagcttcct gatcttgttc acaaagtatg   74640 aagatttaa cactattttt ccactcattt gagataaaat tgaaggagta acatgagtaa   74700
gatcaaagat aggagaagga caaagaaat gaaaagacct aaataactta ctacaggtca   74760
taactgcaag caaacaacaa tgtcaaaatt cagatctaag tctcttaact ccaaagcctt   74820
tgatctttga agtaccatgt acgatttaaa gatcgttacc tgttcagtgt tatatagatc   74880
aaaaatggaa ggaattgaca attgttggca gttaaatttg ggggaaaaaa aataacattt   74940
attacatatt tagcatacat tattaataat actgttatat ttagtattta acatagtatt   75000
aataatttca aatgaaataa atggcaaagg attttgctag ttaccacata tttaacatat   75060
taatattaat aatgaatagg gccaggtggc tctattgtac agtgttctac agtattatac   75120
agtggctcat gcttgtcatc tcagcacttt gggaggccaa ggtgggagga cctcttgagg   75180
ccaggaaacc aacctgggta atgttgcgag accctatctc tataaaaata aaataaaaa   75240 attagccagg tgtgatggca tgcacctatg tttcaactac ttgggaggct gaggtaagag   75300
aatcacctga gcccaggagt tcaagggtgc ggttagctat gataatgcta ctgcattcca   75360
gcctgggcaa cagaacaata actgtttctt tagaaaaatt aataatacta cattaaatat   75420
gtggtaactt gcaaaacact ttgccatata ttattatctc atttgaaata agatattggt   75480
gttacttaat caacctatag tttgtgggca acacacaaga tgctaacagt ggtaatactt   75540
ctgccggctc aaaactcatt gtgtacacac atatatatta ttctaggttc tgtgagttaa   75600
tcaagactag taacctttct gtttgaattt tacattctca cgggagagat tatcaatgtg   75660
ggctttgtga ataaagaact gaaggcctag caagtttcag ggctctttta cttaggagtt   75720
tagacgttct gaacattata atggattttt aaaaaataag ttatctcttt gtattgtgat   75780
aaagtatgca taagataaaa ttccccatgt tgggcatttt taactgtaca attcagtggc   75840
attaagtaca ttcacattgt cttaaaacta ttacctctac tgtgtccaga acttttttcgt   75900 catcctaaac taaactctta aatagtaact ctccatttcc ctgtccagta atcactattc   75960
tttctgtctc tatgaattag actactactc agggtgtttc gtttaagtag attactataa   76020
tatttgtctt tttgtggctg gtttatttca cctagcacaa tgtcttcaag gttcattcat   76080
gtcatagcat gtatcataat attccattgt atggatatac tatatttgt ttatccattt   76140 atccgttaat agacacttaa gattgctatc tcttttagct attgtgaata acaaacagta   76200
gaatacaaat atctgctttc catattatat tacggatatt ttatatccat attaatgtta   76260
tatatatgga tattctgtaa tatccctgtt ttctattaat ttgagtatat acctagaagt   76320
ggaatggcta agtcatatga taattagtta gttttgtaga gacagagtct tgctgtgttg   76380
accaggctag tctcaaactc cagggctcaa gagatcctcc tgcctcagcc tcccaaagtg   76440
```

-continued

| | | | | | |
|---|---|---|---|---|---|
| cagggattgt | aggcatgagc | caccatgctc | agccatatgt | ttaatgtttt | gaggaaatgc | 76500 |
| cataacattc | acaacatttg | caccatttca | cattcccagc | agcagtgcac | caaagtgctg | 76560 |
| ggattgcaga | cgtgagccac | cacgctcagc | catatgttta | atttttttga | ggaaacgcca | 76620 |
| taatagtatc | cacaatgttt | gcaccgtttc | acattcccaa | cggcagtgca | catgggtctg | 76680 |
| gtttctccac | atctccagca | tttgttcttt | tctgttttgt | ttgtttgttt | tttgtgttta | 76740 |
| aatagtagtc | atcctaatgg | atgtgaagtg | gtatctcatt | gtggctttga | ttagcatttc | 76800 |
| tctaatgacc | aggaatggta | aacatcttgt | catgttgctt | attggccatt | cgtatatctt | 76860 |
| ctcttgagag | atttctattc | aagttctttg | cccattttaa | aatttggtgg | tttggttttt | 76920 |
| ttgttgttgt | tgagttatag | gagttcttta | aaaattttgg | atattaatct | cttatcagat | 76980 |
| acatggtttg | cagatatttt | ctattctctg | cactctgtta | ttagtgcttt | caagcacaaa | 77040 |
| atttttaatt | ttgatgagat | ctggtttatt | tcttcttttg | ttgcttgtat | ctttggcttc | 77100 |
| gtatttaaga | aatcattgcc | aaatccaatg | tcatgaaatg | tcttacctat | gttttctttg | 77160 |
| aattttatag | tttcagctag | tatgtttagg | tctttgaccc | attgtgaatt | aattttata | 77220 |
| tagtgtatag | taagggtcca | atttaacatt | tttgtatgtg | gatatccagt | tttcctaaca | 77280 |
| ctatgtgttg | aaaggactgt | cctttccctg | cattgaaagt | tgttggcacc | ttgtatcaat | 77340 |
| cattaaacca | tatacatgag | ggtttatttg | tggggttttt | gttgtattcc | attgatctgt | 77400 |
| ataagtttgt | ttttatgttg | gtaccacact | gtatgattat | ggtagctctg | tagtaagttt | 77460 |
| tgaaatcagg | aaatgtgagt | ctttcaactt | cgttctttt | caaaattgtt | ttgactattt | 77520 |
| gggatctcat | gagatttcat | atgaattta | taatgggttt | ttacgtcttt | gccaaaaagg | 77580 |
| acatagggat | tttgatggag | attgcattga | atctttaaat | tactttgggt | agtattatca | 77640 |
| tcttaacaat | gttatctttt | ccagtccatg | aacacaggat | gtgtccccat | ttatttaagc | 77700 |
| cttctttaat | ttcagcaacg | ttttaagtt | tttggtgcat | aagccttaca | cctccttggt | 77760 |
| taaatttgtt | cctaggtatt | tcttttgac | tttttttc | atttttttt | tttttttga | 77820 |
| gatggagtct | cgctctgtcg | cccaggctgg | agtacagtgg | ctcgatctcg | gctcacggca | 77880 |
| agctccgcct | ccagggttca | tgccattctc | ctgcctcagc | ctcccgagta | gctgggacta | 77940 |
| caggcacccg | ccagcacacc | cggctaattt | ttttttttt | tttttttt | ttttttagt | 78000 |
| agaaacgggg | tttcactgag | ttagccagga | tggtctcgat | ttcctgacct | cgtgatctgc | 78060 |
| ccacctccgc | ctcccaaagt | gctgggatta | caggcgtgag | ccaccgcgcc | tggccttga | 78120 |
| cattatttta | aatggaattg | ttcccttaat | tttcttttca | tattgtttat | tgctagtata | 78180 |
| tagaagtaga | acttttattt | ctgatcttgt | aacctgcaat | tttgttgaat | ttgtctatta | 78240 |
| cctctaatat | attcttttgt | agctccttta | gggtttcta | tgataggatc | atgtcacctg | 78300 |
| caaatagaga | tagttttact | tcttcttttc | caatttatat | gccttttatt | tatcattctt | 78360 |
| gcctaattac | tcagactaga | gcttccagta | aagtgttgaa | tagcagtggt | agaagtgggc | 78420 |
| accttgtctg | ttcctggtca | tagggggaag | cttttagtct | ttcaccgctg | aatataatgt | 78480 |
| tagctgtggg | attttcatta | atgtcctta | tcatattgag | gaagttcctc | tctagtcctt | 78540 |
| gttggccagg | tgttttcaat | catgaagggg | tgttgtgttt | gtcaaatgct | ttttgtatga | 78600 |
| caactgaaat | gatcatatgg | gtttttttc | ttcattttat | tttatttttt | taatagagat | 78660 |
| aaggtcttgc | tctgttgccc | aggctggaat | gcagtgccat | gatcttagct | cactgtattt | 78720 |
| ttgaactctc | agacccaagg | gatcctcctg | cctcagcctc | ctgagtagct | aggaccacgg | 78780 |
| tcatgtgtca | ccacacctgg | ctaattttct | tttaattttc | tgtagagctg | gggtcttgct | 78840 |

```
atgttgccca gactggtttc aaactcctgg tcttaagcca ccctcccttg gccttccaaa    78900
gtgctagggt tacaggtgtg agccactatg gccctatttt gattcttat ttcttttaaa    78960 atagattttg tcagcctgtg ttttctagga atgtctctat ttcatctaag ttatctaatt    79020
tgtcactgta ggccgggtgt ggtggctcac ccctgtaatc ccaacacttt gggaggccaa    79080
ggcaggtgga tcacttgagg ccaggagttc gagatcagcc tggtcaacat ggcaaaacct    79140
catctctaca aaaaaaaaaa aaaaatagc caggcatggt ggtgcactcc tatagtccca    79200
gctacatcag aggctgaggc agagaatcac ttgaacccgg gaggcacagg ttatagtgag    79260
ctgagattgc accactacac tggagtgtag tgcaatgcac tcctgggtgt ttttgagact    79320
ctgtctcaaa aaaaaaaaa aaaaactttc ctatttgttt tctatgtcat atatttcctt    79380
tttattcctc agctaataca ttattgcttt cttttgtgtt tagttttttc ccctagtatg    79440
ctattttgat tccttcttct tttcctttc tgtatatttt ttagtcattt tcttattagt     79500
taacgtggaa ttcacttaa cattctaaat tgaaaacaat ctaggttgaa ttgataccag    79560
tttactttga gtagcttaaa aacctgcttc tgtttacatt tatctaaata gttacctta    79620 ctgatactcc ttttcttct tcatatggct ttgagttaag acagtttgat tatggcatgt    79680
gattatgatg tgtcttcatg tggagctttt ggagttttc atagttggca ttcagcttct    79740
tggatgtgta gatttatatc ttttaccaga ttttggaaagg tttggccatt atttcttcaa    79800
atagtctttc tgccccttc tctccttctg gaactcccat aatgtgtatg ttggtctggt    79860
tgatgccaca gtttccttag tctctgttca cttttcatc cttttcttt ctgttcctca      79920 cacttgataa tttcatttgt cctatcttca agttcactgg ttttttttcc tctgcctgtt    79980
cagatctgct gttgaagcct tctagtgaaa tttaacttc agctattgta cttttcagtg    80040
ctagaatttc tatttggttc tattttcgat ctctttcatg atatttttc tttgttaagt    80100 catcatcttc ctggtacttc atccatagtg ttcatttgct ttttgaacac atttaagaga    80160
gtttaagatt ttgttgagta aatctaatat cttggttcc tcagaggtgg tttctatatt     80220
attttctttt tttttttttt tttttttgag atggagtctc gctctgttgc ccaggctgga    80280
gtgcagtggc acgatcttag ctcactgcaa gctccgcctc ctgggttcac gccattctcc    80340
tgcctcagcc tcccaagtag ctgggactac aggtgcccgc caccacacct ggcttatttt    80400 ttgtatttt tagtagagac ggggtttcac catgttagcc aggatggtct cgatctcctg      80460
accttgtgat ccacctgcct cagcctccca agtgctggg attacaggcg tgagccacca     80520
cgcctggtgg tttctaacat ttttctatat tccctgtgaa tggcccatat tttcttgctt    80580
ctttacatgc tttgtaattt tttgttgtaa actggacatt gttttaaagc agctgtatcc    80640
ttctaagagg gacattttgg atattacagt gttgtaactc tggaaatcag attcttcctc    80700
tttcccccag ggcttgcggt tgttgcttgt tgtgggctgc agtcattcat tcatttagtg    80760
acttttccaa actaattttg caaaatctgt attccttgtc atgtgtattc actgaaatct    80820
ccatttcatt atctcagcca gtgacagaga tttccttaaa tgccaaattt ttatagcctc    80880
tttcttcatt aaacactcct tgcttgttat tagttttta ttagattcca gagttctcag     80940
aaagttgctc tggtcgtttt tgccaactca atggttgctt cagtggaggt atgatttctt    81000
tgagttccct actctgccat ttttgacaac atctgctgga ctctttttta tggaacatga    81060
tttctaaatt aacagttatt taatgaaaac aaattttaa acaaatatat actgatgttt      81120
attccatagt tatctttatt cttattagtt ctgaagtgat taaatggcat tatataaagc    81180
ctaagcatct taatttagaa gcagaaataa ttatttttat aactcttcca atattttccc    81240
```

```
cacttgtatc tcagaattta aacaggtgag aatttgtcat tttagaacta ctgtgaaata    81300
gtgtcattta taaaaagagt aggtccatca gaaacagcaa gagaaaatgc agcacactta    81360
ctctgttctc tctttctgat ataattttaa agcaggtttt ctgagcttta gcagttgaca    81420
gatcattctt tttgtgggga ttatcctaaa cttaaggatg tttagtggca tcctatgact    81480
gtactcatta ggtgctagta acaccttttt tcccattaat gacaaccaga atatgtaccc    81540
agacattgct gaacaccttc cagcaggcaa aagtgtctct gattgagatc actcttttaa    81600
cataaaatgt atgccaagac cataattaac ttctgtattt cccaagggcg gcaactgttt    81660
agtgttttca cctcatttta caaatattag aaagctggcc atgtctaatc agacagttct    81720
gttggccatt aaggaaagtg aatggtggaa aaagccctaa tatccctctt gtgttactgt    81780
tagtactaca gcttcatttg gctaaatgtg ttgtttcgtt ccctaaatat taatttactg    81840
tgtctcagat ggcacaagaa taggtatttc ttgcctgaaa tacccaggtg attgaaaaga    81900
aaattgattc cttttcccta aaagaacatg aggttattgt acctaaaata attttttagt    81960
attttgatga tcataattca gggatgtttt attatactac agtatcttta agctaaaaaa    82020
taaattttct taaaatttta ttttcttaga atttattttt agatgtaccc cttgtaacat    82080
tcaagcccca aaaatagatg ttagtagtat tagttttata tggaattttc tcctatatta    82140
tgaatattta aacgttgtca catacggttt tatattatta agtatctgga agacttggtc    82200
cacatcaaat ttataattct tgaagatgtc atatccattt tttatattac tgccctttttt    82260 tattaacaat gatatcataa atacctcact gcattagtct taatcacttg attctagagg    82320
tagctagtct gaaaatacaa ttccaaatcc attgctcctg tggcttaatc ttatggagat    82380
attggggtgg gagaaaggag tattgatcat ctggattctg agtgagtaaa aatatttcag    82440
taccaaatta tgatgtccag gaagctaaga agtaaccttt atttctggtt tactatacag    82500
cagattaacc aaaaaatact atatttaaag ctaaacaatt ttttcgagta cagtttgtta    82560
tgctttagtt tctaaaaagt ctttttctgta gtcccgaatg cttttgtgta ttttataccct    82620 tggtacattc taaaacaaac cttagtaata cttgatttgt aatagtcaag ttaaacccaa    82680
ggtatagata attataggtg actttgaaga taattgtttc atagaattac ataatgatca    82740
attatcagtt gattttttagt cctggtaaag cttgatgtaa taggattcaa gccaggtgga    82800
atttgtggtt tgcaaggttt tataagagag aaaccatcag tagttggtat ggaatgtgct    82860 tcacttttact tgtatttttaa gtttgaagtg aacaactaat tttgttttgt ctttagctgt    82920
agcaccagtt gtacccgatt taagtagtga cattgatact agtaatttttg atgacttgga    82980 agaagataaa ggagaggaag aaacattccc tattcctaaa gctttcgttg gcaatcaact    83040
accttttgta ggatttacat attatagcaa tcgtaggtaa gtatgctaaa cagtgattat    83100
aggagtaagt gctgattttg ttcttagaaa tatctaaaaa tcatttttaa agtagattta    83160
atgctatata aagatacacc ttattatgca attttttcatt gatgcatgat atttccagta    83220
tttcatattt aatttctctt ggactcatcc atgtttagga cattgttttt caaaattttt    83280
ttgctaaatg atatactata tatcctcaag ttacaacaat taataggtca aaaaatgcca    83340
taaatactga tattttgatc tgtagactta tggtttataa tacattttga aacaacatgt    83400
agactttttt tgttttgttt tgttttgttt ttttccacga tggagtcttg ctctgtcacc    83460
caggctggag tgcagtggca caatctttgc tcactgcaac ctccacctcc tgggttcaag    83520
cagttctcct gcctcagcct cccgagtagc tgggattaca ggtacctgcc accacaccca    83580
gctaattttt gtattttttag tagagatgtg gtttcaccat gttggccagg ctggtcttga    83640
```

```
actcctgacc tcatgatctg cctgcctcgg cctcccaaag tgctgggatt acaggcgtga    83700
cccaccgtgc ctggccagca tgtagacttt tctagcatta tcatcaccat attgatgctg    83760
tatcaatttt tagctcttca aaaattaagt gggccgggcg cggtggctca cgcctgtaat    83820
cccagcactt tgggaggccg aggcgggcgg atcacgaggt caggagatcg agaccatcct    83880
ggctaacacg gtgaaacccc atctctacta aaatacaaa aaattagccg ggcgtggtag     83940
cgggcgcctg tagtcccagc tactcgggag gctgaggcag gagaatggcg tgaacccggg    84000
aggcggagct tgcagtgagc cgagatcgcg ccactgcact ccagcctggg cgacagagcg    84060
agactccgtc tcaaaaaaaa aaaaaaaaa aaaaaaaaa attaagtgat tcctccccaa      84120 atttttaccat gtgttataaa atgtagtatt acctccactg tgaccttgga caaataactt   84180 tggccttttta tgcctccatt tcctcaaaaa tagggatgat gataataaca ataatactgc   84240
ttgcctactt acctcatagg attgttataa ggtttaagta aattaaaaca cagtacagca    84300
cttagaagag ggctttgcat ggtgtaagca ctcagtgtta actattatta ccattagtat    84360
gagttcatgt tagctttact ctaatgtact tgagatttaa gttaaacatt taacattatt    84420
ttagtgtgct gagcattcat tcattccaca gatatctttg ataacttatt atttgtcagg    84480
tatatactga gcaccaaatt gcatggagaa ggatgaataa gatacagtgc cttctcttga    84540
gatgctcaca tcttggtgag aaatgcataa attgtgcaat gtaggttagt aagaactaca    84600
tagtagaaat ctcggccagg cacggtggct cacgcctgta atcgcagcag tttgggaagc    84660
caaggtgggc aggtcacttg aggtcaagag ttcgtgacta gcctggccaa tgtggtgaaa    84720
ccccgtctct actaaaaata caaaaattag ccaggtgtcg tggcgtatgc ctgtaatccc    84780
agctacttgg gagactgagg caggagaatc gcttcaacct gggggcgga ggttacagtg      84840 agcctagatc acgccactgc actccagcct gggcaatgga gcgagactct gtctcaaaaa    84900
aaaaaaaaaa aagaaagaaa aagaaatcta acaaagtgc tataccagta taatgcattg     84960
aactatatga taacacttac tgggtgggtt aaatctactt ttaattaccct caaaaatatg   85020 tacttctaat caaattatac tccttttggaa tggtatcaga taactgattg gcttggagta   85080
aattattaca tttgaggtca ttataactaa tcttattta aagtgaaggg tcttgtcatt     85140
ttagtgtaag agccattcaa gttaatctta gaaaacaaaa agacaattta gtccggcttt    85200
ttgaaacttc ttcagtaatc cactgtaaga tagtacttaa tactttttgt tgcaacatca    85260
atgagatagc tggcacttat ctttttttcc tccctaacac tctgtgagta taatattata    85320
actgtattca attaacatac atatacagaa gagcttcagg gtggttttttg ctgaagcatt   85380 cttttttttt tttttttttt tttttcgag acagagtttt gctcttgttg cccaggctgg     85440
agtgcaatgg cacgatctcg gctcactgca acctccgctt cctgggttca agcgattctc    85500
ctgcctcagc ctcccgagta gctgggatta caggcatgtg ccaccatgcc cggctaattt    85560 tgtatttttta gtagagacag ggtttctcca tgttggtcag gctggtctcg aactcccgac   85620
ctcaggtgat ccgcccacct tggcctccca aagtgctggg attacaggtg tcacccactg    85680
tgcccagcct gctgaagtgt taacttttttg tatttttatc aattattctt tgacttggtt   85740
tctgaaacac tcaagttgtt gatataaaca accgccaatg ttttttgtatt ttctgtagta   85800 gagtccagca gttaataact ttattttaggt ttctctgtat aatggtaacc ttcagttaaa   85860 taaacatttta ttatactatt tgtcctacat tatcatgcac ttgattatgt tctctagctt   85920
ttcttcgtat tcatgttttta tggcccaaac taattttttaa gtttcttaaa agtagaaatt  85980
atactgtgtt cttaactgtc acagcctatt gacaaataaa tatagtattt tttaagtaat    86040
```

```
cacttactac ctgaacaggc aaaggtacgg ttgctgttca taaagaaaga accaacaaaa   86100
tatatatata tttttgaaac aagagtctca ctctgtcgct gaggctggag tgcggtggtg   86160
tgatcttggc tcactgcaat ctctgcctcc tgggttcaag tgattcttgt gcctcagcct   86220
ctgagtagct gggattacag gtgcgtacca ccatgcctgg ctaatctttg tattttatt    86280 agagatgggg ttttgccatg ttggccaggc tgttggccag gctggtctca aaccccctggc  86340 ctcaagtgat ccacccacct tggcctccca aagtaatccc agcggattac aggtgtgagc   86400
cactgcacct ggccctggca aaatattgat tagctttatt gtaatatgta agcataattt   86460
tgaatataca gatatgaaat agaaaacctc tgaaattctt atccctgaaa tccagatata   86520
cttttaatac caagggcaga atcattgtt gcttaattat agctgaatta aacatgattt    86580
ttaaaatagc cttaagctat attcctaata tagtaactcc cgttttgtaa aaagttacct   86640
aaatgaccag attctatgta aaagcaccaa tataatatgc aaatgtacct tgatagagaa   86700
aagacagaag gtgaagaat taatggatgt atacaagtga tgtccttaca tttcctttgc    86760
tgcattcaag cttatattac taattttgca gaagactaaa atgtcagtct cagtcacata   86820
gcatgttaag tttagaaaat atcttagaga tgaaacagtc tcatctaatt tagatgccac   86880
tggcattgct atatgcctta tttatattac ataagcagaa tctcacattg aatttctgag   86940
atgcttagta gtcaatggaa ttaaattgca ccacacctag aatttgtcat tgttatatg    87000 ggacttttcc tctataaagc tgctacacag cccctattat tgtcttaaag ttatttgaat   87060
ctccatttga tctgaataat ttttcaagga aaacctagga agtggcatat ttctagctgt   87120 ttctttata gtaccattgt actgtgtatg tttattgata cttaatggat acttgattat    87180
cttctgttat tcactaattt ttaaaattta cttaaactgt tctttttggaa cattattaat  87240 atctggtgtg ttaacacatg cctccaatag ctatgaagta tactgtaact atttgatctc   87300
cttttgcaat agctctactg gttaatcagg gtgctgactg tagtggtggt gatggtagaa   87360
gtagtgatta tggtagtcgt agcatggtgg cagtaggagc aacactggca gtactagtac   87420
cttaccttta tataatattt ggtagcttaa aaaattgttt acatatatga tctatttaga   87480
ttgtttgaga atcttgtgag acatctaaaa aagacctcta aattagttca ctaatagctt   87540
tatttatata caattctaac tttacactga atttaaagaa ctctgcaagg ctgggagtcc   87600
caaaagatta gcagcatcac ctaaactttg gttctgttat ttcacccaca taggcaaaaa   87660 ctttttttgac ccgaagaggc aatattatgc tttgctgaag gatagttggg tgcaggagag  87720
gtggttatgc atatgtctgc agaagtcagc agtttcttac ccccaattct tatatacaaa   87780
aagctctgaa aactgaatgt ttttaagtta tttgtttggt ggaaaaacct gtcataacct   87840
gctctcatga ccagaaagcc taatctgaac taacttgaga ctatggtttt tatttatcct   87900
acttggtatg aatattctta tgttttgctg caggaatatt aagtcatatg tttacaggct   87960
gctactattt ttagacctaa ctgggtgttt tatttaatat atgtatcatt tctgaattat   88020
gtttataaaa attatgaacc tatacttaat ttttaaaaac aaagttacta taactgaaca   88080
taaaataggc gtgtagtatt tattattggt tgtcatggga tattacagag ttttttgttt   88140
tctttctttt ttaaactttt ctttccctca gatacttatc ttcagcaaat cctaatgata   88200
acagaactag ctccaatgca gataaaagct tggtaggtat tttcttagta ttaagaaaat   88260
tgttttaaaa attgttttgt ggataatata tttgtgggta tgatagtaaa tttatatatt   88320
gtttgtgaag ctgtggttag ctgaacttag atttttatgg cactttcatc tcccatctcc   88380
ttttcagtct gattttttgc tcaaatatca aatggaataa tatatttgga ggcagttagt   88440
```

```
aaactaaatt gttacacaga ttgacagtgg tcatcttttt taatcttcgg aatcaggaac    88500
tatgatatat caatgtatca ttaagggtct tgacaggcaa acagattaca tgttcaaaat    88560
atttaaacag agagttttgt gtgtatggca aatatacgta acatgaaatt taccgtttta    88620 atcatttta agtgtgcagt tcggtggcat taagcacctt cacatagttg tgcagccatc     88680
actgccatcc atctctagaa ccttttcatc atcccaaact aaaaatctat accaattaaa    88740
cagtaactcc tcatttcacc ctcccccag ctcctggtaa ccactgttct actttctgtc     88800
tcaatgaatt tgcctattcc aggtacctca tatgaggtgg aatcatacaa tatttatcca    88860
tatgtgactg gcttatttca tgtagcataa tgtcttcaag gttcatccat gttgtagtat    88920
atattaaaat ttccttcgtg tttaaggctg agtaatattc cattgcatac atatatatac    88980
acacacacac acatatatac acacacacca tattttgca tttattaaat caagagttta     89040
atgaagggat gattaacatg ctgtgaacat cagtagaggg aaacaataaa gggtactaaa    89100
gcacccatgt atgaacaaga gtgggaagcc attgccctat actgaaggag caaagagaga    89160
aaatcttatc gtagctcaga gaaagcctga catcatagaa gaggaatata aaacgtagag    89220
cattgtgaaa accacagtaa agcacaaagg gtgtagggaa atgaatattt ctttctttta    89280
ccttcagatt tctgctggtg tctcctgtgg gttgaaacca accttaaaat catagggcta    89340
cagagtaata caggcaatgc aatctgtaga ttttaaggca aagaagagca gaggatgaat    89400
tttcaaggtt agaagggaat gggggaaatg gagaataacc agtatagtta gcatcatctt    89460
aatttgtcca ctgagaagta tattactcca gaaaatacat tttagttgag ttctttctgt    89520
tgtttatata gctcatgttc tgacacagag gtaaaacaaa atcttacttg cttacatttc    89580
agaaggtcct tttgggttaa caggaatttt ctgaaaaata tccagagtaa ttatctgtcc    89640
attcctagag cattctttga acttttgtc tactatagcc tacatttttt tgtgggggg      89700 cacagagaca ttgcaagcct acatatttt aacagaggag aggaagaggt agcagccatt     89760
tttaaaaagc tgataatgat tcttttcttt ctccttgata tattgactct taaatataag    89820
agaacatgcg gtgaaaaggg aaaatgagaa aaaggtgaag gaactatatg agtactcatt    89880
tggtgttaag ttcatctttc tcttaaattt taatcccagt agagctgttt ggcaagttat    89940
gtattgctaa caagggctca aaaatctttg acctacgtaa taataaggag ttgctgtaag    90000
tcagctctca ctgtgttact tgactgtaga gttagaagtg ccttcggcct tcaaaaatat    90060
tcaaaggatt catgttttct ttgggctgat tttgttcagt ggtgattacc ataagtttat    90120
cagtggttgc tacctttatc ttttgctcta ataatatcag gggggatata ctaattattt    90180
caacctagaa ctaagtacaa aatcaactaa tttaattttc cttgaaaacc tagcagagat    90240
gctattgaac aactttgcaa ttgccaaata cagtggatga ttttcagccc atatcttatt    90300
tttcttcttt gctgtatttg acactgactg cttcctactt cttttggaact tcaaacattt    90360 ctaaatcttc tatgttccta ttgttccct cttttttacc tcccatattt ttgaatttta     90420
tttatttttc aatcctcttt tcaggatctt cctcctctgc tcactttcaa ttattaacat    90480
ttcccaaagt tctgatcttg gctctctgct ctttctctgt aggtaatctc attcatgtcc    90540
agcttgcttg tctgagctcc agtcctgaat cttttctctct cttctgtata cttctcaggc   90600
atatcaaact aggccagagc taaactcact gttttcctgt ccccattccc tccctagcag    90660
tgtgttggct gtcttttcata atggtattat atctattcta acttccagtc ggtttggtca   90720
tacattgtgc tttccaattg atacctttat ccattacttc ctcttcattc ctgtagcctc    90780
tgccttttat cagatcccata ttctcttgtc tgaactgctt tgatagcttt ttaactggtt   90840
```

```
gctcttctta gaacttcact gccctctaag ctgttcatta accttattat tgtagtgatg    90900
tttctgaggt gccagtatta tgtcatttct catttaaaat gcttatgggg taaagtcccc    90960
aactccagtt tgtgcataca aggatcatta ccttcttagg cttaatgtga gttgttttc     91020
ctattacatt ctgtgctctg ctatagtact tgatttcttt ccatttccca aatatatcat    91080
attttcttct gcctttctac ttttgggctc attgttcatt ctagctaaaa tgcctttctt    91140
gtgccacctt ctttgcttta tcagattatc agttcttctt atcttttagg cctcaactca    91200
aggattatat attcttggca gagttagaag tgacctttc tctcctttgg aacactccgt     91260
agataatttt tttattattt accacagtct attgtaatat tttgtgtata tgtctttggg    91320
acattgtagc ttcttttttc tcttccaatt taactttgcc tcactatgta actatttgct    91380
tcatgagaac aggaaccaaa tctttttaat ttttgtattt ctaatggcct aacgtttagt    91440
aaatgttaag aaagtgcttg ttaaattaat aataaaaaaa ttgagataga aagaggtaag    91500
attaaattaa attattttct aaaaaggttt aaaatattaa catagacttg atattttaa     91560
atgtctaaat attcttagta gaatgagttt ttgttttgt tttaaattaa agcaggaaag     91620
tttgcaaaaa acaatctata agctggaaga acagctgcat aatgaaatgc agttaaaaga    91680
tgaaatggag cagaagtgca ggtgagaata tactttaagt ttttcatatt aaaagtttta    91740
tataccaaat acttacttga aagcttatac cctgtaaaca tctgaaagta aatagaaaat    91800
gaggatgtaa agattactac tgataataca ttcatgatgt gtctcggcta gaattgagaa    91860
gttgtattta tgttggctta gttatagatg tattttcctc agaatattta aagtacattt    91920
gttcctggca gtctgtattc ttttttttt ttttaattca tgaaaataat atattgtgta    91980
ctttgtaata tgttccaact gtgttttcat tacagtcatc agaaagtaaa gcagtattct    92040
tttttttttt ttttaagatg gagtctcgct ctgtcgtcca ggctggagtg cagtggcacg    92100
atcttggctc actgcaagct ccgcctcccg ggttcacgcc attctcctgc ctcagcctcc    92160
cgagtagctg ggcctacagg cgcccgccac cacacctggc taatttttt ttttgtattt    92220
ttagtagaga cggggtttca cagtgttagc caggatggtc tcgatctcct gacctcgtga    92280
tctgcccgcc tcggcctcca aaagtgctgg gattacaggt gtgagccacc gcacccggcc    92340
aacagtctgt attcttaaaa aactgtaatg ctaattcatt tagttgcctg acttactgct    92400
tttttctctt tacataatta gctaactaaa agggcaaatt aggctgcaca tggtggatca    92460
cgtgagggca ggagttcaag accagccagg ccaacatggc gaaaccgcat ctctactgaa    92520
aatacaaaaa attagctggg cacgaaggtg tgccctgta gtccctgctg cttgggaggc     92580
tgaggcatga gaattgcttg aacccgggag ggagaggttg caggaagtcg agatcacacc    92640
gttgcactcc agcctgggcg acagagcaag actctgtctc aaaagaaaa ataaataaag     92700
gggaaattag tttacattaa atcaggtgct ttttgaaatg taaaatgttg aagattaaaa    92760
tatactaaat ttttgatgtg gccattctaa tttccactgt ggttcaccag agcagtaact    92820
cagagtatct ttttctgtgg gtctaatttc agcatgttat tgtcattaga ctcacagaaa    92880
aaatatcttt gagttatgct cacgttatt ttaaattacc tagcataata ctgaattact     92940
tatcaattat aagcaataat ttttataat tatttatgtt tttagtgaat agtattgaat     93000
aaatgaaatg caaggtaac acgaaaagta ttcaacaaat aaaattggga acactggtaa     93060
ttttgtgaca gagcaggtgg ggggtttggt acaaaacaga taaaattctc acttttaacc    93120
attcctgata gattatgtgg ttaagtgtat aatacaaatt tcttttaaaa aggcatttga    93180
atataagcaa ataattaact gaccccagga tttggaaaga atttctaagt ataaaatatg    93240
```

```
taaataaggg gaagaactgg gtagatactg ttatataaat gttgggaagt ctctacatcc   93300
aaattttttt tttttttttt tgagacgaaa tctcactctt gtcccccagg ctggagtatg   93360
atggcgcgat cgcggctcac tgcaacctct gcctcccggg ttcaagtgat tctcttgcct   93420
cagtcccccg agtagctggg attacaggct cctgccacca cgcctggcta gttttggtat   93480
ttttagtaga cgggatttt caccatgttg accaggctgg tctcgagctc ctgacctcag    93540
gtgatccacc cacctcagcc tcccgaagtg ttgggattgc aggcgtgagc caccgtgcct   93600
ggcccaaaaa aattttaaa caaaattaaa agacaagtga caaactggta gtaatggtga   93660
gtagggatca gtttgaggaa gtaataagaa tggctgaatt ggctaataat catatgaaag   93720
tatcacctca aggaaataaa attgagatga aactttaaaa aattatatat tgaattggta   93780
aatagttttt aaaataaaaa cctagtgcta gggattgtgg agtgatattt acttgcattt   93840
ctttatttta tttatttttt ttttgttttt atttttttg aggcagagtc tcactctgtc    93900
acccaggctg gagtgcagtg ccgtgatctc agctcactgc aagctccacc tcccgggttc   93960
atggcattct cctgcctcag cctcccgagt agctgggact acaggcgccc gccaccatgc   94020
ctggctaatt ttttgaattc tttagtagag acggggtttc actgtgttaa ccaggatggt   94080
ctcgatctcc tggcctttg atccgcccac ctcggcctcc caaagtgctg ggattacagg    94140
tgtgagccac cacgcccggc cacttgcatt tctttaaatc aaattctctg cattcaaatc   94200
attttagtta cattcattta ttcaataaaa atttcagtta aagtgtcata taatgtgctt   94260
gtcaacaata tagtactgaa taaatcacga catggcccct ctccacaagg agcttgtaat   94320
ttagcaagaa aaacaagtaa gtaattatca agaagtgtgg taggccaggt gcggtggctc   94380
atgcctgtaa tcccagcact tgggaggcc gaggcaggcg gatcacaagg tcaggagatc    94440
aagacatcct ggctcacaag gtgaaaccac atctctacta aaaatacaaa aaattagctg   94500
ggcgcggtgg cgggcgcctg tagtcccagc tactcgggag gctgaggcag gagaatggca   94560
tgaacccggg agacggagct tgcagtgagc tgagattgcg ctgctgcact ccagcatggg   94620
caacagagcg agatttcatc tcaaaaaaaa aaaaaaaaa aaaagaagt gtggtatgtg     94680 ttaattgggg agagaataaa attatacagg aatatcagga atacatcagg agatgcctgt   94740
actgttttgt cagagatcag agaaagctaa accagaagag tcaatggaaa ttattaggag   94800
aagagtggaa ggaagtgtta gggtccagga ggtgagtatc tgtgaaggcc gtgaggtaag   94860
agaccttgac tggccagtaa gatgtgaggg aaggaaaagc ctgagatgag aatggggagg   94920
atggcaaggt ctagattggg gagaattttt ttttctcttt ttttttgcgg gggggctaag   94980
aaatttggaa tttaagtgta atggaaaaac atcaaaagtc attaaactaa taagtaaaaa   95040
atatatatta aatttgctgt tttcaaaaga agttcctgct taattagcag cacttggcac   95100
tttattcagc taaatgggag tgagggagga tgagtcaagg atgattccta ggtgttgtca   95160
tttacttagg gactctagaa gagaagcaaa ttggtattgg ggtgggagtg tggaacagag   95220
gcagtaagtt ctattttgga gatgctgaat gaggtattta atgagacatc cacgtgaaaa   95280
tgttgcatat ataggttttg aagctcagaa ttcattttg aaccaaagaa agcaaatggt    95340
aatgaagata atacactttg agtgttgcca aatggtgcct ttactgattt gatatatact   95400
acctttctct ttgtttactt tatcctgtat taaaggataa atggctaatt tttgagtagt   95460
ggcaagtatt gcatgacgga gtttagggat ccttaacctg aaatccatag acctccccca   95520
aagagtccat ggatgaaatt tgaagtcctt aaacgtggat gacaaaaggt gaacgttttc   95580
tctaacttat aacttaattt tagcacttgt ttcaattctg agcataggca gcaattcagt   95640
```

```
tattagcagt agttgttaat ttttattacc aatagaaatt atagatgttt tcttattaca   95700
gttgttacag ctatctctaa atatcattta tgctcatcaa tactttgaaa tcactgccac   95760
tagatgttgt gatttaatat attaataagg aagcatatat actactgaat tacacatatt   95820
tttttaaagt ttattactgt gtttcaatat aattggcttc tttttttttt ttgagatgga   95880
gtctcactgt atcacccagg ctggagtaca gtagcatgat ctcggctcac tgcaacctcc   95940
acctcccagg ttcaagtgat tctcctgcct tggcctccca aatagctggg attacaggcg   96000
cccgccacca tgccttgcta atttttttttt tttttaattt ttagtagaga cggggtttca   96060
ccatgttggc caagctggtc tcgaactcct gacctcagat gatccacccg cctcagcctc   96120
ccaaagtgct gggattacag gtgtgagcca ctgtacccag cctaattgtc tcttttaatc   96180
atatataatt tttgtgcttc aaaaaatatt ttgaaaaaag gccataggct tcacttgact   96240
gccaaagaga tccatggcac caagaaagga tacaaaactc tagttaagtg gaaaagtaag   96300
gaatgttagt gtttaacact gggcaataag aaatacgtat atttctaatc tgtattgctt   96360
ttgtttttac agaacctcaa acataaaact agacaagata atgaaagaat tggatgaaga   96420
ggtacttttt gttttctaat caagtttcct ttttgagatt tttccctctt tcaaattgtt   96480
tcgtttcctg agaaaattgt atttgaattc tgtagtttga aacacaaaac agagcagaga   96540
attgtgatga aagcctcacc ttggaactgc agtttcaagt ggtacagatt agattataat   96600
ttagtttcct ttgtacaatt gttttctaca gccgtattaa ttttagtacg taaatttcag   96660
ttcagtggtt ctcgatggtt gaaatgtgag aaaggagcca gagaagcaag cgatcagaaa   96720
ttgaatctca aactatgtca gaaagagaca gacaaataag gaaagagag aaatacagtt   96780 taaaatattt ttaaaagatt aacactgaca taatctcatg taatcaaatg gaaaatatat   96840
tgattttaga atgttcatct tttccatggt tacctgtcaa aattttttat tatcagagaa   96900
acaataacaa gcattcataa ttcagatgtt tgtttgcaaa tatgtaatac atttccattc   96960
ctcttagtca acttctaagt atatttctac tgtgtctatg agtcccatga aaagaaatac   97020
actctctgta gtcttctcct aatacattac ttactttgtc cttttttagg tttaatctct   97080
gatagttttt atgctgtgtt aatttttttct tcccttatag aatggtatct gtcaatggct   97140
tgcttgcttt catgggtagc tttggatatc tatgaagatt tagagagcat ttactaactt   97200 gccttttgtac ttaaccttag cagtatatat ttgactctga gtgtttaagg agtccttttt   97260
tgcatatctt ccacttatat ttaactttta aaacacagat aaaattcaga tgtgctagat   97320
ttaagttatt cattttttcca aattagaagt agagagggaa atttgaggta tgaaattaaa   97380
atagtctcac ttctagaaag atggagtaag agtaccttt ctgtattcct cccagtaagt   97440
acagctaaaa accctaaaca ttaaacataa acaaacatg aaaagatttt gaaggtgga   97500 aagaaggcag accaacctgg gttacttgcg tcctgagaaa caacacatga atgagtcttc   97560
agggttttct ttttgctgca tgtatcctag acggggtgcc ggagaagcca gcaacctcga   97620
aatatcaaca gttgcagaca aagctccaaa aaaagctaat ttccttagcc taaagaccaa   97680
aaaaggagca ggctagcaag tcagaaaact tacactatca ctgctctttt cagccaaaca   97740
ccacagaaaa acggtagcct cattcttttt tttttttttt tttttgaga cagagtcttg   97800 ctcttttccc caggctggag tgcagtggcg cgatctctgc tcactgcaag ctccgcctcc   97860
cgggttcacg ctattctcct gcctcagcct cccgagtagc tgggaccaca ggcgcccgcc   97920
accatgcctg gctaattttt tatatatttt tttttagtaga gatggggttt cactgtatta   97980
gccaggattg tctcaatctc ctgaccttga tccacccgcc ttggcctccc aaagtgctgg   98040
```

-continued

```
gattacaggc ctgagccacc gcgcccagcc aactgtagcc ccattcttaa cagcaaaggc    98100
tgagtgggaa gtctagactt ccatctccac tatgctgtag cacacccccaa cttccaatta   98160 gaatagtgtc agagaaggtc cagtaaagga attttcatct cctgtgggca gtaacaaacc    98220
ttctttctct ccccagacag cgtagcagtg accatgtggg gaatctacac ttacacttcc    98280
agctggcagt aagggggtgc cctcccact gccttctggg ttggtatcaa agagacatgg     98340
tagggagtca gaacttttcca ctgaaaataa caagctcccc tccacaatgc agtgtcatct   98400 gtggggcca cataaggagc agccatggtg cactcaatgg aggcctggta gagtgccaga     98460
actcctgctt ccacccagca gtgatgagga tctgctcccc tccctacctg aggtgtcagt    98520
agaggctgag tggaaaacct ggacttctgc aaactccacc tggcagaaaa gaggcagcac    98580
ccccttagtt tcaccagaac agtgtcagag agaccttct aaaagagatt ttaaataaga    98640
tccagaatgt tgtaagatga tgtccaggtt tgaatagcaa actgctcatc ataatcagaa    98700
ctaggaaaat tttaactgga attagaaaca ataataaact aataccaatg ctgagatgac    98760
acagatgtta gagttatctg acaagtattt aaaggaatca ccataaatat gtttcagtga    98820
gcaactgtaa acatacaaac aagcaaaaaa atagtctcag aaagacatag acaatataaa    98880
atagagccaa ccaaaaatta caataactga aataaaagtc tcaatagatg gtgtcagcag    98940
cagagtgaac aatgcagagg agcgaatcag agaccttcaa caaagaaaaa tagaaattat    99000
gcagtctgaa caacagagag aaaatgatca gaaaaaagt gacagagcct ctgggacctg     99060
tagaactata acaataaaat tctaacattt gtgtcactcg aattactaaa ggagaggaga    99120
aagggcgtgg gaagaaatga cgacagaaaa ttcaacaaat ttgacaaaag acctgaactg    99180
acaaaagaca tgaactacca agaagcttag caaaccacaa aaagtgtaaa cccaaagata    99240
tccacaccaa gacacaatag tcagatttct gaaaattaat gacaaaaaag aaatcttaaa    99300
tacaggacac accttaccta gaaaggaaac aacagtgtaa gtgacagctg atttcttatc    99360
agaaaccatg gaggccagga ggaagtggca tgactttttc aggtgctaaa aaacaaaaa    99420 aacaaaccta tcaacctaga attctgtgtt caattaaaac atccttctca aatgaaaaag    99480
aaaatgacaa cattctcaga tgaggaaaaa ctaagataat gtgtcaccag cacaccttcc    99540
ctaaaggaat tgcaaagaa aattctctaa acagaaagga aatgataaaa gaaggaatct    99600
tggccaggta gggtggttca cacctgtaat cccaacactt tgggaggctg aggcgagcag    99660
atcacttgat gccagaagtt taagaccagc ctggccaaca tggcaaaacc ccatctttac    99720
taaaaataca aaaaaaatta gccaagtgtg gtagcgtgta cttgtaatcc tagctactca    99780
ggaggctgag gctgaggcta gagaactgct tgaacctggg aggtggaggt tggagtgagc    99840
caagcgcacc actgcactcc agcctgggtg acacagcaag actctgtctc caaaagaaaa    99900
aggaggaatt ttgaattacc aggaataaag aaacagtaaa agatgggtaa atacattttt    99960
ttctcctctt tatttttat agtaggcagt tgaagcagaa attatattgt ctaatatgat    100020
tctctgtgta tgagaaaaaa tattttagac attataaaca gagagtaatg ggtcataaag   100080
aaaggtaaag ttttttaggtc aagtgtggtg gctcatgtct gtaatcccag cactttggga  100140
ggccaaggcc agcggattgc ttgagcccag gagttcaaga ccagcctgag caacagggtg   100200
aaaccctgtc tctacaaaaa atacaaaaat tagccaggtg tggtagtgca cgcctgtagt   100260
cccagctact agggaggcag aggtgggagg atcgcttgag tccaggaagt tgaggctgca   100320
gtgagccata agcataccac tgtactccag cctgggtgac agagtgagac cctttctcaa   100380
aaataaataa gataaaaatt aaaagaagaa agggaagatg tttatacttt actcaaactg   100440
```

```
gtaagatgcc aataccagtg gagtgtacta tatattaagc tatgcatata caatgtaata  100500
tctagggcag ccactgaaaa ggccttacaa ggagatacat tcaaaaacac catagttaaa  100560
tcaaaaggaa tgctaaaata atgttcaggt aacccacaga aagacaggaa agaaaatgta  100620
gaaataacag agatcaaaca aaaaaacaaa aacggcagac ttaaccctaa catactacca  100680
ataatgacat taaatggaaa ttaaatggaa taccaatcaa aagaggtggt aggggtagat  100740 tttttttaaat cccccattta tatatctgtc agaaactctt caaatataac aatataggca  100800
agttgaacat cggaagatgt gaagagataa cataacaaat attaaaaaga aagcagcata  100860
ttggcaatgt taataccaat taaagtagac ttcagagcaa agaaaattac catgaacata  100920
gaggaatatt acataatgat aagagtcaat ccaccaaaaa taaataaaaa tcctaactgt  100980
acaccaaaca acagagctac aaagtatgtg aagcaaaagt tgataagact ggaaggttaa  101040
atagaccaat ccataattat tgttggagac ttcagcaccc gtaagaatca ccaaacatag  101100
gagaactcaa ctacactgtc agctgtcaga atttgttcaa catttacaga accctctgct  101160
taacagcaca atatgccttc ttttcaagtg cttaaggaac acacaccaag gtagaccaca  101220
tcccaagcta taaacaaac acatttgaaa gcactgaaat catacagttt cctgaccaaa  101280
atgtacagat gagaataaca gaaaaatctg caaacacatg gaaagcaaac aataaacttc  101340
taaataaccc agaggtcaaa gaagaagtct cagtgaaaaa aatacattgg aatgttaatt  101400
atgtctcata aaactgttat ggctctttat ctttacaaaa tatttgaaca atgaagtgaa  101460
aatacatcat caaaatttgt gagatgctgt taacatggtg atgaaggtta atttatagca  101520
ctaaatgctt accttagaaa agaggaaaag tctaaaatca ataatttaaa ctcctacttc  101580
tggaaactag aataagaaga gtgaaataaa cccaaaacaa gcaaaaggaa ggacaagtaa  101640
cgataagagc agagaacaag gcagttaaaa gcagaaaaac aatagagaaa atcagtgaaa  101700 caaaagctg tgtgaaaaga tcaacaaaat taacaaacct ctagcaagac tgataaagga  101760 aaagagagg acacaaatta ccagtatgag gaatgaaata gggcatatac tatagaccat  101820
ataggtatca aaagaatcat aaggaaatcc tatgaacagt tctaaacaca attaagacat  101880
gtagatgaaa gggactaact tctcaaaaat caaactatca caactcatac agtgtgaaat  101940
aggtaatttc agtagcccta tataagtgtt aaggaaagcg aatccatact ttttaaactt  102000
tttagatata tggatgaaaa taaacctatg aaaagaggtt cacataatta gtcatttggg  102060
aagtgcaaat taaaactatc atgaaatatt actccataac catgaaaaaa agtaagtttt  102120
aaaattatgt caatagcaaa ctggcaagga tatggagaaa ctagatcact tggacattgc  102180
agatggggat ataaaatggt acagacattc tggaaaacca attggctgtg ttcctgaaaa  102240
actaaacatg tgcctactat gtgacctagc aattgtattc ttgggcatgt attccagaaa  102300
aatgaaaatg tatattctca caaaaacctg tatactaatg tttataacag ctctatttgt  102360
aatagccaaa aactgaaaac aatcaaaatg tcctacagta ggtgaatggt tgaacaaact  102420
tcggtacatt tgtaccatgg aatactcagc cacaagaagg aataaactgt agatacatac  102480
aatacagaga tggattttaa ggtctttatg ttgagttaaa aaaaaaaaaa acctgtcttg  102540
gccaggcgcg gtgactcacg cctgtaatcc cagcactttg ggaggctgag gcgggcggat  102600
cacgaggtca ggaaatcgag accatcctgg ccaacatggt gaaacccat ctctattaaa  102660 aatacaaaaa aaaaaaaaaa aaaagcctg tctcaaaaag tcatatattg catggttcca  102720
tttatataac attctcaaaa agacaaaatt atagaaatgg agaaccatta gttgccagga  102780
gtatgggtgg tgggaggacg gggatgggtg tggctataac tagtgactgg aaagaaattg  102840
```

```
ttgtgatgac cagttctgta tcttcgttgt ggtggtgctt acatgaacct acatatgtga 102900
taaaatgaga gaatcataca ctccttatac cagtgagaat tttctgattt tgttattgta 102960
ctattgttat atataatgtc tctactgggg gaagctgagt ggaagggcac ttgggacctc 103020
tctgtactat ctttgcaact ttctttgaat gtataattat ctaaaaatta actaaaagtt 103080
agaatgataa actcttagaa tcagaaagac cttgaatgat ttatgtccaa tttctgctta 103140
aagatgagaa agcccagaaa cactgtaaaa caggtttcct aatgtggagt cttaaaaagt 103200
gaagcatcaa aaacaagatt tactgatagt ggtaactcag aaaggtacat ttttaagttg 103260
tgaaaatttg ggtattttag ctgggcaca gtagctcatg cctgttatcc cagtactttg 103320
ggaggctgag gcaggcggat cacctgaggt caagagttca aaaccagcct ggccaacatg 103380
gcaaaagccg tctctaccaa aaatagaaaa attagctgga cgcagtggtg cgtccctgta 103440
gtcccagcta cagaagacag attcccactg tcttcttaaa aggcaagcta cttagaaagt 103500
tgtattagga gatactattt gcgtttgaaa cagaacattc atcttaagtg tttgtctttt 103560
tttttttctt gttttttgtt tttaagaaca aaatactcac ttgaatgaat gaccagagta 103620
ttaatcacag tggtaacttt tatcattata attccaggga aatcaaagaa gaaatctaga 103680
atctacagtg tctcagattg agaaggagaa aatgttgcta cagcatagaa ttaatgagta 103740
ccaaagaaaa gctgaacagg aaaatgagaa gagaagaaat gtagaaaatg aaggtaaatt 103800
gtcactactt ttgaaaaatg atagaatttc taacactgtc atgaggttgt ctttaattta 103860
gtgtccatga tacatacatg aagctacaat cctaagacac tttataagct aaataaccca 103920
ggtctcaggt taaatttata acatattaaa tagtaattaa attaaatatt aaattacata 103980
ttaaagtaaa tagtaagtag catttaacta gagtagtgat tgtcatcatg gtgtgcatac 104040
tggaatctcc tgggaagctt taaagagtac tgatgcctaa atcccagcga ttctaattta 104100
attggtctag atatgtggcc tgagtatcat tattctttac aagcccccta ggtacttcta 104160
acaagcagct gcgtctaaga acttctaaac cagaattcct tgtgttttaa tgcttgtgtt 104220
acaaatatat ttaaaatacc tttctactcc cattgatgca gtaatttcac ttccataagt 104280
tatttcacgt acatactcct actgcaaact gatatataca caaggctatt cattgtagca 104340
ttgtttaaaa tgacaaaaaa aatgcagtca atgctgtata tgaaacataa tgtaatacat 104400
atatgaaaca taaggtaat gaatgctgta ataaatttta gtacatctat atggtagaat 104460
actatgtggc ttataaaaaa taataaatca tctccttaaa tacggttata aaacagtctc 104520
taagacagat ctttaagtga cagaaacgga ttgcttgtgt ttaaaacaag agtacttgtc 104580
tatatatgct taaattaaat atatattagg gaggagagcc agttaaggga gactcagaag 104640
gggcaaaaat gactaaatgg agaaggagg acttattcta tactatctac catttggtac 104700
cttttaaatt ttgtattttt attaagatat tgaattatca agcaattgaa ctcttgaaaa 104760
ataaataata ttaaaactag ctttataagt atactatcag tgatcttata aagggaataa 104820
aggagtttga gatttacaac agtaagaaga aatctttttg cactctgtat tagaagataa 104880
tgttctactt tttaatgaat ttaaaatgca ggtacttcca aattggaatt tggctttggg 104940
agtggaccta atgtagctga ctattatggc ctaagactaa atgtcttttt ttaaaaaagg 105000
atttatatgt ttcccctatg aaaatgttgt aatttctata tattattctt tcatttccta 105060
gtttctacat taaaggatca gttggaagac ttaaagaaag tcagtcagaa ttcacagctt 105120
gctaatgaga agctgtccca gttacaaaag caggtaagtg tttcaaatga ggttcctttt 105180
taaaaaaatt gtagataatt aaattatatc gtactttggt cagaaaccta ttttttttgct 105240
```

```
ttcttttttaa atagctagaa gaagccaatg acttacttag gacagaatcg gacacagctg   105300
taagattgag gaagagtcac acagagatga gcaagtcaat tagtcagtta gagtccctga   105360
acagagagtt gcaagagaga aatcgaattt tagagaattc taagtcacaa acagacaaag   105420
attattacca gctgcaagct atattagaag ctgaacgaag agacagaggt catgattctg   105480
agatgattgg agaccttcaa ggtaatattt tttcttattg tggtaaaata tacgtaacat   105540
gaaatttatt ataacatttt aaccattttt atatatacag ttcagtggga ttaaatgcag   105600
ttcacaatgt atgcaaccat catcatataa gtggaatcat acagtgtttg tccttttgcg   105660
tctggctttt ttcacttagc acaatgtctt caaggtttat ccatgttgtg tgtgtcagat   105720
tttccttcct ttttagggct cagtaatatt ccatggtatg tgtataccac attttgttca   105780
tccactcatc tatcaatgga aggaatattt tataattttt attttttaatt gttaaaaata   105840 tataacataa aatttaccat cttgaccatt tttaagtcta agttaatata tttatgatca   105900
tattaccctc ataaagaaaa tgactttggt gaaaccagaa atggttgcat tcttttttat   105960
tgtttacgtt ttttttgagat aggaacttgc tctgttgcac aggctggagt gcagcggcat   106020
gatcacagct cactgcagcc ttgaactcct gaggtcaagc aattctccca cctcaacctc   106080
ctgagtagct gggactacag gtgcatgcca ccatgcccag ctaattttttg catttttttgt   106140 agagacgggg tttcaccatt ttgcccaggc tggtctcaaa ctcctgagct caagcgatcc   106200
gcccacctcg acctcccaaa gtgctggcat tatgggtgtg agacaccaca ccaggccagc   106260 attcttttctc ttttagaata atgcccacat ttgtatcaca ttgtaatttc ttcaccctca   106320
caggtactcc tgcagggtat gtaatgtgga tattttttcag ttttacagac aaattaacca   106380
aaaacttcat ttaaaaactt gcctaattca taaaggtttt actcaaagtg agactaatcc   106440
aggcaaagag gattatcact attaaaacct aggaattcct catgcatcgt tggtagtaat   106500
agaaagtcag ttgcagaaat aaaatcccat tacacattaa aagttagata cttgggaatg   106560
tttgaactgg agatattgac agtctttgtg aatctaagag gcagaagatt gagtataact   106620
aagtgaataa atgaacagtt tttaaatagt aataaaattc agtttgtttt caaaaagatt   106680 cctggctttta cctactcaca tatttttcta ttttctattc ctgttagcag cagcatccat   106740
actacctaat caaaacaaat atgcatagaa gttgccagat gtctcaggaa aaaattggag   106800
ggaggagttc tttttaacct tagttagaga tgggaacata gtttcaggtc ccttgggggct   106860 tgatgattag ctataattca gtggagagag gtcagggtca gttttttgtga ctaaggaaac   106920 agaaaataca atctcctgtt ggttcttagc tgaggagtgt tgtgcaatca tatttctcag   106980
ggaccaggct taaaatagat ctgattataa ctaagaaagt aaccacttta tatgtaatag   107040
gaaagtcaca gacttcctta aattgttttc ctaggccttt ttatacagct tattagctgt   107100
ttgaaagtct cttcatctcc cttctttatc tgtaaaccaa ggagataaga ataggttacc   107160
tctataaatc cttccaattc taaaattctt ataagtttgt gatctgtgtt tgactgagct   107220
ttaagctcct tgcttcagag gcagagatca tccatgtact atcaacagtg gttttttaact   107280 gaatctattt tttagatatc agtaaaagtt aaggaaaatt tatagcatga tttattgtta   107340
gtttattctt tttcagagtt taatttggaa cttaacgtg aataaaagct cacatacact   107400
aaaataatgc acacaactta tgtgagtttc aacatacata taaaagtgca ttgtgggttt   107460
ttaaaaaaat cacaatgctt atattagtct tttctggtct ttaagaactt tcaggtctct   107520
caagtataaa tttagtttgg gatggtgggc ttctggcaga gtcttgattg ttattcatta   107580
attgaatgtc ctccatatat gatctctgtt gcatagtctt tttatttttt tacttttttat   107640
```

```
aaccttttaa agtataaaaa ccattcttag cttgacatct gtacagaaac aggctgcagc    107700
cctgatgttt gccagtacct ggactagtgc aacagtaagg ctgcaattga ttatagggaa    107760
agtttccaaa agttcaggct atagaggctt aatgaaagtg atcaaaatgt tatggaggat    107820
tgaaatttta actgaattga taagctttca tctagtaagt ttatctctga ttcttcagat    107880
tgaaaggcaa aaatcaattt ttttaaatta accattttta aaagtctttt tctgtttttt    107940
ttaattgttt gcttggaacc agaagtgctt cagatttttgg attttgggtg gtttgtgaga   108000
atatttgcat tatgtatact taccagttga gtatcccaaa tctgaaatcc ttgaatgtca    108060
tgtcagtgct caaaaagttt cagaatttgg agcattttgg attttttggat tttccaatta   108120 aggatgccta acctgtacta tagtgacctc ttgtgtactc attaagcttc aaaaaccttc    108180
atttggtagc cagtcgtgtt tcattttgta cctccacctc cccttcccaa tcctctgaca    108240
ctgaattatt ttgaagctca tatcaggcac cacattgtcc ttttgtaaat acatcctaat    108300
ttgtaaatat ttcattatct taaagatagg gactcttttt taaaaagaca aacataacta    108360
caatgccatt atcaaaggta gaaaataggt gacagttata taatattata aaatatctaa    108420
ttagtgctta agttcctcta gtagtctcat aatttgttct tattgcattt attttgcttg    108480
aatttggatc caaagtttgg acattgcatt tcattaatac gtcccttaag tttattttaa    108540
tctgtatttt cctcctccct tttgtgttct ttgtaatctc ttttgctgt tgttttcggt     108600 taaagaaacc atgttttttt cgtcctgtga gtggctcctg ttcagaattt tactgatttc    108660
atctgctggt atcatttagc atgttgctct gtccgccgta gtactttaaa ctagacgtta    108720
gatctagaga tgtgatctac ttcggtagga cttttgtcaag aatacttgta agtagtattt   108780
aggtaccagg agacacataa acataaaatc tgggctgggt gcagtggctc acacctgtaa    108840
aaccaacact ttgggaggct gaggtgggtg gatctcttga gcccaggagt ttgaggccag    108900
cctgaacaac atgacgaaac ctcatctcta caaaaaataa aaaattagcg aggtatggtg    108960
gcatgcacct gtagtcctag ctacttagga ggctcaggtg gaggattgct tgagcccagg    109020
agatggaggt tgcagtgagc tgaaatcgtg ccactgtact tcagcctggg caacagaaca    109080
agaccctgtc tcaaaaacaa caacaaacaa acgaatgaaa aaacataaag tctggctgta    109140 tcttttttgtg gtgttagtag ccattgatga tcattgccta ggtcctttgt ttctttagga   109200
atttgcagtg gtgatcatct atttttatcc atcttccttc atttgttaat tggaatacta    109260
ctctagagat gaacatttcc tcatcaatta tatagtagtt actttgaggt acagcttata    109320
aaagaaagtc aggttaaata cttaattctt tgtcagtttt tggaacagtg agttattttcc   109380 caggcatcct ccaaagatga ttagtgaatt tttaaaatat atttgtgaac tcatgaattt    109440
taatatattt aatatatgtt agccctttgc attattctta atgatgctca catgaagttt    109500
agtaggaatt ctttaagttt agacactacc ctagtagttt tagatcacat ccttgcttt     109560 tgatatgcat agattttcca gaattatttt ttgtcccaga cctgaaatca cccatttgcc    109620
taggaactcc ggttcctttt gtagcatatg acattcgggg tctataacct gaattctatg    109680
ggtgctcact actgttgggt tggtcaatgt ttgtaggtga ttttaatgga cagaggtagg    109740
aaacaatttt ttttgtaatt aataatttct tattgtgatc aggaactatt aaaagatttc    109800
tactttggga tttctacttt taatgatttt ttttctggct tagtttataa atgatttttg    109860
catttcactg ttacatgggc atttgaaaat tgtcgatttt tgtatgaaac atcttttttgg   109920 gtgaaaagtt gatccgtttt ctaatgtaat ccatcagttt tctaagattg catttattct    109980
ttgtcccttt gttctgtcaa attttaaaat gtgttttaaa agttttcact atcattgtgg    110040
```

```
gttttttctc atagcctccc atgtatttct tttcttttt  tttttttgag acggagcctc  110100
actctgtcac ccaggctaca gtgcagtggc atgatctcgg ctcattgcaa cctctgcctc  110160
ccaggttcaa gtggttctcc tgcctcagcc tcccaagtag ctgggactac aggcatgcgc  110220
caccatgccc agctaattt  tgtatttta  gtagagacag ggtttcacca tgttggccag  110280
gatgtcttga tctcttgacc tcgtgatctg cctgcctcag cctcccaaag tgctgggatt  110340
acaggcgtga gccaccatgc ctggcagcct cccttgtatt ctaacagct  tttgctgtct  110400
atatttta  attaaggtga aattcttgta acaaaaagct aaccatttaa aaatatacaa  110460
ttcaacagca tttactacat tcaaaatgtt cacaaatacc tcctctatgt ggttccaaaa  110520
catttcattt tgaaactaca aaataggatc cattaagctg cccctccta  ttctccgctc  110580
cactatctcc tggcaaccac caattccttt tctgtctctg aatttacccg ttctggtat   110640
ttcgtataaa tggcatcata gaatgtgtga ccttttgtgt caggctttt  tcacttagca  110700
taatgttta  caggttcatc tatattgtag catgtgtcag tagttcattc atttgtggct  110760
gagtaatatt ctgttatatg tatttaccac attttgctta gccattcatc tgttgatgat  110820
atacatataa cagaatatta ctgtggattg attccacctt ttggctattg taaatagcac  110880
tccttcaaca tttgtgtaca agtatttgtt ggagtacctg ttttaattc  tttaggggtg   110940
tatattagg  agtggaattt ctgagtcatc ttgtaattct atgtgtaact ttggaggaat  111000
ttccaaactg ttttctgcaa tggctgcacc attttacatt cctgtcagca atgtacagga  111060
ttccagtttc tccatatccc tgccaacact tggtatttc  cttttttca  gttagttact   111120
ctagtgggta tgtggtggtt gtcccattgc tgtttgtttt gattttcatt gtccctaatg  111180
actaatgata ttgagcatct aatatccagt tgtcccagca acatttgttt gaagagacta  111240
ttcttcctg  tgtaaatggt cttggcatct ttgttgaaaa tcgattggca gccaggtgca   111300
gtagctcaca cctgtaatcc cagcactttg ggaggctgcg ctgggcagat cgcttaagct  111360
caggagtttg agtccagcct gggcaacgtg gcaaaccat  gtctctacta aaaatacaca   111420
aattagccag gcatgatggc acgtgcctgt agtcccagct acttgggga  ctgaggccgg   111480
aggatcactt gagcctggga ggcagcggtt gcagtgagcc aagattgcac cattgcactc  111540
cagcatgggc gaacacagtg agaccctgtc tccaaaaaaa aaaagaaaa  tcaattgact   111600
atagatatca tgcatctatg atattctgga ttctcaaccc tattccattg gtctgtgtgt  111660
ttgtccttat gccagcatgt accacactgt tttgttttgt tcactgtagc tttgtagcaa  111720
gttttgaaat caggaagttt gaaccctcca agtttgttgt tcttcagtat gttttacgta  111780
ttcagggttc tttgcaattc tatgtgaatt tgaggattgg cttttctatt tctgcaaaca  111840
agacctttag aattttgata gcaatttctt tgaatctgta gattactttg tgtagtattg  111900
ccatcttaac aatattaaat cttccagcca ggcgccagtg gctcaagcct gtaatctcag  111960
cattttggga agccaaggta ggcagatcac ttgagcacag gagtttgaga ccccccgag   112020
caacatggcg aagcctgtct ctacaaaaaa taaaaatca  gccaggtgtg gtggtgcacg   112080
cctgttgtcc cagtgctcca gcctggctga cagaggcaga ccttgtctca aaaaaaacca  112140
aaactaatat taagtcttcc aatccatgaa caaggatata ttttcattta tttagatctt  112200
ttaaaatgtg tttcagcagt gttttttgttc atttgtgtgt tgttttttag ttttctatat  112260
acaaatttct tcctgggtat tttattcttt ttgatgctct taaagggaat tttctcaatt  112320
ttcttttggg attgttcatt gagtatgatg ttagctgtgg gtattctcatg aataccttgc  112380
tttacatatt tttaatgcag tgttttttgg tgtgtaagat tttgactcct gtatcttctg  112440
```

-continued

```
ggtggattaa aatttgtatt ataaatgata ttaaatgtat ctgactctga ggcttttcct 112500
taatgtgcat tttcttctta tatcttgccc attaattttat tttaatttt tgtatgttct 112560 tggtgggact caatgccttt ttgtagatta tgcctttttg taaatttat atttattt 112620 ggcattttaa catatttaaa ttagtttttt gctaaaacaa tgatatttca gcaaatggta 112680
tttgtcatga tgaatgaact ttttaatgta ttgtggaatt tggtttgcta gcatcttgtt 112740
gagggttttt gcatgtgtgc tcctcgtgaa tattggctta tagcttttt gtttatttgt 112800 cttttaaaat gtgtcttcat ctggttttgg tatcaaggta atactggcct tgtagaatga 112860
gtttggaaac attctctcct cctctattct ttgaaatagt ttgagtagga ttgttatttg 112920
ttcatcttta aatgtttggt aagggccgga tgcggtggct cacgattgta atcccagcac 112980
tttgagaggc caaggtgggc ggatcacttg aggtctggag ttccagacca gcctggccta 113040
gccaacatgg agaaacccca tctgtactaa aaatacaaaa ttagctgggc atggtggtgc 113100
atgtctataa tcccagctac tcgggaggct gaggcaggag aatcacttga acccggggagg 113160 cggaggtggc agtgagccga gattgcatca ctgcactcca gcctgggtga cagagcaaga 113220
tcctgtctca aaaaaaaaa aaaaaaaaa aaaagtttgg taaaatttag cagtaaagtc 113280
attcagtcct gggcttttat ttgctggaag acttttatt acagcttaga tctcattact 113340
tgttatttgt ctgtttaggt tttggatttc ttcatggttt aatcttggta ggttgcatgt 113400
gtctgatctt tattatttat tttcttctac taattttggg tttgatttgc tctggctttt 113460
ctagttcttt aagatgtatc attaagttgt ttattgaaac ttttctacc ttttgatgt 113520 agatgctcag agctataagc tttcttgtac tgctttcact gtatcccatt ggcttttgta 113580
tgttttgttt tcattatcat ttgtttcagg aaatatttta attttcttct taatttcttc 113640
atcaatccgc tggtcattca ggagcatatt ctttaatttc caggtatttg tatcgtttca 113700
aaaattccgc ttttttggcca ggcatgatgg ctcatgcctg tcatcccagc actttgggag 113760
gccgaggcgg gtggatcact tgaggtcaga agttcgagac cagcctggcc aacatggtga 113820
aaccctgtct ctactaaaaa tacaaaaatt agccaggagt ggttgcaggc acctgtagtc 113880
ccagctagtt aggaggctga ggcaggagaa tcgcttgaac ccgggagtcg gaagttgcag 113940
tgagccaaga tcacgccatt tgtactccag cctggggtac aagagcgaaa cttcgtctca 114000 aaaaaaaaa aaaatccac ttgttgttga tttctagttt tgtttcattg tggtcagaga 114060
agatagatac atgatataat tttactttt ttgaattttt caagacttgc tttgtggagt 114120
aacatatggt ctgtccttga gaatgatcct catgctaagg agaatgtata ttctgtggct 114180
gttggatgaa atgttctgta aatatttatg aggtcccatt tggtctatag tgcagattaa 114240
atctgatttt tctttgttga ttttctgtct aggtgatctg tccagtgctg aaagtgagga 114300
gttgaagtct ccaggattgg ggtctatccc tgtctttagc tctaacaata tctgctttat 114360
atatctggtt gctccagtgt tgggtgcatc tgtatttaca attgttatat tctcttgctg 114420
aattgacccc tttatcatta cattatgacc tttttctgtgc ctttttatag tttttgtctt 114480
gaaatctatt ttgtctgata caagtataac tgctactgct ctttttttgt ttttgttttt 114540 gtttttaattg gcatggaata tctgtttcca tccccttgtt ttttctgtgt atgtctatgt 114600
gtacctttat acatgaagtg tgtttcttgt agtcaacaga tcattgggtt ctgttttttt 114660 gttttttat ttgtttgttt tttggtccat tcagccactc catgtctttc gattgggcag 114720
tttagttcat ctgcattcac tgttattgtt aataagtagg gacatactcc tgccattttg 114780 ttatttttt gtgattgttt tgtggtcttc tcttccttct ttccttcctg tttctgctta 114840
```

```
atgaacatga ttttctctgg tgataggttt taatttcttg ctgcttattt tttgggtatc    114900
tatctgttgt atgtcttttg atttgaggtt accatgaggc ttgcaaataa tatcctctaa    114960
cccgttattt taaactgatg atgacttaac agtgatggca ttaacaaact aacaaacaag    115020
caaagagaaa actaatacaa actctacact ttaacttagt cccctgcatc ttaacttttc    115080
gttgcttcta tttataatct tactgcctct tggaaagtat tatagttgtt attttttgatc   115140
agttctttta gtctctctac ccaagatatg aataatttat acactgcaat tgcagtgtta    115200
cagtagtgtt tttcagtgta cttaccatta ccctatggcc accacctgg aactgtgctg     115260
agtcagacct ctgaacccctt agaaccttct tgtgcttgaa tattggtatc ttttctaga    115320
tttgggaagt tctgtattat tacccctttga gtaaacttc tacccctatc tctctttctg    115380
cctgctcttt aaggctaata actcttagat actctctttt gaggctattt tctagatctt    115440
atatgcatgt tccattcttt ttaattcttt tttgtctcct atgactgtat tttcaaatag    115500
tctgtcttca agctcactaa tactttcttt tgcttgaaca tttctgctgg taagagaccc    115560
tgatgcattc ttcagtatgt cggttgcatt tttcaactcc ggaatttcag cttgattctt    115620
tgtacttatt tcagtctttt tgttaaattt atctgatggg attctgaatt ccttctttgt    115680
tttatcttga atttctttga ttttcctcaa aacagctatt ttaaattctc tgtctgaaag    115740
gtcttatatc tctgtctctc caggattggt ccctggggcc ttatttagtt tctttggtga    115800
gattatgttt tcctgaatgg tcgtgatgtt tgtggttgtt tgttggtgtc tgggcattga    115860
agagttaggt atttattgta gtcattgcag tctgggcttg tttgtacctg tcattttttgg   115920
aaaggctttc caggtattcg aagggactta ggtgttgtga tttaagtttt tggtcactgt    115980
agccatatct gtattaggag gcatccgaag cccagtaata ctgtggctct tgcagactct    116040
tagaggaacc atgttggtgg ttttgggtaa gatgtggaag aattatctgt attataatgc    116100
agaggctctg ttctcttccc tttctcccaa acaaatggag tctctctgcg ctgagctgcc    116160
agggagaggg tggggagggg ttacacaatc acccttgtag ccaccaccac tggaactgtg    116220
ctgggtcaga cctgaagcca gcacagcact gggtctcaat gctgccaggc ttgggactct    116280
cccttcaggg cagtgggctc ctctctggcc cagagcaggt ccagaaatgc catccaagaa    116340
ccaggacctg gaattgggga cccccaagag cctgcttggt gctgtacccc accatggcca    116400
agctgatata tatcactaag ctgattgttg gttcttatga aggtgctttt ctgtgcgaat    116460
ggttgttcaa attggtgttc ctgcagagag acaatcggt ggaggcttct atttggccct     116520
tctctgcctc ccctgttttt attttttaatt gacacataat aattgtacat acttatggga   116580
tgttttggta cgtatatgca atgtgtaatg atcaaattag ggtaattagt atgtacatct    116640
cctcaaacat ttgtcatttc tctatggtga gaacattcaa aatcatctct tctagctatt    116700
ttgaaatatg cagtatgtta ttgttaacta tagtcagtct actgcatggt gggaacattt    116760
tcactcttca gtgctgcttt tggataagca aaaggtctta atttcttgta tttgatgtag    116820
tccagtgtat ctagtttttt ctttattgtt agtgtggttt ttagtgtggc ctatcgaaaa    116880
agtctttgac tagattatga agataatatc ttcattagc ttttagaaat tttgtttaa      116940
tcaacttaga ttatgatacc tagtgtttgg gcccttattc ctcccattat gttttatat     117000
tttctgtata taaagcttct ttgctttcgt gtattgcaca ggtaagttct agtttatttc    117060
cgacatttct tttcagacag agtaaatgag gaaaataaac tatacttaat ttgtctcttt    117120
catgtggttg ctaggaatct tgcgtggatt caacccatat agtttattat cttgtctcct    117180
taggagttgg tttgcagtaa gctgcttcta catgaaaaat tcaaagatta atctgaatta    117240
```

```
ctatctttgt acagattttt taaaatgatt tttaaaacag attttctcct agaactcctg   117300
ggctcaggcg atcctcccac ctcagtctcc caagtagctg ggactataga cttgtgtcac   117360
cacacccagc tgattttgt atttgagaca gggtttcacc atgttggcta agctgatctc   117420
aaactcctga gctcaggcaa tctgcctgcc tcagcctccc aaagtgctga gattacaggc   117480
atgaaccact acacctggcc tattttaaag ataattatat catttatttt ttaaattata   117540
atttctaaat agcacttcaa catttaaaca tcttagcaca tttgctttat ctctgtccac   117600
acaaacacac atatactctg tattttggt caattatttg aaagaaagcg gcagctgttt   117660
ctttctccta catgaactta ctgcaacatg aaaatatctt gagtgtgtaa ataaaattat   117720
ttatttcatt gttttctaga tctagaacta atctagcaga tatgcattat caggtgccaa   117780
agatttaata tttatttgtt tattaaataa ctactttaga aaccctgaaa tatgggaggt   117840
gactagagta catttgagag tgggacaagt acagtaagtc aaactgtact ttgagtagta   117900
cagaagtttt actggcccat ctggtacttc atctatttc cttgtcaaat cctaggccac   117960
tttgaattac aaaatatgaa aatataattt ttattttaag ctagacaata tattaagtca   118020
gatactacat gtgttaaatt tgtgtgttta ttaaatatt atgccttaaa tacctgtaag   118080
gttaaagcat gttttaatga gtagacaatt actaaatata tgagttacta ccattgcaag   118140
gcacgaacat caggtaagtt aaaactaagc tttgttagag tacttgaatt ccttaaaaac   118200
ttagttttct gtgaaaatag agtttggctc cattaagttt aaaagtaatt ttattaaaca   118260
ctttgcagtg tctggcacat atggaccact taatacttgc cttaattaac taaaggctct   118320
cacctttaat gtggttagaa agagcactca gtgccgggcg cggtggctca cacctgtaat   118380
cccagcactt tggaggctg aagcaggcgg atcacgaggt caggggattg agaccatcct   118440
ggctaacaag gtgaaacccc gtctctacta aatatacaaa aattagccgg gctggtggc   118500
aggcgcctgt agtcccagct actcgggagg ctgaggcagg agaatggcgt gaacctggag   118560
gcagagcttg cagtgagctg agcttgtgcc actgcactcc agcctgggca acagagcgag   118620
actccgtctc aaaaaaaaag cactcagtaa ggacttggat ctgatttcta gctcaagctg   118680
aggcttcatc tctttggcta cttgtaaata aggaatatgc actagattat atccaattag   118740
cattaatatt tttattccat atcttgtgtt tattgtgaaa acacttaata aaatcttatc   118800
ggatcaggaa acttaataca ttaaaaaac atttttaaa aactaaattg tcaatactga   118860
acaaaaagac ttctttcaat gactacagac ttgaactttt ttctcacttg atagctcgaa   118920
ttacatcttt acaagaggag gtgaagcatc tcaaacataa tctcgaaaaa gtggaaggag   118980
aaagaaaaga ggctcaagac atgcttaatc actcagaaaa ggtaaatgat ttaacatata   119040
ccaattatta taaaatagta attactgatt atcatagact actaggtggt tttataaaat   119100
agcatttatt cttaatgttt atatagttac atttctaaaa gttttatgt ttgattggtt   119160
gtatgtgggg ctgtatgtat gtcttattta gggttttgtt atttgttatt tttgttttta   119220
ccctagagag cattagatgt ttcatgttaa cagatcatca cagattcctt tggtttggaa   119280
atacctttt ataagtatg ttttcctatt ttctttgtac atgagtaaga tgaatgtgct   119340
gtgagggctt atgaagaagg aaaacaacag atcagtacgt ggtagatgat gagtacctgt   119400
tctgttgttt tacagttagc aaaatagaaa agagcataaa gtgattggcc tttgcattta   119460
gaattttctt aacaataaaa atttcattgg ttattctctg ttatatacct agctaagagt   119520
taaatagatg atatagagat acagctgtca ctttttcaaa gcctctgaaa tgttggaggt   119580
tcaatagaac ctcaggtaaa ttatcagaaa agccactact tatcttgtcc tttggacatg   119640
```

```
ttttgtcaca attagaatag tttttgatgg ccaagctggt gtaaatgtgg acataggata   119700
aaagaagctt gaagagtaga aaagggtacc caaacagaaa tggaatatat tttgactcat   119760
ttttcctttc tatatcaatg acttgccaca ggatactttg tggggttttt ttgtttgttt   119820
tttgttttg tttttttgtg aaagcaaagt aaatgtggat atagatgcaa atgtagataa    119880
agatgattta atatattttt ttaaagtggt agcaggccag gcaaggtggc tcatgcctgt   119940
agacccaaca ctttgggagg ctgacacagg aggattgctt gagcccagga atttgagaat   120000
agcctgggca gtggagcgag accccatctc tacaaaaaaa tgcttaaaaa ttagccaggt   120060
gtggtggcat atgcctgtaa tactagccac tccagaggct aaggctggag atagcttga    120120
gcccaggagt tcaaggctgc agtgagctga aaggtgcca ctgcactcca gcctgggtga     120180
cagagtgaga cctcatctct ttaaaaaaaa aagaaaagaa aaaaaaagat ggtatcagaa   120240
attttaaat aaactgaaaa tttgtcttat tcatttccga tcttagcaat gaactgtcct    120300
gaacataacc accagcacag ccttgttctg ccctccgcca tgattaatga ttcaaatggg   120360
aagggagggg gtaaagaaaa gattatcttt tgcttttaat tatatgtgtt tattgtgatt   120420
tttaaaataa ggcatcatat ctcttccaga atattaaatg taagatttac taacatgcat   120480
gccttctgca cagtttatta catgactcct actcccattt tacaggaaaa gaataattta   120540
gagatagatt taaactacaa acttaaatca ttacaacaac ggttagaaca agaggtaaat   120600
gaacacaaag taaccaaagc tcgtttaact gacaaacatc aatctattga agaggcaaag   120660
tctgtggcaa tgtgtggtaa gtgtcagttt taatatttt acaaaattga ctttaaatag    120720
tgactagaaa aaatttggtt ttggtcaaaa ttttgtactc tttaactcgt agaaagtata   120780
atataaatta taggcctggc acagtggctc atgcctgtaa tcccatcact ttgggaggct   120840
gaagccaatg ggtcacttga ggccgggagt ttgagaccag cctggccaat gtggtgaaac   120900
cccgtctcta ctaaaaataa aaaaattagc caggtgtgtg tcgcacgcct gtaatcccag   120960
ctactgggga ggctgaggca ggagaatcgc ttgaacccag gaggcagagg ttgcagtgag   121020
ccgagatggt gtcactgttc tccagcctgg gcaacagagt gagactgtgt ctcagagaaa   121080
gaaattataa attataatca agaagaggat gccttccttt tgatactttc cttttttttt   121140
tttttttttt ttttttttga gacgaagttt tgctcttgtc tcccatgctg gagtgcaatg   121200
gtgtgatctt ggctcaatgc agtctctgcc tccaggttca agcaattctc ctgcctcagc   121260
ctcccgagta gctgggatta caggcacccg acaccatgcc cggctaattt ttgtattttt   121320
agtagagaca gcgtttcact atgttggaca ggctggtctc gaactcctga cttcggcctc   121380
ccaaagtgct gggattacag gcatgaaaca ccatgcctgg caatgctttc cattttttaa   121440
gatcacaatt tcaccttcta gttccctcag tttactactc tgtttcctat aaaagttagt   121500
ggaatctgtc tttctctgt tttttagtag cccttccctt gattttcttt atgatccact    121560
ctggacctca tcatctgcta attcatctgc tatcttgctt tgtaccctca gttttctcat   121620
ttctttgtac ttccactgtg ttatgcctcc aaacacaacc ctagttcaga ccagccagcc   121680
actttcttca ggcagttgag tgttagtcca atgcattatc tgcaacctga gttgtcaatt   121740
tttttttcaat ttttaaaaat tatttatttt tggtagagaa agagtctcac tatgttgtcc  121800
aggctggtct tgagctcctg ggctcaaggg atccttccac ctcggcctcc caaagtgctg   121860
ggattacagg catgagccac catgcttggc tgtcaatttt ttttgaacat atcggtcata   121920
agttcttct cccagatttt tatttatctt aagtttcctg tgccgtttct ttatcactcc    121980
agttttaggt gaattttatt cttatttcac aagtaaataa tgaaagcata ggtgtgaact   122040
```

```
cctcaaaatc tagttttctt gtcaatctat cctattcttt acctgtcttc attatcttca   122100
ctgttatctt aaaggagggt aagctcctct catctcatct taacttcttt tctcttttc    122160 ttttctatat caaccttttt acctccatta tcttcttact gtaaacatga acaagtctcc   122220
catcttaaaa cagagacaaa tccatgcagc aatctgtcat ccttactaat tactactgtt   122280
ttatttcaaa taaattaata aaatagtcaa acttcaatgg tgtcagattc tttatagaaa   122340
aaaattaaaa aatatccaaa cttctaaaag tcttttcctc accttctgct tattcttaac   122400
ctactacagt ctggatgtgt tggcatctta aattattttt gctcaaaaga aagctcataa   122460
tctcatccat caaacctgct cttattcttt attctcacta acctagttaa tggccatatg   122520
gtctttatga gctaaggctt tggaatcaga cagatcaatg ttgctctgta actattctaa   122580
gttagatgaa aaatgcatgt aaagtgcctg tgcatagaaa gttttcagta gctattatct   122640
tggctactga acatcacatc atcatcttgc caagagttgt tctactcatc agtcattctc   122700
acttaggtta gaacaatttt ccttttagt caaatcgtat tttggttgtc cttaaaatcc    122760
tttagtggct tttcattgtt tgcagggtac ctttcaaact ccttgtatat atagaatctt   122820
taagttgaca cctgcctgtc tttacaatct tactaccta cactttgttg tgtgtaccct    122880
gtgcttcagc catattgagc ttctttatt tccttcactt aagttaatta ttgactgcct    122940
acagacaagg cacagctggg aatatcgcag agaataaaac tgacaggaag cccggagatt   123000
acattcagat agtgaatata gacaaaaaaa aataataata cataaatgaa aatacataca   123060
gcttgtaatt attaatggga aggaaataca tattaatatg attgttttga cttggcactg   123120
ccctggatgg gggttctgag gaaggctttc tgagctagta atatttgagg taagaactga   123180
aagtcaaaat gaaccacctg ttaaatgagc tggagaaagt gcattacagg cagaagtgat   123240
agtaagttca gtattcttat tctaagattt gtattaagcc actagcacat tttaagcttc   123300
tgggatgtgt aatttatatt tttaaaagat cattcccgct gctctgtggg gaatgctttc   123360
aagagtgaga acagtgataa aaagggagat cagttagaaa gctatacgct gtaaacactg   123420
gtagtagtag agagggaaag aagtcgaggt atagaggaga agagtgatga attggataga   123480
aagaggccgg gtgcgggac ccacacctgt aatgctagca ctttgggagg gcaaggcagg    123540
cagattattt gaggtcagga gtttgagacc agcctgggca acatggtgaa accccatct    123600 ctactgaaaa atacaaaaat tagctgcgtg tagtggtgcg tacctgtaat ctcagctact   123660
caggagactg aggcaggagt attcttagaa tccaggaggc ggaagttgca gtgaatcgag   123720
attgcaccac tgtattccat cctgggcaac agagcgagac accatctcaa aaaagaaaa    123780 aaaaagact gagtctaact ggggttggag tggtttgggg ataggccaga agtaaaggca    123840
tctattgtgg atatgttaac tttaataaga ttattagata tctaggtgga gatgttaaat   123900
agtcaattgg tatctaagtc tggagctcag gagagagata ccaagagtca gaagaacata   123960
gtggatggat ttgtgtttga ttaaacagaa gggtcttaag aggtgacagt tttattggtg   124020
cagctaagtt tgtaagtttg gggggaaaga taaggaatag tttatttata tttatttaat   124080
agtttatatt ttgtcaccta gagggtggtc tccaagagtg ggaaagcaca ctttaaataa   124140
acttgaatcc ttatggggca acttactagt tacatgaaca tggaaaagtt aacctctcag   124200
aagcttagtt atatttcaaa aaaggagcct cagtgtagac taatatattc cagtaataat   124260 taaagaggt atactactgt ggaatcttat tcatctgaat tgtataaatt ggagttccta    124320
ccatagcctt aagcctcttc aacctttct ggaacaatgc agggtataaa ttaataacca    124380
cagccttatt tttctgcttt tgcttgatgt atgttcattg ttctttgtta attcacttcc   124440
```

-continued

```
tttctagcta tactcttcac cttcttgtct gaaagtggta ccgattaatc tctcatcact   124500
gggcaagagc tgggtttaga agattttatt actgtattat attttataac tccttttctt   124560
tagagatttc tgctatataa atagtttaca taatgtgaga atttctataa ttactagctc   124620
tattcaagtc ccagaataaa aacaatagag acatttgaaa ccagtttaca gcccatataa   124680
agtgaaatgt gttaaagtac tctttcttta aatgtatgtt tgtaactttt tgctttccca   124740
gagatggaaa aaaagctgaa agaagaaaga gaagctcgag agaaggctga aaatcgggtt   124800
gttcagattg agaaacagtg ttccatgcta gacgttgatc tgaagcaatc tcagcagaaa   124860
ctagaacatt tgactggaaa taaagaaagg atggaggatg aagtaagaaa aatagtactg   124920
actttgttca tctattaaaa gagaaacggt tatataagtt atgactggag ttatctataa   124980
tttaaacacc atgaaggaga tttgaatgaa ataattgaca tgggtctgtg ttcactgctg   125040
tatggtcacc ccagcaccta gaattttcct cttcaaatag ttattgaaca ttcactctgt   125100
gtgatctatg ccattttttca ctatgacagt acaactatat tgaaatgtca tagttccttc   125160
cctgaaaaaa ctgaccatct gctttaaaga aaaaaaagt ctttattata atgcatctta   125220
tatccccaaa gaaaagagca ttgctcttag atttcaataa aagtgtttaa ctgcagtctt   125280
tcctggctta gattgatagc acagggtata cattttataa agcagttaat aaacagataa   125340
aatgacagta tgtcctggtg gttactatat gtactttaga aattatttct aagactgaaa   125400
gtaggaaagc cttttcaaga agatgtaaca tgttacctag attttaaagg ttgagtaaga   125460
cttcaaaagg taatagtttt ggagtcaggg ctttacttgc tagagggaat attatcagta   125520
aagagatgga taataaagtg agtaccggct ggataagaag atgcataagg aaggcataaa   125580
aaggaacttg atagaacttt aacttttga aggaaaaacg aagacatgtt gagtagtcat   125640
gggagaaatt tgtaggccaa agtatcgata ctctttaaaa cttccatggg tggccaggca   125700
cgttggctga cacctgtaat cccagcactt cgggaggctg aggtgggcag atgggcacat   125760
tgcttaagct caggagtttg aaaccagcct aggcaacatg gtgaaaccccc atctcaaata   125820 caaaaatcag ctaggtgtgg tgtcgcatgc ctatagttcc agctactcag gaggctgagg   125880
tgggaggatt ccttgcacct caggaggtcg aggctgcagt gagccaagat tgctccatgg   125940
cactcagcct ggacatcaga gtgagaccct atctctaaaa aataaaaaat aaaacttgca   126000
tgggagctat aggtgaaagc acttttagaa aaatcaatct ggtagtggta tatagaatgg   126060
actagaaaga agagaaatta gagataccta ttaaagctag catgcaggag gaatgtatgt   126120
tcaaaatttg aaagataata ttcagtcatt taaaaaacat aattttttgac tacctatttg   126180 gctctgtgct aggaattggg ggttaccgaa gtgaataaga tataggtatg gtcctgactg   126240
tgttggaact tacagccagg agggaaaaac agatattaaa atagtaacta caagcattgc   126300
aaataattag aaagaaagta cggaatgcta tagggggtgta ttactaatca catttgggag   126360
ttacagaagg ccttgctaag agtatgacat ttgagcctg aagaatgaat aaatgaagga   126420
ggataaaaca ggagtagtgc gtacaagaaa tgtgaggtga gggagaattt gttgcatttg   126480
aggatctgaa gaatatgatt ggattgtaga gaatggccaa tgataggaat agaattagaa   126540
cagatcatga aggccattgt aaaccactgt atgaattttg agttcattgg tcccaacacc   126600
taataaacac ttcagaaata tttgttgagt tgaataaaac atacgttcag tttgtttggt   126660
taagctttga agggttgtag agtagagcac gtagacaggt aaatttaagt actccattca   126720
aatgttcccc caggaatggc tttttttttt ttggagacag agtctcactg tcactccaggc   126780 tggagtgcag tggcgtgatc tcggctcact gcaacctctg actcgtaggc tcaagtgatc   126840
```

```
ctcccatgta gctgggacta caggagtgta ccaccatgcc tggccaattt ttgtattttt   126900
ttgtagagac agggtttcac catgttgacc aggctggtct caaactctgg gttcaagcaa   126960
tccacctgcc tcagcctccc aaagtgctgg gattacagac ataaaccact gtgcctggcc   127020
cagaagtgag ttttataatc accttgtact acagaatttt catgctgatt ggggtagaaa   127080
ggaaccagaa tttttttccc tccacaagat ctcatgtctg aaatttggga attaatttga   127140
cttaatagta aatctactgt aataaacacg tggaacaatg aagactcttt aaaatactaa   127200
tattttctac tagtaccatg aattataatg tacttgattt ggttagtagt ctttcaaata   127260
atgtctaata aattatttaa gagatttaag atcccaatta tttttctcat tcataggtta   127320
agaatctaac cctgcaactg gagcaggaat caaataagcg gctgttgtta caaaatgaat   127380
tgaagactca agcatttgag gcagacaatt taaaaggttt agaaaagcag atgaaacagg   127440
aaataaatac tttattggaa gcaaagagat tattagaatt tgagttagct cagcttacga   127500
agtaagtctt taaaataaca ttgtgatttc tttctttttt gtgttcatca ttgacttgtg   127560
tgtttgacat tttacatatg tacagattat gtacttagag tttgtgaaag acagaaaaaa   127620
agtatttaga agtaaaagaa tttacttgca aaggttttca ggggagttca ggctttggaa   127680
agaccacagt tttctcatct gattttcatg tccacaaaag tcatcacatt tcttcaggtt   127740
agaattacaa aaatcacggt gccttgtagg agatgttcaa ggtttatttc agaggctaga   127800
attagacatg acactttgtt cgttttgttt tgtgtctttg gttcatctca aaatgcaaaa   127860
atgtcttttt tctttttctg ttactcttgg gatgtgatat gcctccttat ttgaaatgga   127920
gaacaagcaa gatcaggaac gctttcacaa tttgtcgaag aatatgcttc acaagtttaa   127980
tatcaaaagt ggatatatct tatgccaagt cttgtgtttt tatttcctcc acgtttattt   128040
tatcatatca tcacttgcta gcttcattta caaaagtgat tcttggatta aattgtcagt   128100
tttcataaaa ttggatttat attggtgaaa ttcttttcct cttttagggc caccgttttc   128160
gcaaaagtgt gttttatatt ttttttctcc aaaaatactc tcgctcagca ttcagtggag   128220
attggtgtag actttctgtc agccacatgc cttttgagat actgagaata caaagctatt   128280 actgtcaat atgaaagtct agccgctaga ttttcaagcc tagctgctag gctttcatat   128340
tatacagtaa ataattattg aaaatctgtg tctttgggtt acattgggtt tccatctttt   128400
ggactctgct cctatgtgag ttgtgtttat gtatgtatta tatacatgca gttgtctatc   128460
tgcgttcctc cttgtttgtc agtttgttgt tcttgctttc ccttcttacc tgatggttca   128520
tttccaccag cccctttctt gtgcttaatt ggccataata tctagtatgc agtactgaat   128580
tattacttat taaatatagt actatgatat gtagcactga attattatta aattttcat   128640 gcccccctct ttttttattt actgtacaag acatttcctt ccctatgact gcttttctct   128700
gtaaaaattt accaaaaata tggtatcaat tttattttt cattttggat agatccacaa   128760
ttaatattct ccaaaaagtg atcatcagta gaaaagggtt ctcactactt ttgcatagcg   128820
tcattttata aggagcaaga tagaaccggt gtggcctgac caagttaatt agtaaaataa   128880
tgaataatga agtatgtttt taaaaaataa agattgtttt agtaaacttt tttatattag   128940
caactttaac aaactaagaa aaaatgaagt ctagtataag taggagcgtt tgttcacttg   129000
ttttttcttt catctgaaga cagtatagag gaaatgaagg acagatgcgg gagctacaag   129060
atcagcttga agctgagcaa tatttctcgg taagtgagaa tcatttttaa catacacact   129120
gtttcaaaac ctgacttaaa acaaggtatt tagattcttt tatgtgaact gtaattcttt   129180
ttcaaatgac tcttcatctt ctaataaaca ttgtgacttt tctgcttttt gtttgtccat   129240
```

```
ttgtttcttg gcatattagg ctatcattgg tatatgtttt taaattgtaa aaacttttca   129300
ggccaggtgc ggtggctcac acctgtcatc ccagcacttt gggaggccga ggcgagtgga   129360
tcacttgagg tcaggagttc aagaccagcc tggccaacat ggtgaaaccc cgtctctact   129420
acaaatacaa aaattagccg attgtggtgg caggcacctg tagtcgcagc tactcaggag   129480
gctgaggcag gagaattgct tgagtccagt agttggacat tataataagc caaggtcatc   129540
tgtgctgcag cctgggtgac agcaagactc tgtctcataa acaaaatgaa agactttttaa   129600 atattgttga aaactctttc cctgagtgtt tgctaaacgt aattattcaa agtatctact   129660
gctaacttct gcaaagtgat cggtagcatc ccatatgctt tcttgccata tgcttccaca   129720
gagcagtcat ccagtgcctc caaatgtttg gatgggtgtc aaatgacttg tggtgattct   129780
tgtggatttt tgattttgct tctagaaaat agtacaaaac ctgaccctat ctcagttctg   129840
atttattcca ttgcttgtgg gcattggatt aaatagcatt caattcaata agctgttatg   129900
aaccaaattt taagatttgt cttttttctg ggttttcaaa tcagattatt tttctttta   129960 tcccttcatt gatttactta tttgaatttc agtatttgaa gtcagagaga taagaatctg   130020
agtcctaaag gccaaataga ttaattttag aaattataaa tacttaacct agagtaagcc   130080
cttattcttt tttcatttgc attcccatgg acatttatgt attttttgc ctaggaaagt   130140 gctgtttctt agtgtaataa ataagtgtta aaagtagttc tccacagctg tttcctggcc   130200
cttgctattt cttcccttc tcttttttctt ttaaaatgaa gagggtagtt aaaaagaaat   130260
agacatcaga actggaagtt cactctgtaa cttcagcaac taacacaata tgagtctgat   130320
gtgttaaata ttttcactg gcgttggcaa aagcttagtg aattttgtaa gagccattgt   130380
tctgaaataa gcatatatta tagatatgtt agcagaatac ttgataaatc ttatttgtgg   130440
atatttcttt ttttttgag acggagtttc accctcttgc ccaggctgga gagcaagtgg   130500
cacgatcttg gctcactgca agctctgcct cccgggttca cgccattctc ctgcctcagc   130560
atcccgagta gctggaacta caggcgcccg ccaccatgcc tagctaattt tttgtacttt   130620
tagtagagac ggggtttcac catgttaacc aggatggttt cgatctcctg acccatgat   130680 ctgcccgcct cggcctccca aagtgctgga attacaggcg tgagccactg cgcccggccc   130740
ttttgtggat atttctttac ctgtctctca actacccagt acatcccacc cctcaaaaca   130800
gaagtgattt ttctaacatt agtcaagaat tgatctaacc tttaaattag taatatgtgt   130860
taaatttctt tataacgtct tcccaaatct ataatacact ttattaagct ataatgtctt   130920
tttttttttt tttttgaga tggaatctca ctctgtcgcc caggctggag agtagtggca   130980
tgatcttggc tcactgcaac ctcccactcc tgggttcaag cgattctcct gcctcagcct   131040
cctgagtagc tgggattaca gtagcatgcc accacgccca gctaatttt tgtattttta   131100 gtagaaacga ggtttcactg tgttagccag gatgctctca atctcctgac cttgtgatct   131160
gcccgccttg gcctcccaaa gtgctgggat tacaggcgtg agccaccgca cctggccatt   131220
aagctataat ttctatataa tatacccatt ttaagtgtac tggttagtaa attttgacaa   131280
atatgtacat ctgtgtgacc accaccacag tcaacatgtg gaacatttt tttcactgc   131340 aaaaagttcc cttatggccc ttcactctac attttcccca cccacctcta tacacagaca   131400
atgactgttt ttccatgatt attgattatt ttcacctgtc ctagaatttc atctacatgg   131460
agtcacagta tacactcttt aacacgtggt ttctttcact cagcatattt tttagatttc   131520
ttagatttac atgttgtatg tatcagtagt tcattccttt ttattgctga gtaatatgaa   131580
ttaaccacag ttttgttttt tgttttttt ttaacccatg tattgatgga tgtctgggtc   131640
```

```
atttccagtt tggagctgtt ataaataaaa ccataaggga aattcatgtg taagactagg    131700
tgttgacata tatttgcatt tgtcatgggt aaatacttga gagtggaatt gttggatcat    131760
atgttaattt tttaaattta taagaaactg ccaaattgtt tttaacccac cataaacact    131820
tatttctcct tgtcacttgt tttgcagaca ctttataaaa cccaggtaaa ggaacttaaa    131880
gaagaaattg aagaaaaaaa cagagaaaat ttaaagaaaa tacaggaact acaaatgaa     131940
aagtatgtcc attttacttt agaacaagaa tcagtactgc aacaggcatt cttaagtttt    132000
aagttagtga atagatgtgc cattattctg gtgggaatgg tatagaacac agtttattgg    132060
gctaattcag aacaaatcag attaggctga aatttgcctt tatggtgaaa aaaacagtgc    132120
tataaatcaa cactgtacca attgcagaga ttcattaaac tgacaaaaag ttggtttgac    132180
aattgttttc aggggtattg caattttat ttttttaatt tttttttttt gagatggagt     132240
cttgctctgt cactcaggct ggagtgcagt ggcatgatct cggctcactg caacttccac    132300
ctcccgggtt caagcgattc tcctgcctca gcctcctgag tagctgggat tacaggcgtg    132360
cgccaccacg ctccgctaat ttttgtattt ttagtagaga cagggtttca ccatgttggt    132420
caggttggtc tcaaactcct gacctcatat tccgtccacc ttggcctccc aaagtgctgg    132480
gattataggc attagccacc acgcctgggc tagtatcaat tttaaaagat ctatttatat    132540
ataaatcatg ctgtctttgc aaatcattat tttaagttag ataaaggtat ttaaggtctt    132600
cttaggatta ctatgcaggt tatggccggg catggtggct catgcctgta ataccagcat    132660
tttgggaggc taaggtgaga ggatcacttg agcccaagag ttcaagacca gcctgggcaa    132720
cataatgaga ccccatctcc aaggagaaaa ccttataaag ctatttcaag tgtaacagct    132780
tcattttaga attcagctga caggcgcaac aagatagtaa ctcctgcgga gtatctcata    132840
gctaggtaat gtcagaacag acactagaac tagttttcca acattgttat attctcttta    132900
catttaatca cctttgaaag actgttgttg aaacaaacaa ttacagaaaa cagcaaaact    132960
aatacagttc ttatgaacta tgacaaatgt cattataacc atcatcatcc atgaaagaga    133020
accttgctat ccacttcaga agcccactat atcccacctc ctaattatgc cttctttcct    133080
ccccacctca agagtaatca ccatcctaaa actaatttgt tgaagaaact ggattttttt    133140
gtcctgtaga tgttccctca gttgcgattt tattgattgc atttctgtag ttggttgaac    133200
attccccatt tccctatgt ttcctggaag tcagtagttg tatctagagc tcctctgccc     133260
aatatggtgg ccagtagcca catgtagtta cttaaattta aattcaatta cgtaaaatta    133320
aaacttagtt cctcagatgt actagtcgta tttcaggtgc tcagtagtca catgcagtta    133380
gtgtctacca tattataata gatggtacag atatagaaca tttctgacat cctggaaagt    133440
tttattggac atttctgatt tagaagctta atcagattca aatctgattt ttaggaggaa    133500
gaagactaat tcatatatag ccttgtactt tctggttgcc tatttctgtt gttaaccact    133560
atggcattca atgttagatc cttaatacat taggtgttgc aaactggaga tactcacttt    133620
tatcattctt cattttttt tttttttgtt ggaatacata acttttattt tcactagttt     133680
tataaataaa cttagacttt ttgttgttta actttgttga cttgattaca attaagtata    133740
attgcatctt tttgcaatta agttgcctta atcgagttga ttatattgat taaaatattt    133800
aaggtccaaa attgacaata gtttgttgca gagctgtata ttatcttaaa ttttagcatc    133860
acagcgggta taaacatact aattcggtgg ccaagtatca tagttagata acctaattaa    133920
ctggaagcta aggtagacac aaagctgcat ttcctggtta ttctctgata tagtcatatt    133980
gtagaatcta gtctgttacc taccatttgt gtggtattca cagtgcaata tgcaatccca    134040
```

```
ggtgtatgca ttcactgtga aggggacagt ttaggcagaa gccaatcagt gatctgagga  134100
acagaaagag aaagtgatta aaagtgccaa atattcaatc catactatat tgtttcagag  134160
ttgatatatt ttcccttttt catctattca agacaaatat atggatcacc agtattgtgc  134220
tataagtact gtgctttgtg cagctatcca attattagta agttatgatt cttcaggtgc  134280
ttcagaatca agttaggaga gatataatca aggtatagtg gctatgccaa aggatacctc  134340
atcttaccat gtgggattca gagaacattt cctaacagag atcacaaccg atggaaagta  134400
gaattagcca gggaatggga tgtggggaac aagggacaat ataggcagaa gccaatctgt  134460
gatctgagga acagcaaatg gttagttcgt gacagataag gctggagaga gaaaactgag  134520
tcagattaca aaggaccttg tgtatcatgc tgaagagttt aaaatattga aagtgggga   134580 cttttgtttc ttctattgtt gtctattgtc tattcccagc actccaatca gggactttca  134640
gagaataagt attcaataaa tattgaatga ataaatgaaa atcctaagct agtgactgat  134700
aagtatttta gaaaactcac tctaaggagt ggagaatgaa ttgaagtaag ggaaagctgg  134760
gtggatgcag ggagcccaat tatataaccg ctggcaaaac ttagatgtaa aattatagtg  134820
gaagttggca gtaggaggca agtgcataaa acgaagtagg aagtaaaaga agtaggattt  134880
gtagatttgg aggcataggg gtaaaggtta ggataatttt caggctgact cccaagtttc  134940
tgaccagagc tgttgagttg atggtagtgc tggtccctga gctaaggaat gccaaaattg  135000
tgagatgaga ggagagaaga ttattttaat ttcaggccta ttgagtttga ggtgcctatg  135060
ggatgtccaa acagaaatgg ataccactgt atttgggctt attgctttag aatgcagata  135120
aaagataaga acttgaagct gatttgatag tctttgcata cagaaaccac taatatagag  135180
atctgttaag gtgattgtgt atctcagagt ttataaactc atgagcctat gatgccatag  135240
gtgtaactag gctgtaatta gtggggtcta agtgcagata tattcgttaa tgtaagttgt  135300
aaggattgta acaaactgaa gatctcgcct tctcagttcc agccatttgt taccacatga  135360
taacactggc ccagtatgtc aggatcttct gattttcaa gagaaaccaa gaatctgaat   135420
ttttatgtaa aaggttgacc caaaactctt ttaggtgtat gtttgtgtat gtgtgtctgg  135480
atccctccag acaattttct aggcatttga aatatacctg tgtgaacaag aacaaagcca  135540
ctctttataa tcttataatc cagaagaata tggaattatt gattattgaa ttcttttaag  135600
aggtaggaga ataagggtga gagattgacc ttaaatatta ttaaagacag tctttcatta  135660
tggagagttg taaggaagt ctggatgaat atatagatgc aggggcact gttgtaggct     135720 catttggtcc tctcaggtag caaattgtaa tccatagtgt aggatcagaa gacacaaagg  135780
ctgaggaaag actactagct cctagacttt taaggaatgg gcagaggaag ggaaaccaat  135840
aagctaccaa cagtgtaaga gaagatcaga gcaggatatc acaaaagctg gggtaagaga  135900
atatttccag aaagagaaag tgattaaaag tgccacatat tggccgggca tggtggctca  135960
cgcctgtaat cccagcactt tgggaggccg aggcaggcgg atcacaatat caggagattg  136020
agaccatcct ggctaacagg gtgaaacccc gtctctactg aaaatacaaa aaattagcc   136080 gggcgtggtg gcaggtgcct gtagtcccag ctactcggga ggctgaggca ggagaatggc  136140
gtgaacctgg gaggcggagc ttgcagtgag cctagatggt gccacggcac tccatcctgg  136200
gcaacagagt gagactgtct caaaaaaaga ataaataaat aaaaattaaa ttaaatttta  136260
aaaagtgcca catacccaca aaggtcaaga aaaacagtca taaattgtcc atttatttat  136320
attgaaggtt attcattatc ttggtgagaa cagcttctaa atagagatga gaataggtat  136380
taaagtagat tgagactgaa tggaaagggt aaaacaagag acagagtata tctaacagcc  136440
```

```
tgattagcct tatttctatt caacaaacca attagtcact ctcctacttc caggtatgta   136500
cattgctctt ctctctgcct ggaacagttt cctccaagta tctacatggc ttgctccttg   136560
gcccttctcc aggtccacat catttgacaa ggccttccct gaatatgctt tttaaattgc   136620
aaacatcccc accccactac cgtggtgccc agttcatcct tccctatttt attttctct   136680 gcagcactta ttccctccta atatataatt ttcttacctg ttgtatttat tgttttgtt    136740 tttccgctag aaacaaagct ctatggtagg aggaatttc agatatttca ttcttaggtt    136800
caattcattg ctgtatgtct agcacctaca attgtaactg cagcattgtg atgctcagca   136860
agtgtttgtt aaattaaaca attcaggaga cttggctgtt atggcaaggg gatgtagcag   136920
tagctagagg agagtgtgaa ggagagcact ttcttttta cagtagtgta aacttgagca    136980
tatttaaatg gagcatggga aggagatcag agtaggaaca gccccacatc tattcattca   137040
aataaataaa atttctgagc gcattctatg ggccagagaa ttttctaggc atttgaaata   137100
tacctgtaaa caagaacaaa gccattcttt ataatcttat aatccagaag aatatggaat   137160
tattgattat tgaattcttt taagaggtag gagaataagg gtgagagatt gaccttaaat   137220
attagtaaag acagtctttc attatggaga gttgtaaagg aagtctggat gaatgtatag   137280
atgcaggtaa ttttaccctg aaccatctaa ttctttcttg cttttctct tgcacagtag    137340 cataaccagg gatagaaata tattctggat taaataggtt ttctggtgtc ttaaagtata   137400
acccagatac ttttatctta acacaaagca gaaactccag ataagaacat gtcgtgaacc   137460
tgaagccctg tattatagta gctagcagaa ccactcccaa tattcttaga tttggcattg   137520
gcagcatatc ctttctttc ctaaagtact aactctacta ctctcctaag aaaattattt     137580
cacatctcgt ctctactcag atctccagct tttccttatt cttgtactta gctaatggcc   137640
ttgcttccta aaaatcagaa gagaacatct attctcttc accaccatag ctactaactt    137700
gtctgcatca gagtagagta tcacaaaaac tgggggagga ggatatttca agaaagagaa   137760
agtgattaaa agtgccaaat attgctgggc acggtggctc acgcctgtaa tcccagcact   137820
ttgggaggct gaggcggggg gatcacgagg tcaggagatc gagaccattc tggctaacat   137880
ggagaaaccc cgtctctact aaaaatacaa aaaattacgg gcgggcgcct gtagtcccag   137940
ctactcggga ggctgaggca ggagaatggc gtgaacccgg gaggagccga gatcacacca   138000
ctgcactcca gcctgggtga cagagcaaga ctccatctca aaaaaaaaaa aaagtgcca    138060 aatattgaga aaggtcacaa aaaagtcata aattgtccat tgtatttatt ttgaaggcta   138120
ctcattatct tggtgagaat agcttctaag tagagaatag tacctataaa ccctgccttc   138180
cttctgatga tgtaaatgga catcatgagc taacgctctt atctaatgct agtccctcga   138240
tcctatctct tcctgcctac ttaagaatat gacttggtcg ggtgtggtga ctcatgcccg   138300
taatcccagc aatttgggag gccaggtgg gtggatcact tgggtcaaga gttcgctacc    138360
agcctggcta acacggtgaa accccgtctc tactaaaaat gcaaaaatta gccgggcatg   138420
gtggcacatg cctgtagtcc cagctgcttg gaaggctgag gcaggagaat cgcttgaacc   138480
tgggaggcga agattgcagt gtgccgagat tgcgccattg cactccagcc tgggcgcag    138540 agactgagtc tccaaaaaaa attatgattc caacaattct cttatctttt ctacatcaat   138600
ttttaccttt ttgtagtcat tatcattgtt atgtaaacat atttagatat ctcctctaaa   138660
aacaaccctc ttacaccggg cgtggtggct cacgcctgta atcccagcac tttgggaggc   138720
caaggcgggt ggattcctg aggtcggag ttcaagacca gcctgaccaa catggagaaa     138780
ccccatctgt actaaaaata caaaattagc tgggcgtggt ggcacatgcc tgtaatccca   138840
```

```
actactcggg aggctgaggc aggggaattg cttcaaccca ggaggcggag tttgcagtga  138900
gccaagatca caccattgcg ctccagcctg ggcaacaaga gcgaaactgc gtcttttaac  138960
tacattatct acatggtagc caccatccca ctttttcttt ttttatagcc aacttacttg  139020
aaaagtgaca taccaggtat cttccaccgt cttctttcat tctctcttga gctcactcca  139080
gtcatacttt tgcattcatc atgctaacag aacaactctt ctcaaggtca gtggggtctt  139140
cctaatagtg acttctcagt tctcacctta tttcatagca ggatttgact tagttgatta  139200
ctctcttgag aaaatgtctt catttggctt ctgtgacacc acatgctgta ttttccttat  139260
tgaactggct actctttctc agcctccttt gttccttttt ccattctaat tgctgagacc  139320
gttaaaagtt tggagtgctc aagggattac tccctacttg ttctcatcca gccttgtggc  139380
tttaaatggt gtcagagtcc aagtacatcc tcccttgaat tccagactta cgtatccagc  139440
tgtctaattg acatctctgc ttgagtgtta agcaccccac atttaacgtg tccagaaaaa  139500
cttcctgatt ccctgacctt gcgaactgct ccttcctgtc ttcctcattt cagtcctgaa  139560
caattctgtt attcctagtt gtttaagtga aaaatttaga gtcatcctag actcttcttt  139620 tttcttaca ctctaaatgc agtccaccaa caaattttcc cagtgttaac taaaaattat  139680
gtatagactc taatcacttc tcaccacttg taccatttac tgacctggtc caaactgcca  139740
tcatctccaa tcttgattat ttcagtagtc tcctaactgg tatcccagct tctgccattg  139800 tcccctact gtctgatctt aatacagcag ccagaatgat ctttctaaaa caccagagta  139860
ccagaataaa agtcaaagtc cttgtattgc cttggaaagc cttacagtat ctgttgttct  139920
cttcccccta cttttcttct actgttgtct tagcagagag gcctccttga tcaacctgta  139980 ataaagtga tcatattcat aactttccat atttatctt gtattattct ctgtggcata  140040
ctatatagca cttgttcatt ttttaaattg cctgtacggc cccactaatg catgctccct  140100
gagggcagga actttgttac tgctgtgtct ctttatttat ttatttattt atttatttat  140160
ttatttattt atttatttat ttatttttga gacggagtct tgcactgtca cctcagcctc  140220
ccaagtagcc gggattacag gcacacacca ccacacctgg ctaatttttt gtattttag  140280 tagagatggg gttccactac gttggcagac tggtctccaa ctcctgacct catgatctgc  140340
ccgcctcagc ctcccaaagg gctgggatta tggggtgag ccactgcttc cggcctgctg  140400
tatctcttaa ttcctagaac agcgtgatgc atagtaaaca tagtgtagta cttagtaaac  140460
cttcaagtaa atagctgttg ggtgaattaa tgaattttct gtgtgtatgt gtgtgtgtgt  140520
gtgtgtgtgt gtgtgtgtgt gtgtgtatgt ttactatatg tctccctctt gaggcttcag  140580
gcagaaaatt tgaattgtaa tactcactag aaaataggag gtggaagtta ctcattcaga  140640
acatatttat tgagcaccta ctctgttcag ggaatacagt agtgactaag agagcttatc  140700
caagagaggc tctttgagaa gagtaggcaa actggagttg tcttggtctg aatgtcagtt  140760
ctgaaatgtt ttagtatcat ttccaggag cattctcaga ttagtttgta gtgatttgca  140820
aatctcttat aagttttcat aatctcattt aatttcagag ctggaaggga ctagtttaac  140880
catctcattt tacagatttg atgaaactga actgcaggaa gtgtaaggga cttgcccagt  140940
gtctctactc aattagttaa tgataaaaca gagataaagt tctgggtcta gcctgctgat  141000
taacaagtca atgactttc cactatgcca cgctgcctc cattccaaat ctgcaagaaa  141060 ttcttttca aaagcagact atttgctatt gctttatgac cttttttagt taagcacaat  141120
atgggataga aaactaaata gttctttat aattttcaa catgtgagag gttaaattca  141180
ttacttttat agaaagtttg caatggattt aaatttattt taagcaataa ataattctt  141240
```

```
tttatcattt aaagttaatt gtgttttaa gaatatgatt aagttggaag gatgaactga   141300
atttgtttac atcagtttct cttaaaaaat tgttgcagag aaactcttgc tactcagttg   141360
gatctagcag aaacaaaagc tgagtctgag cagttggcgc gaggccttct ggaagaacag   141420
tattttgaat tgacgcaaga aagcaagaaa gctgcttcaa gaaatagaca agagattaca   141480
gataaagatc acactgttag tcgggtaagt gtgatagtca ggtaagttat ataaaattta   141540
tttaaatcac aataggtcac atcttaaaat attagggtaa gtgtgtgtgc aagtgtattt   141600
acttctatgt taatacatag tggtcattct gtactcatgt ataaaatagt ttgtataata   141660
ccaaacattt gttaattatt gaaattcttg ttcaagatat tgggcttttg tttgtatagg   141720
cacagaacca atgcaatatt gggctgtttt tctggctgta gatcttatta gttatatttc   141780
atatgaagta atggcttagc ttaaattcat ttgttgttct cttaatacat tgcaactgat   141840
tttatgggcc agaattctgt gaaatataga gaaaccattt gggaatgagg aattcttggg   141900
ataatatata aatccattat aagaaaacca atactccaaa caattaccta ttcctgaggt   141960
ttatactgta atctatatag aatcatgcga ctaaaaagag gagttagatt tttcttgtaa   142020
agccactatc agtcactctg ggttccagtt ttgcccctaa gaagttatat ggtcttggca   142080
aagttggctt taacttctct aagcctcaga tttctcatct ataaaataga aatagtaata   142140
tctcttccac atgattgtta tgaggattaa ataagacagt agacatagaa tgattaatat   142200
aacatataac aagtaatgat tatatattac taaaagtaat ctataaataa atgttttat   142260 tatcgttttc atcatcaata ttcagataaa gatattgaag tccagaaaaa gtatgacttg   142320
ctcggggtca catactaggt taatcgcaga gctagaacta aatacaaatt tcttagtttg   142380
caatctagtt atcttgccat tacatatgcc ccccttttgt tcatacatat atctatatgc   142440
atacaatgaa ataattttg gatgctgtta actacttta aatattttg atgtaattac   142500 atattttaag ctggaaacca gacatttgct gtagttcagc agtgtctgac ctgtctttat   142560
ctagcagtat atttaaaggt tactgcctga aatacgagaa tagcaaagag ctggagctt   142620 aaacttttgt gtgctttgtt tagcttgaag aagcaaacag catgctaacc aaagatattg   142680
aaatattaag aagagagaat gaagagctaa cagagaaaat gaagaaggca gaggaaggta   142740
tgtagaattt ttaaaaatc atcatgttaa atcaaattca gtgatttatc tttacctatg   142800
ttgtgttagg tttctaagat acctgttttc atatattaag taacttctgt agccttaaga   142860
attatcttaa tgaagttact gaaagttact atgtaatgta tacttatttg aataattaaa   142920
gacattgtta gtttgaaatg cagaaattaa attaatacca tacaataaca tttaatataa   142980
tttgttgaca gaatataaac tggagaagga ggaggagatc agtaatctta aggctgcctt   143040
tgaaaagaat atcaacactg aacgaaccct aaaacacag gtatacatgc tttcgatctt   143100
ttccacatgt tcatttttga gttaatcatt gctctttatg cacttttttcc taaaaccaag   143160 gcttataagg ttcaagcttt tcatcagaac aaataaattc tctccccgct aactataaaa   143220
aacttatttg tgaaatagaa tttcaaggcc aggcgcggtg gctcatgcct gtaatcccaa   143280
cactttagga ggctgaggcc agcagaacac ttaaggccag gagttcgaga gcagcctggc   143340
tgacatcgaa accccagtct ctactaaaaa tacaaaaatt agccgggcgt ggtggtgcgc   143400
tccagtaata ccagctagtc aggtggctga ggcacgagaa ttgcttgaac ccaggaggca   143460
gaggttgcag tgagcaaaga tcatgccact gcatgccagc ctgggcgaca gagcaagacc   143520
cagtctcaaa aaaaaaaaaa gaaataggat ttcagttaag aaagctaact tgcctagtaa   143580
tattgtatag ttgtagaaga taagagtatg tggccaaggc atagaagctt tatttgctag   143640
```

```
tacccaacat cagagtagga ttagcatact cttgattcag tactgggttg taaagttaac 143700
caaagaaagg ctcctggttc ttacatttaa gtagtgtgat aagtcagtgt tagttacttg 143760
tgctaccagt tatcatgtct caaccatcat gaagttgtcc taattttcat acacacagaa 143820
agtcctgctt cctgattttg aagaaaaaaa tacatttag tattaaattg gatgactaca 143880
ctattgatct ttattaataa tattttaata ggctgttaac aaattggcag aaataatgaa 143940
tcgaaaagat tttaaaattg atagaaagaa agctaataca caagatttga gaaagaaaga 144000
aaaggaaaat cgaaagctgc aactggaact caaccaagaa agagagaaat tcaaccagat 144060
ggtagtgaaa catcagaagg aactgaatga catgcaagcg gtaaggtttc tgtgtgtgta 144120
tggatatgag tgtgaaggat tattttctta aattatttct gtatatactt gttatctatt 144180
tatcttgttt agattgggaa caatcaaggg ttctgcctgt ttggtttcag actgaaattg 144240
ggatatggct gttataatat taactataat tggggtagag gttttgaagt attgtagctt 144300
atttattttc tctagtcaag actcactttt ttgaaatcaa aataacaagc ttaattttt 144360 gataccccctt ggcttgttaa tagaacaaaa ttgagaacct ggtctcgggc acttagatct 144420
aagcttttta gctccatcag ttatggtttt ctgaagtttt ctatacccttt aaagctactt 144480 catttggagc cagaaaagca ttttcttttg ttgtaacttt tttgttttga tggcttatgt 144540
ttgaaaacaa aaacaaaaac tcttttttaag gcaaggagaa aaggaatttg tccgagcatt 144600
gtattactga gaaagaactt gacatttctg tagtgtatca aaatctgtgg tagcaaacat 144660
tcatgaagtt tactgtacat ttttagtatt agcaatttaa attatcatat ttcaattagt 144720
aatgttggaa attgttttag cttgattata ttatcttgat acttttcaaa attagcaatt 144780
ggtagaagaa tgtgcacata ggaatgagct tcagatgcag ttggccagca aagagagtga 144840
tattgagcaa ttgcgtgcta aacttttgga cctctcggat tctacaagtg ttgctagttt 144900
tcctagtgct gatgaaactg atggtaacct cccaggtaag aataattctg tatcattcaa 144960
acatgtataa atgtcatgga aattagtgta tatttctttc atttggtttt ctacctcctt 145020
gtcattttgt ccatggattc ctaagaagga attcttattt ctgatagcca aggcctgatg 145080
atgattatac acttggtgta ttttgtggag tagagcagtt gtaagcaatc ttaggctatt 145140
taaatagacc taagaagctt tacctgaata aaaaccataa gaggtttatg aacctatttt 145200
gagcagccta agtccacagt gagagtcaaa gctgctacta cacatctcac tattttttaa 145260
aagttgtaca tttttgtgag taatagctct ttaacatttt atgtattctt gtgctaaaac 145320
taagaactgt actttatcat cagaaccaca gcagctacat atagaaccct atctagtgga 145380
gtagtgatca acttcagtca gactttgcta agttttaagt ttggggaaat agataaaatg 145440
ggttgggcag tgcagtaaga ggccgggggt gtcaaataaa ggcaggaatg agtggctaag 145500
atttgagact ttttctgtg tcttcttttt cccagtggag aatcaattta aaataaaaca 145560
caacctcatt cttggtttaa tcgtcatgta aactataata cctttatgta ctttacagag 145620
atgagaaata cacatactat aagttcaatt tagaaataaa atgagtaggt tatcattatt 145680
aaaacatgca tttacatata cacagagtct tagttcagag tcttggaagt tttgtataca 145740
tgataataca cttgaaaata gatttttaatt agtgtatttt ctgaataata cataaatagg 145800
aagatattta tgaagcagca tgtttgatat tgggattctg ttttaacaga tattacttgt 145860
tattgtgaat ttgatataag gaactagagg agtcactcag aaaattttat agtatctttc 145920
ttggtcaaga aagtgggact caaagtggga aatgaattca gctcctctct gtatgctatg 145980
tgatccctgg cctcattctt gtgtggcttt gctaggtcaa aatcaggtat ctgggaatgg 146040
```

```
aaaggcagcg aagaaatatt tcttatttta gtggtcaagg aactcctctg tttacctatt  146100
tttggctctc tgaaactgcc tacctcttga gaaacttgca ggtacacacg attcattatt  146160
gtaggatcac tttgaattta ataagaacct gtagctttag ttattgtttg aacatctttc  146220
taaagttaga cttaatcatc actaagaata tgacttttag aagtgtttgg ctacattctt  146280
tcaattgttg aactgaattg gtaggttaga ttcccacttc attaaccctg agatacttct  146340
ggagttattt agtataggga ttcttactct atgtatgtat gtatgtatac attcttactc  146400
tatgtatata tgtatgtatg tatgtatgta tgtatgtatg tatgtatata tgtatgtatg  146460
tatgtatgaa acagtctcac tctgttgccc aggctagagt gcagtggcgt gatcttggtt  146520
catgatcctg cctcctgggc tcaagcgatc ctcctgcccc aacctcctga gtagctggga  146580
ctacaggtgc acatcaccac acccggctaa ttttttttaat tttttgtaga cgggatttt  146640 caccatattg cccaggctgg ttttgaactc ctgagctcaa gctatctgcc tgccttggcc  146700
ttccaaagtg ctgagattac aggcatgagc cacccgcctg ccgacccttg ctctatttag  146760
tgtcagttcg aaatcctgac caattttatt tttattccac ccatttccct ttaactattt  146820
ataatgcctt tatgcacct tagtgttctt agtattgggt taaatatgtc agaaatggac  146880
acattattgg tgaatgctag ttagaagatt tgagttgaaa ggtgagctgg tgggactgct  146940
aatgaggaaa gtgattaatt ttacccacca tcgtggctga ttcagaaagg ctaagctcat  147000
agtgccatca gctggcttca ttggcagact taggctggga atccatttag gtttcagaat  147060
cctgacctaa taaattgact tattgagcaa agagattttt aaatgtttct actagctcca  147120
ttttcagtat atttcttaga atattagtgt actttcagga attttgtttt taaggttatc  147180
aaagtccaaa ccaagtgggg cggggagtac tggtagccat tctcccttgc tagaagaggc  147240
cagttaatac ctcttttcct attactgtgt tcttaatttt gagactttat aaaatctcaa  147300
cagtgctgaa ccttgacttt catattggaa gtagaaatta atggatagtc tttgtcaata  147360
ttatttacct ctctgtgggt cagatatttt gctagtaaat tgaaaatctg tattaaatcc  147420
accatttact agatgctcaa aaatggtccc tggcaaataa agttaaggtt ttgcattcat  147480
atctaggaag aattgttaaa gaatgttgat attcattctt aatattagat agttacatat  147540
cattcaagtg tctaaaaaat ttcttgaagg taatggctaa tgattaattt ttacttcagt  147600
ttagaaaata agtaaatgaa tatacgtact aaaaaggaga gggctttgaa tagattaagt  147660
ttactccaag ttaaaatgat ggcttttga aatatgggtc acattttca gtttttttt  147720 aagtagttgg atggataaac tgacactgca acttttatta tttctcttat atttcatcat  147780
tcagtataaa gattataatt taattatctt gcacatctag aacgcagcct ctatgaatcc  147840
ttagtggcca ttttgttatt aactagctta aatattaaat ctcccttcta aaattcccaa  147900
ttctaaaaac tttatttaaa aaatgttact ccttctctga cttataactc tttgaagttc  147960
ttgaagtcac cttcattctc ttaattcttt tatgtcttta tcttctcttt ggttctgtag  148020
caggttgtga cctagcacac aatacaaaca taaagattac ccttacggtt atgggtgcct  148080
gttgcctaga tgacaaaaaa ctttaatgtg taaactgttt cttttcctca ttctttctct  148140
ttccttcttt tggaactgtt aacctagaca tctgaagaga atgtagaaat agatgatgga  148200
ttaggaaaac ttggtattga tactccagta atattcatta tctcttatgg attatttgta  148260 tcatacccctt ttccatccag cttgacctta ggttatgtaa cttaaacctg aaaatggtgg  148320
atctcttggt gtgttcccca atatttgaat atatgaatgt ttctgacctt gcccaaatct  148380
agtgatttga agttggtgta tctgacttgt tgagtattaa ttaattttct tttttatatc  148440
```

```
acttttgaat ttaattaaag tgttttgaaa tggttctttta gccctgtttc ttaagcagta   148500
tgtttgtggt atagctaaat aaattaggta gtcttcagag gttagctctg atgtttgaat   148560
tggctatatc gagtattgat gtacatgtag ttagattgtc tcttatttgg gtaaagaaat   148620
cgctgatatt gcagtaatat acatctaact tcttataagt taaaattgtt ctacaaatat   148680
attgtataaa atttagagcc aagttgtttt tgtacatatg tagaatatta ttaaggataa   148740
tccagactta gaggttctct cagtgggagt ttcatttagt tatctggaga agctgttttc   148800
tgtgcttgtg atataaaaga tggaatttac agcgttatac ctccagatca ccacttaagt   148860
tacaggtggt cccgatttta gaggaggtct ttatatattt taaaaactgg taagtatatt   148920
atcttgcaac tatggtaggc gtaaggaaag gaaacgcagg agaagctagt atgtatttt   148980 ttatctgtta ttattgagct tagttcagtt gcttctctga gggaattcac cagatggaaa   149040
aactaaaatt ttctcccatg acattgttgt aaattggcaa aaaccttcac atattcttga   149100
cacctttatt tgcattccag atttcttcat ttaatttatt ttctccctga ccctcttcat   149160
ttaatttaaa tatgagcaaa tgtagaattc tggcttattt gactcataag attcccttga   149220
tatataaaat ttctaaggaa cactgaaatg acagataaag ccataccata taacaactta   149280
ttgaagatat attaaaactg gcaggttaac ccacatctag agccagaaag cataaatatt   149340
tttgacattg attgtcacaa agaaataatg tgaaagtata gggtattttg gcatacaaat   149400
tttgtgtaaa tgtcaagaat tcaaaggctt ttatatcttt gttttggtg aggaattact    149460 aatactaaac aactttgtat tatcagatat taagactcct tttcattctc actaatgttc   149520
atcttaatgt tttccaaact acactttaaa accagagctg caatttctac cacactaatg   149580
ggaaaatttc tggcaataac ttttttgctt ttataagata aaatattggt gaatgatcaa   149640
tatgtgatca acagtcttct gcatgctatt tagtataaaa ctgcctgttt ggtttttaaa   149700
ctggaaccac tatttacaaa ggatgacttt aattggctaa ttcagaaaaa tgcagaatta   149760
caaaataatc aacaaatatc tgtcaagtac cacctcgttg tgtcatttgc catgggatat   149820
ataaaatcaa gtgttaagat atggtccttg ctctcacaaa acttaccaag gaactaccta   149880
agcaacaaaa taattacttc atgaactaaa ttgcagcaat taaagccagg tgctgtggta   149940
catgccactg cttaggaagc tgaggctcag gagtttgagg ccagcctgga caacgtaaca   150000
agacttcatg tcaaaaaaaa aaaaaaaaaa aaaggaaaaa gaaaatgtt gggagaagag    150060 agggatcatt ttgaactaaa gttacctcac catttcctcc attttaacaa tttatatgaa   150120
gaggaataac acaagcaaag gtgtggagac attacgtacc tggtgggagt aggggaaaaa   150180
aatatttccc acaattcagt caactgcaga gcttgtttgc gaacagaata tgttgtgct    150240 ctagaaacat aagctcagaa attagactgc cggggttga aaccatagag ctttgataga    150300
tactgataga gttgccttgc ccaagtccgt ttaccctgct aagcttagt ctcttctttt    150360 gtaagtgaaa gatgacagta gaaccttttc cgaattcctc ggaatataat atcctgtatt   150420
catggactta tacataggtt aaatatgaga tattataaag catgtggcaa atagtaaatt   150480
tatgaataaa taaatcagta aatgttacct attgttaact gttactgtaa gactgagttt   150540
atagctttta aattatatga aggcggacaa tatattgcct taggattacc atttgaatga   150600
tagtataatc tcatatttta gtgtcatact ttgaaattgg ttattttct attcttttgt    150660 gtttcaaata taaggtagat acggaaaata gttaaattga atggattttc ttatttccaa   150720
cctgatctaa aataactatt tctaatggag ttgtctttat cccccagata tttctagtag   150780
acattagtta tatttaaaca atagtaataa ttattataaa atgccttgat caaatagtca   150840
```

```
aggaattcct ggtatgcacg tactagttga ataatggca gtagaccaaa tggattctgt    150900
gttgttttta ctgttgatca aattgtgata tcagaaactt aagaggcttt aaaactcttt    150960
agtttgagta gaattgcaat tgaacttagc actagagtta agtgctcccc tcaaccaaat    151020
ttgggcaatt ttattgaaat agttacaaat tcaaattgaa gttgttttac caaaaagctt    151080
aatcagaata ttgtactgag aaaacaaata aaatacttgt ctcttattct ttatatctag    151140
ttgattctgc ctgcattcct tatttattta tcttctattc ttgtcttctg tgagtaatag    151200
gacacttcta tacttttgct tgctctttct tgtgtaaatc atggctctga tttgttccac    151260
ttgctgcatt attttttct ttcttttttt tgctgatta tttttatatg aatgttaaat     151320
gataaagtct tctacatcat atcccattta agctgcaatc cattccagtc ttgcctggct    151380
cttaagggta ttgttacttc atactttttgt aattgattac taaatgttaa attgtatggg   151440
aaaagtggct tggaattttt ttctgcaata tttgtatggc cattaaagtt gatttgtgtg    151500
attgaagcat ggaagagcaa attatagcac ttattcattt agttgtgttc aattgcttgt    151560
tgctgcatgc tgtcagacaa cttttaatag tttttcttt gttacaattt aagactgact     151620
aatacatata ttctttttct cctagagtca agaattgaag gttggctttc agtaccaaat    151680
agaggaaata tcaaacgata tggctggaag aaacaggtac catataccta attatttttct   151740 aactggtatt ttgttctata ttttactttg gagcatagaa cttatattag ctacttttt    151800 ttactagcat ttatttttaca ttaatacagt ataatctaga tattagtggc aaatattatg   151860
cttatcactt taaaccaagt taatgttgct cttgtaactc ttccccctt tttcttattt     151920 cagtatgttg tggtaagcag caaaaaaatt ttgttctata atgacgaaca agataaggag    151980
caatccaatc catctatggt attggacata gagtaagttg cctttgattg aattttaaag    152040
gggttgagag ctaacttttg ataattattt ttagacttaa aatttatttt atattttgtg    152100
ttacttcagc actgttacct acttttctgt ttttcttaag cataaatgtt gacattatat    152160
taaatcttca gcaaaatgtg agaaggaaaa atgtatatac ttatttcatg tatttggaag    152220
acaacttttt tagttcaagt gtttagtagt ttgagttcag agagcatttc aaaaagtata    152280
gtcagctgtg tatcagtggg ttccatatcc acaactgtgg atagaaaata tttgaaagag    152340
ggccgggtgc ggtgactcac acctgtaacc ccagcacttt gggaggtcga ggcaggtgga    152400
tcacctgagg tcaggaattc aagaccagcc tgaccaacat ggtgaaaccc catctctact    152460
aaaaatccaa aaattagctg gcgtggtgg caggcgcctg tagtcccagc tactcagaag     152520
gctgaggcag gagaatcact tgaacctggg aggcagaggt tgcagtgagc ctagattcg     152580 ccactgcact ccagcctggg ccacaagagc gaaactctgt ctcaaaaaaa aaatatatat    152640
attatatgta ttatatatat tatatataat attatatata ttatataata tataatatat    152700
atattttata taatatatat aatatatata ttatataata tatatataat atatatatta    152760
tataaaatat atatattata taatataaaa tataatatat atattatata ttatataaaa    152820
tatatatatt atatatatta tataaaatat atatattatt ttttataaaa tatatatatt    152880
atatatatta tataaaatat atatattatt ttttatataa tatatatata aaatatataa    152940
aatatatata tataaataaa tatatatatt tatatatata atatatatat tttataacta    153000
ttaataatag aaatttcttt aaaaaataca gtataacaac tgtttacatc gcatttatac    153060
tgtattatgt cttatgagta atacagagat gattttaaag catacaggag gatgtgccta    153120
ggttatatgc aaataccaca ccatttata taagagcctt gagcatactt ggactttgat     153180
atttttggag ttcctggaat cagttccctg tggatataaa agaacaactg tgtaggattc    153240
```

```
tttggtcatt attaagggga aatataaata tatctgttct tttgtaatga taggtcaaag   153300
aggcctataa tatagtattt tttcttatat tcattctaaa atcttttctt aattattgct   153360
gcttatatta tcatagatta tgtagtatgt ataaagatga gtaaattcca tcattaagga   153420
ccttaccgac tagcaggaga aaaggcaaaa catattcaac aaaatatata ttcaaagtca   153480
agtctggtaa ctgcttttta aaagaaatat atatataaaa taaagtatta tcatcccttt   153540
ggaattaagt atttgtggag ctggttatag ttagaatgtg aaaagaatta agcaagttct   153600
agagaatact ctttctttat tttctgtttt tttaataaac agctttagtt gtcaaaattt   153660
aaattatcag cttaagcgaa ataatacata aacactagta tgaaagatac tatcttttcaa  153720 ctaagttaaa tacttttag attgatgaga gatttctttc ctctctttat taaggtataa   153780
tttcccacaa taaagttcat agatcttaag tgttctcttc agtaacttt tacagttgta    153840 aacattcata taatcactca atacaagatt taaaaaaatc gtatttcttt agaaaactca   153900
cttgtggctg ggcacagtgg ttatgcctct aatcccagca ctttgggaga ccaaggtggg   153960
cggttggcct gagttcaatt tgagaccagc ctgggcaaca tagcgagacc ctgtctctga   154020
aaaaagaatt tttttttttt tttttaattt atgaagaaag ctcacttggg ccagttgtgg   154080
tggctcacac ctgtaatccc agcactttgg aaggctgagg tgggaggatc acgaggtcag   154140
gagttcattc gagaccagtc tggccaacat ggtgaaaccc tgtctctact aaaaatacaa   154200
aaaattagct gggcgtggtg gcaggtgcct gtaatcccag ctactcggga ggctgaggca   154260
ggagaatcgc ttgaacccag gaggctgagg ttgcggtgag ccaagattgc gccactgcac   154320
tgcagcccgg gtgacagagc gagactccat ctcaaaaaaa aaaaagaaa aaggaaagct    154380 cacttgtgcc tcttcccatg atctgatttc tattgccaag attagttttg cctgttctag   154440
aactttatat aaatggaatt aaacagtaat gtacactttt gtgcctagca tctttcactc   154500
agcctgcacc tgtggtggtg tctgtattga ttgttctttg tattgctgaa tagtataaca   154560
ttgcatgaat ttgtttatcc attttgtgt tgattgacat ttgggttgct tccaatttgg    154620
ggctatcgta aataagactt atgagcattc ctttttttaa cttatgtttt catttctcat   154680 gggtaaaatac ccaggattgg aatcctgggt tataaagtag atctgtgttt aacttttta   154740 aaatctacca aacaattctc aaaaattatt atgtcacact attttatat caccaacagt    154800 atgagtttca gttgctccac atcctcacca acatttggtg atatcaacct ttgatttag    154860 cttttctagt ggatgttaaa tgttatttca ttgttatttt aatttgcatt ctcctcataa   154920
ctaataatac caagaatctt tcatgtcgtt attagccatt gtatatcttt tcttttttca   154980 agtctttttgc ccgtttttaa attgggttgc ttatgttttt aagattggtt tttaagagtt  155040
ctagatatat tctgaataag aatcctatgt tagaaatatg taatgcaaat atttcccaat   155100
ctgttgctta cctgttgatt ttgttaatgg tgtctttaa tgaggatcag tgtaccaatt    155160
tttaaaatgt tttctgcctt ttgtggtctg tgtttggtaa gaggtggatg tttaggtcag   155220
gttggctttt ttccccccac ataggtatct ggttgttcca acagtatttg tttttatatg   155280
ttgaccttga atcatttaat cttgcttgc acttaacagt tttatagggt tgtgggtt      155340 tgggatcaat tccacagagc ttttctacac acagtcagcc ctctgtatcc atgggttctg   155400
catctgtata ttcatccaaa catggattga aaatgtagtt aggccattg tggttgtgtc    155460 tgtacttaat atgtacagtt ttgttttttct ctaaacaata taatataata acaatttcca  155520 tagcattac attatattag atattatcta gagacaattt taaatataca ggaaggtgta   155580
cttaggttat atacaaatac tacaccattt cttatctttt ctttttttcc tgtctcttcc   155640
```

```
ctccttccct ctctttctct ctctttctct ttcactctct ctcttcaaaa tcctcctggg    155700
tcctgggacc aatctgccac agataccacg agacaactgc atacaatcat gtcatcgcca    155760
aataaagagt tttactcctt tctttccaat ctgtatgcct ttctcacgtg tatagatttg    155820
tatgaccacc accacactca aaatacagaa caattccatc acaagtgtcc ctgtgctact    155880 cctttgtag tcaaaaggca gcttccttcc tccacctctc cctaatccat agcaacatta     155940
atctgttctc catctccata attttgtctc ttcaagagtg ttatatgaat ggaatcaaat    156000
aatgtgtaat cttttctgat cagcttttt tcccattcag tataattccc ttaagatcaa     156060
tccaagtata atttgttttt ttcttgttga gtagtattcc atagtataga tgtatcacag    156120
tttgcttacc catttatttg ggttgtttct aggttttggt tattatgaat aaagctccta    156180
tgaacatcta tgtgcaggtt tttttaaata gatataaaat gttatatgaa ttttgtttc     156240 ttgaaattaa aggcccaaca gtgcaatttg ctgggttata tggtaagcat atgtttagtt    156300
ttctaagaaa ttgccatatt cttttccag agtggctgtg taattttatg tttccatcag     156360
cagtatatga gtgatttact ttctctgcat tctcacaagc atttgatgtt actactgttt    156420
ttattttttt taactctgat agatgtgtag tgacacttat tgtggtttta atttgcattt    156480
ctctaatgac tgatgatgtt gaatatcttt ttgtgtgctt atttatcacc catatgtcct    156540
ctttagtgaa atgtctttta caataaatga gttttgtaa atggcctgta ttatttca      156600 ttttagtaaa ctgtttcacg ttagacctgt aacccaagga gatgtgtata gagctgaaac    156660
tgaagaaatt cctaaaatat tccaggtaaa aatctgaagt tataatttta aagaatctaa    156720
gtcctaagcg ttttgtgaa gtaaatgtaa aatataccaa tgcttaagat ttttaaaatc     156780
ttttcctttc accattcctg aatgtagata ctatatgcaa atgaaggtga atgtagaaaa    156840
gatgtagaga tggaaccagt acaacaagct gaaaaaacta atttccaaaa tcacaaaggc    156900
catgagttta ttcctacact ctaccacttt cctgccaatt gtgatgcctg tgccaaacct    156960
ctctggcatg ttttaagcc acccctgcc ctagagtgtc gaagatgcca tgttaagtgc      157020
cacagagatc acttagataa gaaagaggac ttaatttgtc catgtaaagg taaggcatgg    157080
taattattgt tacaacttat aacaaattta attttaagtc tcaatgaact aacttatgtg    157140
tagtgatttc tataccaagt tgaaaagaga ttatagaaag tattattttg acactggtgg    157200
ggcaatatgc agctatttac agatttagct tttaaaaatg ttttattta ttttattga     157260 ttgactgatt gattgagatg gattctcact ctgtctcgcc caggctggag tgcagtggcg    157320
tgatctcagc tcactgcagc ctctgcctcc caggttcaag tgattctcct atctcagcct    157380
cctgagtagc tgggactata ggcgtgtgcc accacacccg gctaattttg tattttagt     157440 agagatggag tttcaccatg ttgtccaggc tggtttcgaa ctcctgacat caggtgatcc    157500
acccacctcg gcctcccaaa gtgctgggat tacaggtgtg agccattgca cgcccggcca    157560
acagtgtttt taaagagaat caccccttg taaacaaaca aaacaaaca aacatgctgc     157620 taagaaatta ttccaagttg gagagaagag caacaggtga gttccactct attcctccct    157680
tgagtttttc ctcttctttt tgtctggcat tcactgcctg gatcagcatg catgctgtat    157740
cacagaatat cttctagttt tacagaggta gcttgaggga aagaatacag accatagcta    157800
ttttcagata agaagcttat gttctttaaa tacatttatt tgttttacat tttgttatat    157860
ttctgatttt actttattag tttgactaat ttttttttt aatttcagcc ttatttaact    157920
taaggagaat gagatattgt tcatgcttaa ttaagcatat taaaacttt aaaaccttaa     157980 gaacttgaaa aactatgcat ttgataggtt ggattttaaa aaactatatg gctttaatta    158040
```

```
tgcttttttt ttcctcctta acatagtaag ttatgatgta acatcagcaa gagatatgct   158100
gctgttagca tgttctcagg atgaacaaaa aaaatgggta actcatttag taaagaaaat   158160
ccctaagaat ccaccatctg gttttgttcg tgcttcccct cgaacgcttt ctacaagatc   158220
cactgcaaat cagtctttcc ggaaagtggt caaaaataca tctggaaaaa ctaggtaagg   158280
atttgaaatg ctaacgtttt taacaatgtg aaaatgattg gataacagct attaaaatca   158340
gaaatctaat tgtgcttttc accacagagg gcatcatttt taggtatttg tatgtgaatt   158400
gcagtgactt tataaattag tttaacttat tcttgttaga gtttaataat aataatacat   158460
gcaatattat atttatttag ttctgtgtct aattttattg tcataagttg ctgtacatgg   158520
catagtttta gcccttaatg ctttaaccaa cttaattttt ttaatgcaga aattcatata   158580
aaacttttca tcatcttttc tgttttttaa ctgtgttggc atagtttttc tacaaaaacc   158640
aaaattgttt ttcccttttt tgttaacttc ccatactatc ccaacataca aaattatttg   158700
gtattatcag tgactatgtt ttttaatta ttatacttta agttctggga tatatgtgca   158760
gaacatgcag gtttgttaca tgggtataca cgtgccatgg tggtttgctg cacccatcaa   158820
cccatcatct acattaggta tttctcctaa tgctatccct gccctagccc cccatcccctc   158880 gacaggccct ggtgcgtgac gttcccctcc ctgtgtccat gttttctcat tgttcaactc   158940
ccacttacga gtgagaacct gtggtgtttg gttttctatt cctgtgttag tttgctgaga   159000
atgatggttt ccagcttcat ccatgtccct tcaaggatg tgaactcatg acccccttttt  159060 ttttttttgtt ttttgagaca gagtctcact ctgtcaccca ggctggagtg cagtggtggc   159120
gctatctcag ctcactgcaa cctccacctc ccaagttcaa gcaattctcc agcctcagcc   159180
tcccaagtag cggggattac agacgcatgc cacgcctggc taattttttgt atttttagta   159240 gagagagggt ttcatcatgt tggccaggct gatctcaaac tcctgacctc aaatgatctg   159300
catgccccag cctcccaaag tgctgggatt acaggcgtga gccaccatgc ctggctgttt   159360
aactattttt gatggacttt ttttccaaaaa tatgttttat gccatgataa acaattataa   159420
ggcataacca ttcattcatt cattcattca ttcattcatt cattcatttt gagacagagt   159480
ctcgctctgt cacccaggcc agagtgcagt ggcgcaatct cagctcactg caacctctgc   159540
ctcccaggtt caagctattc tcccacctca gcctcctgag tagctggaat acaggcaca   159600 tgccaccacg gcctgctaat ttttgtattt ttagtagaga tggagtttaa catgttggcc   159660
aggctggtct tgaactcctg acctcaggtg atgcaccttc ctgggcctcc caaagtgctg   159720
cgattacagg catgagccac cgcaccaggc agttaactct ttcttggaga gaaataatga   159780
aatctcatct cattaagttc tcattttaca cattagtaaa taaggctcag agaaattaag   159840
cagtttgctc aatcacacag ccaatggatt ggaaaccatt tctgtccaat tctaaagcct   159900
atgttgtcca attccaaagc ctctattcta ccacatacca ccttccctag agtgtactcc   159960
ctagattaat agggccactc gaattagaag ctgagaccta acactgattt gcctcgctgc   160020
caatgtcacc tacatcttcc aagcaggctt aaagccatct tgaattcatc ccttttgttc   160080 atgcccctatt gtcagtaacc aggcctaatt ctttgaaatg acttatatcc tttcctttct   160140
cagccaccat actatgccag gtattatcac cttactgcta acttaattct gtagaatgct   160200
atgtcagcct tctcctgagc ataggttgta aactggatct aaaatgattt gaatgagat    160260 tatagctgag taagaaaatg tgtagaaaca aagaggagag aatactaagt atatttttcc   160320
tattccttgt tttccaaatt ttgtgtaatt gttaattatt ttatgtaaag ataatgtata   160380
tttacctttc ctcctaatgt tgtttcttg tatttttaaa ctgagtgcat ttcttaaatt    160440
```

```
agttttttcc ccctccctca acagttaacc atgtgactga gtgccctgtg gaatcgtgtg   160500
ggatgctacc tgataaacca ggcttcttta accatgcaga gcagacaggc tgtttctttg   160560
acacaaatat cacaggcttc agggttaaga ttgctgtttt tctgtccttg ctttggcaca   160620
acacactgag ggttttttt attgcgggtt tgcctacagg tagattagat taattattac    160680
tatgtaatgc aagtacagtt gggggaaagc ttaggtagat atatttttt taaaaggtgc    160740
tgccttttg gatttataag aaaatgcctg tcagtcgtga tagaacagag ttttcctcat    160800
atgagtaaga ggaagggact ttcactttca gtggaacag ccatcactat caagatcagc    160860
tcatggaagt agtaaagaaa atatctcaaa atgagacaaa ctgaagtttt gtttttttt    160920
taatgactta agttttgtg ctcttgcaag actatacaaa actattttaa gaaagcagtg    160980
atatcacttg aacttcagtg ccctcactgt agaatttaaa agccttactg ttgattgccc    161040
atgttggact tgatggagaa attaaatatc tttcattatg ctttacaaaa tactgtatat    161100
gtttcagcaa gtttggggaa tgggagagga caaaaaaaag ttacatttaa tctatgcatt    161160
tttgccaagc catattgagt tattttacta ctagagacat taggaaacta actgtacaaa    161220
agaaccaagt ttaaaagcat tttgtggggt acatcatttc tataattgta taatgtattt    161280
ctttgtggtt ttaaatgata aagacattaa gttaacaaac atataagaaa tgtatgcact    161340
gtttgaaatg taaattattc ttagaacact ttcaatgggg gttgcattgt ccttttagtg    161400
ccttaatttg agataattat tttactgcca tgagtaagta tagaaatttc aaaaaatgta    161460
ttttcaaaaa attatgtgtg tcagtgagtt tttcattgat aattggttta atttaaaata    161520
tttagaggtt tgttggactt tcataaattg agtacaatct ttgcatcaaa ctacctgcta    161580
caataatgac tttataaaac tgcaaaaaat gtagaaggtt gcaccaacat aaaaaggaaa    161640
tatggcaata catccatgat gttttccagt taacatagga attaccagat aaatactgtt    161700
aaactcttgt ccagtaacaa gagttgattc atatggacag tatgatttat tgtttatttt    161760
tttaaccaaa tacctcctca gtaatttata atggctttgc agtaatgtgt atcagataag    161820
aagcactgga aaaccgatcg tctctaggat gatatgcatg tttcaagtgg tattgaaagc    161880
cgcactgatg gatatgtaat aataaacata tctgttatta atatactaat gactctgtgc    161940
tcatttaatg agaaataaaa gtaatttatg gatgggtatc tttaattttt actgcaatgt    162000
gttttctcat ggctgaaatg aatggaaaac atacttcaaa ttagtctctg attgtatata    162060
aatgtttgtg aaattccatg gttagattaa agtgtatttt taaaagataa aa            162112
```

<210> SEQ ID NO 2
<211> LENGTH: 1354
<212> TYPE: PRT
<213> ORGANISM: Homo sapiens

<400> SEQUENCE: 2

```
Met Ser Thr Gly Asp Ser Phe Glu Thr Arg Phe Glu Lys Met Asp Asn
1               5                   10                  15

Leu Leu Arg Asp Pro Lys Ser Glu Val Asn Ser Asp Cys Leu Leu Asp
            20                  25                  30

Gly Leu Asp Ala Leu Val Tyr Asp Leu Asp Phe Pro Ala Leu Arg Lys
        35                  40                  45

Asn Lys Asn Ile Asp Asn Phe Leu Ser Arg Tyr Lys Asp Thr Ile Asn
    50                  55                  60

Lys Ile Arg Asp Leu Arg Met Lys Ala Glu Asp Tyr Glu Val Val Lys
65                  70                  75                  80

Val Ile Gly Arg Gly Ala Phe Gly Glu Val Gln Leu Val Arg His Lys
```

```
            85                  90                  95
Ser Thr Arg Lys Val Tyr Ala Met Lys Leu Leu Ser Lys Phe Glu Met
            100                 105                 110

Ile Lys Arg Ser Asp Ser Ala Phe Phe Trp Glu Glu Arg Asp Ile Met
            115                 120                 125

Ala Phe Ala Asn Ser Pro Trp Val Val Gln Leu Phe Tyr Ala Phe Gln
            130                 135                 140

Asp Asp Arg Tyr Leu Tyr Met Val Met Glu Tyr Met Pro Gly Gly Asp
145                 150                 155                 160

Leu Val Asn Leu Met Ser Asn Tyr Asp Val Pro Glu Lys Trp Ala Arg
                    165                 170                 175

Phe Tyr Thr Ala Glu Val Val Leu Ala Leu Asp Ala Ile His Ser Met
                    180                 185                 190

Gly Phe Ile His Arg Asp Val Lys Pro Asp Asn Met Leu Leu Asp Lys
                    195                 200                 205

Ser Gly His Leu Lys Leu Ala Asp Phe Gly Thr Cys Met Lys Met Asn
            210                 215                 220

Lys Glu Gly Met Val Arg Cys Asp Thr Ala Val Gly Thr Pro Asp Tyr
225                 230                 235                 240

Ile Ser Pro Glu Val Leu Lys Ser Gln Gly Gly Asp Gly Tyr Tyr Gly
                    245                 250                 255

Arg Glu Cys Asp Trp Trp Ser Val Gly Val Phe Leu Tyr Glu Met Leu
                    260                 265                 270

Val Gly Asp Thr Pro Phe Tyr Ala Asp Ser Leu Val Gly Thr Tyr Ser
                    275                 280                 285

Lys Ile Met Asn His Lys Asn Ser Leu Thr Phe Pro Asp Asp Asn Asp
290                 295                 300

Ile Ser Lys Glu Ala Lys Asn Leu Ile Cys Ala Phe Leu Thr Asp Arg
305                 310                 315                 320

Glu Val Arg Leu Gly Arg Asn Gly Val Glu Glu Ile Lys Arg His Leu
                    325                 330                 335

Phe Phe Lys Asn Asp Gln Trp Ala Trp Glu Thr Leu Arg Asp Thr Val
                    340                 345                 350

Ala Pro Val Val Pro Asp Leu Ser Ser Asp Ile Asp Thr Ser Asn Phe
                    355                 360                 365

Asp Asp Leu Glu Glu Asp Lys Gly Glu Glu Glu Thr Phe Pro Ile Pro
            370                 375                 380

Lys Ala Phe Val Gly Asn Gln Leu Pro Phe Val Gly Phe Thr Tyr Tyr
385                 390                 395                 400

Ser Asn Arg Arg Tyr Leu Ser Ser Ala Asn Pro Asn Asp Asn Arg Thr
                    405                 410                 415

Ser Ser Asn Ala Asp Lys Ser Leu Gln Glu Ser Leu Gln Lys Thr Ile
            420                 425                 430

Tyr Lys Leu Glu Glu Gln Leu His Asn Glu Met Gln Leu Lys Asp Glu
            435                 440                 445

Met Glu Gln Lys Cys Arg Thr Ser Asn Ile Lys Leu Asp Lys Ile Met
450                 455                 460

Lys Glu Leu Asp Glu Glu Gly Asn Gln Arg Arg Asn Leu Glu Ser Thr
465                 470                 475                 480

Val Ser Gln Ile Glu Lys Glu Lys Met Leu Leu Gln His Arg Ile Asn
                    485                 490                 495

Glu Tyr Gln Arg Lys Ala Glu Gln Glu Asn Glu Lys Arg Arg Asn Val
                    500                 505                 510
```

-continued

```
Glu Asn Glu Val Ser Thr Leu Lys Asp Gln Leu Glu Asp Leu Lys Lys
            515                 520                 525
Val Ser Gln Asn Ser Gln Leu Ala Asn Glu Lys Leu Ser Gln Leu Gln
        530                 535                 540
Lys Gln Leu Glu Glu Ala Asn Asp Leu Leu Arg Thr Glu Ser Asp Thr
545                 550                 555                 560
Ala Val Arg Leu Arg Lys Ser His Thr Glu Met Ser Lys Ser Ile Ser
                565                 570                 575
Gln Leu Glu Ser Leu Asn Arg Glu Leu Gln Glu Arg Asn Arg Ile Leu
            580                 585                 590
Glu Asn Ser Lys Ser Gln Thr Asp Lys Asp Tyr Tyr Gln Leu Gln Ala
        595                 600                 605
Ile Leu Glu Ala Glu Arg Arg Asp Arg Gly His Asp Ser Glu Met Ile
610                 615                 620
Gly Asp Leu Gln Ala Arg Ile Thr Ser Leu Gln Glu Glu Val Lys His
625                 630                 635                 640
Leu Lys His Asn Leu Glu Lys Val Glu Gly Glu Arg Lys Glu Ala Gln
                645                 650                 655
Asp Met Leu Asn His Ser Glu Lys Glu Lys Asn Asn Leu Glu Ile Asp
            660                 665                 670
Leu Asn Tyr Lys Leu Lys Ser Leu Gln Gln Arg Leu Glu Gln Glu Val
        675                 680                 685
Asn Glu His Lys Val Thr Lys Ala Arg Leu Thr Asp Lys His Gln Ser
690                 695                 700
Ile Glu Glu Ala Lys Ser Val Ala Met Cys Glu Met Glu Lys Lys Leu
705                 710                 715                 720
Lys Glu Glu Arg Glu Ala Arg Glu Lys Ala Glu Asn Arg Val Val Gln
                725                 730                 735
Ile Glu Lys Gln Cys Ser Met Leu Asp Val Asp Leu Lys Gln Ser Gln
            740                 745                 750
Gln Lys Leu Glu His Leu Thr Gly Asn Lys Glu Arg Met Glu Asp Glu
        755                 760                 765
Val Lys Asn Leu Thr Leu Gln Leu Glu Gln Glu Ser Asn Lys Arg Leu
770                 775                 780
Leu Leu Gln Asn Glu Leu Lys Thr Gln Ala Phe Glu Ala Asp Asn Leu
785                 790                 795                 800
Lys Gly Leu Glu Lys Gln Met Lys Gln Glu Ile Asn Thr Leu Leu Glu
                805                 810                 815
Ala Lys Arg Leu Leu Glu Phe Glu Leu Ala Gln Leu Thr Lys Gln Tyr
            820                 825                 830
Arg Gly Asn Glu Gly Gln Met Arg Glu Leu Gln Asp Gln Leu Glu Ala
        835                 840                 845
Glu Gln Tyr Phe Ser Thr Leu Tyr Lys Thr Gln Val Lys Glu Leu Lys
850                 855                 860
Glu Glu Ile Glu Glu Lys Asn Arg Glu Asn Leu Lys Lys Ile Gln Glu
865                 870                 875                 880
Leu Gln Asn Glu Lys Glu Thr Leu Ala Thr Gln Leu Asp Leu Ala Glu
                885                 890                 895
Thr Lys Ala Glu Ser Glu Gln Leu Ala Arg Gly Leu Leu Glu Glu Gln
            900                 905                 910
Tyr Phe Glu Leu Thr Gln Glu Ser Lys Lys Ala Ala Ser Arg Asn Arg
        915                 920                 925
Gln Glu Ile Thr Asp Lys Asp His Thr Val Ser Arg Leu Glu Glu Ala
930                 935                 940
```

Asn Ser Met Leu Thr Lys Asp Ile Glu Ile Leu Arg Arg Glu Asn Glu
945                 950                 955                 960

Glu Leu Thr Glu Lys Met Lys Lys Ala Glu Glu Tyr Lys Leu Glu
            965                 970                 975

Lys Glu Glu Glu Ile Ser Asn Leu Lys Ala Ala Phe Glu Lys Asn Ile
                980                 985                 990

Asn Thr Glu Arg Thr Leu Lys Thr Gln Ala Val Asn Lys Leu Ala Glu
            995                 1000                1005

Ile Met Asn Arg Lys Asp Phe Lys Ile Asp Arg Lys Lys Ala Asn
    1010                1015                1020

Thr Gln Asp Leu Arg Lys Lys Glu Lys Glu Asn Arg Lys Leu Gln
    1025                1030                1035

Leu Glu Leu Asn Gln Glu Arg Glu Lys Phe Asn Gln Met Val Val
    1040                1045                1050

Lys His Gln Lys Glu Leu Asn Asp Met Gln Ala Gln Leu Val Glu
    1055                1060                1065

Glu Cys Ala His Arg Asn Glu Leu Gln Met Gln Leu Ala Ser Lys
    1070                1075                1080

Glu Ser Asp Ile Glu Gln Leu Arg Ala Lys Leu Leu Asp Leu Ser
    1085                1090                1095

Asp Ser Thr Ser Val Ala Ser Phe Pro Ser Ala Asp Glu Thr Asp
    1100                1105                1110

Gly Asn Leu Pro Glu Ser Arg Ile Glu Gly Trp Leu Ser Val Pro
    1115                1120                1125

Asn Arg Gly Asn Ile Lys Arg Tyr Gly Trp Lys Lys Gln Tyr Val
    1130                1135                1140

Val Val Ser Ser Lys Lys Ile Leu Phe Tyr Asn Asp Glu Gln Asp
    1145                1150                1155

Lys Glu Gln Ser Asn Pro Ser Met Val Leu Asp Ile Asp Lys Leu
    1160                1165                1170

Phe His Val Arg Pro Val Thr Gln Gly Asp Val Tyr Arg Ala Glu
    1175                1180                1185

Thr Glu Glu Ile Pro Lys Ile Phe Gln Ile Leu Tyr Ala Asn Glu
    1190                1195                1200

Gly Glu Cys Arg Lys Asp Val Glu Met Glu Pro Val Gln Gln Ala
    1205                1210                1215

Glu Lys Thr Asn Phe Gln Asn His Lys Gly His Glu Phe Ile Pro
    1220                1225                1230

Thr Leu Tyr His Phe Pro Ala Asn Cys Asp Ala Cys Ala Lys Pro
    1235                1240                1245

Leu Trp His Val Phe Lys Pro Pro Ala Leu Glu Cys Arg Arg
    1250                1255                1260

Cys His Val Lys Cys His Arg Asp His Leu Asp Lys Lys Glu Asp
    1265                1270                1275

Leu Ile Cys Pro Cys Lys Val Ser Tyr Asp Val Thr Ser Ala Arg
    1280                1285                1290

Asp Met Leu Leu Leu Ala Cys Ser Gln Asp Glu Gln Lys Lys Trp
    1295                1300                1305

Val Thr His Leu Val Lys Lys Ile Pro Lys Asn Pro Pro Ser Gly
    1310                1315                1320

Phe Val Arg Ala Ser Pro Arg Thr Leu Ser Thr Arg Ser Thr Ala
    1325                1330                1335

Asn Gln Ser Phe Arg Lys Val Val Lys Asn Thr Ser Gly Lys Thr

Ser

<210> SEQ ID NO 3
<211> LENGTH: 6650
<212> TYPE: DNA
<213> ORGANISM: Homo sapiens
<220> FEATURE:
<221> NAME/KEY: misc_feature
<223> OTHER INFORMATION: mRNA

<400> SEQUENCE: 3

| | | | | | |
|---|---|---|---|---|---|
| gctggttccc | cttccgagcg | tccgcgcccc | gcatgcgcag | tctgccccgg | cggtctccgt | 60 |
| ttgtttgaac | aggaaggcgg | acatattagt | ccctctcagc | cccctcgcc | ccacccccca | 120 |
| ggcattcgcc | gccgcgactc | gcccttcc | cggctggac | cgcagcccct | cccagaagct | 180 |
| cccccatcag | cagccgccgg | gacccaacta | tcgtcttcct | cttcgcccgc | tctccagcct | 240 |
| ttcctctgct | aagtctccat | cgggcatcga | cctcgcctg | ccccaccgga | caccgtagca | 300 |
| gcagccccag | cagcgacggg | acaaaatggg | agagtgaggc | tgtcctgcgt | ggaccagctc | 360 |
| gtggccgaga | ctgatcggtg | cgtcgggccg | ggccgagtag | agccggggac | gcggggctag | 420 |
| accgtctaca | gcgcctctga | gcggagcggg | cccggcccgt | ggcccgagcg | gcggccgcag | 480 |
| ctggcacagc | tcctcacccg | cccttttgctt | tcgccttcc | tcttctccct | ccccttgttgc | 540 |
| ccggagggag | tctccaccct | gcttctcttt | ctctacccgc | tcctgcccat | ctcgggacgg | 600 |
| ggaccctcc | atggcgacgg | cggccgggc | ccgctagact | gaagcacctc | gccggagcga | 660 |
| cgaggctggt | ggcgacggcg | ctgtcggctg | tcgtgagggg | ctgccgggtg | ggatgcgact | 720 |
| tgggcgtcc | gagcggctgt | gggtcgctgt | tgccccccggc | ccggggtctg | gagagcggag | 780 |
| gtccctcag | tgaggggaag | acggggggaac | cgggcgcacc | tggtgaccct | gaggttccgg | 840 |
| ctcctccgcc | ccgcggctgc | gaacccaccg | cggaggaagt | tggttgaaat | tgcttcccgc | 900 |
| tgctggtgct | ggtaagaggg | cattgtcaca | gcagcagcaa | catgtcgact | ggggacagtt | 960 |
| ttgagactcg | atttgaaaaa | atggacaacc | tgctgcggga | tcccaaatcg | gaagtgaatt | 1020 |
| cggattgttt | gctggatgga | ttggatgctt | tggtatatga | tttggatttt | cctgccttaa | 1080 |
| gaaaaaacaa | aaatattgac | aacttttttaa | gcagatataa | agacacaata | aataaaatca | 1140 |
| gagatttacg | aatgaaagct | gaagattatg | aagtagtgaa | ggtgattggt | agaggtgcat | 1200 |
| ttggagaagt | tcaattggta | aggcataaat | ccaccaggaa | ggtatatgct | atgaagcttc | 1260 |
| tcagcaaatt | tgaaatgata | aagagatctg | attctgcttt | tttctgggaa | gaaagggaca | 1320 |
| tcatggcttt | tgccaacagt | ccttgggttg | ttcagctttt | ttatgcattc | caagatgatc | 1380 |
| gttatctcta | catggtgatg | gaatacatgc | ctggtggaga | tcttgtaaac | ttaatgagca | 1440 |
| actatgatgt | gcctgaaaaa | tgggcacgat | tctatactgc | agaagtagtt | cttgcattgg | 1500 |
| atgcaatcca | ttcatgggt | tttattcaca | gagatgtgaa | gcctgataac | atgctgctgg | 1560 |
| ataaatctgg | acatttgaag | ttagcagatt | ttggtacttg | tatgaagatg | aataaggaag | 1620 |
| gcatggtacg | atgtgataca | gcggttggaa | cacctgatta | tatttccccct | gaagtattaa | 1680 |
| aatcccaagg | tggtgatggt | tattatggaa | gagaatgtga | ctggtggtcg | gttgggtat | 1740 |
| ttttatacga | aatgcttgta | ggtgatacac | cttttatgc | agattctttg | gttgaacttt | 1800 |
| acagtaaaat | tatgaaccat | aaaaattcac | ttaccttttcc | tgatgataat | gacatatcaa | 1860 |
| aagaagcaaa | aaacccttatt | tgtgccttcc | ttactgacag | ggaagtgagg | ttagggcgaa | 1920 |
| atggtgtaga | agaaatcaaa | cgacatctct | tcttcaaaaa | tgaccagtgg | gcttgggaaa | 1980 |

```
cgctccgaga cactgtagca ccagttgtac ccgatttaag tagtgacatt gatactagta    2040
attttgatga cttggaagaa gataaaggag aggaagaaac attccctatt cctaaagctt    2100
tcgttggcaa tcaactacct tttgtaggat ttacatatta tagcaatcgt agatacttat    2160
cttcagcaaa tcctaatgat aacagaacta gctccaatgc agataaaagc ttgcaggaaa    2220
gtttgcaaaa aacaatctat aagctggaag aacagctgca taatgaaatg cagttaaaag    2280
atgaaatgga gcagaagtgc agaacctcaa acataaaact agacaagata atgaaagaat    2340
tggatgaaga gggaaatcaa agaagaaatc tagaatctac agtgtctcag attgagaagg    2400
agaaaatgtt gctacagcat agaattaatg agtaccaaag aaaagctgaa caggaaaatg    2460
agaagagaag aaatgtagaa aatgaagttt ctacattaaa ggatcagttg gaagacttaa    2520
agaaagtcag tcagaattca cagcttgcta atgagaagct gtcccagtta caaaagcagc    2580
tagaagaagc caatgactta cttaggacag aatcggacac agctgtaaga ttgaggaaga    2640
gtcacacaga gatgagcaag tcaattagtc agttagagtc cctgaacaga gagttgcaag    2700
agagaaatcg aattttagag aattctaagt cacaaacaga caaagattat taccagctgc    2760
aagctatatt agaagctgaa cgaagagaca gaggtcatga ttctgagatg attggagacc    2820
ttcaagctcg aattacatct ttacaagagg aggtgaagca tctcaaacat aatctcgaaa    2880
aagtggaagg agaaagaaaa gaggctcaag acatgcttaa tcactcagaa aaggaaagaa    2940
ataatttaga gatagattta aactacaaac ttaaatcatt acaacaacgg ttagaacaag    3000
aggtaaatga acacaaagta accaaagctc gtttaactga caaacatcaa tctattgaag    3060
aggcaaagtc tgtggcaatg tgtgagatgg aaaaaaagct gaaagaagaa agagaagctc    3120
gagagaaggc tgaaaatcgg gttgttcaga ttgagaaaca gtgttccatg ctagacgttg    3180
atctgaagca atctcagcag aaactagaac atttgactgg aaataaagaa aggatggagg    3240
atgaagttaa gaatctaacc ctgcaactgg agcaggaatc aaataagcgg ctgttgttac    3300
aaaatgaatt gaagactcaa gcatttgagg cagacaattt aaaaggttta gaaaagcaga    3360
tgaaacagga aataaatact ttattggaag caaagagatt attagaattt gagttagctc    3420
agcttacgaa acagtataga ggaaatgaag gacagatgcg ggagctacaa gatcagcttg    3480
aagctgagca atatttctcg acactttata aacccaggt aaaggaactt aaagaagaaa    3540
ttgaagaaaa aaacagagaa aatttaagga aaatacagga actacaaaat gaaaagagaa    3600
ctcttgctac tcagttggat ctagcagaaa caaaagctga gtctgagcag ttggcgcgag    3660
gccttctgga agaacagtat tttgaattga cgcaagaaag caagaaagct gcttcaagaa    3720
atagacaaga gattacagat aaagatcaca ctgttagtcg gcttgaagaa gcaaacagca    3780
tgctaaccaa agatattgaa atattaagaa gagagaatga agagctaaca gagaaaatga    3840
agaaggcaga ggaagaatat aaactggaga aggaggagga gatcagtaat cttaaggctg    3900
cctttgaaaa gaatatcaac actgaacgaa cccttaaaac acaggctgtt aacaaattgg    3960
cagaaataat gaatcgaaaa gattttaaaa ttgatagaaa gaaagctaat acacaagatt    4020
tgagaaagaa agaaaaggaa aatcgaaagc tgcaactgga actcaaccaa gaaagagaga    4080
aattcaacca gatggtagtg aaacatcaga aggaactgaa tgacatgcaa gcgcaattgg    4140
tagaagaatg tgcacatagg aatgagcttc agatgcagtt ggccagcaaa gagagtgata    4200
ttgagcaatt gcgtgctaaa ctttttggacc tctcggattc tacaagtgtt gctagttttc    4260
ctagtgctga tgaaactgat ggtaacctcc cagagtcaag aattgaaggt tggctttcag    4320
taccaaatag aggaaatatc aaacgatatg gctggaagaa acagtatgtt gtggtaagca    4380
```

```
gcaaaaaaat tttgttctat aatgacgaac aagataagga gcaatccaat ccatctatgg    4440
tattggacat agataaactg tttcacgtta gacctgtaac ccaaggagat gtgtatagag    4500
ctgaaactga agaaattcct aaaatattcc agatactata tgcaaatgaa ggtgaatgta    4560 gaaagatgt agagatggaa ccagtacaac aagctgaaaa aactaatttc caaaatcaca     4620
aaggccatga gtttattcct acactctacc actttcctgc caattgtgat gcctgtgcca    4680
aacctctctg gcatgttttt aagccacccc ctgccctaga gtgtcgaaga tgccatgtta    4740
agtgccacag agatcactta gataagaaag aggacttaat ttgtccatgt aaagtaagtt    4800
atgatgtaac atcagcaaga gatatgctgc tgttagcatg ttctcaggat gaacaaaaaa    4860
aatgggtaac tcatttagta aagaaaatcc ctaagaatcc accatctggt tttgttcgtg    4920
cttcccctcg aacgctttct acaagatcca ctgcaaatca gtctttccgg aaagtggtca    4980
aaaatacatc tggaaaaact agttaaccat gtgactgagt gccctgtgga atcgtgtggg    5040
atgctacctg ataaaccagg cttcttTaac catgcagagc agacaggctg tttctttgac    5100
acaaatatca caggcttcag ggttaagatt gctgttTttc tgtccttgct ttggcacaac    5160
acactgaggg tttttTtTat tgcgggtttg cctacaggta gattagatta attattacta    5220
tgtaatgcaa gtacagttgg gggaaagctt aggtagatat attttTtTta aaggtgctg     5280 cctTtTtgga tttataagaa aatgcctgtc agtcgtgata gaacagagtt ttcctcatat    5340
gagtaagagg aagggacttt cactTtcaag tggaacagcc atcactatca agatcagctc    5400
atggaaggag taaagaaaat atctcaaaat gagacaaact gaagttttgt tttTtTtTta    5460
atgacttaag ttTtTgtgct cttgcaagac tatacaaaac tattTaaga aagcagtgat    5520 atcacttgaa cttcagtgcc ctcactgtag aatttaaaag ccttactgtt gattgcccat    5580
gttggacttg atgagagaat taaatatctt tcattatgct ttacaaaata ctgtatatgt    5640
ttcagcaagt ttggggaatg ggagaggaca aaaaaaagtt acatttaatc tatgcattTt    5700
tgccaagcca tattgagtta ttTtactact agagacatta ggaaactaac tgtacaaaag    5760
aaccaagttt aaaagcattt tgtgggtac atcatttcta taattgtata atgtattTct     5820
ttgtggtttt aaatgataaa gacattaagt taacaaacat ataagaaatg tatgcactgt    5880
ttgaaatgta aattattctt agaacacttt caatgggggt tgcattgtcc ttttagtgcc    5940
ttaatTtgag ataattattT tactgccatg agtaagtata gaaatttcaa aaaatgtatt    6000
ttcaaaaaat tatgtgtgtc agtgagttTt tcattgataa ttggtttaat ttaaaatatt    6060
tagaggtttg ttggactttc ataaattgag tacaatcttt gcatcaaact acctgctaca    6120
ataatgactt tataaaactg caaaaaatgt agaaggttgc accaacataa aaaggaaata    6180
tggcaataca tccatgatgt tttccagtta acataggaat taccagataa atactgttaa    6240
actcttgtcc agtaacaaga gttgattcat atggacagta tgatttattg tttatttttt    6300
taaccaaata cctcctcagt aatttataat ggctttgcag taatgtgtat cagataagaa    6360
gcactggaaa accgatcgtc tctaggatga tatgcatgtt tcaagtggta ttgaaagccg    6420
cactgatgga tatgtaataa taaacatatc tgttattaat atactaatga ctctgtgctc    6480
atttaatgag aaataaaagt aatttatgga tgggtatctt taattttTac tgcaatgtgt    6540
tttctcatgg ctgaaatgaa tggaaaacat acttcaaatt agtctctgat tgtatataaa    6600
tgtttgtgaa attccatggt tagattaaag tgtatttTta aaagataaaa                6650
```